US007622301B2

(12) United States Patent
Ren et al.

(10) Patent No.: US 7,622,301 B2
(45) Date of Patent: Nov. 24, 2009

(54) COMPOSITIONS AND METHODS USING RNA INTERFERENCE FOR CONTROL OF NEMATODES

(75) Inventors: Peifeng Ren, Cary, NC (US); Xiang Huang, Apex, NC (US); Sumita Chaudhuri, Cary, NC (US); Lawrence Talton, Sanford, NC (US); John McMillan, Raleigh, NC (US)

(73) Assignee: BASF Plant Science GmbH (DE)

( * ) Notice: Subject to any disclaimer, the term of this patent is extended or adjusted under 35 U.S.C. 154(b) by 488 days.

(21) Appl. No.: 10/906,472

(22) Filed: Feb. 22, 2005

(65) Prior Publication Data

US 2005/0188438 A1 Aug. 25, 2005

Related U.S. Application Data

(60) Provisional application No. 60/547,418, filed on Feb. 24, 2004, provisional application No. 60/601,344, filed on Aug. 13, 2004.

(51) Int. Cl.
*C12N 15/82* (2006.01)
*C12N 5/10* (2006.01)
(52) U.S. Cl. ..................... 435/468; 800/285
(58) Field of Classification Search ............ None
See application file for complete search history.

(56) References Cited

U.S. PATENT DOCUMENTS

| 5,589,622 | A | 12/1996 | Gurr et al. | 800/279 |
| 5,824,876 | A | 10/1998 | Gurr et al. | 800/279 |
| 6,506,559 | B1 | 1/2003 | Fire et al. | 435/6 |
| 6,521,438 | B1 | 2/2003 | Davis et al. | |
| 6,753,139 | B1 | 6/2004 | Baulcombe et al. | 435/6 |
| 6,784,337 | B1 | 8/2004 | Atkinson et al. | |
| 2002/0086356 | A1 | 7/2002 | Tuschl et al. | |
| 2003/0150017 | A1 | 8/2003 | Mesa et al. | |
| 2003/0235898 | A1 | 12/2003 | Kloek et al. | 435/193 |
| 2004/0091467 | A1 | 5/2004 | Williams et al. | 424/94.5 |
| 2004/0098761 | A1 | 5/2004 | Trick et al. | 800/279 |
| 2004/0133943 | A1 | 7/2004 | Plaetinck et al. | 800/279 |
| 2005/0091713 | A1 | 4/2005 | Atkinson et al. | |

FOREIGN PATENT DOCUMENTS

| EP | 0983370 B1 | 9/2003 |
| EP | 1080208 B1 | 3/2005 |
| WO | WO 99/53050 | 10/1999 |
| WO | WO 01/37654 A2 | 5/2001 |
| WO | WO 01/96584 A2 | 12/2001 |
| WO | WO 03/052110 A2 | 6/2003 |
| WO | WO 2004/005485 A2 | 1/2004 |

OTHER PUBLICATIONS

Terami et al., J. Cell Biol. 1999, vol. 146, pp. 193-202.*
Yan et al., GenBank Accession No. AF249890, Jul. 12, 2000.*
Leroux, MR, "Characterization of four new tcp-1-related cct genes from the nematode Caernorhabditis elegans.," DNA Cell Biol., Nov. 1995, pp. 95-60, 14(11), Abstract Only.
Hammond et al., "Post-transcriptional gene silencing by double-stranded RNA," Nature Reviews, Feb. 2001, pp. 110-119, vol. 2.
Bass, BL, "The short answer," Nature, May 24, 2001, pp. 428-429, vol. 411.
Elbashir et al., "Duplexes of 21-nucleotide RNAs mediate RNA interference in cultured mammalian cells,"Nature, May 24, 2001, pp. 494-498, vol. 411.
Wesley et al., "Construct design for efficient, effective and high-throughput gene silencing in plants," The Plant Journal, 2001, pp. 581-590, 27:6.
Bass, BL, "Double-stranded RNA as a template for gene silencing," Cell, Apr. 28, 2000, pp. 235-238, vol. 101.
Birnby et al., "A transmembrane Guanylyl Cyclase (DAF-11) and Hsp90 (DAF-21) regulate a common set of chemosensory behaviors in . . . " Genetics, May 2000, pp. 85-104, vol. 155.
Young LD, "Managing soybean resistance to heterodera glycines," Suppl. to Journal of Nematology, 1998, pp. 525-529, vol. 30:4S.
Davis et al., "Nematode parasitism genes," Annu. Rev. Phytopathol., Sep. 2000, pp. 341-372, vol. 38.
Boutla et al., "Induction of RNA interference in Caenorhabditis elegans by RNAs derived from plants exhibiting . . . ," Nucleic Acids Res., 2002, pp. 1688-1694, 30:7.
Urwin et al., "Ingestion of double-stranded RNA by preparasitic juvenile cyst nematodes leads to RNA interference,"MPMI, 2002, pp. 747-752, 15:8.
Leroux et al., "Characterization of C. elegans CCT, a hetero-oligomeric cytosolic chaperonin containing two related proteins, CCT-1 . . . ," Early 1995 Int'l Worm Mtg. Abstract.
Goenczy et al., "Functional genomic analysis of cell division in C. elegans using RNAi of genes on chromosome III," Nature, Nov. 16, 2000, 331-336, 408.
Kamath et al., "Systematic functional analysis of the Caenorhabditis elegans genome using RNAi," Nature, Jan. 16, 2003, 231-237, 421.
Gao et al., "Identification of Putative Parasitism Genes Expressed in the Esophageal Gland Cells of the Soybean Cyst Nematode Heterodera . . . " MPMI, 2001, pp. 1247-1254, 14.
Database UniProt 'Online!, Chaperonin containing tcp-1 protein 6, isoform b. XP002328417 retrieved from EBI accession No. UniProt:Q8MYQ9, Oct. 1, 2002.
Atkinson et al., "Engineering Plants for Nematode Resistance," Annu. Rev. Phytopathol., 2003, 615-639, 41.
Simmer et al., "Genome-wide RNAi of C. elegans using the hyper-sensitive rrf-3 strain reveals novel gene functions," 2003, PloS Biology, 1(1), pp. 77-84.

(Continued)

*Primary Examiner*—Ashwin Mehta
(74) *Attorney, Agent, or Firm*—Patricia A. McDaniels

(57) ABSTRACT

The present invention concerns double stranded RNA compositions and transgenic plants capable of inhibiting expression of essential genes in parasitic nematodes, and methods associated therewith. Specifically, the invention relates to the use of RNA interference to inhibit expression of a target essential parasitic nematode gene selected from the group consisting of a parasitic nematode cytosolic chaperonin gene, a parasitic nematode gene encoding heat shock protein-90, a parasitic nematode gene homologous to the *C. elegans* Y65B4BR.5a gene, and a parasitic nematode gene homologous to a *C. elegans* pat-10 gene, and relates to the generation of plants that have increased tolerance to parasitic nematodes.

20 Claims, 14 Drawing Sheets

OTHER PUBLICATIONS

David P. Bartel, "MicroRNAs: Genomics, Biogenesis, Mechanism, and Function", journal, Jan. 23, 2004, Cell, vol. 116, 281-297, Cell Press, Cambridge, Massachusetts.

Yukio Kurihara and Yuichiro Watanabe, "Arabidopsis micro-RNA biogenesis through Dicer-like 1 protein functions", journal, Aug. 24, 2004, 12753-12758, vol. 101, No. 34, PNAS.

* cited by examiner

SEQ ID NO:1
(*H. glycines cct-6* full-length cDNA, long form)
ggtttaattacccaagtttgagcttcaataacctttaattggaagccatttgtctgcttacctgttaaatggctt
ccatcgcatgtttgaacccaaaagcggagttggcccggcacgcggccgcactggagatgaacatcagcggtgcta
aagggttgcaggaagtgatgaagaccaacctcgggccgaagggcacgctgaaaatgcttgtctccggttcgggtg
accttaaagtgactaaggacggcaatgttttactccatgaaatgcaaatccaacatccgactgcttcactgatcg
ccaaggcgtgcaccgcgcaaaacgacgtcaccggcgacgggaccacgtcgaccgttctgctgattggcgaactgc
tcaaacaggccgagaattacgtcagcgagggtgtccacccccatttggtcaccgagggtttccaattggcccatg
accatttgctccaactgttggccgcctccaaaaagacgttgcctatcgaccggccgctgctcatcgaagtggcca
ggacgacgttgcgcacaaaattggaccaaaagttggccgaccacgtcacggaatgtgttgtggacgccgttttgg
caattcgtcgggatgaaaacgacacggagcccgacttgcatatgattgaaattcagcaaatggaacacgagatgg
agacggacacgcagctgatccgtggcctcgtgcttgaccacggcggccgacacccggacatgccgaagagtgtgc
gaaacgtgcacattttgacatgcaatgtttcgttggagtttgagaaaactgaggtcaattcgggcctttttctaca
agacggcggctgagcgtgaacgtttgctgcaagcggagcgcgaatacatcacacgacgggtgctgaaaattgtgg
aactgaaggagacggtctgtgccggtggagatcaaggatttgtggtgattaatcaaaagggcattgatccgccgt
cgttggatttgttggcacagcacggcattttggccctgcgacgtgccaagcgtcggaacatggaacggctgcagt
tggcctgcggcggcgaggcggtcaattcggtggacgacctgacgcccgatgtgctcggctgggcaggcagtgttt
atgagcatgtgctgggcgaggacaaatacacttttgtggaggagtgcaaaagtcccaggtcggtcactttgctgc
tcaaagggcccaacaagcacagcatcacgcagctgaaggacgccatttatgacggacagcgggcggttgccaatg
cgttgaaagacggtgccgttttgcccggcgccggtgcatttgaaattgcgggatattgtgcactgaaaaagcttg
ccgacaatgtgaaagggcgtgccaaactcggtgttttggcttttgctgaggctttgctggttattccgaaaactt
tggcggtcaatgccggattcgacgcccaggaggccattgtcaagctggtggagacgttcagtgctgctggtgagc
tggtcggattggacctggagagcggagagccgtgtgttcctcagagcgtttgggacaatgtgtgcgtgaagcagg
cgagtctgaacgcctgtcagaacatcgcctccaatctgctggaggtggacgaggtgatgcgtgccggcatgcgcg
acttgaagggggacagtgaaaatgaacggaacggaaatgaaggagcaacaccaataaatcacaaaatgttaatg
gctttttctttgttgaactctgcgctttattgtttgaatcagaccactgctgtttttgctttttcaatctcgctt
ttctgaacgaatgaaaattttgacaat SEQ ID NO:2
(*H. glycines cct-6* full-length cDNA, short form)
gtttaattacccaagtttgaggctgagcgtgagcgtttgctgcaggcggagcgcgaatacatcacacgacgggtg
ctgaaaattgtggaactgaaggagacggtctgtgccggtggagatcaaggatttgtggtgattaatcaaaagggc
attgatccgccgtcgttggatttgttggcacagcacggcattttggccctgcgacgtgccaagcgtcggaacatg
gaacggctgcagttggcctgcggcggcgaggcggtcaattcggtggacgacctgacgcccgatgtgctcggctgg
gcaggcagtgtttatgagcatgtgctgggcgaggacaaatacacttttgtggaggagtgcaaaagtcccaggtcg
gtcactttgctgctcaaagggcccaacaagcacagcatcacgcagctgaaggacgccatttatgacggacagcgg
gcggttgccaatgcgttgaaagacggtgccgttttgcccggcgccggtgcatttgaaattgcgggatattgtgca
ctgaaaaagcttgccgacaatgtgaaagggcgtgccaaactcggtgttttggcttttgctgaggctttgctggtt
attccgaaaactttggcggtcaatgccggattcgacgcccaggaggccattgtcaagctggtggagacgttcagt
gctgctggtgagctggtcggattggacctggagagcggagagccgtgtgttcctcagagcgtttgggacaatgtg
tgcgtgaagcaggcgagtctgaacgcctgtcagaacatcgcctccaatctgctggaggtggacgaggtgatgcgt
gccggcatgcgcgacttgaagggggacagtgaaaatgaacggaacggaaatgaaggagcaacaccaataaatca
caaaatgttaatggctttttctttgttgaactctgcgctttattgtttgaatcagaccactgctgtttttgcttt
ttcaatctcgcttttctgaacgaatgaaaattttgacaat

FIGURE 1A

SEQ ID NO:3
( H. glycines daf-21 full-length cDNA), (agcgcggcttcgaggtcatctacatggtcgacccgattgacgagtact)gcgtccagcagctcaaagaatacgacg
ggaagaagttggtcagtgtgaccaaggaaggccttgagctgccagagagtgaggaggagaagaagaaatttgaagag
gacaaggtcaagttcgagaagctgtgcaaagtcattaaggacatcttggacaagaaagtccaaaaggtttctgtctc
aaaccgtttggtctcttctccgtgttgcattgtgaccggagagtacggatggtctgccaacatggaacggatcatga
aggcccaggcattgcgtgactcctccacaatgggatacatggcgtccaaaaagaacctggagatcaaccctgaccat
tcaatcatcaagtctttgcgcgaccgtgttgagaaggagcaggacgacaaaactgcaaaggacctcgttgtgctgct
gtacgaaacttctctgctcacctccggcttttcattggaggacccgcaacagcatgcgtcgcgaatttaccgaatgg
tgaaacttggacttgacatccccgacgaggaggagccggccgagcaacagccgagcacttcgggcgagccgacaatt
gcggagaaaattgctggtgccgaagaggaggcctcgagaatggaggaagttgactgaatggtgacatcgtctatcca
ttcttggatctcggctattcaatattttgattcattgttttttgttttcttgtttgacataaatttgaatt SEQ ID NO:4
( H. glycines Y65BR.5a full-length cDNA)
ggtttaattacccaagtttgagcaattcgagtgctacaaatagttcgaaatggtaactgcggaagataccgttaaaa
caaaggaagaagacccccaaaaaaacgacaacggacgacggatcgagttcagaggaagaagtgcccgagctcgaagag
ggcgacgttactgaagagcagaaaaaagttgctgaggcggccggactcagtgagcaggttgccgaaaagggctccaa
acaatcgcgttctgaaaagaaggctcgtaaactattcagcaaacttggcctcaagcaagtgcacggcgtttcgcgcg
tatgcatccgtaaatcgaagagcattttgttcgtcatcaacaagccggacgtgtacaaaagtccgggctccgacaca
tacgtcgtttttggcgaggcaaaaattgaagatttggcacaacacgctcaaatcactgacgtggagaatttgaaacc
gccctcaatcattcgcgatgttcgcaaccgaatcacaccggcggaggaggaaagcgatggcgaagaggctgatgcta
ctggaattgaagaaaaggatattgagttggtgatgtcgcaagcaaatgtttctcgaaacaaagctatcaaagcattg
aaaaaggctgacaatgatttggtgaacgctattatggcattgacaatgtaggaggaagccagaggaattcagagaaa
acattgttgaccttcgaattttttgcttcaatattttcctacgggaatcggttcttttaccattgctgattatgtta
ctttacgaatttttgcttataaaaattaaaaagcgt

FIGURE 1B

SEQ ID NO:5
(*H. glycines pat-10* full-length cDNA variant 1)
accgttttgtcctcctacccatttcctaaatcaaataacaatccacagatcgctgagaactggccgagaacatcg
aagaaatccttgccgaaatcgacggctcccaaattgaggagtaccaacgcttttcgatatgttcgaccgcggaa
agaacggttacataatggccactcaaattgggcaaattatgaacgcgatggagcaggactttgacgagaagaccc
tcagaaaattgatccgaaaatttgacgcggaccgctcgggcaaattggaattcgacgaattctgcgcgttggtgt
acactgtggccaacactgtggacaaagacacgttgcgaaaagagctgagagaggcattccgactgtttgacaagg
agggcaatggttacatttcgcgccccacgctcaaaggactgctgcatgaaattgcacccgatctcagcgacaagg
atttggaggcggcggtggacgaaattgacgaggacggcagcggaaagatcgaatttgaggaattttgggaactga
tggcgggcgaaacggactaaacgaacgatcagaaagaggaaagaagaacgaaagaaagtgatcaattggcggaa
acggcggaacgtacaaaaaacgtcctcaaaacaaaaataaataaataattcgccaattattattttttgcagcgga
atttcccattaaaattcagtgaaagt SEQ ID NO:6
(*H. glycines pat-10* full-length cDNA variant 2)

GGTTTAATTACCCAAGTTTGAGATCGCTGAGAAATGGCCGAGAACATCGAAGAAATCCTTGCCGAAATCGACGGCTC
CCAAATTGAGGAGTACCAACGCTTTTTCGATATGTTCGACCGCGGAAAGAACGGTTACATAATGGCCACTCAAATTG
GGCAAATTATGAACGCGATGGAGCAGGACTTTGACGAGAAGACCCTCAGAAAATTGATCCGAAAATTTGACGCGGAC
GGCTCGGGCAAATTGGAATTCGACGAATTCTGCGCGTTGGTGTACACTGTGGCCAACACTGTGGACAAAGACACGTT
GCGAAAAGAGCTGAGAGAGGCATTCCGACTGTTTGACAAGGAGGGCAATGGTTACATTTCGCGCCCCACGCTCAAAG
GACTGCTGCATGAAATTGCACCCGATCTCAGCGACAAGGATTTGGAGGCGGCGGTGGACGAAATTGACGAGGACGGC
AGCGGAAAGATCGAATTTGAGGAATTTTGGGAACTGATGGCGGGCGAAACGGACTAAACGAACGATCAGAAAGAGGA
AAGAAGAACGAAAGAAAGTGATCAATTGGCGGAAACGGCGGAACGTACAAAAAACGTCCTCAAAACAAAAATAAAT
AAATAATTCGCCAATTATTATTTTTGCAGCGGAATTTCCCATTAAAATTCAGTGAAAGT

SEQ ID NO:7
(*H. glycines pat-10* 5'UTR)
CCTTTTCGATCGTCCTTCCTTTTCTTCCCTCTTTTTTTTTGCTCCTTTAACTCATTTTCTTGATCCACC

FIGURE 1C

| EST contig | SEQ ID NO | Forward Primer | SEQ ID NO | Reverse Primer |
|---|---|---|---|---|
| H. glycines cct-6 middle | 8 | CGGAGCGCGAATACATCACA | 9 | AAGCCTCAGCAAAAGCCAAA |
| H. glycines daf-21 middle | 10 | ACGGGAAGAAGTTGGTCAGT | 11 | GAAGTTTCGTACAGCAGCAC |
| H. glycines Y65BR.5a middle | 12 | AAAAAACGACAACGGACGAC | 13 | TCGAGAAACATTTGCTTGCG |
| H. glycines pat-10 middle | 14 | ACCGTTTTGTCCTCCTACCC | 15 | GGGCGCGAAATGTAACCATT |
| F01F1.8a | 16 | AAAGTTGGGCTTGTTGAACG | 17 | GCACCACGACAGTGATATGG |
| C47E8.5 | 18 | AATACGTTTCCCGCATGAAG | 19 | AATGATGCAGCAAACAGCAC |
| Y65B4BR.5a | 20 | GGCTTAATTTTGGCTCAGATTTT | 21 | AAAGTTCTCGATCAATAGAGGGG |
| F54C1.7 | 22 | AACTCCTCGAACTCAATCTTTCC | 23 | AAGAATGTGTTTTGTGGAGGAGA |

| Common Primers | SEQ ID NO | |
|---|---|---|
| SL1 | 24 | GGTTTAATTACCCAAGTTTGA |
| GeneRacer 5' Primer | 25 | CGACTGGAGCACGAGGACACTGA |
| GeneRacer 5' Nested Primer | 26 | GGACACTGACATGGACTGAAGGAGTA |
| GeneRacer 3' Primer | 27 | GCTGTCAACGATACGCTACGTAACG |
| GeneRacer 3' Nested Primer | 28 | CGCTACGTAACGGCATGACAGTG |
| GeneRacer Oligo dT | 29 | GCTGTCAACGATACGCTACGTAACGGCATGACAGTG(T)$_{24}$ |

FIGURE 2A

| Gene | SEQ ID NO | Forward Primer | SEQ ID NO | Reverse Primer |
|---|---|---|---|---|
| H. glycines cct-6 5' | 24 | SL1 | 30 | GGTGCACTCCTCCACAAAAGTGTA |
| H. glycines cct-6 5' nested | 24 | SL1 | 31 | ATGCTCATAAACACTGCCTGC |
| H. glycines cct-6 3' | 32 | GGATTTGTTGGCACAGCACGGCAT | 27 | GeneRacer 3' Primer |
| H. glycines cct-6 3' nested | 33 | GCTCGGCTGGGCAGGCAGTGTTT | 28 | GeneRacer 3' Nested Primer |
| H. glycines pat-10 5' nested | 24 | SL1 | 34 | CGTCGAATTCCAATTTGCC |
| H. glycines pat-10 3' | 35 | TGAACGCGATGGAGCAGGACTTTGA | 27 | GeneRacer 3' Primer |
| H. glycines pat-10 3' nested | 36 | GACGAATTCTGCGCGTTGGTGTACA | 28 | GeneRacer 3' Nested Primer |
| H. glycines Y65BR.5a 5' | 24 | SL1 | 37 | TACACGTCCGGCTTGTTGATGA |
| H. glycines Y65BR.5a 5' nested | 24 | SL1 | 38 | TCGATTTACGGATGCATACGCG |
| H. glycines Y65BR.5a 3' | 39 | GTCATCAACAAGCCGGACGTGTACA | 27 | GeneRacer 3' Primer |
| H. glycines Y65BR.5a 3' nested | 40 | CATTCGCGATGTTCGCAACCGAAT | 28 | GeneRacer 3' Nested Primer |
| H. glycines daf-21 5' | 25 | GeneRacer 5' Primer | 41 | ATTGTGGAGGAGTCACGCAATG |
| H. glycines daf-21 5' nested | 26 | GeneRacer 5' Nested Primer | 42 | TGATCCGTTCCATGTTGGCAGA |
| H. glycines daf-21 3' | 43 | GTCTGCCAACATGGAACGGATCATGA | 27 | GeneRacer 3' Primer |
| daf-21 3' nested | 44 | GGCATTGCGTGACTCCTCCACAAT | 27 | GeneRacer 3' Nested Primer |

FIGURE 2B

SEQ ID NO:45 - F01F1.8a (homolog of *H. glycines cct-6*)

aaagttgggcttgttgaacgggatggggaatattatcaaacacggcaacagatcatagaaacggacacactgggggaatagaaaaacaa
ttttaatatttattctggttgtggctgcttcaagttggtcataccagcgcgcatcacttcatcaacaagcaagagattgcatgcaagtactgtcgc
cgacgagatactgttcttcttcaccgtcacattgtcccaaattccttgtggctcgacagctcctccggtttcgagatcgagtccaacggcgatat
ctggtccagcggcggttttctcctcaataagcttaacaagtgtttcctgagcatcatatcctccatttacggccagtgtctttggaataacgagaa
gagcttgagcaaacgcttcagctccgagcttggcacgtcccttcaggttctcaacatctttttcaacatcacgtaggcagcaatttcgaaagc
agcagctccagggagaacagcctctgaaaataggttactagaacagaagttaataaaatttaaactcactgtcaacgatggtgttgaaaaca
gcacgaagtccatcatgaatagcatccttgatttgagtgatggtatgcttgtttggtcccttgataagaagagtcacagattttggagcacggca
ttcctcgataaacgtgtatttctcttctccaagggaatgctcgtaaacgagtccagcccatccaagatcctctggagtcaaatcatcaactgagt
tgacggcttctcctccgacggccagctgaagacgttccatgttacgtctcttggcacgacgaagagcaagaattccttcggaagcaagcaa
gtcaagagatggaggatcgattcctttctggttgataacaacgaatcccttattcttaccatctggagaattatcaataaccttcttcttcaactca
ataatcttgtgaacacgacgagtaatgaattcacgttcggcagcgagaagtgcctcacgttccttggcggtcttgtagaaaagtcccgagttg
acttcagtcttctcgtattccaaagaaacgttgcaagtgagaatgtaagcgtctttaacgtgtcttggcatatctgggtgacgagctccatgatc
gagaactaatccacgaacaagtgtggtatccatatcactgtcgtggtgc

FIGURE 3A

SEQ ID NO:46 - C47E8.5 (homolog of SCN daf-21)

aatacgtttcccgcatgaaggagaaccaaactcaaatctactacatcaccggagagtccaaggatgttgttgctgcttcagctttcgtcgagc
gtgttaagagccgcggattcgaagtcctctacatgtgcgacccaattgatgagtactgcgtccaacaactcaaggagtatgatggaaagaag
cttgtctccgtcaccaaggaaggactcgagctcccagaaaccgaggaggagaagaagaagttcgaagaggacaaggttgcctacgaaaa
cctttgcaaggtcatcaaggacattttggagaagaaggttgagaaggttggagtttctaaccgtcttgtctcttccccatgctgcattgtcacttc
cgagtacggatggtccgctaacatggagcgcatcatgaaagctcaagctcttcgtgattcctctactatgggatacatggccgccaagaagc
atctcgaaatcaacccagaccacgctatcatgaagtaagttacccaaaaactattttaaaatgaacattcacaaacgttttgctatttcaggaca
cttcgtgatcgtgtcgaggtcgataagaatgacaagaccgttaaggatttggttgttcttcttttcgagactgctcttctcgcttccggattctccct
tgaggagccacaatctcacgcttcccgcatctacagaatgatcaagcttggtctcgatatcggagatgacgaaattgaagattctgctgttcca
tcatcgtgcaccgctgaggccaagattgagggagctgaggaggatgcttcccgcatggaggaggtcgactaaacatcctatttaatttatcat
ttgttacgagaagatctccccaaaagcccctccacagttttattcattgttttcctgtctatcgaacccaaataaagttccgtaattaatttcatcaat
gtttttttttgcaaacgtgaacttttgaagaagcacatttgaacagtttagatactcgagggaaattaaacagttttagtttatacgaaacatgattg
caatcttattcgagttggcatgtttcctgatcttggccagtgctgtttgctgcatcatt

FIGURE 3B

SEQ ID NO:47 - Y65B4BR.5a (homolog of SCN Y65BR.5a)

ggcttaattttggctcagattttcctcaaaaacatgaaaatccaatctagaataagtagtaatgggtatattctaagattgtgcaaaagttagcttg
aatttcctcgattaaagctttcctaccaagaaaaatgtgtggatattttgaatttacaagttttcatctttttttgtaatattctctttgaaactcctgttt
ctctcaaatttgtaaactttcataaacgttttttcagggttaccacattaaacaatgaccggaagcaccgaaactcgccagaaggaagtcaag
gaggttggttgttcaaagtgacgtctaaaatatttaaatttctatatttcagccacaagttgacgtttcggatgattccgacaacgaggccgtcga
gcaagagctcaccgaggagcaaagacgtgtggccgaggctgctggacttggagatcacatcgacaagcaggccaagcaaagccgctcc
gagaagaaggcccgcaagctcttctccaagctcggactcaagcaagtgactggtgtctcccgtgtctgcattcgcaagtcgaagaacatcct
cttcgtcataaacaagccagacgtgttcaagagcccaggatctgacacctacatcatcttcggagaagccaagatcgaggatctcacccaa
cacgcccagatgtctgctattgagaacttgaagccaactcgtgaggccccacaactcaagactgtcgaagaggacgagaatgaggatgttg
aggtaattcagtaacttaatcggatttattacattaattgtacggtttaaggaggattccaccggcattgaggagaaggacatcgagcttgtcatt
tcccaagccaacaccacccgcaacaaggccatcagggcgcttaaggaagctgacaatgacatcgtcaatgccatcatgagccttaccatgt
agcttgtttcctgatgaccttgcagatactcttgttatcgttgtatctcttgcttatcccgttttccgttccaagtaaacgtttatcagtcttttttaacttt
tttgttatgtttaaaaaacaattgcatcttcgaattgacctaccttttacagaaaagaacaattaaatcactgtttgtgtaaaacacccctctattgat
cgagaacttt

FIGURE 3C

SEQ ID NO:48 - F57C1.7 (homolog of SCN pat-10)

aactcctcgaactcaatctttccggaaccgtcctcgtcaatctcgtcgacagcctcctcgagttgttgatcggtgaggtcatcggcgatttctttg
agaagagccttcagagttggtcgagaaatatatccgttaccctgaaaaattaataattaaagaataaaaagcaaaatctaaaagtacaaacct
ccttgtcgaaaagacggaaagcttcacgaagttctttctccaatgtttccttgtcgacagtgtttgcaacggtgtacacgagagcgcagaactc
gtcaaactcgagctttccggaaccgtcagcgtcgaacttgcggatcagtttacgaagggtctaaaagaatgaagttagatgccacatagattt
agaaaaatcaaaatcatcaattctataactaaatttcataacatatagttatatcttactttagtcgacataataaatgctttgttcagatggaatatc
aaaattaattatttcacaaacattagtaacatgttttagtggcgaaaattaattgaattcagttgagaaacaagccgcagaagataggtcggata
aaaacaaaattttaggcaagagtaacccatttatattttcggttatcttactcagttggcctacctaatcattaccgtgaaacctaaatttaaaaga
gttgaaaacttcctaatttgaattatcactcttctgaagatcccctaactctacataaaccaaaagttccaaaatgatttaccttctcatcgaaatcc
tgttccattccatgcatgatttgaccgatctgagtggccatgatgtatccttgctttcctctgtcgaaggcatcgaagaacttttggtattctagaa
agttttaatgatgatttttcaatcataaatataaaatatcttaccctcaatttgggatccgtcgatttcagcaagaatctcttcgatatcctcagcctat
aaaagtataaacatataaaaattcaaaaagaaatttattgaagacatgagaaagcgggactcaccatgttgtcggagtttgttgtgctctggata
agcttcgtcgggcagaagcaacggcgggagcgagtaggcggaggaacccgagggcgggcttttctttctcacaacggcatcatcgtctc
ctccacaaaacacattctt

FIGURE 3D

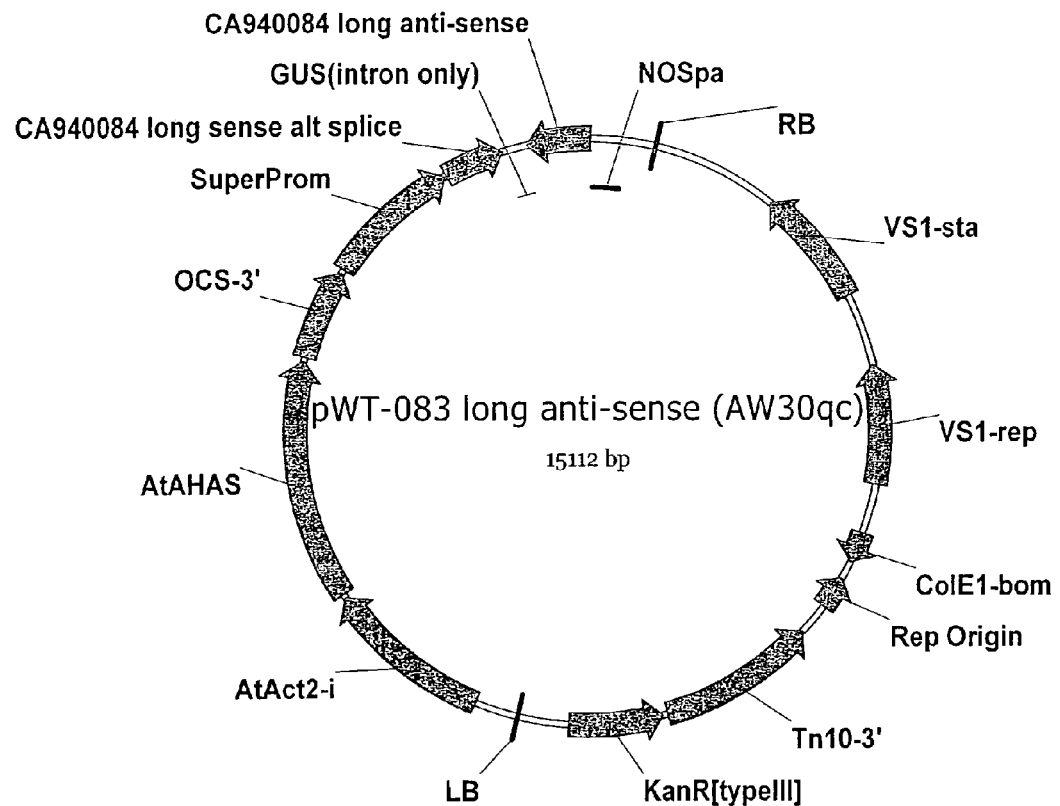
Fig: 4D

COMPOSITIONS AND METHODS USING RNA INTERFERENCE FOR CONTROL OF NEMATODES

CROSS REFERENCE TO RELATED APPLICATIONS

This application claims the benefit of U.S. provisional application Nos. 60/547,418, filed Feb. 24, 2004; and 60/601,344, filed Aug. 13, 2004.

BACKGROUND OF THE INVENTION

1. Field of the Invention

The field of this invention is the control of nematodes, in particular the control of soybean cyst nematodes. The invention also relates to the introduction of genetic material into plants that are susceptible to nematodes in order to increase tolerance to nematodes.

2. Background Art

Nematodes are microscopic wormlike animals that feed on the roots, leaves, and stems of more than 2,000 vegetables, fruits, and ornamental plants causing an estimated $100 billion crop loss worldwide. One common type of nematode is the root-knot nematode, whose feeding causes the characteristic galls on roots. Other root-feeding nematodes are the cyst- and lesion-types, which are more host specific.

Nematodes are present throughout the United States, but are mostly a problem in warm, humid areas of the South and West, and in sandy soils. Soybean cyst nematode (SCN), *Heterodera glycines*, was first discovered in the United States in North Carolina in 1954. It is the most serious pest of soybean plants. Some areas are so heavily infested by SCN that soybean production is no longer economically possible without control measures. Although soybean is the major economic crop attacked by SCN, SCN parasitizes some fifty hosts in total, including field crops, vegetables, ornamentals, and weeds.

Signs of nematode damage include stunting and yellowing of leaves, and wilting of the plants during hot periods. However, nematodes, including SCN, can cause significant yield loss without obvious above-ground symptoms. In addition, roots infected with SCN are dwarfed or stunted. SCN can decrease the number of nitrogen-fixing nodules on the roots, and may make the roots more susceptible to attacks by other soil-borne plant pathogens.

The SCN life cycle has three major stages: egg, juvenile, and adult. The life cycle can be completed in 24 to 30 days under optimum conditions. When temperature and moisture levels become adequate in the spring, worm-shaped juveniles hatch from eggs in the soil. These juveniles are the only life stage of the nematode that can infect soybean roots.

After penetrating the soybean roots, juveniles move through the root until they contact vascular tissue, where they stop and start to feed. The nematode injects secretions that modify certain root cells and transform them into specialized feeding sites. The root cells are morphologically transformed into large multinucleate syncytia or giant cells, which are used as a source of nutrients for the nematodes. The actively feeding nematodes thus steal essential nutrients from the plant resulting in yield loss. As the nematodes feed, they swell and eventually female nematodes become so large that they break through the root tissue and are exposed on the surface of the root.

Male nematodes, which are not swollen as adults, migrate out of the root into the soil and fertilize the lemon-shaped adult females. The males then die, while the females remain attached to the root system and continue to feed. The swollen females begin producing eggs, initially in a mass or egg sac outside the body, then later within the body cavity. Eventually the entire body cavity of the adult female is filled with eggs, and the female nematode dies. It is the egg-filled body of the dead female that is referred to as the cyst. Cysts eventually dislodge and are may be found free in the soil. The walls of the cyst become very tough, providing excellent protection for the 200 to 400 eggs contained within. SCN eggs survive within the cyst until proper hatching conditions occur. Although many of the eggs may hatch within the first year, many also will survive within the cysts for several years.

SCN can move through the soil only a few inches per year on its own power. However, SCN can be spread substantial distances in a variety of ways. Anything that can move infested soil is capable of spreading SCN, including farm machinery, vehicles and tools, wind, water, animals, and farm workers. Seed sized particles of soil often contaminate harvested seed. Consequently, SCN can be spread when seed from infested fields is planted in non-infested fields. There is even evidence that SCN can be spread by birds. Only some of these causes can be prevented.

Traditional practices for managing SCN include: maintaining proper fertility and soil pH levels in SCN-infested land; controlling other plant diseases, as well as insect and weed pests; using sanitation practices such as plowing, planting, and cultivating of SCN-infested fields only after working non-infested fields; cleaning equipment thoroughly with high pressure water or steam after working in infested fields; not using seed grown on infested land for planting non-infested fields unless the seed has been properly cleaned; rotating infested fields and alternating host crops with non-host crops, such as, corn, oat and alfalfa; using nematicides; and planting resistant soybean varieties.

Methods have been proposed for the genetic transformation of plants in order to confer increased resistance to plant parasitic nematodes. U.S. Pat. Nos. 5,589,622 and 5,824,876 are directed to the identification of plant genes expressed specifically in or adjacent to the feeding site of the plant after attachment by the nematode. The promoters of these plant target genes can then be used to direct the specific expression of toxic proteins or enzymes, or the expression of antisense RNA to the target gene or to general cellular genes. The plant promoters may also be used to confer cyst nematode resistance specifically at the feeding site by transforming the plant with a construct comprising the promoter of the plant target gene linked to a gene whose product induces lethality in the nematode after ingestion. However, these patents do not provide any specific nematode genes that are useful for conferring resistance to nematode infection, and the methods are only useful for expressing genes specifically at the feeding sites for nematodes after attachment to the plant.

Recently, RNA interference (RNAi), also referred to as gene silencing, has been proposed as a method for controlling nematodes. When double-stranded RNA (dsRNA) corresponding essentially to the sequence of a target gene or mRNA is introduced into a cell, expression from the target gene is inhibited (See e.g., U.S. Pat. No. 6,506,559). U.S. Pat. No. 6,506,559 demonstrates the effectiveness of RNAi against known genes in *C. elegans*, but does not teach or suggest any novel genes that are essential for plant parasitic nematodes, and does not demonstrate the usefulness of RNAi for controlling plant parasitic nematodes.

In addition, RNAi was used in PCT Publication WO 01/96584 to target nematode genes, preferably in root-knot nematodes and potato cyst nematodes. Preferred targets included molecules involved in ribosome assembly; neurotransmitter receptors and ligands; electron transport proteins; metabolic pathway proteins; and proteins involved in protein and polynucleotide production, folding, and processing. However, none of the sequences provided in PCT Publication WO 01/96584 were demonstrated to be down-regulated using RNAi, and moreover, they were not shown to be useful in conferring resistance to plant parasitic nematodes.

PCT Publication WO 01/17654 A2 also proposed the use of RNAi for targeting essential plant pathogenic and parasitic nematode genes. The host plant is preferably transformed with a construct for expressing dsRNA that has substantial sequence identity to an endogenous and essential nematode gene. The publication proposes that the invention is particularly useful for targeting a vascular acetylcholine transporter protein, a choline acetyltransferase, and a ubiquinone oxidoreductase. WO 01/17654 demonstrated that RNAi was effective in reducing expression of sec-1, involved in vesicle trafficking, in *Meloidogyne incognita*. However, sec-1 was not shown to be essential for plant parasitic nematodes or useful for conferring plant resistance to nematodes. In addition, the patent publication does not teach or suggest any novel genes that are essential for plant parasitic nematodes.

A number of models have been proposed for the action of RNAi. See, e.g., Hammond et al. (2001) *Nature Reviews Genetics* 2, 110-119, and references cited therein. In mammalian systems, dsRNAs larger than 30 nucleotides trigger induction of interferon synthesis and a global shut-down of protein syntheses, in a non-sequence-specific manner. See, e.g., Bass (2001) *Nature* 411, 428-429; Elbashir, et al. (2001) *Nature* 411, 494-498. However, U.S. Pat. No. 6,506,559 discloses that in nematodes, the length of the dsRNA corresponding to the target gene sequence may be at least 25, 50, 100, 200, 300 or 400 bases, and that even larger dsRNAs (742 nucleotides, 1033 nucleotides, 785 nucleotides, 531 nucleotides, 576 nucleotides, 651 nucleotides, 1015 nucleotides, 1033 nucleotides 730 nucleotides, 830 nucleotides, see Table 1) were also effective at inducing RNAi in *C. elegans*. Moreover, Wesley, et al. (2001) *The Plant Journal* 27, 581-590 discloses that when hairpin RNA constructs having double stranded regions ranging from 98 to 854 nucleotides were transformed into a number of plant species, the target plant genes were efficiently silenced. There is general agreement that in many organisms, including nematodes and plants, large pieces of dsRNA are cleaved into 21-23 nucleotide fragments (siRNA) within cells, and that these siRNAs are the actual mediators of the RNAi phenomenon.

Notwithstanding the foregoing, there is a need to identify safe and effective compositions and methods for the controlling plant parasitic nematodes using RNAi, and for the production of plants having increased resistance to plant parasitic nematodes.

SUMMARY OF THE INVENTION

The present invention provides nucleic acids, transgenic plants, and methods to overcome, or at least alleviate, nematode infestation of valuable agricultural crops such as soybeans. The nucleic acids of the invention are capable of modulating expression of parasitic nematode target genes by RNA interference (RNAi). In accordance with the invention, the parasitic nematode target gene is selected from the group consisting of a parasitic nematode cytosolic chaperonin gene, a parasitic nematode gene encoding heat shock protein-90, a parasitic nematode gene homologous to a *C. elegans* Y65B4BR.5a gene, and a parasitic nematode pat-10 gene. The nucleic acid of the invention encodes a double stranded RNA comprising (a) a first strand having a sequence substantially identical to from about 19 to about 400 or 500 consecutive nucleotides of a target gene having a sequence selected from the group of SEQ ID NO:1, SEQ ID NO:2, SEQ ID NO:3; SEQ ID NO:4, SEQ ID NO:5, SEQ ID NO:6 and SEQ ID NO:7 and (b) a second strand having a sequence substantially complementary to the first strand.

The invention is further embodied as a pool of double stranded RNA molecules comprising a multiplicity of short interfering RNA molecules each comprising a double stranded region having a length of about 19 nucleotides, wherein said RNA molecules are derived from a polynucleotide selected from the group consisting of (a) a polynucleotide having a sequence as set forth in SEQ ID NO:1; (b) a polynucleotide from a parasitic nematode that hybridizes under stringent conditions to a polynucleotide having a sequence as set forth in SEQ ID NO:1; (c) a polynucleotide having a sequence as set forth in SEQ ID NO:2; (d) a polynucleotide from a parasitic nematode that hybridizes under stringent conditions to a polynucleotide having a sequence as set forth in SEQ ID NO:2; (e) a polynucleotide having a sequence as set forth in SEQ ID NO:3; (f) a polynucleotide from a parasitic nematode that hybridizes under stringent conditions to a polynucleotide having a sequence as set forth in SEQ ID NO:3; (g) a polynucleotide having a sequence as set forth in SEQ ID NO:4; (h) a polynucleotide from a parasitic nematode that hybridizes under stringent conditions to a polynucleotide having a sequence as set forth in SEQ ID NO:4; (i) a polynucleotide having a sequence as set forth in SEQ ID NO:5; (j) a polynucleotide from a parasitic nematode that hybridizes under stringent conditions to a polynucleotide having a sequence as set forth in SEQ ID NO:5; (k) a polynucleotide having a sequence as set forth in SEQ ID NO:6; (l) a polynucleotide from a parasitic nematode that hybridizes under stringent conditions to a polynucleotide having a sequence as set forth in SEQ ID NO:6; (m) a polynucleotide comprising a sequence as set forth in SEQ ID NO:7; and (n) a polynucleotide from a parasitic nematode that hybridizes under stringent conditions to a polynucleotide comprising a sequence as set forth in SEQ ID NO:7.

In another embodiment, the invention provides a transgenic plant resistant to parasitic nematode infection, the plant comprising a nucleic acid construct that encodes a dsRNA capable of specifically modulating a parasitic nematode target gene selected from the group consisting of a parasitic nematode cytosolic chaperonin gene, a parasitic nematode gene encoding heat shock protein-90, a parasitic nematode gene homologous to the *C. elegans* Y65B4BR.5a gene, and a parasitic nematode pat-10 gene.

In another embodiment, the invention provides a method for controlling the infection of a plant by a parasitic nematode, comprising the steps of contacting the nematode with a dsRNA molecule comprising one strand that is substantially identical to a portion of a target gene essential to the nematode, thereby controlling the infection of the plant by the nematode, wherein the target gene is selected from the group consisting of a parasitic nematode cytosolic chaperonin gene, a parasitic nematode gene encoding heat shock protein-90, a parasitic nematode gene homologous to the *C. elegans* Y65B4BR.5a gene, and a parasitic nematode pat-10 gene.

The invention further encompasses a method of making a transgenic plant capable of expressing a dsRNA that is substantially identical to a target gene in a parasitic nematode, said method comprising the steps of: (a) selecting a target gene from the group consisting of a parasitic nematode cytosolic chaperonin gene, a parasitic nematode gene encoding heat shock protein-90, a parasitic nematode gene homologous to the *C. elegans* Y65B4BR.5a gene, and a parasitic nematode pat-10 gene; (b) preparing a nucleic acid sequence comprising a region that is substantially identical to a portion of the selected target gene, wherein the nucleic acid is able to form a double-stranded transcript once expressed in the plant; (c) contacting a recipient plant with said nucleic acid; (d) producing one or more offspring of said recipient plant; and (e) testing the offspring for expression of said double-stranded transcript.

In preferred embodiments of the foregoing, the double stranded RNA molecule comprises one strand substantially identical to from about 21 to about 400 or 500 consecutive nucleotides of a sequence selected from the group consisting of: (a) a polynucleotide having a sequence as set forth in SEQ ID NO:1; (b) a polynucleotide from a parasitic nematode that hybridizes under stringent conditions to a polynucleotide having a sequence as set forth in SEQ ID NO:1; (c) a polynucleotide having a sequence as set forth in SEQ ID NO:2; (d) a polynucleotide from a parasitic nematode that hybridizes under stringent conditions to a polynucleotide having a sequence as set forth in SEQ ID NO:2; (e) a polynucleotide having a sequence as set forth in SEQ ID NO:3; (f) a polynucleotide from a parasitic nematode that hybridizes under stringent conditions to a polynucleotide having a sequence as set forth in SEQ ID NO:3; (g) a polynucleotide having a sequence as set forth in SEQ ID NO:4; (h) a polynucleotide from a parasitic nematode that hybridizes under stringent conditions to a polynucleotide having a sequence as set forth in SEQ ID NO:4; (i) a polynucleotide having a sequence as set forth in SEQ ID NO:5; (j) a polynucleotide from a parasitic nematode that hybridizes under stringent conditions to a polynucleotide having a sequence as set forth in SEQ ID NO:5; (k) a polynucleotide having a sequence as set forth in SEQ ID NO:6; (l) a polynucleotide from a parasitic nematode that hybridizes under stringent conditions to a polynucleotide having a sequence as set forth in SEQ ID NO:6; (m) a polynucleotide comprising a sequence as set forth in SEQ ID NO:7; and (n) a polynucleotide from a parasitic nematode that hybridizes under stringent conditions to a polynucleotide comprising a sequence as set forth in SEQ ID NO:7.

BRIEF DESCRIPTION OF THE DRAWINGS

FIGS. 1A through 1C show cDNA sequences of the SCN target genes of the invention. FIG. 1A shows two different forms of the full-length cDNAs of *H. glycines* target gene cct-6 as SEQ ID NOs:1 and 2; FIG. 1B shows the full-length cDNA of *H. glycines* target gene daf-21 as SEQ ID NO:3 and the full-length cDNA of *H. glycines* target gene Y65B4BR.5a as SEQ IN NO:4; and FIG. 1C shows two variants of the *H. glycines* target gene pat-10 as SEQ ID NO:5 (full-length cDNA variant 1) and SEQ ID NO:6 (full-length cDNA variant 2), and SEQ ID NO:7 (5' UTR of pat-10 EST disclosed in the GENBANK database).

FIGS. 2A and 2B provide the sets of primers that were used to isolate target soybean cyst nematode genes (SEQ ID NOs: 8-15 and 24-44) and *C. elegans* homologs of the soybean cyst nematode target genes (SEQ ID NOs:16-23) by PCR.

FIGS. 3A through 3D show the sequences of the *C. elegans* gene fragments (SEQ ID NOs:45-48) used in the RNAi feeding assay of Example 3.

FIGS. 4A through 4E show the binary vectors useful for transformation of soybean cells to produce the dsRNA of the invention in soybean plants, thereby inhibiting any of the four soybean cyst nematode target genes identified herein.

DETAILED DESCRIPTION OF THE INVENTION

Figure 4A:
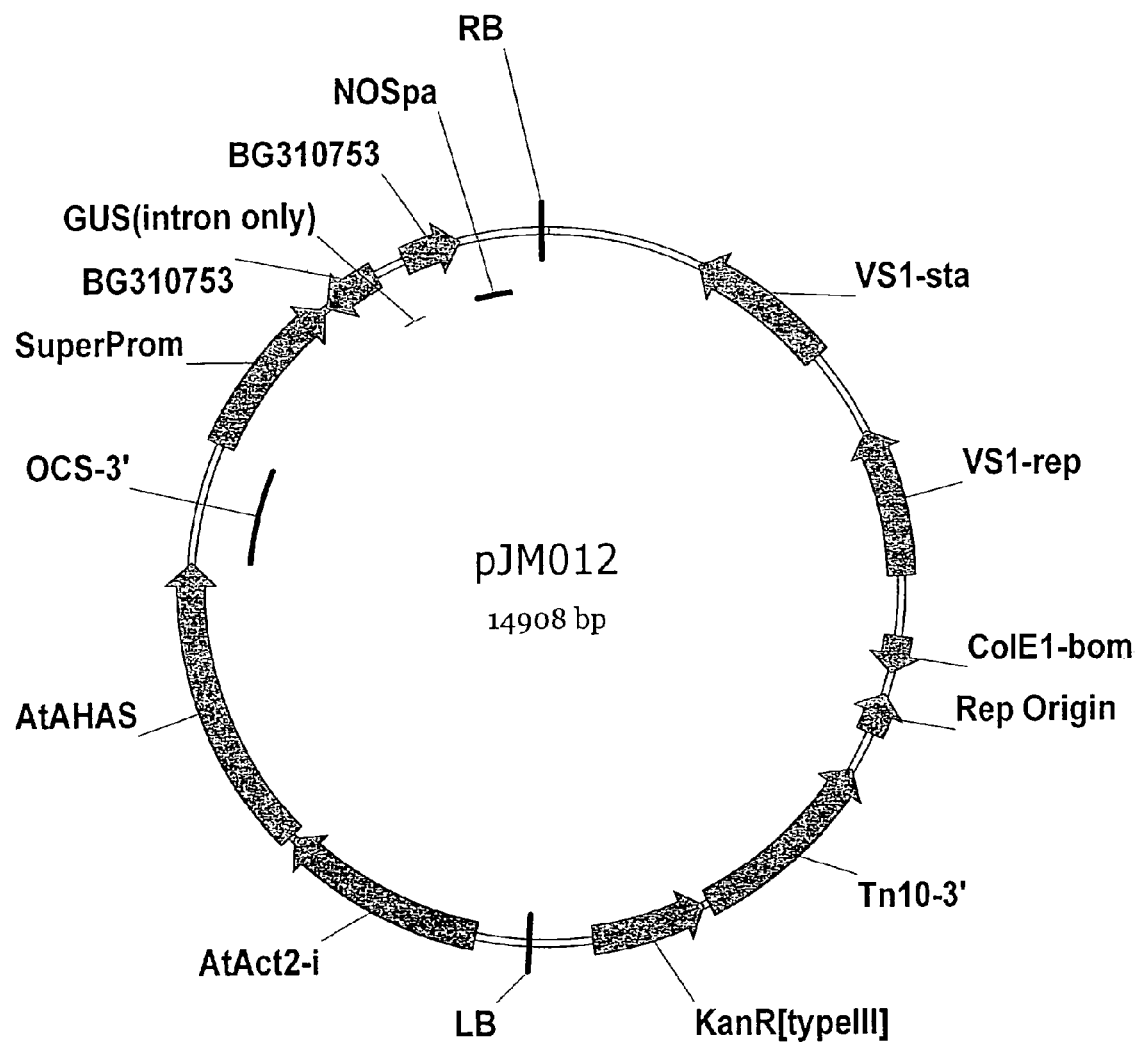

The present invention may be understood more readily by reference to the following detailed description of the preferred embodiments of the invention and the examples included herein. Unless otherwise noted, the terms used herein are to be understood according to conventional usage by those of ordinary skill in the relevant art. In addition to the definitions of terms provided below, definitions of common terms in molecular biology may also be found in Rieger et al., 1991 Glossary of genetics: classical and molecular, $5^{th}$ Ed., Berlin: Springer-Verlag; and in Current Protocols in Molecular Biology, F. M. Ausubel et al., Eds., Current Protocols, a joint venture between Greene Publishing Associates, Inc. and John Wiley & Sons, Inc., (1998 Supplement). It is to be understood that as used in the specification and in the claims, "a" or "an" can mean one or more, depending upon the context in which it is used. Thus, for example, reference to "a cell" can mean that at least one cell can be utilized. It is to be understood that this invention is not limited to specific nucleic acids, specific cell types, specific host cells, specific conditions, or specific methods, etc., as such may, of course, vary, and the numerous modifications and variations therein will be apparent to those skilled in the art. It is also to be understood that the terminology used herein is for the purpose of describing specific embodiments only and is not intended to be limiting.

Throughout this application, various publications are referenced. The disclosures of all of these publications and those references cited within those publications in their entireties are hereby incorporated by reference into this application in order to more fully describe the state of the art to which this invention pertains. Standard techniques for cloning, DNA isolation, amplification and purification, for enzymatic reactions involving DNA ligase, DNA polymerase, restriction endonucleases and the like, and various separation techniques are those known and commonly employed by those skilled in the art. A number of standard techniques are described in Sambrook et al., 1989 Molecular Cloning, Second Edition, Cold Spring Harbor Laboratory, Plainview, N.Y.; Maniatis et al., 1982 Molecular Cloning, Cold Spring Harbor Laboratory, Plainview, N.Y.; Wu (Ed.) 1993 Meth. Enzymol. 218, Part I; Wu (Ed.) 1979 Meth Enzymol. 68; Wu et al., (Eds.) 1983 Meth. Enzymol. 100 and 101; Grossman and Moldave (Eds.) 1980 Meth. Enzymol. 65; Miller (Ed.) 1972 Experiments in Molecular Genetics, Cold Spring Harbor Laboratory, Cold Spring Harbor, N.Y.; Old and Primrose, 1981 Principles of Gene Manipulation, University of California Press, Berkeley; Schleif and Wensink, 1982 Practical Methods in Molecular Biology; Glover (Ed.) 1985 DNA Cloning Vol. I and II, IRL Press, Oxford, UK; Hames and Higgins (Eds.) 1985 Nucleic Acid Hybridization, IRL Press, Oxford, UK; and Setlow and Hollaender 1979 Genetic Engineering: Principles and Methods, Vols. 1-4, Plenum Press, New York. Abbreviations and nomenclature, where employed, are deemed standard in the field and commonly used in professional journals such as those cited herein.

As used herein, "RNAi" or "RNA interference" refers to the process of sequence-specific post-transcriptional gene silencing in nematodes, mediated by double-stranded RNA (dsRNA). As used herein, "dsRNA" refers to RNA that is partially or completely double stranded. Double stranded RNA is also referred to as short interfering RNA (siRNA), short interfering nucleic acid (siNA), micro-RNA (mRNA), and the like. In the RNAi process, dsRNA comprising a first strand that is substantially identical to a portion of a target gene and a second strand that is complementary to the first strand is introduced into a nematode, preferably by soaking and more preferably by feeding. After introduction into the nematode, the target gene-specific dsRNA is processed into relatively small fragments (siRNAs) and can subsequently become distributed throughout the nematode, leading to a loss-of-function mutation having a phenotype that, over the period of a generation, may come to closely resemble the phenotype arising from a complete or partial deletion of the target gene. Alternatively, the target gene-specific dsRNA is processed into relatively small fragments by a plant cell containing the RNAi processing machinery; and when the plant-processed small dsRNA is ingested by a parasitic nematode, the loss-of-function phenotype is obtained.

As used herein, taking into consideration the substitution of uracil for thymine when comparing RNA and DNA sequences, the terms "substantially identical" and "corresponding to" mean that the nucleotide sequence of one strand of the dsRNA is at least about 80%-90% identical to 19 or more contiguous nucleotides of the target gene, more preferably, at least about 90-95% identical to 19 or more contiguous nucleotides of the target gene, and most preferably at least about 95-99% identical or absolutely identical to 19 or more contiguous nucleotides of the target gene.

As used herein, "complementary" polynucleotides are those that are capable of base pairing according to the standard Watson-Crick complementarity rules. Specifically, purines will base pair with pyrimidines to form a combination of guanine paired with cytosine (G:C) and adenine paired with either thymine (A:T) in the case of DNA, or adenine paired with uracil (A:U) in the case of RNA. It is understood that two polynucleotides may hybridize to each other even if they are not completely complementary to each other, provided that each has at least one region that is substantially complementary to the other. As used herein, the term "substantially complementary" means that two nucleic acid sequences are complementary at least at 80% of their nucleotides. Preferably, the two nucleic acid sequences are complementary at least at 85%, 90%, 95%, 96%, 97%, 98%, 99% or more of their nucleotides. Alternatively, "substantially complementary" means that two nucleic acid sequences can hybridize under high stringency conditions. As used herein, the term "substantially identical" means that two nucleic acid sequences have at least 80% sequence identity. Preferably, two nucleic acid sequences, which are substantially identical, have at least 85%, 90%, 95%, 96%, 97%, 98%, 99% or 100% of sequence identity.

Also as used herein, the terms "nucleic acid" and "polynucleotide" refer to RNA or DNA that is linear or branched, single or double stranded, or a hybrid thereof. The term also encompasses RNA/DNA hybrids. When dsRNA is produced synthetically, less common bases, such as inosine, 5-methylcytosine, 6-methyladenine, hypoxanthine and others can also be used for antisense, dsRNA and ribozyme pairing. For example, polynucleotides that contain C-5 propyne analogues of uridine and cytidine have been shown to bind RNA with high affinity and to be potent antisense inhibitors of gene expression. Other modifications, such as modification to the phosphodiester backbone, or the 2'-hydroxy in the ribose sugar group of the RNA can also be made.

As used herein, the terms "contacting" and "administering" are used interchangeably, and refer to a process by which dsRNA of the present invention is delivered to a cell of a parasitic nematode, in order to inhibit expression of an essential target gene in the nematode. The dsRNA may be administered in a number of ways, including, but not limited to, direct introduction into a cell (i.e., intracellularly); or extracellular introduction into a cavity, interstitial space, or into the circulation of the nematode, oral introduction, the dsRNA may be introduced by bathing the nematode in a solution containing dsRNA, or the dsRNA may be present in a food source. Methods for oral introduction include direct mixing of dsRNA with food of the nematode, as well as engineered approaches in which a species that is used as food is engineered to express a dsRNA, then fed to the organism to be affected. For example, the dsRNA may be sprayed onto a plant, or the dsRNA may be applied to soil in the vicinity of roots, taken up by the plant and/or the parasitic nematode, or a plant may be genetically engineered to express the dsRNA in an amount sufficient to kill some or all of the parasitic nematode to which the plant is exposed.

As used herein, the term "control", when used in the context of an infection, refers to the reduction or prevention of an infection. Reducing or preventing an infection by a nematode will cause a plant to have increased tolerance to the nematode, however, such increased tolerance does not imply that the plant necessarily has 100% tolerance to infection. In preferred embodiments, the tolerance to infection by a nematode in a resistant plant is greater than 10%, 20%, 30%, 40%, 50%, 60%, 70%, 80%, 90% or 95% in comparison to a wild type plant that is not resistant to nematodes. The plant's tolerance to infection by the nematode may be due to the death, sterility, arrest in development, or impaired mobility of the nematode upon exposure to the dsRNA specific to an essential gene.

The term "plant" is intended to encompass plants at any stage of maturity or development, as well as any tissues or organs (plant parts) taken or derived from any such plant unless otherwise clearly indicated by context. Plant parts include, but are not limited to, stems, roots, flowers, ovules, stamens, leaves, embryos, meristematic regions, callus tissue, anther cultures, gametophytes, sporophytes, pollen, microspores, protoplasts, hairy root cultures, and the like. The present invention also includes seeds produced by the plants of the present invention. In one embodiment, the seeds are true breeding for an increased tolerance to nematode infection as compared to a wild-type variety of the plant seed. As used herein, a "plant cell" includes, but is not limited to, a protoplast, gamete producing cell, and a cell that regenerates into a whole plant. Tissue culture of various tissues of plants, and regeneration of plants therefrom, is well known in the art and is widely published.

As used herein, the term "transgenic" refers to any plant, plant cell, callus, plant tissue, or plant part that contains all or part of at least one recombinant polynucleotide. In many cases, all or part of the recombinant polynucleotide is stably integrated into a chromosome or stable extra-chromosomal element, so that it is passed on to successive generations. For the purposes of the invention, the term "recombinant polynucleotide" refers to a polynucleotide that has been altered, rearranged or modified by genetic engineering. Examples include any cloned polynucleotide, or polynucleotides, that are linked or joined to heterologous sequences. The term "recombinant" does not refer to alterations of polynucleotides that result from naturally occurring events, such as spontaneous mutations, or from non-spontaneous mutagenesis followed by selective breeding.

As used herein, the term "amount sufficient to inhibit expression" refers to a concentration or amount of the dsRNA that is sufficient to reduce levels or stability of mRNA or protein produced from a target gene in a parasitic nematode. As used herein, "inhibiting expression" refers to the absence or observable decrease in the level of protein and/or mRNA product from a target gene. Inhibition of target gene expression may be lethal to the parasitic nematode, or such inhibition may delay or prevent entry into a particular developmental step (e.g., metamorphosis), if plant disease is associated with a particular stage of the parasitic nematode's life cycle. The consequences of inhibition can be confirmed by examination of the outward properties of the nematode (as presented below in the examples).

The present invention may be used to reduce crop destruction by a variety of plant parasitic nematodes. Some such plants and their pathogens are listed in Index of Plant Diseases in the United States (U.S. Dept. of Agriculture Handbook No. 165, 1960); Distribution of Plant-Parasitic Nematode Species in North America (Society of Nematologists, 1985); and Fungi on Plants and Plant Products in the United States (American Phytopathological Society, 1989). In a preferred embodiment, the present invention uses RNAi to reduce crop destruction by parasitic nematodes, and most particularly, by cyst nematodes, for example, *Heterodera glycines, Heterodera shachtii, Heterodera avenae, Heterodera oryzae, Globodera pallida, Globodera rostochiensis,* or *Globodera tabacum.*

In accordance with the invention, a parasitic nematode is contacted with a dsRNA which specifically inhibits expression of a target gene which is essential for survival, metamorphosis, or reproduction of the nematode. Preferably, the parasitic nematode comes into contact with the dsRNA after entering a plant which expresses the dsRNA. In one embodiment, the dsRNA is encoded by a vector which has been transformed into an ancestor of the infected plant. Preferably, the nucleic acid sequence expressing said dsRNA is under the transcriptional control of a root specific promoter or a parasitic nematode feeding cell-specific promoter.

In one embodiment, the parasitic nematode target gene is a homolog of the *C. elegans* cct-6gene, which encodes one of the subunits of a cytosolic chaperonin. The chaperonins are a diverse class of proteins that assist the process of protein folding within cells. The *C. elegans* cct genes (cct-1, cct-2, cct-4, cct-5, and cct-6) are expressed constitutively during all life stages, indicating that they perform necessary functions throughout development of the nematode. Example 3 below shows that feeding *C. elegans* RNAi molecules specific for the *C. elegans* cct-6gene results in arrest at the L2 larval stage. As shown in Example 1, two forms of the *H. glycines* cct-6 gene were isolated, as represented in SEQ ID NOs: 1 and 2, which are believed to be alternatively spliced variants of the *H. glycines* cct-6gene. In this embodiment of the present invention, the parasitic nematode cct-6 target gene has a sequence selected from the group consisting of: the sequence set forth in SEQ ID NO:1 a polynucleotide from a parasitic nematode that hybridizes under stringent conditions to the sequence set forth in SEQ ID NO:1; the sequence set forth in SEQ ID NO:2; and a polynucleotide from a parasitic nematode that hybridizes under stringent conditions to the sequence set forth in SEQ ID NO:2. Example 2 below shows that soaking J2 stage *H. glycines* in RNAi molecules corresponding to nucleotides 859-1404 of the sequence set forth in SEQ ID NO:1 results in immobilization of the nematode larvae.

In another embodiment, the parasitic nematode target gene is a homolog of the *C. elegans* daf-21 gene, which encodes heat shock protein 90 (Hsp90). Hsp90 is an essential chaperone protein in *C. elegans*, believed to mediate refolding of a variety of other proteins when they are denatured or misfolded as a result of stress. Hsp90 may also bind stably to specific target proteins and help them to achieve their mature structures, in the absence of stress. Example 3 below shows that feeding *C. elegans* RNAi molecules specific for the daf-21 gene results in arrest at the L3/L4 stage. In this embodiment of the invention, the parasitic nematode daf-21 target gene has a sequence selected from the group consisting of: a sequence set forth in SEQ ID NO:3 and a polynucleotide from a parasitic nematode that hybridizes under stringent conditions to a sequence set forth in SEQ ID NO:3. Example 2 below shows that soaking J2 stage *H. glycines* in RNAi molecules corresponding to nucleotides 73-472 of SEQ ID NO:3 results in immobilization of the nematode larvae.

In another embodiment, the parasitic nematode target gene is a homolog of the *C. elegans* Y65B4BR.5a gene, which encodes a protein involved in forming nascent polypeptide-associated complexes. Example 3 below shows that feeding *C. elegans* RNAi molecules specific for the Y65B4BR.5a gene results in arrest at the young adult stage. In this embodiment of the invention, the parasitic nematode target gene has a sequence selected from the group consisting of: a sequence set forth in SEQ ID NO:4 and a polynucleotide from a parasitic nematode that hybridizes under stringent conditions to a sequence set forth in SEQ ID NO:4. Example 2 below shows that soaking J2 stage *H. glycines* in RNAi molecules corresponding to nucleotides 96-595 of SEQ ID NO:4 results in immobilization of the nematode larvae.

In yet another embodiment, the parasitic nematode target gene is a homolog of the *C. elegans* pat-10 gene, which encodes a muscle troponin C expressed in body wall and in vulval and anal muscles. The PAT-10 protein is the calcium-binding component of the troponin complex of actin thin filaments and is essential for muscle contraction and for completion of embryonic morphogenesis and elongation. Expression of PAT-10 in body wall muscle begins during early embryonic morphogenesis and is concurrent with expression of other body wall muscle structural components. Example 3 below shows that feeding *C. elegans* RNAi molecules specific for the pat-10 gene results in arrest at the L4 larval and young adult stage. In this embodiment of the invention, the parasitic nematode target gene has a sequence selected from the group consisting of a polynucleotide having a sequence as set forth in SEQ ID NO:5; a polynucleotide from a parasitic nematode that hybridizes under stringent conditions to a polynucleotide having a sequence as set forth in SEQ ID NO:5; a polynucleotide having a sequence as set forth in SEQ ID NO:6; a polynucleotide from a parasitic nematode that hybridizes under stringent conditions to a polynucleotide having a sequence as set forth in SEQ ID NO:6; a polynucleotide having a sequence as set forth in SEQ ID NO:7; and a polynucleotide from a parasitic nematode that hybridizes under stringent conditions to a polynucleotide having a sequence as set forth in SEQ ID NO:7. Example 2 below shows that soaking J2 stage *H. glycines* in RNAi molecules corresponding to nucleotides 1-400 of SEQ ID NO:5 results in immobilization of the nematode larvae.

The nucleotide sequences determined from the cloning of the genes from soybean cyst nematode as disclosed herein allow for the generation of probes and primers designed for use in identifying and/or cloning homologs in other cell types and organisms, as well as homologs from other parasitic nematode races and species. For example, a nucleic acid molecule having a nucleotide sequence as set forth in SEQ ID NO:1, SEQ ID NO:2, SEQ ID NO:3, SEQ ID NO:4, SEQ ID NO:5, SEQ ID NO:6, or SEQ ID NO:7 or a nucleic acid molecule from a parasitic nematode that hybridizes under stringent conditions to a nucleotide sequence of SEQ ID NO:1, SEQ ID NO:2, SEQ ID NO:3, SEQ ID NO:4, SEQ ID NO:5, SEQ ID NO:6, or SEQ ID NO:7 can be isolated from parasitic nematode cDNA libraries. Alternatively, mRNA can be isolated from parasitic nematode cells (e.g., by the guanidinium-thiocyanate extraction procedure of Chirgwin et al., 1979, Biochemistry 18:5294-5299), and cDNA can be prepared using reverse transcriptase (e.g., Moloney MLV reverse transcriptase, available from Gibco/BRL, Bethesda, Md.; or AMV reverse transcriptase, available from Seikagaku America, Inc., St. Petersburg, Fla.). Synthetic oligonucleotide primers for polymerase chain reaction amplification can be designed based upon the nucleotide sequence shown in SEQ ID NO:1, SEQ ID NO:2, SEQ ID NO:3, SEQ ID NO:4; SEQ ID NO:5, SEQ ID NO:6, or SEQ ID NO:7. Nucleic acid molecules corresponding to the parasitic nematode target genes of the invention can be amplified using cDNA or, alternatively, genomic DNA, as a template and appropriate oligonucleotide primers according to standard PCR amplification techniques. The nucleic acid molecules so amplified can be cloned into appropriate vectors and characterized by DNA sequence analysis.

Accordingly, the dsRNA of the invention is substantially identical to a portion of a target gene of a parasitic nematode genome, the target gene being selected from the group consisting of a *H. glycines* cct-6 gene, a *H. glycines* daf-21 gene, a *H. glycines* homolog of the *C. elegans* Y65B4BR.5a gene, and a *H. glycines* pat-10 gene. In preferred embodiments, the target gene is selected from the group consisting of: (a) a polynucleotide having the sequence set forth in SEQ ID NO:1; (b) a polynucleotide from a parasitic nematode that hybridizes under stringent conditions to a polynucleotide having the sequence set forth in SEQ ID NO:1; (c) a polynucleotide having the sequence set forth in SEQ ID NO:2; (d) a polynucleotide from a parasitic nematode that hybridizes under stringent conditions to a polynucleotide having the sequence set forth in SEQ ID NO:2; (e) a polynucleotide having the sequence set forth in SEQ ID NO:3; (f) a polynucleotide from a parasitic nematode that hybridizes under stringent conditions to a polynucleotide having the sequence set forth in SEQ ID NO:3; (g) a polynucleotide having a sequence as set forth in SEQ ID NO:4; (h) a polynucleotide from a parasitic nematode that hybridizes under stringent conditions to a polynucleotide having a sequence as set forth in SEQ ID NO:4; (i) a polynucleotide having a sequence as set forth in SEQ ID NO:5; (j) a polynucleotide from a parasitic nematode that hybridizes under stringent conditions to a polynucleotide having a sequence as set forth in SEQ ID NO:5; (k) a polynucleotide having a sequence as set forth in SEQ ID NO:6; (l) a polynucleotide from a parasitic nematode that hybridizes under stringent conditions to a polynucleotide having a sequence as set forth in SEQ ID NO:6; (m) a polynucleotide comprising a sequence as set forth in SEQ ID NO:7; and (n) a polynucleotide from a parasitic nematode that hybridizes under stringent conditions to a polynucleotide comprising a sequence as set forth in SEQ ID NO:7. Preferably, the dsRNA of the invention comprises (a) a first strand comprising a sequence that is substantially identical to from about 21 to about 400 or 500 consecutive nucleotides of the target gene and (b) a second strand comprising a sequence substantially complementary to the first strand.

As discussed above, fragments of dsRNA larger than about 19-21 nucleotides in length are cleaved intracellularly by nematodes and plants to siRNAs of about 19-21 nucleotides in length, and these siRNAs are the actual mediators of the RNAi phenomenon. Example 6 demonstrates that siRNAs are generated when vectors containing fragments of the target genes of the invention are transformed into soybean hairy roots. Example 5 demonstrates that cyst count is reduced when *H. glycines* is inoculated onto transgenic soybean hairy root lines containing fragments of the target genes of the invention, as compared to a *H. glycines*-inoculated transgenic control hairy root line that does not contain such target gene fragments. Thus the dsRNA of the present invention may range in length from about 19-21 nucleotides to about 2000 nucleotides. Preferably, the dsRNA of the invention has a length from about 19-21 nucleotides to about 1500 nucleotides. More preferably, the dsRNA of the invention has a length from about 19-21 nucleotides to about 1000 nucleotides, or from about 19-21 nucleotides to about 400 or 500 nucleotides.

When dsRNA of the invention has a length longer than about 19-21 nucleotides, for example from about 50 nucleotides to about 1000 nucleotides, it will be cleaved to dsRNAs of about 19-21 nucleotides within the plant or parasitic nematode cell, the siRNAs. The cleavage of a longer dsRNA of the invention will yield a pool of 19 mer to 21 mer dsRNAs, derived from the longer dsRNA. This pool of 19 mer to 21 mer dsRNAs is also encompassed within the scope of the present invention, whether generated intracellularly within the plant or nematode or synthetically using known methods of oligonucleotide synthesis.

The siRNAs of the invention have sequences corresponding to fragments of about 19-21 contiguous nucleotides across the entire sequence of each target gene cDNA. For example, a pool of siRNA of the invention derived from the *H. glycines* cct-6 gene as set forth in SEQ ID NO:1 may comprise a multiplicity of RNA molecules which are selected from the group consisting of oligonucleotides substantially identical to nucleotides 1 to 21 of SEQ ID NO:1, nucleotides 2 to 23 of SEQ ID NO:1, nucleotides 3 to 24 of SEQ ID NO:1, nucleotides 4 to 25 of SEQ ID NO:1, nucleotides 5 to 26 of SEQ ID NO:1, nucleotides 6 to 27 of SEQ ID NO:1, nucleotides 7 to 28 of SEQ ID NO:1, nucleotides 8 to 29 of SEQ ID NO:1, nucleotides 9 to 30 of SEQ ID NO:1, nucleotides 10 to 31 of SEQ ID NO:1, nucleotides 11 to 32 of SEQ ID NO:1, nucleotides 12 to 33 of SEQ ID NO:1, nucleotides 13 to 34 of SEQ ID NO:1, nucleotides 14 to 35 of SEQ ID NO:1, nucleotides 15 to 36 of SEQ ID NO:1, nucleotides 16 to 37 of SEQ ID NO:1, nucleotides 17 to 38 of SEQ ID NO:1, nucleotides 18 to 39 of SEQ ID NO:1, nucleotides 19 to 40 of SEQ ID NO:1, nucleotides 20 to 41 of SEQ ID NO:1, nucleotides 21 to 42 of SEQ ID NO:1, nucleotides 22 to 43 of SEQ ID NO:1, nucleotides 23 to 44 of SEQ ID NO:1, nucleotides 24 to 45 of SEQ ID NO:1, nucleotides 25 to 46 of SEQ ID NO:1, nucleotides 26 to 47 of SEQ ID NO:1, nucleotides 27 to 48 of SEQ ID NO:1, nucleotides 28 to 49 of SEQ ID NO:1, nucleotides 29 to 50 of SEQ ID NO:1, nucleotides 30 to 51 of SEQ ID NO:1, nucleotides 31 to 52 of SEQ ID NO:1, nucleotides 32 to 53 of SEQ ID NO:1, nucleotides 33 to 54 of SEQ ID NO:1, nucleotides 34 to 55 of SEQ ID NO:1, nucleotides 35 to 56 of SEQ ID NO:1, nucleotides 36 to 57 of SEQ ID NO:1, nucleotides 37 to 58 of SEQ ID NO:1, nucleotides 38 to 59 of SEQ ID NO:1, nucleotides 39 to 60 of SEQ ID NO:1, nucleotides 40 to 61 of SEQ ID NO:1, nucleotides 41 to 62 of SEQ ID NO:1, nucleotides 42 to 63 of SEQ ID NO:1, nucleotides 43 to 64 of SEQ ID NO:1, nucleotides 44 to 65 of SEQ ID NO:1, nucleotides 45 to 66 of SEQ ID NO:1, nucleotides 46 to 67 of SEQ ID NO:1, nucleotides 47 to 68 of SEQ ID NO:1, nucleotides 48 to 69 of SEQ ID NO:1, nucleotides 49 to 70 of SEQ ID NO:1, and nucleotides 50 to 71 of SEQ ID NO:1.

As another example, a pool of siRNA of the invention derived from the *H. glycines* cct-6 gene of SEQ ID NO:1 may comprise a multiplicity of RNA molecules selected from the group of oligonucleotides substantially identical to nucleotides 51 to 72 of SEQ ID NO:1, nucleotides 52 to 73 of SEQ ID NO:1, nucleotides 53 to 74 of SEQ ID NO:1, nucleotides 54 to 75 of SEQ ID NO:1, nucleotides 55 to 76 of SEQ ID NO:1, nucleotides 56 to 77 of SEQ ID NO:1, nucleotides 57 to 78 of SEQ ID NO:1, nucleotides 58 to 79 of SEQ ID NO:1, nucleotides 59 to 80 of SEQ ID NO:1, nucleotides 60 to 81 of SEQ ID NO:1, nucleotides 61 to 82 of SEQ ID NO:1, nucleotides 62 to 83 of SEQ ID NO:1, nucleotides 63 to 84 of SEQ ID NO:1, nucleotides 64 to 85 of SEQ ID NO:1, nucleotides 65 to 86 of SEQ ID NO:1, nucleotides 66 to 87 of SEQ ID NO:1, nucleotides 67 to 88 of SEQ ID NO:1, nucleotides 68 to 89 of SEQ ID NO:1, nucleotides 69 to 90 of SEQ ID NO:1, nucleotides 70 to 91 of SEQ ID NO:1, nucleotides 71 to 92 of SEQ ID NO:1, nucleotides 72 to 93 of SEQ ID NO:1, nucleotides 73 to 94 of SEQ ID NO:1, nucleotides 74 to 95 of SEQ ID NO:1, nucleotides 75 to 96 of SEQ ID NO:1, nucleotides 76 to 97 of SEQ ID NO:1, nucleotides 77 to 98 of SEQ ID NO:1, nucleotides 78 to 99 of SEQ ID NO:1, nucleotides 79 to 100 of SEQ ID NO:1, nucleotides 80 to 101 of SEQ ID NO:1, nucleotides 81 to 102 of SEQ ID NO:1, nucleotides 82 to 103 of SEQ ID NO:1, nucleotides 83 to 104 of SEQ ID NO:1, nucleotides 84 to 105 of SEQ ID NO:1, nucleotides 85 to 106 of SEQ ID NO:1, nucleotides 86 to 107 of SEQ ID NO:1, nucleotides 87 to 108 of SEQ ID NO:1, nucleotides 88 to 109 of SEQ ID NO:1, nucleotides 89 to 110 of SEQ ID NO:1, nucleotides 90 to 111 of SEQ ID NO:1, nucleotides 91 to 112 of SEQ ID NO:1, nucleotides 92 to 113 of SEQ ID NO:1, nucleotides 93 to 114 of SEQ ID NO:1, nucleotides 94 to 115 of SEQ ID NO:1, nucleotides 95 to 116 of SEQ ID NO:1, nucleotides 96 to 117 of SEQ ID NO:1, nucleotides 97 to 118 of SEQ ID NO:1, nucleotides 98 to 119 of SEQ ID NO:1, nucleotides 99 to 120 of SEQ ID NO:1, and nucleotides 100 to 121 of SEQ ID NO:1.

As another example, a pool of siRNA of the invention derived from the *H. glycines* cct-6 gene of SEQ ID NO:1 may comprise a multiplicity of RNA molecules selected from the group of oligonucleotides substantially identical to nucleotides 101 to 122 of SEQ ID NO:1, nucleotides 102 to 123 of SEQ ID NO:1, nucleotides 103 to 124 of SEQ ID NO:1, nucleotides 104 to 125 of SEQ ID NO:1, nucleotides 105 to 126 of SEQ ID NO:1, nucleotides 106 to 127 of SEQ ID NO:1, nucleotides 107 to 128 of SEQ ID NO:1, nucleotides 108 to 129 of SEQ ID NO:1, nucleotides 109 to 130 of SEQ ID NO:1, nucleotides 110 to 131 of SEQ ID NO:1, nucleotides 111 to 132 of SEQ ID NO:1, nucleotides 112 to 133 of SEQ ID NO:1, nucleotides 113 to 134 of SEQ ID NO:1, nucleotides 114 to 135 of SEQ ID NO:1, nucleotides 115 to 136 of SEQ ID NO:1, nucleotides 116 to 137 of SEQ ID NO:1, nucleotides 117 to 138 of SEQ ID NO:1, nucleotides 118 to 139 of SEQ ID NO:1, nucleotides 119 to 140 of SEQ ID NO:1, nucleotides 120 to 141 of SEQ ID NO:1, nucleotides 121 to 142 of SEQ ID NO:1, nucleotides 122 to 143 of SEQ ID NO:1, nucleotides 123 to 144 of SEQ ID NO:1, nucleotides 124 to 145 of SEQ ID NO:1, nucleotides 125 to 146 of SEQ ID NO:1, nucleotides 126 to 147 of SEQ ID NO:1, nucleotides 127 to 148 of SEQ ID NO:1, nucleotides 128 to 149 of SEQ ID NO:1, nucleotides 129 to 150 of SEQ ID NO:1, nucleotides 130 to 151 of SEQ ID NO:1, nucleotides 131 to 152 of SEQ ID NO:1, nucleotides 132 to 153 of SEQ ID NO:1, nucleotides 133 to 154 of SEQ ID NO:1, nucleotides 134 to 155 of SEQ ID NO:1, nucleotides 135 to 156 of SEQ ID NO:1, nucleotides 136 to 157 of SEQ ID NO:1, nucleotides 137 to 158 of SEQ ID NO:1, nucleotides 138 to 159 of SEQ ID NO:1, nucleotides 139 to 160 of SEQ ID NO:1, nucleotides 140 to 161 of SEQ ID NO:1, nucleotides 141 to 162 of SEQ ID NO:1, nucleotides 142 to 163 of SEQ ID NO:1, nucleotides 143 to 164 of SEQ ID NO:1, nucleotides 144 to 165 of SEQ ID NO:1, nucleotides 145 to 166 of SEQ ID NO:1, nucleotides 146 to 167 of SEQ ID NO:1, nucleotides 147 to 168 of SEQ ID NO:1, nucleotides 148 to 169 of SEQ ID NO:1, nucleotides 149 to 170 of SEQ ID NO:1, and nucleotides 150 to 171 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 151 to 172 of SEQ ID NO:1, nucleotides 152 to 173 of SEQ ID NO:1, nucleotides 153 to 174 of SEQ ID NO:1, nucleotides 154 to 175 of SEQ ID NO:1, nucleotides 155 to 176 of SEQ ID NO:1, nucleotides 156 to 177 of SEQ ID NO:1, nucleotides 157 to 178 of SEQ ID NO:1, nucleotides 158 to 179 of SEQ ID NO:1, nucleotides 159 to 180 of SEQ ID NO:1, nucleotides 160 to 181 of SEQ ID NO:1, nucleotides 161 to 182 of SEQ ID NO:1, nucleotides 162 to 183 of SEQ ID NO:1, nucleotides 163 to 184 of SEQ ID NO:1, nucleotides 164 to 185 of SEQ ID NO:1, nucleotides 165 to 186 of SEQ ID NO:1, nucleotides 166 to 187 of SEQ ID NO:1, nucleotides 167 to 188 of SEQ ID NO:1, nucleotides 168 to 189 of SEQ ID NO:1, nucleotides 169 to 190 of SEQ ID NO:1, nucleotides 170 to 191 of SEQ ID NO:1, nucleotides 171 to 192 of SEQ ID NO:1, nucleotides 172 to 193 of SEQ ID NO:1, nucleotides 173 to 194 of SEQ ID NO:1, nucleotides 174 to 195 of SEQ ID NO:1, nucleotides 175 to 196 of SEQ ID NO:1, nucleotides 176 to 197 of SEQ ID NO:1, nucleotides 177 to 198 of SEQ ID NO:1, nucleotides 178 to 199 of SEQ ID NO:1, nucleotides 179 to 200 of SEQ ID NO:1, nucleotides 180 to 201 of SEQ ID NO:1, nucleotides 181 to 202 of SEQ ID NO:1, nucleotides 182 to 203 of SEQ ID NO:1, nucleotides 183 to 204 of SEQ ID NO:1, nucleotides 184 to 205 of SEQ ID NO:1, nucleotides 185 to 206 of SEQ ID NO:1, nucleotides 186 to 207 of SEQ ID NO:1, nucleotides 187 to 208 of SEQ ID NO:1, nucleotides 188 to 209 of SEQ ID NO:1, nucleotides 189 to 210 of SEQ ID NO:1, nucleotides 190 to 211 of SEQ ID NO:1, nucleotides 191 to 212 of SEQ ID NO:1, nucleotides 192 to 213 of SEQ ID NO: 1, nucleotides 193 to 214 of SEQ ID NO: 1, nucleotides 194 to 215 of SEQ ID NO:1, nucleotides 195 to 216 of SEQ ID NO:1, nucleotides 196 to 217 of SEQ ID NO:1, nucleotides 197 to 218 of SEQ ID NO:1, nucleotides 198 to 219 of SEQ ID NO:1, nucleotides 199 to 220 of SEQ ID NO:1, and nucleotides 200 to 221 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 201 to 222 of SEQ ID NO:1, nucleotides 202 to 223 of SEQ ID NO:1, nucleotides 203 to 224 of SEQ ID NO:1, nucleotides 204 to 225 of SEQ ID NO:1, nucleotides 205 to 226 of SEQ ID NO:1, nucleotides 206 to 227 of SEQ ID NO:1, nucleotides 207 to 228 of SEQ ID NO:1, nucleotides 208 to 229 of SEQ ID NO:1, nucleotides 209 to 230 of SEQ ID NO:1, nucleotides 210 to 231 of SEQ ID NO:1, nucleotides 211 to 232 of SEQ ID NO:1, nucleotides 212 to 233 of SEQ ID NO:1, nucleotides 213 to 234 of SEQ ID NO:1, nucleotides 214 to 235 of SEQ ID NO:1, nucleotides 215 to 236 of SEQ ID NO:1, nucleotides 216 to 237 of SEQ ID NO:1, nucleotides 217 to 238 of SEQ ID NO:1, nucleotides 218 to 239 of SEQ ID NO:1, nucleotides 219 to 240 of SEQ ID NO:1, nucleotides 220 to 241 of SEQ ID NO:1, nucleotides 221 to 242 of SEQ ID NO:1, nucleotides 222 to 243 of SEQ ID NO:1, nucleotides 223 to 244 of SEQ ID NO:1, nucleotides 224 to 245 of SEQ ID NO:1, nucleotides 225 to 246 of SEQ ID NO:1, nucleotides 226 to 247 of SEQ ID NO:1, nucleotides 227 to 248 of SEQ ID NO:1, nucleotides 228 to 249 of SEQ ID NO:1, nucleotides 229 to 250 of SEQ ID NO:1, nucleotides 230 to 251 of SEQ ID NO:1, nucleotides 231 to 252 of SEQ ID NO:1, nucleotides 232 to 253 of SEQ ID NO:1, nucleotides 233 to 254 of SEQ ID NO:1, nucleotides 234 to 255 of SEQ ID NO:1, nucleotides 235 to 256 of SEQ ID NO:1, nucleotides 236 to 257 of SEQ ID NO:1, nucleotides 237 to 258 of SEQ ID NO:1, nucleotides 238 to 259 of SEQ ID NO:1, nucleotides 239 to 260 of SEQ ID NO:1, nucleotides 240 to 261 of SEQ ID NO:1, nucleotides 241 to 262 of SEQ ID NO:1, nucleotides 242 to 263 of SEQ ID NO:1, nucleotides 243 to 264 of SEQ ID NO:1, nucleotides 244 to 265 of SEQ ID NO:1, nucleotides 245 to 266 of SEQ ID NO:1, nucleotides 246 to 267 of SEQ ID NO:1, nucleotides 247 to 268 of SEQ ID NO:1, nucleotides 248 to 269 of SEQ ID NO:1, nucleotides 249 to 270 of SEQ ID NO:1, and nucleotides 250 to 271 of SEQ ID NO:1.

As another example, a pool of siRNA of the invention derived from the *H. glycines* cct-6 gene of SEQ ID NO:1 may comprise a multiplicity of RNA molecules selected from the group of oligonucleotides substantially identical to nucleotides 251 to 272 of SEQ ID NO:1, nucleotides 252 to 273 of SEQ ID NO:1, nucleotides 253 to 274 of SEQ ID NO:1, nucleotides 254 to 275 of SEQ ID NO:1, nucleotides 255 to 276 of SEQ ID NO:1, nucleotides 256 to 277 of SEQ ID NO:1, nucleotides 257 to 278 of SEQ ID NO:1, nucleotides 258 to 279 of SEQ ID NO:1, nucleotides 259 to 280 of SEQ ID NO:1, nucleotides 260 to 281 of SEQ ID NO:1, nucleotides 261 to 282 of SEQ ID NO:1, nucleotides 262 to 283 of SEQ ID NO:1, nucleotides 263 to 284 of SEQ ID NO:1, nucleotides 264 to 285 of SEQ ID NO:1, nucleotides 265 to 286 of SEQ ID NO:1, nucleotides 266 to 287 of SEQ ID NO:1, nucleotides 267 to 288 of SEQ ID NO:1, nucleotides 268 to 289 of SEQ ID NO:1, nucleotides 269 to 290 of SEQ ID NO:1, nucleotides 270 to 291 of SEQ ID NO:1, nucleotides 271 to 292 of SEQ ID NO:1, nucleotides 272 to 293 of SEQ ID NO:1, nucleotides 273 to 294 of SEQ ID NO:1, nucleotides 274 to 295 of SEQ ID NO:1, nucleotides 275 to 296 of SEQ ID NO:1, nucleotides 276 to 297 of SEQ ID NO:1, nucleotides 277 to 298 of SEQ ID NO:1, nucleotides 278 to 299 of SEQ ID NO:1, nucleotides 279 to 300 of SEQ ID NO:1, nucleotides 280 to 301 of SEQ ID NO:1, nucleotides 281 to 302 of SEQ ID NO:1, nucleotides 282 to 303 of SEQ ID NO:1, nucleotides 283 to 304 of SEQ ID NO:1, nucleotides 284 to 305 of SEQ ID NO:1, nucleotides 285 to 306 of SEQ ID NO:1, nucleotides 286 to 307 of SEQ ID NO:1, nucleotides 287 to 308 of SEQ ID NO:1, nucleotides 288 to 309 of SEQ ID NO:1, nucleotides 289 to 310 of SEQ ID NO:1, nucleotides 290 to 311 of SEQ ID NO:1, nucleotides 291 to 312 of SEQ ID NO:1, nucleotides 292 to 313 of SEQ ID NO:1, nucleotides 293 to 314 of SEQ ID NO:1, nucleotides 294 to 315 of SEQ ID NO:1, nucleotides 295 to 316 of SEQ ID NO:1, nucleotides 296 to 317 of SEQ ID NO:1, nucleotides 297 to 318 of SEQ ID NO:1, nucleotides 298 to 319 of SEQ ID NO:1, nucleotides 299 to 320 of SEQ ID NO:1, and nucleotides 300 to 321 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 301 to 322 of SEQ ID NO:1, nucleotides 302 to 323 of SEQ ID NO:1, nucleotides 303 to 324 of SEQ ID NO:1, nucleotides 304 to 325 of SEQ ID NO:1, nucleotides 305 to 326 of SEQ ID NO:1, nucleotides 306 to 327 of SEQ ID NO:1, nucleotides 307 to 328 of SEQ ID NO:1, nucleotides 308 to 329 of SEQ ID NO:1, nucleotides 309 to 330 of SEQ ID NO:1, nucleotides 310 to 331 of SEQ ID NO:1, nucleotides 311 to 332 of SEQ ID NO:1, nucleotides 312 to 333 of SEQ ID NO:1, nucleotides 313 to 334 of SEQ ID NO:1, nucleotides 314 to 335 of SEQ ID NO:1, nucleotides 315 to 336 of SEQ ID NO:1, nucleotides 316 to 337 of SEQ ID NO:1, nucleotides 317 to 338 of SEQ ID NO:1, nucleotides 318 to 339 of SEQ ID NO:1, nucleotides 319 to 340 of SEQ ID NO:1, nucleotides 320 to 341 of SEQ ID NO:1, nucleotides 321 to 342 of SEQ ID NO:1, nucleotides 322 to 343 of SEQ ID NO:1, nucleotides 323 to 344 of SEQ ID NO:1, nucleotides 324 to 345 of SEQ ID NO:1, nucleotides 325 to 346 of SEQ ID NO:1, nucleotides 326 to 347 of SEQ ID NO:1, nucleotides 327 to 348 of SEQ ID NO:1, nucleotides 328 to 349 of SEQ ID NO:1, nucleotides 329 to 350 of SEQ ID NO:1, nucleotides 330 to 351 of SEQ ID NO:1, nucleotides 331 to 352 of SEQ ID NO:1, nucleotides 332 to 353 of SEQ ID NO:1, nucleotides 333 to 354 of SEQ ID NO:1, nucleotides 334 to 355 of SEQ ID NO:1, nucleotides 335 to 356 of SEQ ID NO:1, nucleotides 336 to 357 of SEQ ID NO:1, nucleotides 337 to 358 of SEQ ID NO:1, nucleotides 338 to 359 of SEQ ID NO:1, nucleotides 339 to 360 of SEQ ID NO:1, nucleotides 340 to 361 of SEQ ID NO:1, nucleotides 341 to 362 of SEQ ID NO:1, nucleotides 342 to 363 of SEQ ID NO:1, nucleotides 343 to 364 of SEQ ID NO:1, nucleotides 344 to 365 of SEQ ID NO:1, nucleotides 345 to 366 of SEQ ID NO:1, nucleotides 346 to 367 of SEQ ID NO:1, nucleotides 347 to 368 of SEQ ID NO:1, nucleotides 348 to 369 of SEQ ID NO:1, nucleotides 349 to 370 of SEQ ID NO:1, and nucleotides 350 to 371 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 351 to 372 of SEQ ID NO:1, nucleotides 352 to 373 of SEQ ID NO:1, nucleotides 353 to 374 of SEQ ID NO:1, nucleotides 354 to 375 of SEQ ID NO:1, nucleotides 355 to 376 of SEQ ID NO:1, nucleotides 356 to 377 of SEQ ID NO:1, nucleotides 357 to 378 of SEQ ID NO:1, nucleotides 358 to 379 of SEQ ID NO:1, nucleotides 359 to 380 of SEQ ID NO:1, nucleotides 360 to 381 of SEQ ID NO:1, nucleotides 361 to 382 of SEQ ID NO:1, nucleotides 362 to 383 of SEQ ID NO:1, nucleotides 363 to 384 of SEQ ID NO:1, nucleotides 364 to 385 of SEQ ID NO:1, nucleotides 365 to 386 of SEQ ID NO:1, nucleotides 366 to 387 of SEQ ID NO:1, nucleotides 367 to 388 of SEQ ID NO:1, nucleotides 368 to 389 of SEQ ID NO:1, nucleotides 369 to 390 of SEQ ID NO:1, nucleotides 370 to 391 of SEQ ID NO:1, nucleotides 371 to 392 of SEQ ID NO:1, nucleotides 372 to 393 of SEQ ID NO:1, nucleotides 373 to 394 of SEQ ID NO:1, nucleotides 374 to 395 of SEQ ID NO:1, nucleotides 375 to 396 of SEQ ID NO:1, nucleotides 376 to 397 of SEQ ID NO:1, nucleotides 377 to 398 of SEQ ID NO:1, nucleotides 378 to 399 of SEQ ID NO:1, nucleotides 379 to 400 of SEQ ID NO:1; nucleotides 380 to 401 of SEQ ID NO:1, nucleotides 381 to 402 of SEQ ID NO:1, nucleotides 382 to 403 of SEQ ID NO:1, nucleotides 383 to 404 of SEQ ID NO:1, nucleotides 384 to 405 of SEQ ID NO:1, nucleotides 385 to 406 of SEQ ID NO:1, nucleotides 386 to 407 of SEQ ID NO:1, nucleotides 387 to 408 of SEQ ID NO:1, nucleotides 388 to 409 of SEQ ID NO:1, nucleotides 389 to 410 of SEQ ID NO:1, nucleotides 390 to 411 of SEQ ID NO:1, nucleotides 391 to 412 of SEQ ID NO:1, nucleotides 392 to 413 of SEQ ID NO:1, nucleotides 393 to 414 of SEQ ID NO:1, nucleotides 394 to 415 of SEQ ID NO:1, nucleotides 395 to 416 of SEQ ID NO:1, nucleotides 396 to 417 of SEQ ID NO:1, nucleotides 397 to 418 of SEQ ID NO:1, nucleotides 398 to 419 of SEQ ID NO:1, nucleotides 399 to 420 of SEQ ID NO:1, and nucleotides 400 to 421 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 401 to 422 of SEQ ID NO:1, nucleotides 402 to 423 of SEQ ID NO:1, nucleotides 403 to 424 of SEQ ID NO:1, nucleotides 404 to 425 of SEQ ID NO:1, nucleotides 405 to 426 of SEQ ID NO:1, nucleotides 406 to 427 of SEQ ID NO:1, nucleotides 407 to 428 of SEQ ID NO:1, nucleotides 408 to 429 of SEQ ID NO:1, nucleotides 409 to 430 of SEQ ID NO:1, nucleotides 410 to 431 of SEQ ID NO:1, nucleotides 411 to 432 of SEQ ID NO:1, nucleotides 412 to 433 of SEQ ID NO:1, nucleotides 413 to 434 of SEQ ID NO:1, nucleotides 414 to 435 of SEQ ID NO:1, nucleotides 415 to 436 of SEQ ID NO:1, nucleotides 416 to 437 of SEQ ID NO:1, nucleotides 417 to 438 of SEQ ID NO:1, nucleotides 418 to 439 of SEQ ID NO:1, nucleotides 419 to 440 of SEQ ID NO:1, nucleotides 420 to 441 of SEQ ID NO:1, nucleotides 421 to 442 of SEQ ID NO:1, nucleotides 422 to 443 of SEQ ID NO:1, nucleotides 423 to 444 of SEQ ID NO:1, nucleotides 424 to 445 of SEQ ID NO:1, nucleotides 425 to 446 of SEQ ID NO:1, nucleotides 426 to 447 of SEQ ID NO:1, nucleotides 427 to 448 of SEQ ID NO:1, nucleotides 428 to 449 of SEQ ID NO:1, nucleotides 429 to 450 of SEQ ID NO:1, nucleotides 430 to 451 of SEQ ID NO:1, nucleotides 431 to 452 of SEQ ID NO:1, nucleotides 432 to 453 of SEQ ID NO:1, nucleotides 433 to 454 of SEQ ID NO:1, nucleotides 434 to 455 of SEQ ID NO:1, nucleotides 435 to 456 of SEQ ID NO:1, nucleotides 436 to 457 of SEQ ID NO:1, nucleotides 437 to 458 of SEQ ID NO:1, nucleotides 438 to 459 of SEQ ID NO:1, nucleotides 439 to 460 of SEQ ID NO:1, nucleotides 440 to 461 of SEQ ID NO:1, nucleotides 441 to 462 of SEQ ID NO:1, nucleotides 442 to 463 of SEQ ID NO:1, nucleotides 443 to 464 of SEQ ID NO:1, nucleotides 444 to 465 of SEQ ID NO:1, nucleotides 445 to 466 of SEQ ID NO:1, nucleotides 446 to 467 of SEQ ID NO:1, nucleotides 447 to 468 of SEQ ID NO:1, nucleotides 448 to 469 of SEQ ID NO:1, nucleotides 449 to 470 of SEQ ID NO:1, and nucleotides 450 to 471 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 451 to 472 of SEQ ID NO:1, nucleotides 452 to 473 of SEQ ID NO:1, nucleotides 453 to 474 of SEQ ID NO:1, nucleotides 454 to 475 of SEQ ID NO:1, nucleotides 455 to 476 of SEQ ID NO:1, nucleotides 456 to 477 of SEQ ID NO:1, nucleotides 457 to 478 of SEQ ID NO:1, nucleotides 458 to 479 of SEQ ID NO:1, nucleotides 459 to 480 of SEQ ID NO:1, nucleotides 460 to 481 of SEQ ID NO:1, nucleotides 461 to 482 of SEQ ID NO:1, nucleotides 462 to 483 of SEQ ID NO:1, nucleotides 463 to 484 of SEQ ID NO:1, nucleotides 464 to 485 of SEQ ID NO:1, nucleotides 465 to 486 of SEQ ID NO:1, nucleotides 466 to 487 of SEQ ID NO:1, nucleotides 467 to 488 of SEQ ID NO:1, nucleotides 468 to 489 of SEQ ID NO:1, nucleotides 469 to 490 of SEQ ID NO:1, nucleotides 470 to 491 of SEQ ID NO:1, nucleotides 471 to 492 of SEQ ID NO:1, nucleotides 472 to 493 of SEQ ID NO:1, nucleotides 473 to 494 of SEQ ID NO:1, nucleotides 474 to 495 of SEQ ID NO:1, nucleotides 475 to 496 of SEQ ID NO:1, nucleotides 476 to 497 of SEQ ID NO:1, nucleotides 477 to 498 of SEQ ID NO:1, nucleotides 478 to 499 of SEQ ID NO:1, nucleotides 479 to 500 of SEQ ID NO:1, nucleotides 480 to 501 of SEQ ID NO:1, nucleotides 481 to 502 of SEQ ID NO:1, nucleotides 482 to 503 of SEQ ID NO:1, nucleotides 483 to 504 of SEQ ID NO:1, nucleotides 484 to 505 of SEQ ID NO:1, nucleotides 485 to 506 of SEQ ID NO:1, nucleotides 486 to 507 of SEQ ID NO:1, nucleotides 487 to 508 of SEQ ID NO:1, nucleotides 488 to 509 of SEQ ID NO:1, nucleotides 489 to 510 of SEQ ID NO:1, nucleotides 490 to 511 of SEQ ID NO:1, nucleotides 491 to 512 of SEQ ID NO:1, nucleotides 492 to 513 of SEQ ID NO:1, nucleotides 493 to 514 of SEQ ID NO:1, nucleotides 494 to 515 of SEQ ID NO:1, nucleotides 495 to 516 of SEQ ID NO:1, nucleotides 496 to 517 of SEQ ID NO:1, nucleotides 497 to 518 of SEQ ID NO:1, nucleotides 498 to 519 of SEQ ID NO:1, nucleotides 499 to 520 of SEQ ID NO:1, and nucleotides 500 to 521 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 501 to 522 of SEQ ID NO:1, nucleotides 502 to 523 of SEQ ID NO:1, nucleotides 503 to 524 of SEQ ID NO:1, nucleotides 504 to 525 of SEQ ID NO:1, nucleotides 505 to 526 of SEQ ID NO:1, nucleotides 506 to 527 of SEQ ID NO:1, nucleotides 507 to 528 of SEQ ID NO:1, nucleotides 508 to 529 of SEQ ID NO:1, nucleotides 509 to 530 of SEQ ID NO:1, nucleotides 510 to 531 of SEQ ID NO:1, nucleotides 511 to 532 of SEQ ID NO:1, nucleotides 512 to 533 of SEQ ID NO:1, nucleotides 513 to 534 of SEQ ID NO:1, nucleotides 514 to 535 of SEQ ID NO:1, nucleotides 515 to 536 of SEQ ID NO:1, nucleotides 516 to 537 of SEQ ID NO:1, nucleotides 517 to 538 of SEQ ID NO:1, nucleotides 518 to 539 of SEQ ID NO:1, nucleotides 519 to 540 of SEQ ID NO:1, nucleotides 520 to 541 of SEQ ID NO:1, nucleotides 521 to 542 of SEQ ID NO:1, nucleotides 522 to 543 of SEQ ID NO:1, nucleotides 523 to 544 of SEQ ID NO:1; nucleotides 524 to 545 of SEQ ID NO:1, nucleotides 525 to 546 of SEQ ID NO:1, nucleotides 526 to 547 of SEQ ID NO:1, nucleotides 527 to 548 of SEQ ID NO:1, nucleotides 528 to 549 of SEQ ID NO:1, nucleotides 529 to 550 of SEQ ID NO:1, nucleotides 530 to 551 of SEQ ID NO:1, nucleotides 531 to 552 of SEQ ID NO:1, nucleotides 532 to 553 of SEQ ID NO:1, nucleotides 533 to 554 of SEQ ID NO:1, nucleotides 534 to 555 of SEQ ID NO:1, nucleotides 535 to 556 of SEQ ID NO:1, nucleotides 536 to 557 of SEQ ID NO:1, nucleotides 537 to 558 of SEQ ID NO:1, nucleotides 538 to 559 of SEQ ID NO:1, nucleotides 539 to 560 of SEQ ID NO:1, nucleotides 540 to 561 of SEQ ID NO:1, nucleotides 541 to 562 of SEQ ID NO:1, nucleotides 542 to 563 of SEQ ID NO:1, nucleotides 543 to 564 of SEQ ID NO:1, nucleotides 544 to 565 of SEQ ID NO:1, nucleotides 545 to 566 of SEQ ID NO:1, nucleotides 546 to 567 of SEQ ID NO:1, nucleotides 547 to 568 of SEQ ID NO:1, nucleotides 548 to 569 of SEQ ID NO:1, nucleotides 549 to 570 of SEQ ID NO:1, and nucleotides 550 to 571 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 551 to 572 of SEQ ID NO:1, nucleotides 552 to 573 of SEQ ID NO:1, nucleotides 553 to 574 of SEQ ID NO:1, nucleotides 554 to 575 of SEQ ID NO:1, nucleotides 555 to 576 of SEQ ID NO:1, nucleotides 556 to 577 of SEQ ID NO:1, nucleotides 557 to 578 of SEQ ID NO:1, nucleotides 558 to 579 of SEQ ID NO:1, nucleotides 559 to 580 of SEQ ID NO:1, nucleotides 560 to 581 of SEQ ID NO:1, nucleotides 561 to 582 of SEQ ID NO:1, nucleotides 562 to 583 of SEQ ID NO:1, nucleotides 563 to 584 of SEQ ID NO:1, nucleotides 564 to 585 of SEQ ID NO:1, nucleotides 565 to 586 of SEQ ID NO:1, nucleotides 566 to 587 of SEQ ID NO:1, nucleotides 567 to 588 of SEQ ID NO:1, nucleotides 568 to 589 of SEQ ID NO:1, nucleotides 569 to 590 of SEQ ID NO:1, nucleotides 570 to 591 of SEQ ID NO:1, nucleotides 571 to 592 of SEQ ID NO:1, nucleotides 572 to 593 of SEQ ID NO:1, nucleotides 573 to 594 of SEQ ID NO:1, nucleotides 574 to 595 of SEQ ID NO:1, nucleotides 575 to 596 of SEQ ID NO:1, nucleotides 576 to 597 of SEQ ID NO:1, nucleotides 577 to 598 of SEQ ID NO:1, nucleotides 578 to 599 of SEQ ID NO:1, nucleotides 579 to 600 of SEQ ID NO:1, nucleotides 580 to 601 of SEQ ID NO:1, nucleotides 581 to 602 of SEQ ID NO:1, nucleotides 582 to 603 of SEQ ID NO:1, nucleotides 583 to 604 of SEQ ID NO:1, nucleotides 584 to 605 of SEQ ID NO:1, nucleotides 585 to 606 of SEQ ID NO:1, nucleotides 586 to 607 of SEQ ID NO:1, nucleotides 587 to 608 of SEQ ID NO:1, nucleotides 588 to 609 of SEQ ID NO:1, nucleotides 589 to 610 of SEQ ID NO:1, nucleotides 590 to 611 of SEQ ID NO:1, nucleotides 591 to 612 of SEQ ID NO:1, nucleotides 592 to 613 of SEQ ID NO:1, nucleotides 593 to 614 of SEQ ID NO:1, nucleotides 594 to 615 of SEQ ID NO:1, nucleotides 595 to 616 of SEQ ID NO:1, nucleotides 596 to 617 of SEQ ID NO:1, nucleotides 597 to 618 of SEQ ID NO:1, nucleotides 598 to 619 of SEQ ID NO:1, nucleotides 599 to 620 of SEQ ID NO:1, and nucleotides 600 to 621 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 601 to 622 of SEQ ID NO:1, nucleotides 602 to 623 of SEQ ID NO:1, nucleotides 603 to 624 of SEQ ID NO:1, nucleotides 604 to 625 of SEQ ID NO:1, nucleotides 605 to 626 of SEQ ID NO:1, nucleotides 606 to 627 of SEQ ID NO:1, nucleotides 607 to 628 of SEQ ID NO:1, nucleotides 608 to 629 of SEQ ID NO:1, nucleotides 609 to 630 of SEQ ID NO:1, nucleotides 610 to 631 of SEQ ID NO:1, nucleotides 611 to 632 of SEQ ID NO:1, nucleotides 612 to 633 of SEQ ID NO:1, nucleotides 613 to 634 of SEQ ID NO:1, nucleotides 614 to 635 of SEQ ID NO:1, nucleotides 615 to 636 of SEQ ID NO:1, nucleotides 616 to 637 of SEQ ID NO:1, nucleotides 617 to 638 of SEQ ID NO:1, nucleotides 618 to 639 of SEQ ID NO:1, nucleotides 619 to 640 of SEQ ID NO:1, nucleotides 620 to 641 of SEQ ID NO:1, nucleotides 621 to 642 of SEQ ID NO:1, nucleotides 622 to 643 of SEQ ID NO:1, nucleotides 623 to 644 of SEQ ID NO:1, nucleotides 624 to 645 of SEQ ID NO:1, nucleotides 625 to 646 of SEQ ID NO:1, nucleotides 626 to 647 of SEQ ID NO:1, nucleotides 627 to 648 of SEQ ID NO:1, nucleotides 628 to 649 of SEQ ID NO:1, nucleotides 629 to 650 of SEQ ID NO:1, nucleotides 630 to 651 of SEQ ID NO:1, nucleotides 631 to 652 of SEQ ID NO:1, nucleotides 632 to 653 of SEQ ID NO:1, nucleotides 633 to 654 of SEQ ID NO:1, nucleotides 634 to 655 of SEQ ID NO:1, nucleotides 635 to 656 of SEQ ID NO:1, nucleotides 636 to 657 of SEQ ID NO:1, nucleotides 637 to 658 of SEQ ID NO:1, nucleotides 638 to 659 of SEQ ID NO:1, nucleotides 639 to 660 of SEQ ID NO:1, nucleotides 640 to 661 of SEQ ID NO:1, nucleotides 641 to 662 of SEQ ID NO:1, nucleotides 642 to 663 of SEQ ID NO:1, nucleotides 643 to 664 of SEQ ID NO:1, nucleotides 644 to 665 of SEQ ID NO:1, nucleotides 645 to 666 of SEQ ID NO:1, nucleotides 646 to 667 of SEQ ID NO:1, nucleotides 647 to 668 of SEQ ID NO:1, nucleotides 648 to 669 of SEQ ID NO:1, nucleotides 649 to 670 of SEQ ID NO:1, and nucleotides 650 to 671 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 651 to 672 of SEQ ID NO:1, nucleotides 652 to 673 of SEQ ID NO:1, nucleotides 653 to 674 of SEQ ID NO:1, nucleotides 654 to 675 of SEQ ID NO:1, nucleotides 655 to 676 of SEQ ID NO:1, nucleotides 656 to 677 of SEQ ID NO:1, nucleotides 657 to 678 of SEQ ID NO:1, nucleotides 658 to 679 of SEQ ID NO:1, nucleotides 659 to 680 of SEQ ID NO:1, nucleotides 660 to 681 of SEQ ID NO:1, nucleotides 661 to 682 of SEQ ID NO:1, nucleotides 662 to 683 of SEQ ID NO:1, nucleotides 663 to 684 of SEQ ID NO:1, nucleotides 664 to 685 of SEQ ID NO:1, nucleotides 665 to 686 of SEQ ID NO:1, nucleotides 666 to 687 of SEQ ID NO:1, nucleotides 667 to 688 of SEQ ID NO:1, nucleotides 668 to 689 of SEQ ID NO:1, nucleotides 669 to 690 of SEQ ID NO:1, nucleotides 670 to 691 of SEQ ID NO:1, nucleotides 671 to 692 of SEQ ID NO:1, nucleotides 672 to 693 of SEQ ID NO:1, nucleotides 673 to 694 of SEQ ID NO:1, nucleotides 674 to 695 of SEQ ID NO:1, nucleotides 675 to 696 of SEQ ID NO:1, nucleotides 676 to 697 of SEQ ID NO:1, nucleotides 677 to 698 of SEQ ID NO:1, nucleotides 678 to 699 of SEQ ID NO:1, nucleotides 679 to 700 of SEQ ID NO:1, nucleotides 680 to 701 of SEQ ID NO:1, nucleotides 681 to 702 of SEQ ID NO:1, nucleotides 682 to 703 of SEQ ID NO:1, nucleotides 683 to 704 of SEQ ID NO:1, nucleotides 684 to 705 of SEQ ID NO:1, nucleotides 685 to 706 of SEQ ID NO:1, nucleotides 686 to 707 of SEQ ID NO:1, nucleotides 687 to 708 of SEQ ID NO:1, nucleotides 688 to 709 of SEQ ID NO:1, nucleotides 689 to 710 of SEQ ID NO:1, nucleotides 690 to 711 of SEQ ID NO:1, nucleotides 691 to 712 of SEQ ID NO:1, nucleotides 692 to 713 of SEQ ID NO:1, nucleotides 693 to 714 of SEQ ID NO:1, nucleotides 694 to 715 of SEQ ID NO:1, nucleotides 695 to 716 of SEQ ID NO:1, nucleotides 696 to 717 of SEQ ID NO:1, nucleotides 697 to 718 of SEQ ID NO:1, nucleotides 698 to 719 of SEQ ID NO:1, nucleotides 699 to 720 of SEQ ID NO:1, and nucleotides 700 to 721 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 701 to 722 of SEQ ID NO:1, nucleotides 702 to 723 of SEQ ID NO:1, nucleotides 703 to 724 of SEQ ID NO:1, nucleotides 704 to 725 of SEQ ID NO:1, nucleotides 705 to 726 of SEQ ID NO:1, nucleotides 706 to 727 of SEQ ID NO:1, nucleotides 707 to 728 of SEQ ID NO:1, nucleotides 708 to 729 of SEQ ID NO:1, nucleotides 709 to 730 of SEQ ID NO:1, nucleotides 710 to 731 of SEQ ID NO:1, nucleotides 711 to 732 of SEQ ID NO:1, nucleotides 712 to 733 of SEQ ID NO:1, nucleotides 713 to 734 of SEQ ID NO:1, nucleotides 714 to 735 of SEQ ID NO:1, nucleotides 715 to 736 of SEQ ID NO:1, nucleotides 716 to 737 of SEQ ID NO:1, nucleotides 717 to 738 of SEQ ID NO:1, nucleotides 718 to 739 of SEQ ID NO:1, nucleotides 719 to 740 of SEQ ID NO:1, nucleotides 720 to 741 of SEQ ID NO:1, nucleotides 721 to 742 of SEQ ID NO:1, nucleotides 722 to 743 of SEQ ID NO:1, nucleotides 723 to 744 of SEQ ID NO:1, nucleotides 724 to 745 of SEQ ID NO:1, nucleotides 725 to 746 of SEQ ID NO:1, nucleotides 726 to 747 of SEQ ID NO:1, nucleotides 727 to 748 of SEQ ID NO:1, nucleotides 728 to 749 of SEQ ID NO:1, nucleotides 729 to 750 of SEQ ID NO:1, nucleotides 730 to 751 of SEQ ID NO:1, nucleotides 731 to 752 of SEQ ID NO:1, nucleotides 732 to 753 of SEQ ID NO:1, nucleotides 733 to 754 of SEQ ID NO:1, nucleotides 734 to 755 of SEQ ID NO:1, nucleotides 735 to 756 of SEQ ID NO:1, nucleotides 736 to 757 of SEQ ID NO:1, nucleotides 737 to 758 of SEQ ID NO:1, nucleotides 738 to 759 of SEQ ID NO:1, nucleotides 739 to 760 of SEQ ID NO:1, nucleotides 740 to 761 of SEQ ID NO:1, nucleotides 741 to 762 of SEQ ID NO:1, nucleotides 742 to 763 of SEQ ID NO:1, nucleotides 743 to 764 of SEQ ID NO:1, nucleotides 744 to 765 of SEQ ID NO:1, nucleotides 745 to 766 of SEQ ID NO:1, nucleotides 746 to 767 of SEQ ID NO:1, nucleotides 747 to 768 of SEQ ID NO:1, nucleotides 748 to 769 of SEQ ID NO:1, nucleotides 749 to 770 of SEQ ID NO:1, and nucleotides 750 to 771 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 751 to 772 of SEQ ID NO:1, nucleotides 752 to 773 of SEQ ID NO:1, nucleotides 753 to 774 of SEQ ID NO:1, nucleotides 754 to 775 of SEQ ID NO:1, nucleotides 755 to 776 of SEQ ID NO:1, nucleotides 756 to 777 of SEQ ID NO:1, nucleotides 757 to 778 of SEQ ID NO:1, nucleotides 758 to 779 of SEQ ID NO:1, nucleotides 759 to 780 of SEQ ID NO:1, nucleotides 760 to 781 of SEQ ID NO:1, nucleotides 761 to 782 of SEQ ID NO:1, nucleotides 762 to 783 of SEQ ID NO:1, nucleotides 763 to 784 of SEQ ID NO:1, nucleotides 764 to 785 of SEQ ID NO:1, nucleotides 765 to 786 of SEQ ID NO:1, nucleotides 766 to 787 of SEQ ID NO:1, nucleotides 767 to 788 of SEQ ID NO:1, nucleotides 768 to 789 of SEQ ID NO:1, nucleotides 769 to 790 of SEQ ID NO:1, nucleotides 770 to 791 of SEQ ID NO:1, nucleotides 771 to 792 of SEQ ID NO:1, nucleotides 772 to 793 of SEQ ID NO:1, nucleotides 773 to 794 of SEQ ID NO:1, nucleotides 774 to 795 of SEQ ID NO:1, nucleotides 775 to 796 of SEQ ID NO:1, nucleotides 776 to 797 of SEQ ID NO:1, nucleotides 777 to 798 of SEQ ID NO:1, nucleotides 778 to 799 of SEQ ID NO:1, nucleotides 779 to 800 of SEQ ID NO:1, nucleotides 780 to 801 of SEQ ID NO:1, nucleotides 781 to 802 of SEQ ID NO:1, nucleotides 782 to 803 of SEQ ID NO:1, nucleotides 783 to 804 of SEQ ID NO:1, nucleotides 784 to 805 of SEQ ID NO:1, nucleotides 785 to 806 of SEQ ID NO:1, nucleotides 786 to 807 of SEQ ID NO:1, nucleotides 787 to 808 of SEQ ID NO:1, nucleotides 788 to 809 of SEQ ID NO:1, nucleotides 789 to 810 of SEQ ID NO:1, nucleotides 790 to 811 of SEQ ID NO:1, nucleotides 791 to 812 of SEQ ID NO:1, nucleotides 792 to 813 of SEQ ID NO:1, nucleotides 793 to 814 of SEQ ID NO:1, nucleotides 794 to 815 of SEQ ID NO:1, nucleotides 795 to 816 of SEQ ID NO:1, nucleotides 796 to 817 of SEQ ID NO:1, nucleotides 797 to 818 of SEQ ID NO:1, nucleotides 798 to 819 of SEQ ID NO:1, nucleotides 799 to 820 of SEQ ID NO:1, and nucleotides 800 to 821 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 801 to 822 of SEQ ID NO:1, nucleotides 802 to 823 of SEQ ID NO:1, nucleotides 803 to 824 of SEQ ID NO:1, nucleotides 804 to 825 of SEQ ID NO:1, nucleotides 805 to 826 of SEQ ID NO:1, nucleotides 806 to 827 of SEQ ID NO:1, nucleotides 807 to 828 of SEQ ID NO:1, nucleotides 808 to 829 of SEQ ID NO:1, nucleotides 809 to 830 of SEQ ID NO:1, nucleotides 810 to 831 of SEQ ID NO:1, nucleotides 811 to 832 of SEQ ID NO:1, nucleotides 812 to 833 of SEQ ID NO:1, nucleotides 813 to 834 of SEQ ID NO:1, nucleotides 814 to 835 of SEQ ID NO:1, nucleotides 815 to 836 of SEQ ID NO:1, nucleotides 816 to 837 of SEQ ID NO:1, nucleotides 817 to 838 of SEQ ID NO:1, nucleotides 818 to 839 of SEQ ID NO:1, nucleotides 819 to 840 of SEQ ID NO:1, nucleotides 820 to 841 of SEQ ID NO:1, nucleotides 821 to 842 of SEQ ID NO:1, nucleotides 822 to 843 of SEQ ID NO:1, nucleotides 823 to 844 of SEQ ID NO:1, nucleotides 824 to 845 of SEQ ID NO:1, nucleotides 825 to 846 of SEQ ID NO:1, nucleotides 826 to 847 of SEQ ID NO:1, nucleotides 827 to 848 of SEQ ID NO:1, nucleotides 828 to 849 of SEQ ID NO:1, nucleotides 829 to 850 of SEQ ID NO:1, nucleotides 830 to 851 of SEQ ID NO:1, nucleotides 831 to 852 of SEQ ID NO:1, nucleotides 832 to 853 of SEQ ID NO:1, nucleotides 833 to 854 of SEQ ID NO:1, nucleotides 834 to 855 of SEQ ID NO:1, nucleotides 835 to 856 of SEQ ID NO:1, nucleotides 836 to 857 of SEQ ID NO:1, nucleotides 837 to 858 of SEQ ID NO:1, nucleotides 838 to 859 of SEQ ID NO:1, nucleotides 839 to 860 of SEQ ID NO:1, nucleotides 840 to 861 of SEQ ID NO:1, nucleotides 841 to 862 of SEQ ID NO:1, nucleotides 842 to 863 of SEQ ID NO:1, nucleotides 843 to 864 of SEQ ID NO:1, nucleotides 844 to 865 of SEQ ID NO:1, nucleotides 845 to 866 of SEQ ID NO:1, nucleotides 846 to 867 of SEQ ID NO:1, nucleotides 847 to 868 of SEQ ID NO:1, nucleotides 848 to 869 of SEQ ID NO:1, nucleotides 849 to 870 of SEQ ID NO:1, and nucleotides 850 to 871 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 851 to 872 of SEQ ID NO:1, nucleotides 852 to 873 of SEQ ID NO:1, nucleotides 853 to 874 of SEQ ID NO:1, nucleotides 854 to 875 of SEQ ID NO:1, nucleotides 855 to 876 of SEQ ID NO:1, nucleotides 856 to 877 of SEQ ID NO:1, nucleotides 857 to 878 of SEQ ID NO:1, nucleotides 858 to 879 of SEQ ID NO:1, nucleotides 859 to 880 of SEQ ID NO:1, nucleotides 860 to 881 of SEQ ID NO:1, nucleotides 861 to 882 of SEQ ID NO:1, nucleotides 862 to 883 of SEQ ID NO:1, nucleotides 863 to 884 of SEQ ID NO:1, nucleotides 864 to 885 of SEQ ID NO:1, nucleotides 865 to 886 of SEQ ID NO:1, nucleotides 866 to 887 of SEQ ID NO:1, nucleotides 867 to 888 of SEQ ID NO:1, nucleotides 868 to 889 of SEQ ID NO:1, nucleotides 869 to 890 of SEQ ID NO:1, nucleotides 870 to 891 of SEQ ID NO:1, nucleotides 871 to 892 of SEQ ID NO:1, nucleotides 872 to 893 of SEQ ID NO:1, nucleotides 873 to 894 of SEQ ID NO:1, nucleotides 874 to 895 of SEQ ID NO:1, nucleotides 875 to 896 of SEQ ID NO:1, nucleotides 876 to 897 of SEQ ID NO:1, nucleotides 877 to 898 of SEQ ID NO:1, nucleotides 878 to 899 of SEQ ID NO:1, nucleotides 879 to 900 of SEQ ID NO:1, nucleotides 880 to 901 of SEQ ID NO:1, nucleotides 881 to 902 of SEQ ID NO:1, nucleotides 882 to 903 of SEQ ID NO:1, nucleotides 883 to 904 of SEQ ID NO:1, nucleotides 884 to 905 of SEQ ID NO:1, nucleotides 885 to 906 of SEQ ID NO:1, nucleotides 886 to 907 of SEQ ID NO:1, nucleotides 887 to 908 of SEQ ID NO:1, nucleotides 888 to 909 of SEQ ID NO:1, nucleotides 889 to 910 of SEQ ID NO:1, nucleotides 890 to 911 of SEQ ID NO:1, nucleotides 891 to 912 of SEQ ID NO:1, nucleotides 892 to 913 of SEQ ID NO:1, nucleotides 893 to 914 of SEQ ID NO:1, nucleotides 894 to 915 of SEQ ID NO:1, nucleotides 895 to 916 of SEQ ID NO:1, nucleotides 896 to 917 of SEQ ID NO:1, nucleotides 897 to 918 of SEQ ID NO:1, nucleotides 898 to 919 of SEQ ID NO:1, nucleotides 899 to 920 of SEQ ID NO:1, and nucleotides 900 to 921 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 901 to 922 of SEQ ID NO:1, nucleotides 902 to 923 of SEQ ID NO:1; nucleotides 903 to 924 of SEQ ID NO:1, nucleotides 904 to 925 of SEQ ID NO:1, nucleotides 905 to 926 of SEQ ID NO:1, nucleotides 906 to 927 of SEQ ID NO:1, nucleotides 907 to 928 of SEQ ID NO:1, nucleotides 908 to 929 of SEQ ID NO:1, nucleotides 909 to 930 of SEQ ID NO:1, nucleotides 910 to 931 of SEQ ID NO:1, nucleotides 911 to 932 of SEQ ID NO:1, nucleotides 912 to 933 of SEQ ID NO:1, nucleotides 913 to 934 of SEQ ID NO:1, nucleotides 914 to 935 of SEQ ID NO:1, nucleotides 915 to 936 of SEQ ID NO:1, nucleotides 916 to 937 of SEQ ID NO:1, nucleotides 917 to 938 of SEQ ID NO:1, nucleotides 918 to 939 of SEQ ID NO:1, nucleotides 919 to 940 of SEQ ID NO:1, nucleotides 920 to 941 of SEQ ID NO:1, nucleotides 921 to 942 of SEQ ID NO:1, nucleotides 922 to 943 of SEQ ID NO:1, nucleotides 923 to 944 of SEQ ID NO:1, nucleotides 924 to 945 of SEQ ID NO:1, nucleotides 925 to 946 of SEQ ID NO:1, nucleotides 926 to 947 of SEQ ID NO:1, nucleotides 927 to 948 of SEQ ID NO:1, nucleotides 928 to 949 of SEQ ID NO:1, nucleotides 929 to 950 of SEQ ID NO:1, nucleotides 930 to 951 of SEQ ID NO:1, nucleotides 931 to 952 of SEQ ID NO:1, nucleotides 932 to 953 of SEQ ID NO:1, nucleotides 933 to 954 of SEQ ID NO:1, nucleotides 934 to 955 of SEQ ID NO:1, nucleotides 935 to 956 of SEQ ID NO:1, nucleotides 936 to 957 of SEQ ID NO:1, nucleotides 937 to 958 of SEQ ID NO:1, nucleotides 938 to 959 of SEQ ID NO:1, nucleotides 939 to 960 of SEQ ID NO:1, nucleotides 940 to 961 of SEQ ID NO:1, nucleotides 941 to 962 of SEQ ID NO:1, nucleotides 942 to 963 of SEQ ID NO:1, nucleotides 943 to 964 of SEQ ID NO:1, nucleotides 944 to 965 of SEQ ID NO:1, nucleotides 945 to 966 of SEQ ID NO:1, nucleotides 946 to 967 of SEQ ID NO:1, nucleotides 947 to 968 of SEQ ID NO:1, nucleotides 948 to 969 of SEQ ID NO:1, nucleotides 949 to 970 of SEQ ID NO:1, and nucleotides 950 to 971 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 951 to 972 of SEQ ID NO:1, nucleotides 952 to 973 of SEQ ID NO:1, nucleotides 953 to 974 of SEQ ID NO:1, nucleotides 954 to 975 of SEQ ID NO:1, nucleotides 955 to 976 of SEQ ID NO:1, nucleotides 956 to 977 of SEQ ID NO:1, nucleotides 957 to 978 of SEQ ID NO:1, nucleotides 958 to 979 of SEQ ID NO:1, nucleotides 959 to 980 of SEQ ID NO:1, nucleotides 960 to 981 of SEQ ID NO:1, nucleotides 961 to 982 of SEQ ID NO:1, nucleotides 962 to 983 of SEQ ID NO:1, nucleotides 963 to 984 of SEQ ID NO:1, nucleotides 964 to 985 of SEQ ID NO:1, nucleotides 965 to 986 of SEQ ID NO:1, nucleotides 966 to 987 of SEQ ID NO:1, nucleotides 967 to 988 of SEQ ID NO:1, nucleotides 968 to 989 of SEQ ID NO:1, nucleotides 969 to 990 of SEQ ID NO:1, nucleotides 970 to 991 of SEQ ID NO:1, nucleotides 971 to 992 of SEQ ID NO:1, nucleotides 972 to 993 of SEQ ID NO:1, nucleotides 973 to 994 of SEQ ID NO:1, nucleotides 974 to 995 of SEQ ID NO:1, nucleotides 975 to 996 of SEQ ID NO:1, nucleotides 976 to 997 of SEQ ID NO:1, nucleotides 977 to 998 of SEQ ID NO:1, nucleotides 978 to 999 of SEQ ID NO:1, and nucleotides 979 to 1000 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 980 to 1001 of SEQ ID NO:1, nucleotides 981 to 1002 of SEQ ID NO:1, nucleotides 982 to 1003 of SEQ ID NO:1, nucleotides 983 to 1004 of SEQ ID NO:1, nucleotides 984 to 1005 of SEQ ID NO:1, nucleotides 985 to 1006 of SEQ ID NO:1, nucleotides 986 to 1007 of SEQ ID NO:1, nucleotides 987 to 1008 of SEQ ID NO:1, nucleotides 988 to 1009 of SEQ ID NO:1, nucleotides 989 to 1010 of SEQ ID NO:1, nucleotides 990 to 1011 of SEQ ID NO:1, nucleotides 991 to 1012 of SEQ ID NO:1, nucleotides 992 to 1013 of SEQ ID NO:1, nucleotides 993 to 1014 of SEQ ID NO:1, nucleotides 994 to 1015 of SEQ ID NO:1, nucleotides 995 to 1016 of SEQ ID NO:1, nucleotides 996 to 1017 of SEQ ID NO:1, nucleotides 997 to 1018 of SEQ ID NO:1, nucleotides 998 to 1019 of SEQ ID NO:1, nucleotides 999 to 1020 of SEQ ID NO:1, nucleotides 1000 to 1021 of SEQ ID NO:1, nucleotides 1001 to 1022 of SEQ ID NO:1, nucleotides 1002 to 1023 of SEQ ID NO:1, nucleotides 1003 to 1024 of SEQ ID NO:1, nucleotides 1004 to 1025 of SEQ ID NO:1, nucleotides 1005 to 1026 of SEQ ID NO:1, nucleotides 1006 to 1027 of SEQ ID NO:1, nucleotides 1007 to 1028 of SEQ ID NO:1, nucleotides 1008 to 1029 of SEQ ID NO:1, nucleotides 1009 to 1030 of SEQ ID NO:1, nucleotides 1010 to 1031 of SEQ ID NO:1, nucleotides 1011 to 1032 of SEQ ID NO:1, nucleotides 1012 to 1033 of SEQ ID NO:1, nucleotides 1013 to 1034 of SEQ ID NO:1, nucleotides 1014 to 1035 of SEQ ID NO:1, nucleotides 1015 to 1036 of SEQ ID NO:1, nucleotides 1016 to 1037 of SEQ ID NO:1, nucleotides 1017 to 1038 of SEQ ID NO:1, nucleotides 1018 to 1039 of SEQ ID NO:1, nucleotides 1019 to 1040 of SEQ ID NO:1, nucleotides 1020 to 1041 of SEQ ID NO:1, nucleotides 1021 to 1042 of SEQ ID NO:1, nucleotides 1022 to 1043 of SEQ ID NO:1, nucleotides 1023 to 1044 of SEQ ID NO:1, nucleotides 1024 to 1045 of SEQ ID NO:1, nucleotides 1025 to 1046 of SEQ ID NO:1, nucleotides 1026 to 1047 of SEQ ID NO:1, nucleotides 1027 to 1048 of SEQ ID NO:1, nucleotides 1028 to 1049 of SEQ ID NO:1, nucleotides 1029 to 1050 of SEQ ID NO:1, nucleotides 1030 to 1051 of SEQ ID NO:1, nucleotides 1031 to 1052 of SEQ ID NO:1, nucleotides 1032 to 1053 of SEQ ID NO:1, nucleotides 1033 to 1054 of SEQ ID NO:1, nucleotides 1034 to 1055 of SEQ ID NO:1, nucleotides 1035 to 1056 of SEQ ID NO:1, nucleotides 1036 to 1057 of SEQ ID NO:1, nucleotides 1037 to 1058 of SEQ ID NO:1, nucleotides 1038 to 1059 of SEQ ID NO:1, nucleotides 1039 to 1060 of SEQ ID NO:1, nucleotides 1040 to 1061 of SEQ ID NO:1, nucleotides 1041 to 1062 of SEQ ID NO:1, nucleotides 1042 to 1063 of SEQ ID NO:1, nucleotides 1043 to 1064 of SEQ ID NO:1, nucleotides 1044 to 1065 of SEQ ID NO:1, nucleotides 1045 to 1066 of SEQ ID NO:1, nucleotides 1046 to 1067 of SEQ ID NO:1, nucleotides 1047 to 1068 of SEQ ID NO:1, nucleotides 1048 to 1069 of SEQ ID NO:1, nucleotides 1049 to 1070 of SEQ ID NO:1, and nucleotides 1050 to 1071 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 1051 to 1072 of SEQ ID NO:1, nucleotides 1052 to 1073 of SEQ ID NO:1, nucleotides 1053 to 1074 of SEQ ID NO:1, nucleotides 1054 to 1075 of SEQ ID NO:1, nucleotides 1055 to 1076 of SEQ ID NO:1, nucleotides 1056 to 1077 of SEQ ID NO:1, nucleotides 1057 to 1078 of SEQ ID NO:1, nucleotides 1058 to 1079 of SEQ ID NO:1, nucleotides 1059 to 1080 of SEQ ID NO:1, nucleotides 1060 to 1081 of SEQ ID NO:1, nucleotides 1061 to 1082 of SEQ ID NO:1, nucleotides 1062 to 1083 of SEQ ID NO:1, nucleotides 1063 to 1084 of SEQ ID NO:1, nucleotides 1064 to 1085 of SEQ ID NO:1, nucleotides 1065 to 1086 of SEQ ID NO:1, nucleotides 1066 to 1087 of SEQ ID NO:1, nucleotides 1067 to 1088 of SEQ ID NO:1, nucleotides 1068 to 1089 of SEQ ID NO:1, nucleotides 1069 to 1090 of SEQ ID NO:1, nucleotides 1070 to 1091 of SEQ ID NO:1, nucleotides 1071 to 1092 of SEQ ID NO:1, nucleotides 1072 to 1093 of SEQ ID NO:1, nucleotides 1073 to 1094 of SEQ ID NO:1, nucleotides 1074 to 1095 of SEQ ID NO:1, nucleotides 1075 to 1096 of SEQ ID NO:1, nucleotides 1076 to 1097 of SEQ ID NO:1, nucleotides 1077 to 1098 of SEQ ID NO:1, nucleotides 1078 to 1099 of SEQ ID NO:1, nucleotides 1079 to 1100 of SEQ ID NO:1, nucleotides 1080 to 1101 of SEQ ID NO:1, nucleotides 1081 to 1102 of SEQ ID NO:1, nucleotides 1082 to 1103 of SEQ ID NO:1, nucleotides 1083 to 1104 of SEQ ID NO:1, nucleotides 1084 to 1105 of SEQ ID NO:1, nucleotides 1085 to 1106 of SEQ ID NO:1, nucleotides 1086 to 1107 of SEQ ID NO:1, nucleotides 1087 to 1108 of SEQ ID NO:1, nucleotides 1088 to 1109 of SEQ ID NO:1, nucleotides 1089 to 1110 of SEQ ID NO:1, nucleotides 1090 to 1111 of SEQ ID NO:1, nucleotides 1091 to 1112 of SEQ ID NO:1, nucleotides 1092 to 1113 of SEQ ID NO:1, nucleotides 1093 to 1114 of SEQ ID NO:1, nucleotides 1094 to 1115 of SEQ ID NO:1, nucleotides 1095 to 1116 of SEQ ID NO:1, nucleotides 1096 to 1117 of SEQ ID NO:1, nucleotides 1097 to 1118 of SEQ ID NO:1, nucleotides 1098 to 1119 of SEQ ID NO:1, nucleotides 1099 to 1120 of SEQ ID NO:1, and nucleotides 1100 to 1121 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 1101 to 1122 of SEQ ID NO:1, nucleotides 1102 to 1123 of SEQ ID NO:1, nucleotides 1103 to 1124 of SEQ ID NO:1, nucleotides 1104 to 1125 of SEQ ID NO:1, nucleotides 1105 to 1126 of SEQ ID NO:1, nucleotides 1106 to 1127 of SEQ ID NO:1, nucleotides 1107 to 1128 of SEQ ID NO:1, nucleotides 1108 to 1129 of SEQ ID NO:1, nucleotides 1109 to 1130 of SEQ ID NO:1, nucleotides 1110 to 1131 of SEQ ID NO:1, nucleotides 1111 to 1132 of SEQ ID NO:1, nucleotides 1112 to 1133 of SEQ ID NO:1, nucleotides 1113 to 1134 of SEQ ID NO:1, nucleotides 1114 to 1135 of SEQ ID NO:1, nucleotides 1115 to 1136 of SEQ ID NO:1, nucleotides 1116 to 1137 of SEQ ID NO:1, nucleotides 1117 to 1138 of SEQ ID NO:1, nucleotides 1118 to 1139 of SEQ ID NO:1, nucleotides 1119 to 1140 of SEQ ID NO:1, nucleotides 1120 to 1141 of SEQ ID NO:1, nucleotides 1121 to 1142 of SEQ ID NO:1, nucleotides 1122 to 1143 of SEQ ID NO:1, nucleotides 1123 to 1144 of SEQ ID NO:1, nucleotides 1124 to 1145 of SEQ ID NO:1, nucleotides 1125 to 1146 of SEQ ID NO:1, nucleotides 1126 to 1147 of SEQ ID NO:1, nucleotides 1127 to 1148 of SEQ ID NO:1, nucleotides 1128 to 1149 of SEQ ID NO:1, nucleotides 1129 to 1150 of SEQ ID NO:1, nucleotides 1130 to 1151 of SEQ ID NO:1, nucleotides 1131 to 1152 of SEQ ID NO:1, nucleotides 1132 to 1153 of SEQ ID NO:1, nucleotides 1133 to 1154 of SEQ ID NO:1, nucleotides 1134 to 1155 of SEQ ID NO:1, nucleotides 1135 to 1156 of SEQ ID NO:1, nucleotides 1136 to 1157 of SEQ ID NO:1, nucleotides 1137 to 1158 of SEQ ID NO:1, nucleotides 1138 to 1159 of SEQ ID NO:1, nucleotides 1139 to 1160 of SEQ ID NO:1, nucleotides 1140 to 1161 of SEQ ID NO:1, nucleotides 1141 to 1162 of SEQ ID NO:1, nucleotides 1142 to 1163 of SEQ ID NO:1, nucleotides 1143 to 1164 of SEQ ID NO:1, nucleotides 1144 to 1165 of SEQ ID NO:1, nucleotides 1145 to 1166 of SEQ ID NO:1, nucleotides 1146 to 1167 of SEQ ID NO:1, nucleotides 1147 to 1168 of SEQ ID NO:1, nucleotides 1148 to 1169 of SEQ ID NO:1, nucleotides 1149 to 1170 of SEQ ID NO:1, and nucleotides 1150 to 1171 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 1151 to 1172 of SEQ ID NO:1, nucleotides 1152 to 1173 of SEQ ID NO:1, nucleotides 1153 to 1174 of SEQ ID NO:1, nucleotides 1154 to 1175 of SEQ ID NO:1, nucleotides 1155 to 1176 of SEQ ID NO:1, nucleotides 1156 to 1177 of SEQ ID NO:1, nucleotides 1157 to 1178 of SEQ ID NO:1, nucleotides 1158 to 1179 of SEQ ID NO:1, nucleotides 1159 to 1180 of SEQ ID NO:1, nucleotides 1160 to 1181 of SEQ ID NO:1, nucleotides 1161 to 1182 of SEQ ID NO:1, nucleotides 1162 to 1183 of SEQ ID NO:1, nucleotides 1163 to 1184 of SEQ ID NO:1, nucleotides 1164 to 1185 of SEQ ID NO:1, nucleotides 1165 to 1186 of SEQ ID NO:1, nucleotides 1166 to 1187 of SEQ ID NO:1, nucleotides 1167 to 1188 of SEQ ID NO:1, nucleotides 1168 to 1189 of SEQ ID NO:1, nucleotides 1169 to 1190 of SEQ ID NO:1, nucleotides 1170 to 1191 of SEQ ID NO:1, nucleotides 1171 to 1192 of SEQ ID NO:1, nucleotides 1172 to 1193 of SEQ ID NO:1, nucleotides 1173 to 1194 of SEQ ID NO:1, nucleotides 1174 to 1195 of SEQ ID NO:1, nucleotides 1175 to 1196 of SEQ ID NO:1, nucleotides 1176 to 1197 of SEQ ID NO:1, nucleotides 1177 to 1198 of SEQ ID NO:1, nucleotides 1178 to 1199 of SEQ ID NO:1, nucleotides 1179 to 1200 of SEQ ID NO:1, nucleotides 1180 to 1201 of SEQ ID NO:1, nucleotides 1181 to 1202 of SEQ ID NO:1, nucleotides 1182 to 1203 of SEQ ID NO:1, nucleotides 1183 to 1204 of SEQ ID NO:1, nucleotides 1184 to 1205 of SEQ ID NO:1, nucleotides 1185 to 1206 of SEQ ID NO:1, nucleotides 1186 to 1207 of SEQ ID NO:1, nucleotides 1187 to 1208 of SEQ ID NO:1, nucleotides 1188 to 1209 of SEQ ID NO:1, nucleotides 1189 to 1210 of SEQ ID NO:1, nucleotides 1190 to 1211 of SEQ ID NO:1, nucleotides 1191 to 1212 of SEQ ID NO:1, nucleotides 1192 to 1213 of SEQ ID NO:1, nucleotides 1193 to 1214 of SEQ ID NO:1, nucleotides 1194 to 1215 of SEQ ID NO:1, nucleotides 1195 to 1216 of SEQ ID NO:1, nucleotides 1196 to 1217 of SEQ ID NO:1, nucleotides 1197 to 1218 of SEQ ID NO:1, nucleotides 1198 to 1219 of SEQ ID NO:1, nucleotides 1199 to 1220 of SEQ ID NO:1, and nucleotides 1200 to 1221 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 1201 to 1222 of SEQ ID NO:1, nucleotides 1202 to 1223 of SEQ ID NO:1, nucleotides 1203 to 1224 of SEQ ID NO:1, nucleotides 1204 to 1225 of SEQ ID NO:1, nucleotides 1205 to 1226 of SEQ ID NO:1, nucleotides 1206 to 1227 of SEQ ID NO:1, nucleotides 1207 to 1228 of SEQ ID NO:1, nucleotides 1208 to 1229 of SEQ ID NO:1, nucleotides 1209 to 1230 of SEQ ID NO:1, nucleotides 1210 to 1231 of SEQ ID NO:1, nucleotides 1211 to 1232 of SEQ ID NO:1, nucleotides 1212 to 1233 of SEQ ID NO:1, nucleotides 1213 to 1234 of SEQ ID NO:1, nucleotides 1214 to 1235 of SEQ ID NO:1, nucleotides 1215 to 1236 of SEQ ID NO:1, nucleotides 1216 to 1237 of SEQ ID NO:1, nucleotides 1217 to 1238 of SEQ ID NO:1, nucleotides 1218 to 1239 of SEQ ID NO:1, nucleotides 1219 to 1240 of SEQ ID NO:1, nucleotides 1220 to 1241 of SEQ ID NO:1, nucleotides 1221 to 1242 of SEQ ID NO:1, nucleotides 1222 to 1243 of SEQ ID NO:1, nucleotides 1223 to 1244 of SEQ ID NO:1, nucleotides 1224 to 1245 of SEQ ID NO:1, nucleotides 1225 to 1246 of SEQ ID NO:1, nucleotides 1226 to 1247 of SEQ ID NO:1, nucleotides 1227 to 1248 of SEQ ID NO:1, nucleotides 1228 to 1249 of SEQ ID NO:1, nucleotides 1229 to 1250 of SEQ ID NO:1, nucleotides 1230 to 1251 of SEQ ID NO:1, nucleotides 1231 to 1252 of SEQ ID NO:1, nucleotides 1232 to 1253 of SEQ ID NO:1, nucleotides 1233 to 1254 of SEQ ID NO:1, nucleotides 1234 to 1255 of SEQ ID NO:1, nucleotides 1235 to 1256 of SEQ ID NO:1, nucleotides 1236 to 1257 of SEQ ID NO:1, nucleotides 1237 to 1258 of SEQ ID NO:1, nucleotides 1238 to 1259 of SEQ ID NO:1, nucleotides 1239 to 1260 of SEQ ID NO:1, nucleotides 1240 to 1261 of SEQ ID NO:1, nucleotides 1241 to 1262 of SEQ ID NO:1, nucleotides 1242 to 1263 of SEQ ID NO:1, nucleotides 1243 to 1264 of SEQ ID NO:1, nucleotides 1244 to 1265 of SEQ ID NO:1, nucleotides 1245 to 1266 of SEQ ID NO:1, nucleotides 1246 to 1267 of SEQ ID NO:1, nucleotides 1247 to 1268 of SEQ ID NO:1, nucleotides 1248 to 1269 of SEQ ID NO:1, nucleotides 1249 to 1270 of SEQ ID NO:1, and nucleotides 1250 to 1271 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 1251 to 1272 of SEQ ID NO:1, nucleotides 1252 to 1273 of SEQ ID NO:1, nucleotides 1253 to 1274 of SEQ ID NO:1, nucleotides 1254 to 1275 of SEQ ID NO:1, nucleotides 1255 to 1276 of SEQ ID NO:1, nucleotides 1256 to 1277 of SEQ ID NO:1, nucleotides 1257 to 1278 of SEQ ID NO:1, nucleotides 1258 to 1279 of SEQ ID NO:1, nucleotides 1259 to 1280 of SEQ ID NO:1, nucleotides 1260 to 1281 of SEQ ID NO:1, nucleotides 1261 to 1282 of SEQ ID NO:1, nucleotides 1262 to 1283 of SEQ ID NO:1, nucleotides 1263 to 1284 of SEQ ID NO:1, nucleotides 1264 to 1285 of SEQ ID NO:1, nucleotides 1265 to 1286 of SEQ ID NO:1, nucleotides 1266 to 1287 of SEQ ID NO:1, nucleotides 1267 to 1288 of SEQ ID NO:1, nucleotides 1268 to 1289 of SEQ ID NO:1, nucleotides 1269 to 1290 of SEQ ID NO:1, nucleotides 1270 to 1291 of SEQ ID NO:1, nucleotides 1271 to 1292 of SEQ ID NO:1, nucleotides 1272 to 1293 of SEQ ID NO:1, nucleotides 1273 to 1294 of SEQ ID NO:1, nucleotides 1274 to 1295 of SEQ ID NO:1, nucleotides 1275 to 1296 of SEQ ID NO:1, nucleotides 1276 to 1297 of SEQ ID NO:1, nucleotides 1277 to 1298 of SEQ ID NO:1, nucleotides 1278 to 1299 of SEQ ID NO:1, nucleotides 1279 to 1300 of SEQ ID NO:1, nucleotides 1280 to 1301 of SEQ ID NO:1, nucleotides 1281 to 1302 of SEQ ID NO:1, nucleotides 1282 to 1303 of SEQ ID NO:1, nucleotides 1283 to 1304 of SEQ ID NO:1, nucleotides 1284 to 1305 of SEQ ID NO:1, nucleotides 1285 to 1306 of SEQ ID NO:1, nucleotides 1286 to 1307 of SEQ ID NO:1, nucleotides 1287 to 1308 of SEQ ID NO:1, nucleotides 1288 to 1309 of SEQ ID NO:1, nucleotides 1289 to 1310 of SEQ ID NO:1, nucleotides 1290 to 1311 of SEQ ID NO:1, nucleotides 1291 to 1312 of SEQ ID NO:1, nucleotides 1292 to 1313 of SEQ ID NO:1, nucleotides 1293 to 1314 of SEQ ID NO:1, nucleotides 1294 to 1315 of SEQ ID NO:1, nucleotides 1295 to 1316 of SEQ ID NO:1, nucleotides 1296 to 1317 of SEQ ID NO:1, nucleotides 1297 to 1318 of SEQ ID NO:1, nucleotides 1298 to 1319 of SEQ ID NO:1, nucleotides 1299 to 1320 of SEQ ID NO:1, and nucleotides 1300 to 1321 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 1301 to 1322 of SEQ ID NO:1, nucleotides 1302 to 1323 of SEQ ID NO:1, nucleotides 1303 to 1324 of SEQ ID NO:1, nucleotides 1304 to 1325 of SEQ ID NO:1, nucleotides 1305 to 1326 of SEQ ID NO:1, nucleotides 1306 to 1327 of SEQ ID NO:1, nucleotides 1307 to 1328 of SEQ ID NO:1, nucleotides 1308 to 1329 of SEQ ID NO:1, nucleotides 1309 to 1330 of SEQ ID NO:1, nucleotides 1310 to 1331 of SEQ ID NO:1, nucleotides 1311 to 1332 of SEQ ID NO:1, nucleotides 1312 to 1333 of SEQ ID NO:1, nucleotides 1313 to 1334 of SEQ ID NO:1, nucleotides 1314 to 1335 of SEQ ID NO:1, nucleotides 1315 to 1336 of SEQ ID NO:1, nucleotides 1316 to 1337 of SEQ ID NO:1, nucleotides 1317 to 1338 of SEQ ID NO:1, nucleotides 1318 to 1339 of SEQ ID NO:1, nucleotides 1319 to 1340 of SEQ ID NO:1, nucleotides 1320 to 1341 of SEQ ID NO:1, nucleotides 1321 to 1342 of SEQ ID NO:1, nucleotides 1322 to 1343 of SEQ ID NO:1, nucleotides 1323 to 1344 of SEQ ID NO:1, nucleotides 1324 to 1345 of SEQ ID NO:1, nucleotides 1325 to 1346 of SEQ ID NO:1, nucleotides 1326 to 1347 of SEQ ID NO:1, nucleotides 1327 to 1348 of SEQ ID NO:1, nucleotides 1328 to 1349 of SEQ ID NO:1, nucleotides 1329 to 1350 of SEQ ID NO:1, nucleotides 1330 to 1351 of SEQ ID NO:1, nucleotides 1331 to 1352 of SEQ ID NO:1, nucleotides 1332 to 1353 of SEQ ID NO:1, nucleotides 1333 to 1354 of SEQ ID NO:1, nucleotides 1334 to 1355 of SEQ ID NO:1, nucleotides 1335 to 1356 of SEQ ID NO:1, nucleotides 1336 to 1357 of SEQ ID NO:1, nucleotides 1337 to 1358 of SEQ ID NO:1, nucleotides 1338 to 1359 of SEQ ID NO:1, nucleotides 1339 to 1360 of SEQ ID NO:1, nucleotides 1340 to 1361 of SEQ ID NO:1, nucleotides 1341 to 1362 of SEQ ID NO:1, nucleotides 1342 to 1363 of SEQ ID NO:1, nucleotides 1343 to 1364 of SEQ ID NO:1, nucleotides 1344 to 1365 of SEQ ID NO:1, nucleotides 1345 to 1366 of SEQ ID NO:1, nucleotides 1346 to 1367 of SEQ ID NO:1, nucleotides 1347 to 1368 of SEQ ID NO:1, nucleotides 1348 to 1369 of SEQ ID NO:1, nucleotides 1349 to 1370 of SEQ ID NO:1, and nucleotides 1350 to 1371 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 1351 to 1372 of SEQ ID NO:1, nucleotides 1352 to 1373 of SEQ ID NO:1, nucleotides 1353 to 1374 of SEQ ID NO:1, nucleotides 1354 to 1375 of SEQ ID NO:1, nucleotides 1355 to 1376 of SEQ ID NO:1, nucleotides 1356 to 1377 of SEQ ID NO:1, nucleotides 1357 to 1378 of SEQ ID NO:1, nucleotides 1358 to 1379 of SEQ ID NO:1, nucleotides 1359 to 1380 of SEQ ID NO:1, nucleotides 1360 to 1381 of SEQ ID NO:1, nucleotides 1361 to 1382 of SEQ ID NO:1, nucleotides 1362 to 1383 of SEQ ID NO:1, nucleotides 1363 to 1384 of SEQ ID NO:1, nucleotides 1364 to 1385 of SEQ ID NO:1, nucleotides 1365 to 1386 of SEQ ID NO:1, nucleotides 1366 to 1387 of SEQ ID NO:1, nucleotides 1367 to 1388 of SEQ ID NO:1, nucleotides 1368 to 1389 of SEQ ID NO:1, nucleotides 1369 to 1390 of SEQ ID NO:1, nucleotides 1370 to 1391 of SEQ ID NO:1, nucleotides 1371 to 1392 of SEQ ID NO:1, nucleotides 1372 to 1393 of SEQ ID NO:1, nucleotides 1373 to 1394 of SEQ ID NO:1, nucleotides 1374 to 1395 of SEQ ID NO:1, nucleotides 1375 to 1396 of SEQ ID NO:1, nucleotides 1376 to 1397 of SEQ ID NO:1, nucleotides 1377 to 1398 of SEQ ID NO:1, nucleotides 1378 to 1399 of SEQ ID NO:1, nucleotides 1379 to 1400 of SEQ ID NO:1, nucleotides 1380 to 1401 of SEQ ID NO:1, nucleotides 1381 to 1402 of SEQ ID NO:1, nucleotides 1382 to 1403 of SEQ ID NO:1, nucleotides 1383 to 1404 of SEQ ID NO:1, nucleotides 1384 to 1405 of SEQ ID NO:1, nucleotides 1385 to 1406 of SEQ ID NO:1, nucleotides 1386 to 1407 of SEQ ID NO:1, nucleotides 1387 to 1408 of SEQ ID NO:1, nucleotides 1388 to 1409 of SEQ ID NO:1, nucleotides 1389 to 1410 of SEQ ID NO:1, nucleotides 1390 to 1411 of SEQ ID NO:1, nucleotides 1391 to 1412 of SEQ ID NO:1, nucleotides 1392 to 1413 of SEQ ID NO:1, nucleotides 1393 to 1414 of SEQ ID NO:1, nucleotides 1394 to 1415 of SEQ ID NO:1, nucleotides 1395 to 1416 of SEQ ID NO:1, nucleotides 1396 to 1417 of SEQ ID NO:1, nucleotides 1397 to 1418 of SEQ ID NO:1, nucleotides 1398 to 1419 of SEQ ID NO:1, nucleotides 1399 to 1420 of SEQ ID NO:1, and nucleotides 1400 to 1421 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 1401 to 1422 of SEQ ID NO:1, nucleotides 1402 to 1423 of SEQ ID NO:1, nucleotides 1403 to 1424 of SEQ ID NO:1, nucleotides 1404 to 1425 of SEQ ID NO:1, nucleotides 1405 to 1426 of SEQ ID NO:1, nucleotides 1406 to 1427 of SEQ ID NO:1, nucleotides 1407 to 1428 of SEQ ID NO:1, nucleotides 1408 to 1429 of SEQ ID NO:1, nucleotides 1409 to 1430 of SEQ ID NO:1, nucleotides 1410 to 1431 of SEQ ID NO:1, nucleotides 1411 to 1432 of SEQ ID NO:1, nucleotides 1412 to 1433 of SEQ ID NO:1, nucleotides 1413 to 1434 of SEQ ID NO:1, nucleotides 1414 to 1435 of SEQ ID NO:1, nucleotides 1415 to 1436 of SEQ ID NO:1, nucleotides 1416 to 1437 of SEQ ID NO:1, nucleotides 1417 to 1438 of SEQ ID NO:1, nucleotides 1418 to 1439 of SEQ ID NO:1, nucleotides 1419 to 1440 of SEQ ID NO:1, nucleotides 1420 to 1441 of SEQ ID NO:1, nucleotides 1421 to 1442 of SEQ ID NO:1, nucleotides 1422 to 1443 of SEQ ID NO:1, nucleotides 1423 to 1444 of SEQ ID NO:1, nucleotides 1424 to 1445 of SEQ ID NO:1, nucleotides 1425 to 1446 of SEQ ID NO:1, nucleotides 1426 to 1447 of SEQ ID NO:1, nucleotides 1427 to 1448 of SEQ ID NO:1, nucleotides 1428 to 1449 of SEQ ID NO:1, nucleotides 1429 to 1450 of SEQ ID NO:1, nucleotides 1430 to 1451 of SEQ ID NO:1, nucleotides 1431 to 1452 of SEQ ID NO:1, nucleotides 1432 to 1453 of SEQ ID NO:1, nucleotides 1433 to 1454 of SEQ ID NO:1, nucleotides 1434 to 1455 of SEQ ID NO:1, nucleotides 1435 to 1456 of SEQ ID NO:1, nucleotides 1436 to 1457 of SEQ ID NO:1, nucleotides 1437 to 1458 of SEQ ID NO:1, nucleotides 1438 to 1459 of SEQ ID NO:1, nucleotides 1439 to 1460 of SEQ ID NO:1, nucleotides 1440 to 1461 of SEQ ID NO:1, nucleotides 1441 to 1462 of SEQ ID NO:1, nucleotides 1442 to 1463 of SEQ ID NO:1, nucleotides 1443 to 1464 of SEQ ID NO:1, nucleotides 1444 to 1465 of SEQ ID NO:1, nucleotides 1445 to 1466 of SEQ ID NO:1, nucleotides 1446 to 1467 of SEQ ID NO:1, nucleotides 1447 to 1468 of SEQ ID NO:1, nucleotides 1448 to 1469 of SEQ ID NO:1, nucleotides 1449 to 1470 of SEQ ID NO:1, and nucleotides 1450 to 1471 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 1451 to 1472 of SEQ ID NO:1, nucleotides 1452 to 1473 of SEQ ID NO:1, nucleotides 1453 to 1474 of SEQ ID NO:1, nucleotides 1454 to 1475 of SEQ ID NO:1, nucleotides 1455 to 1476 of SEQ ID NO:1, nucleotides 1456 to 1477 of SEQ ID NO:1, nucleotides 1457 to 1478 of SEQ ID NO:1, nucleotides 1458 to 1479 of SEQ ID NO:1, nucleotides 1459 to 1480 of SEQ ID NO:1, nucleotides 1460 to 1481 of SEQ ID NO:1, nucleotides 1461 to 1482 of SEQ ID NO:1, nucleotides 1462 to 1483 of SEQ ID NO:1, nucleotides 1463 to 1484 of SEQ ID NO:1, nucleotides 1464 to 1485 of SEQ ID NO:1, nucleotides 1465 to 1486 of SEQ ID NO:1, nucleotides 1466 to 1487 of SEQ ID NO:1, nucleotides 1467 to 1488 of SEQ ID NO:1, nucleotides 1468 to 1489 of SEQ ID NO:1, nucleotides 1469 to 1490 of SEQ ID NO:1, nucleotides 1470 to 1491 of SEQ ID NO:1, nucleotides 1471 to 1492 of SEQ ID NO:1, nucleotides 1472 to 1493 of SEQ ID NO:1, nucleotides 1473 to 1494 of SEQ ID NO:1, nucleotides 1474 to 1495 of SEQ ID NO:1, nucleotides 1475 to 1496 of SEQ ID NO:1, nucleotides 1476 to 1497 of SEQ ID NO:1, nucleotides 1477 to 1498 of SEQ ID NO:1, nucleotides 1478 to 1499 of SEQ ID NO:1, nucleotides 1479 to 1500 of SEQ ID NO:1, nucleotides 1480 to 1501 of SEQ ID NO:1, nucleotides 1481 to 1502 of SEQ ID NO:1, nucleotides 1482 to 1503 of SEQ ID NO:1, nucleotides 1483 to 1504 of SEQ ID NO:1, nucleotides 1484 to 1505 of SEQ ID NO:1, nucleotides 1485 to 1506 of SEQ ID NO:1, nucleotides 1486 to 1507 of SEQ ID NO:1, nucleotides 1487 to 1508 of SEQ ID NO:1, nucleotides 1488 to 1509 of SEQ ID NO:1, nucleotides 1489 to 1510 of SEQ ID NO:1, nucleotides 1490 to 1511 of SEQ ID NO:1, nucleotides 1491 to 1512 of SEQ ID NO:1, nucleotides 1492 to 1513 of SEQ ID NO:1, nucleotides 1493 to 1514 of SEQ ID NO:1, nucleotides 1494 to 1515 of SEQ ID NO:1, nucleotides 1495 to 1516 of SEQ ID NO:1, nucleotides 1496 to 1517 of SEQ ID NO:1, nucleotides 1497 to 1518 of SEQ ID NO:1, nucleotides 1498 to 1519 of SEQ ID NO:1, nucleotides 1499 to 1520 of SEQ ID NO:1, and nucleotides 1500 to 1521 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 1501 to 1522 of SEQ ID NO:1, nucleotides 1502 to 1523 of SEQ ID NO:1, nucleotides 1503 to 1524 of SEQ ID NO:1, nucleotides 1504 to 1525 of SEQ ID NO:1, nucleotides 1505 to 1526 of SEQ ID NO:1, nucleotides 1506 to 1527 of SEQ ID NO:1, nucleotides 1507 to 1528 of SEQ ID NO:1, nucleotides 1508 to 1529 of SEQ ID NO:1, nucleotides 1509 to 1530 of SEQ ID NO:1, nucleotides 1510 to 1531 of SEQ ID NO:1, nucleotides 1511 to 1532 of SEQ ID NO:1, nucleotides 1512 to 1533 of SEQ ID NO:1, nucleotides 1513 to 1534 of SEQ ID NO:1, nucleotides 1514 to 1535 of SEQ ID NO:1, nucleotides 1515 to 1536 of SEQ ID NO:1, nucleotides 1516 to 1537 of SEQ ID NO:1, nucleotides 1517 to 1538 of SEQ ID NO:1, nucleotides 1518 to 1539 of SEQ ID NO:1, nucleotides 1519 to 1540 of SEQ ID NO:1, nucleotides 1520 to 1541 of SEQ ID NO:1, nucleotides 1521 to 1542 of SEQ ID NO:1, nucleotides 1522 to 1543 of SEQ ID NO:1, nucleotides 1523 to 1544 of SEQ ID NO:1, nucleotides 1524 to 1545 of SEQ ID NO:1, nucleotides 1525 to 1546 of SEQ ID NO:1, nucleotides 1526 to 1547 of SEQ ID NO:1, nucleotides 1527 to 1548 of SEQ ID NO:1, nucleotides 1528 to 1549 of SEQ ID NO:1, nucleotides 1529 to 1550 of SEQ ID NO:1, nucleotides 1530 to 1551 of SEQ ID NO:1, nucleotides 1531 to 1552 of SEQ ID NO:1, nucleotides 1532 to 1553 of SEQ ID NO:1, nucleotides 1533 to 1554 of SEQ ID NO:1, nucleotides 1534 to 1555 of SEQ ID NO:1, nucleotides 1535 to 1556 of SEQ ID NO:1, nucleotides 1536 to 1557 of SEQ ID NO:1, nucleotides 1537 to 1558 of SEQ ID NO:1, nucleotides 1538 to 1559 of SEQ ID NO:1, nucleotides 1539 to 1560 of SEQ ID NO:1, nucleotides 1540 to 1561 of SEQ ID NO:1, nucleotides 1541 to 1562 of SEQ ID NO:1, nucleotides 1542 to 1563 of SEQ ID NO:1, nucleotides 1543 to 1564 of SEQ ID NO:1, nucleotides 1544 to 1565 of SEQ ID NO:1, nucleotides 1545 to 1566 of SEQ ID NO:1, nucleotides 1546 to 1567 of SEQ ID NO:1, nucleotides 1547 to 1568 of SEQ ID NO:1, nucleotides 1548 to 1569 of SEQ ID NO:1, nucleotides 1549 to 1570 of SEQ ID NO:1, and nucleotides 1550 to 1571 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 1551 to 1572 of SEQ ID NO:1, nucleotides 1552 to 1573 of SEQ ID NO:1, nucleotides 1553 to 1574 of SEQ ID NO:1, nucleotides 1554 to 1575 of SEQ ID NO:1, nucleotides 1555 to 1576 of SEQ ID NO:1, nucleotides 1556 to 1577 of SEQ ID NO:1, nucleotides 1557 to 1578 of SEQ ID NO:1, nucleotides 1558 to 1579 of SEQ ID NO:1, nucleotides 1559 to 1580 of SEQ ID NO:1, nucleotides 1560 to 1581 of SEQ ID NO:1, nucleotides 1561 to 1582 of SEQ ID NO:1, nucleotides 1562 to 1583 of SEQ ID NO:1, nucleotides 1563 to 1584 of SEQ ID NO:1, nucleotides 1564 to 1585 of SEQ ID NO:1, nucleotides 1565 to 1586 of SEQ ID NO:1, nucleotides 1566 to 1587 of SEQ ID NO:1, nucleotides 1567 to 1588 of SEQ ID NO:1, nucleotides 1568 to 1589 of SEQ ID NO:1, nucleotides 1569 to 1590 of SEQ ID NO:1, nucleotides 1570 to 1591 of SEQ ID NO:1, nucleotides 1571 to 1592 of SEQ ID NO:1, nucleotides 1572 to 1593 of SEQ ID NO:1, nucleotides 1573 to 1594 of SEQ ID NO:1, nucleotides 1574 to 1595 of SEQ ID NO:1, nucleotides 1575 to 1596 of SEQ ID NO:1, nucleotides 1576 to 1597 of SEQ ID NO:1, nucleotides 1577 to 1598 of SEQ ID NO:1, nucleotides 1578 to 1599 of SEQ ID NO:1, nucleotides 1579 to 1600 of SEQ ID NO:1, nucleotides 1580 to 1601 of SEQ ID NO:1, nucleotides 1581 to 1602 of SEQ ID NO:1, nucleotides 1582 to 1603 of SEQ ID NO:1, nucleotides 1583 to 1604 of SEQ ID NO:1, nucleotides 1584 to 1605 of SEQ ID NO:1, nucleotides 1585 to 1606 of SEQ ID NO:1, nucleotides 1586 to 1607 of SEQ ID NO:1, nucleotides 1587 to 1608 of SEQ ID NO:1, nucleotides 1588 to 1609 of SEQ ID NO:1, nucleotides 1589 to 1610 of SEQ ID NO:1, nucleotides 1590 to 1611 of SEQ ID NO:1, nucleotides 1591 to 1612 of SEQ ID NO:1, nucleotides 1592 to 1613 of SEQ ID NO:1, nucleotides 1593 to 1614 of SEQ ID NO:1, nucleotides 1594 to 1615 of SEQ ID NO:1, nucleotides 1595 to 1616 of SEQ ID NO:1, nucleotides 1596 to 1617 of SEQ ID NO:1, nucleotides 1597 to 1618 of SEQ ID NO:1, nucleotides 1598 to 1619 of SEQ ID NO:1, nucleotides 1599 to 1620 of SEQ ID NO:1, and nucleotides 1600 to 1621 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 1601 to 1622 of SEQ ID NO:1, nucleotides 1602 to 1623 of SEQ ID NO:1, nucleotides 1603 to 1624 of SEQ ID NO:1, nucleotides 1604 to 1625 of SEQ ID NO:1, nucleotides 1605 to 1626 of SEQ ID NO:1, nucleotides 1606 to 1627 of SEQ ID NO:1, nucleotides 1607 to 1628 of SEQ ID NO:1, nucleotides 1608 to 1629 of SEQ ID NO:1, nucleotides 1609 to 1630 of SEQ ID NO:1, nucleotides 1610 to 1631 of SEQ ID NO:1, nucleotides 1611 to 1632 of SEQ ID NO:1, nucleotides 1612 to 1633 of SEQ ID NO:1, nucleotides 1613 to 1634 of SEQ ID NO:1, nucleotides 1614 to 1635 of SEQ ID NO:1, nucleotides 1615 to 1636 of SEQ ID NO:1, nucleotides 1616 to 1637 of SEQ ID NO:1, nucleotides 1617 to 1638 of SEQ ID NO:1, nucleotides 1618 to 1639 of SEQ ID NO:1, nucleotides 1619 to 1640 of SEQ ID NO:1, nucleotides 1620 to 1641 of SEQ ID NO:1, nucleotides 1621 to 1642 of SEQ ID NO:1, nucleotides 1622 to 1643 of SEQ ID NO:1, nucleotides 1623 to 1644 of SEQ ID NO:1, nucleotides 1624 to 1645 of SEQ ID NO:1, nucleotides 1625 to 1646 of SEQ ID NO:1, nucleotides 1626 to 1647 of SEQ ID NO:1, nucleotides 1627 to 1648 of SEQ ID NO:1, nucleotides 1628 to 1649 of SEQ ID NO:1, nucleotides 1629 to 1650 of SEQ ID NO:1, nucleotides 1630 to 1651 of SEQ ID NO:1, nucleotides 1631 to 1652 of SEQ ID NO:1, nucleotides 1632 to 1653 of SEQ ID NO:1, nucleotides 1633 to 1654 of SEQ ID NO:1, nucleotides 1634 to 1655 of SEQ ID NO:1, nucleotides 1635 to 1656 of SEQ ID NO:1, nucleotides 1636 to 1657 of SEQ ID NO:1, nucleotides 1637 to 1658 of SEQ ID NO:1, nucleotides 1638 to 1659 of SEQ ID NO:1, nucleotides 1639 to 1660 of SEQ ID NO:1, nucleotides 1640 to 1661 of SEQ ID NO:1, nucleotides 1641 to 1662 of SEQ ID NO:1, nucleotides 1642 to 1663 of SEQ ID NO:1, nucleotides 1643 to 1664 of SEQ ID NO:1, nucleotides 1644 to 1665 of SEQ ID NO:1, nucleotides 1645 to 1666 of SEQ ID NO:1, nucleotides 1646 to 1667 of SEQ ID NO:1, nucleotides 1647 to 1668 of SEQ ID NO:1, nucleotides 1648 to 1669 of SEQ ID NO:1, nucleotides 1649 to 1670 of SEQ ID NO:1, and nucleotides 1650 to 1671 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 1651 to 1672 of SEQ ID NO:1, nucleotides 1652 to 1673 of SEQ ID NO:1, nucleotides 1653 to 1674 of SEQ ID NO:1, nucleotides 1654 to 1675 of SEQ ID NO:1, nucleotides 1655 to 1676 of SEQ ID NO:1, nucleotides 1656 to 1677 of SEQ ID NO:1, nucleotides 1657 to 1678 of SEQ ID NO:1, nucleotides 1658 to 1679 of SEQ ID NO:1, nucleotides 1659 to 1680 of SEQ ID NO:1, nucleotides 1660 to 1681 of SEQ ID NO:1, nucleotides 1661 to 1682 of SEQ ID NO:1, nucleotides 1662 to 1683 of SEQ ID NO:1, nucleotides 1663 to 1684 of SEQ ID NO:1, nucleotides 1664 to 1685 of SEQ ID NO:1, nucleotides 1665 to 1686 of SEQ ID NO:1, nucleotides 1666 to 1687 of SEQ ID NO:1, nucleotides 1667 to 1688 of SEQ ID NO:1, nucleotides 1668 to 1689 of SEQ ID NO:1, nucleotides 1669 to 1690 of SEQ ID NO:1, nucleotides 1670 to 1691 of SEQ ID NO:1, nucleotides 1671 to 1692 of SEQ ID NO:1, nucleotides 1672 to 1693 of SEQ ID NO:1, nucleotides 1673 to 1694 of SEQ ID NO:1, nucleotides 1674 to 1695 of SEQ ID NO:1, nucleotides 1675 to 1696 of SEQ ID NO:1, nucleotides 1676 to 1697 of SEQ ID NO:1, nucleotides 1677 to 1698 of SEQ ID NO:1, nucleotides 1678 to 1699 of SEQ ID NO:1, nucleotides 1679 to 1700 of SEQ ID NO:1, nucleotides 1680 to 1701 of SEQ ID NO:1, nucleotides 1681 to 1702 of SEQ ID NO:1, nucleotides 1682 to 1703 of SEQ ID NO:1, nucleotides 1683 to 1704 of SEQ ID NO:1, nucleotides 1684 to 1705 of SEQ ID NO:1, nucleotides 1685 to 1706 of SEQ ID NO:1, nucleotides 1686 to 1707 of SEQ ID NO:1, nucleotides 1687 to 1708 of SEQ ID NO:1, nucleotides 1688 to 1709 of SEQ ID NO:1, nucleotides 1689 to 1710 of SEQ ID NO:1, nucleotides 1690 to 1711 of SEQ ID NO:1, nucleotides 1691 to 1712 of SEQ ID NO:1, nucleotides 1692 to 1713 of SEQ ID NO:1, nucleotides 1693 to 1714 of SEQ ID NO:1, nucleotides 1694 to 1715 of SEQ ID NO:1, nucleotides 1695 to 1716 of SEQ ID NO:1, nucleotides 1696 to 1717 of SEQ ID NO:1, nucleotides 1697 to 1718 of SEQ ID NO:1, nucleotides 1698 to 1719 of SEQ ID NO:1, nucleotides 1699 to 1720 of SEQ ID NO:1, and nucleotides 1700 to 1721 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 1701 to 1722 of SEQ ID NO:1, nucleotides 1702 to 1723 of SEQ ID NO:1, nucleotides 1703 to 1724 of SEQ ID NO:1, nucleotides 1704 to 1725 of SEQ ID NO:1, nucleotides 1705 to 1726 of SEQ ID NO:1, nucleotides 1706 to 1727 of SEQ ID NO:1, nucleotides 1707 to 1728 of SEQ ID NO:1, nucleotides 1708 to 1729 of SEQ ID NO:1, nucleotides 1709 to 1730 of SEQ ID NO:1, nucleotides 1710 to 1731 of SEQ ID NO:1, nucleotides 1711 to 1732 of SEQ ID NO:1, nucleotides 1712 to 1733 of SEQ ID NO:1, nucleotides 1713 to 1734 of SEQ ID NO:1, nucleotides 1714 to 1735 of SEQ ID NO:1, nucleotides 1715 to 1736 of SEQ ID NO:1, nucleotides 1716 to 1737 of SEQ ID NO:1, nucleotides 1717 to 1738 of SEQ ID NO:1, nucleotides 1718 to 1739 of SEQ ID NO:1, nucleotides 1719 to 1740 of SEQ ID NO:1, nucleotides 1720 to 1741 of SEQ ID NO:1, nucleotides 1721 to 1742 of SEQ ID NO:1, nucleotides 1722 to 1743 of SEQ ID NO:1, nucleotides 1723 to 1744 of SEQ ID NO:1, nucleotides 1724 to 1745 of SEQ ID NO:1, nucleotides 1725 to 1746 of SEQ ID NO:1, nucleotides 1726 to 1747 of SEQ ID NO:1, nucleotides 1727 to 1748 of SEQ ID NO:1, nucleotides 1728 to 1749 of SEQ ID NO:1, nucleotides 1729 to 1750 of SEQ ID NO:1, nucleotides 1730 to 1751 of SEQ ID NO:1, nucleotides 1731 to 1752 of SEQ ID NO:1, nucleotides 1732 to 1753 of SEQ ID NO:1, nucleotides 1733 to 1754 of SEQ ID NO:1, nucleotides 1734 to 1755 of SEQ ID NO:1, nucleotides 1735 to 1756 of SEQ ID NO:1, nucleotides 1736 to 1757 of SEQ ID NO:1, nucleotides 1737 to 1758 of SEQ ID NO:1, nucleotides 1738 to 1759 of SEQ ID NO:1, nucleotides 1739 to 1760 of SEQ ID NO:1, nucleotides 1740 to 1761 of SEQ ID NO:1, nucleotides 1741 to 1762 of SEQ ID NO:1, nucleotides 1742 to 1763 of SEQ ID NO:1, nucleotides 1743 to 1764 of SEQ ID NO:1, nucleotides 1744 to 1765 of SEQ ID NO:1, nucleotides 1745 to 1766 of SEQ ID NO:1, nucleotides 1746 to 1767 of SEQ ID NO:1, nucleotides 1747 to 1768 of SEQ ID NO:1, nucleotides 1748 to 1769 of SEQ ID NO:1, nucleotides 1749 to 1770 of SEQ ID NO:1, and nucleotides 1750 to 1771 of SEQ ID NO:1.

As another example, a pool of siRNA of the invention derived from the *H. glycines* cct-6gene of SEQ ID NO:1 may comprise a multiplicity of RNA molecules selected from the group of oligonucleotides substantially identical to nucleotides 1751 to 1772 of SEQ ID NO:1, nucleotides 1752 to 1773 of SEQ ID NO:1, nucleotides 1753 to 1774 of SEQ ID NO:1, nucleotides 1754 to 1775 of SEQ ID NO:1, nucleotides 1755 to 1776 of SEQ ID NO:1, nucleotides 1756 to 1777 of SEQ ID NO:1, nucleotides 1757 to 1778 of SEQ ID NO:1, nucleotides 1758 to 1779 of SEQ ID NO:1, nucleotides 1759 to 1780 of SEQ ID NO:1, nucleotides 1760 to 1781 of SEQ ID NO:1, nucleotides 1761 to 1782 of SEQ ID NO:1, nucleotides 1762 to 1783 of SEQ ID NO:1, nucleotides 1763 to 1784 of SEQ ID NO:1, nucleotides 1764 to 1785 of SEQ ID NO:1, nucleotides 1765 to 1786 of SEQ ID NO:1, nucleotides 1766 to 1787 of SEQ ID NO:1, nucleotides 1767 to 1788 of SEQ ID NO:1, nucleotides 1768 to 1789 of SEQ ID NO:1, nucleotides 1769 to 1790 of SEQ ID NO:1, nucleotides 1770 to 1791 of SEQ ID NO:1, nucleotides 1771 to 1792 of SEQ ID NO:1, nucleotides 1772 to 1793 of SEQ ID NO:1, nucleotides 1773 to 1794 of SEQ ID NO:1, nucleotides 1774 to 1795 of SEQ ID NO:1, nucleotides 1775 to 1796 of SEQ ID NO:1, nucleotides 1776 to 1797 of SEQ ID NO:1, nucleotides 1777 to 1798 of SEQ ID NO:1, nucleotides 1778 to 1799 of SEQ ID NO:1, nucleotides 1779 to 1800 of SEQ ID NO:1, nucleotides 1780 to 1801 of SEQ ID NO:1, nucleotides 1781 to 1802 of SEQ ID NO:1, nucleotides 1782 to 1803 of SEQ ID NO:1, nucleotides 1783 to 1804 of SEQ ID NO:1, nucleotides 1784 to 1805 of SEQ ID NO:1, nucleotides 1785 to 1806 of SEQ ID NO:1, nucleotides 1786 to 1807 of SEQ ID NO:1, nucleotides 1787 to 1808 of SEQ ID NO:1, nucleotides 1788 to 1809 of SEQ ID NO:1, nucleotides 1789 to 1810 of SEQ ID NO:1, nucleotides 1790 to 1811 of SEQ ID NO:1, nucleotides 1791 to 1812 of SEQ ID NO:1, nucleotides 1792 to 1813 of SEQ ID NO:1, nucleotides 1793 to 1814 of SEQ ID NO:1, nucleotides 1794 to 1815 of SEQ ID NO:1, nucleotides 1795 to 1816 of SEQ ID NO:1, nucleotides 1796 to 1817 of SEQ ID NO:1, nucleotides 1797 to 1818 of SEQ ID NO:1, nucleotides 1798 to 1819 of SEQ ID NO:1, nucleotides 1799 to 1820 of SEQ ID NO:1, nucleotides 1800 to 1821 of SEQ ID NO:1, nucleotides 1801 to 1822 of SEQ ID NO:1, nucleotides 1802 to 1823 of SEQ ID NO:1, nucleotides 1803 to 1824 of SEQ ID NO:1, nucleotides 1804 to 1825 of SEQ ID NO:1, nucleotides 1805 to 1826 of SEQ ID NO:1, and nucleotides 1806 to 1827 of SEQ ID NO:1.

A pool of siRNA of the invention derived from the *H. glycines* cct-6gene of SEQ ID NO:1 may also comprise any combination of the specific RNA molecules having any of the 21 contiguous nucleotide sequences derived from SEQ ID NO:1 set forth above. Similarly, a pool of siRNA of the invention may comprise a multiplicity of RNA molecules having any 19 contiguous nucleotide sequences derived from SEQ ID NO:1, or a multiplicity of RNA molecules having any 20 contiguous nucleotide sequences derived from SEQ ID NO:1. Alternatively, the pool of siRNA of the invention may comprise a multiplicity of RNA molecules having a combination of any 19, 20, and/or 21 contiguous nucleotide sequences derived from SEQ ID NO:1.

In another embodiment, a pool of siRNA of the invention derived from the *H. glycines* cct-6gene of SEQ ID NO:2 may comprise a multiplicity of RNA molecules which are selected from the group consisting of oligonucleotides substantially identical to nucleotides 1 to 21 of SEQ ID NO:2, nucleotides 2 to 23 of SEQ ID NO:2, nucleotides 3 to 24 of SEQ ID NO:2, nucleotides 4 to 25 of SEQ ID NO:2, nucleotides 5 to 26 of SEQ ID NO:2, nucleotides 6 to 27 of SEQ ID NO:2, nucleotides 7 to 28 of SEQ ID NO:2, nucleotides 8 to 29 of SEQ ID NO:2, nucleotides 9 to 30 of SEQ ID NO:2, nucleotides 10 to 31 of SEQ ID NO:2, nucleotides 11 to 32 of SEQ ID NO:2, nucleotides 12 to 33 of SEQ ID NO:2, nucleotides 13 to 34 of SEQ ID NO:2, nucleotides 14 to 35 of SEQ ID NO:2, nucleotides 15 to 36 of SEQ ID NO:2, nucleotides 16 to 37 of SEQ ID NO:2, nucleotides 17 to 38 of SEQ ID NO:2, nucleotides 18 to 39 of SEQ ID NO:2, nucleotides 19 to 40 of SEQ ID NO:2, nucleotides 20 to 41 of SEQ ID NO:2, nucleotides 21 to 42 of SEQ ID NO:2, nucleotides 22 to 43 of SEQ ID NO:2, nucleotides 23 to 44 of SEQ ID NO:2, nucleotides 24 to 45 of SEQ ID NO:2, nucleotides 25 to 46 of SEQ ID NO:2, nucleotides 26 to 47 of SEQ ID NO:2, nucleotides 27 to 48 of SEQ ID NO:2, nucleotides 28 to 49 of SEQ ID NO:2, nucleotides 29 to 50 of SEQ ID NO:2, nucleotides 30 to 51 of SEQ ID NO:2, nucleotides 31 to 52 of SEQ ID NO:2, nucleotides 32 to 53 of SEQ ID NO:2, nucleotides 33 to 54 of SEQ ID NO:2, nucleotides 34 to 55 of SEQ ID NO:2, nucleotides 35 to 56 of SEQ ID NO:2, nucleotides 36 to 57 of SEQ ID NO:2, nucleotides 37 to 58 of SEQ ID NO:2, nucleotides 38 to 59 of SEQ ID NO:2, nucleotides 39 to 60 of SEQ ID NO:2, nucleotides 40 to 61 of SEQ ID NO:2, nucleotides 41 to 62 of SEQ ID NO:2, nucleotides 42 to 63 of SEQ ID NO:2, nucleotides 43 to 64 of SEQ ID NO:2, nucleotides 44 to 65 of SEQ ID NO:2, nucleotides 45 to 66 of SEQ ID NO:2, nucleotides 46 to 67 of SEQ ID NO:2, nucleotides 47 to 68 of SEQ ID NO:2, nucleotides 48 to 69 of SEQ ID NO:2, nucleotides 49 to 70 of SEQ ID NO:2, and nucleotides 50 to 71 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 51 to 72 of SEQ ID NO:2, nucleotides 52 to 73 of SEQ ID NO:2, nucleotides 53 to 74 of SEQ ID NO:2, nucleotides 54 to 75 of SEQ ID NO:2, nucleotides 55 to 76 of SEQ ID NO:2, nucleotides 56 to 77 of SEQ ID NO:2, nucleotides 57 to 78 of SEQ ID NO:2, nucleotides 58 to 79 of SEQ ID NO:2, nucleotides 59 to 80 of SEQ ID NO:2, nucleotides 60 to 81 of SEQ ID NO:2, nucleotides 61 to 82 of SEQ ID NO:2, nucleotides 62 to 83 of SEQ ID NO:2, nucleotides 63 to 84 of SEQ ID NO:2, nucleotides 64 to 85 of SEQ ID NO:2, nucleotides 65 to 86 of SEQ ID NO:2, nucleotides 66 to 87 of SEQ ID NO:2, nucleotides 67 to 88 of SEQ ID NO:2, nucleotides 68 to 89 of SEQ ID NO:2, nucleotides 69 to 90 of SEQ ID NO:2, nucleotides 70 to 91 of SEQ ID NO:2, nucleotides 71 to 92 of SEQ ID NO:2, nucleotides 72 to 93 of SEQ ID NO:2, nucleotides 73 to 94 of SEQ ID NO:2, nucleotides 74 to 95 of SEQ ID NO:2, nucleotides 75 to 96 of SEQ ID NO:2, nucleotides 76 to 97 of SEQ ID NO:2, nucleotides 77 to 98 of SEQ ID NO:2, nucleotides 78 to 99 of SEQ ID NO:2, nucleotides 79 to 100 of SEQ ID NO:2, nucleotides 80 to 101 of SEQ ID NO:2, nucleotides 81 to 102 of SEQ ID NO:2, nucleotides 82 to 103 of SEQ ID NO:2, nucleotides 83 to 104 of SEQ ID NO:2, nucleotides 84 to 105 of SEQ ID NO:2, nucleotides 85 to 106 of SEQ ID NO:2, nucleotides 86 to 107 of SEQ ID NO:2, nucleotides 87 to 108 of SEQ ID NO:2, nucleotides 88 to 109 of SEQ ID NO:2, nucleotides 89 to 110 of SEQ ID NO:2, nucleotides 90 to 111 of SEQ ID NO:2, nucleotides 91 to 112 of SEQ ID NO:2, nucleotides 92 to 113 of SEQ ID NO:2, nucleotides 93 to 114 of SEQ ID NO:2, nucleotides 94 to 115 of SEQ ID NO:2, nucleotides 95 to 116 of SEQ ID NO:2, nucleotides 96 to 117 of SEQ ID NO:2, nucleotides 97 to 118 of SEQ ID NO:2, nucleotides 98 to 119 of SEQ ID NO:2, nucleotides 99 to 120 of SEQ ID NO:2, and nucleotides 100 to 121 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 101 to 122 of SEQ ID NO:2, nucleotides 102 to 123 of SEQ ID NO:2, nucleotides 103 to 124 of SEQ ID NO:2, nucleotides 104 to 125 of SEQ ID NO:2, nucleotides 105 to 126 of SEQ ID NO:2, nucleotides 106 to 127 of SEQ ID NO:2, nucleotides 107 to 128 of SEQ ID NO:2, nucleotides 108 to 129 of SEQ ID NO:2, nucleotides 109 to 130 of SEQ ID NO:2, nucleotides 110 to 131 of SEQ ID NO:2, nucleotides 111 to 132 of SEQ ID NO:2, nucleotides 112 to 133 of SEQ ID NO:2, nucleotides 113 to 134 of SEQ ID NO:2, nucleotides 114 to 135 of SEQ ID NO:2, nucleotides 115 to 136 of SEQ ID NO:2, nucleotides 116 to 137 of SEQ ID NO:2, nucleotides 117 to 138 of SEQ ID NO:2, nucleotides 118 to 139 of SEQ ID NO:2, nucleotides 119 to 140 of SEQ ID NO:2, nucleotides 120 to 141 of SEQ ID NO:2, nucleotides 121 to 142 of SEQ ID NO:2, nucleotides 122 to 143 of SEQ ID NO:2, nucleotides 123 to 144 of SEQ ID NO:2, nucleotides 124 to 145 of SEQ ID NO:2, nucleotides 125 to 146 of SEQ ID NO:2, nucleotides 126 to 147 of SEQ ID NO:2, nucleotides 127 to 148 of SEQ ID NO:2, nucleotides 128 to 149 of SEQ ID NO:2, nucleotides 129 to 150 of SEQ ID NO:2, nucleotides 130 to 151 of SEQ ID NO:2, nucleotides 131 to 152 of SEQ ID NO:2, nucleotides 132 to 153 of SEQ ID NO:2, nucleotides 133 to 154 of SEQ ID NO:2, nucleotides 134 to 155 of SEQ ID NO:2, nucleotides 135 to 156 of SEQ ID NO:2, nucleotides 136 to 157 of SEQ ID NO:2, nucleotides 137 to 158 of SEQ ID NO:2, nucleotides 138 to 159 of SEQ ID NO:2, nucleotides 139 to 160 of SEQ ID NO:2, nucleotides 140 to 161 of SEQ ID NO:2, nucleotides 141 to 162 of SEQ ID NO:2, nucleotides 142 to 163 of SEQ ID NO:2, nucleotides 143 to 164 of SEQ ID NO:2, nucleotides 144 to 165 of SEQ ID NO:2, nucleotides 145 to 166 of SEQ ID NO:2, nucleotides 146 to 167 of SEQ ID NO:2, nucleotides 147 to 168 of SEQ ID NO:2, nucleotides 148 to 169 of SEQ ID NO:2, nucleotides 149 to 170 of SEQ ID NO:2, and nucleotides 150 to 171 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 151 to 172 of SEQ ID NO:2, nucleotides 152 to 173 of SEQ ID NO:2, nucleotides 153 to 174 of SEQ ID NO:2, nucleotides 154 to 175 of SEQ ID NO:2, nucleotides 155 to 176 of SEQ ID NO:2, nucleotides 156 to 177 of SEQ ID NO:2, nucleotides 157 to 178 of SEQ ID NO:2, nucleotides 158 to 179 of SEQ ID NO:2, nucleotides 159 to 180 of SEQ ID NO:2, nucleotides 160 to 181 of SEQ ID NO:2, nucleotides 161 to 182 of SEQ ID NO:2, nucleotides 162 to 183 of SEQ ID NO:2, nucleotides 163 to 184 of SEQ ID NO:2, nucleotides 164 to 185 of SEQ ID NO:2, nucleotides 165 to 186 of SEQ ID NO:2, nucleotides 166 to 187 of SEQ ID NO:2, nucleotides 167 to 188 of SEQ ID NO:2, nucleotides 168 to 189 of SEQ ID NO:2, nucleotides 169 to 190 of SEQ ID NO:2, nucleotides 170 to 191 of SEQ ID NO:2, nucleotides 171 to 192 of SEQ ID NO:2, nucleotides 172 to 193 of SEQ ID NO:2, nucleotides 173 to 194 of SEQ ID NO:2, nucleotides 174 to 195 of SEQ ID NO:2, nucleotides 175 to 196 of SEQ ID NO:2, nucleotides 176 to 197 of SEQ ID NO:2, nucleotides 177 to 198 of SEQ ID NO:2, nucleotides 178 to 199 of SEQ ID NO:2, nucleotides 179 to 200 of SEQ ID NO:2, nucleotides 180 to 201 of SEQ ID NO:2, nucleotides 181 to 202 of SEQ ID NO:2, nucleotides 182 to 203 of SEQ ID NO:2, nucleotides 183 to 204 of SEQ ID NO:2, nucleotides 184 to 205 of SEQ ID NO:2, nucleotides 185 to 206 of SEQ ID NO:2, nucleotides 186 to 207 of SEQ ID NO:2, nucleotides 187 to 208 of SEQ ID NO:2, nucleotides 188 to 209 of SEQ ID NO:2, nucleotides 189 to 210 of SEQ ID NO:2, nucleotides 190 to 211 of SEQ ID NO:2, nucleotides 191 to 212 of SEQ ID NO:2, nucleotides 192 to 213 of SEQ ID NO:2, nucleotides 193 to 214 of SEQ ID NO:2, nucleotides 194 to 215 of SEQ ID NO:2, nucleotides 195 to 216 of SEQ ID NO:2, nucleotides 196 to 217 of SEQ ID NO:2, nucleotides 197 to 218 of SEQ ID NO:2, nucleotides 198 to 219 of SEQ ID NO:2, nucleotides 199 to 220 of SEQ ID NO:2, and nucleotides 200 to 221 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 201 to 222 of SEQ ID NO:2, nucleotides 202 to 223 of SEQ ID NO:2, nucleotides 203 to 224 of SEQ ID NO:2, nucleotides 204 to 225 of SEQ ID NO:2, nucleotides 205 to 226 of SEQ ID NO:2, nucleotides 206 to 227 of SEQ ID NO:2, nucleotides 207 to 228 of SEQ ID NO:2, nucleotides 208 to 229 of SEQ ID NO:2, nucleotides 209 to 230 of SEQ ID NO:2, nucleotides 210 to 231 of SEQ ID NO:2, nucleotides 211 to 232 of SEQ ID NO:2, nucleotides 212 to 233 of SEQ ID NO:2, nucleotides 213 to 234 of SEQ ID NO:2, nucleotides 214 to 235 of SEQ ID NO:2, nucleotides 215 to 236 of SEQ ID NO:2, nucleotides 216 to 237 of SEQ ID NO:2, nucleotides 217 to 238 of SEQ ID NO:2, nucleotides 218 to 239 of SEQ ID NO:2, nucleotides 219 to 240 of SEQ ID NO:2, nucleotides 220 to 241 of SEQ ID NO:2, nucleotides 221 to 242 of SEQ ID NO:2, nucleotides 222 to 243 of SEQ ID NO:2, nucleotides 223 to 244 of SEQ ID NO:2, nucleotides 224 to 245 of SEQ ID NO:2, nucleotides 225 to 246 of SEQ ID NO:2, nucleotides 226 to 247 of SEQ ID NO:2, nucleotides 227 to 248 of SEQ ID NO:2, nucleotides 228 to 249 of SEQ ID NO:2, nucleotides 229 to 250 of SEQ ID NO:2, nucleotides 230 to 251 of SEQ ID NO:2, nucleotides 231 to 252 of SEQ ID NO:2, nucleotides 232 to 253 of SEQ ID NO:2, nucleotides 233 to 254 of SEQ ID NO:2, nucleotides 234 to 255 of SEQ ID NO:2, nucleotides 235 to 256 of SEQ ID NO:2, nucleotides 236 to 257 of SEQ ID NO:2, nucleotides 237 to 258 of SEQ ID NO:2, nucleotides 238 to 259 of SEQ ID NO:2, nucleotides 239 to 260 of SEQ ID NO:2, nucleotides 240 to 261 of SEQ ID NO:2, nucleotides 241 to 262 of SEQ ID NO:2, nucleotides 242 to 263 of SEQ ID NO:2, nucleotides 243 to 264 of SEQ ID NO:2, nucleotides 244 to 265 of SEQ ID NO:2, nucleotides 245 to 266 of SEQ ID NO:2, nucleotides 246 to 267 of SEQ ID NO:2, nucleotides 247 to 268 of SEQ ID NO:2, nucleotides 248 to 269 of SEQ ID NO:2, nucleotides 249 to 270 of SEQ ID NO:2, and nucleotides 250 to 271 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 251 to 272 of SEQ ID NO:2, nucleotides 252 to 273 of SEQ ID NO:2, nucleotides 253 to 274 of SEQ ID NO:2, nucleotides 254 to 275 of SEQ ID NO:2, nucleotides 255 to 276 of SEQ ID NO:2, nucleotides 256 to 277 of SEQ ID NO:2, nucleotides 257 to 278 of SEQ ID NO:2, nucleotides 258 to 279 of SEQ ID NO:2, nucleotides 259 to 280 of SEQ ID NO:2, nucleotides 260 to 281 of SEQ ID NO:2, nucleotides 261 to 282 of SEQ ID NO:2, nucleotides 262 to 283 of SEQ ID NO:2, nucleotides 263 to 284 of SEQ ID NO:2, nucleotides 264 to 285 of SEQ ID NO:2, nucleotides 265 to 286 of SEQ ID NO:2, nucleotides 266 to 287 of SEQ ID NO:2, nucleotides 267 to 288 of SEQ ID NO:2, nucleotides 268 to 289 of SEQ ID NO:2, nucleotides 269 to 290 of SEQ ID NO:2, nucleotides 270 to 291 of SEQ ID NO:2, nucleotides 271 to 292 of SEQ ID NO:2, nucleotides 272 to 293 of SEQ ID NO:2, nucleotides 273 to 294 of SEQ ID NO:2, nucleotides 274 to 295 of SEQ ID NO:2, nucleotides 275 to 296 of SEQ ID NO:2, nucleotides 276 to 297 of SEQ ID NO:2, nucleotides 277 to 298 of SEQ ID NO:2, nucleotides 278 to 299 of SEQ ID NO:2, nucleotides 279 to 300 of SEQ ID NO:2, nucleotides 280 to 301 of SEQ ID NO:2, nucleotides 281 to 302 of SEQ ID NO:2, nucleotides 282 to 303 of SEQ ID NO:2, nucleotides 283 to 304 of SEQ ID NO:2, nucleotides 284 to 305 of SEQ ID NO:2, nucleotides 285 to 306 of SEQ ID NO:2, nucleotides 286 to 307 of SEQ ID NO:2, nucleotides 287 to 308 of SEQ ID NO:2, nucleotides 288 to 309 of SEQ ID NO:2, nucleotides 289 to 310 of SEQ ID NO:2, nucleotides 290 to 311 of SEQ ID NO:2, nucleotides 291 to 312 of SEQ ID NO:2, nucleotides 292 to 313 of SEQ ID NO:2, nucleotides 293 to 314 of SEQ ID NO:2, nucleotides 294 to 315 of SEQ ID NO:2, nucleotides 295 to 316 of SEQ ID NO:2, nucleotides 296 to 317 of SEQ ID NO:2, nucleotides 297 to 318 of SEQ ID NO:2, nucleotides 298 to 319 of SEQ ID NO:2, nucleotides 299 to 320 of SEQ ID NO:2, and nucleotides 300 to 321 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 301 to 322 of SEQ ID NO:2, nucleotides 302 to 323 of SEQ ID NO:2, nucleotides 303 to 324 of SEQ ID NO:2, nucleotides 304 to 325 of SEQ ID NO:2, nucleotides 305 to 326 of SEQ ID NO:2, nucleotides 306 to 327 of SEQ ID NO:2, nucleotides 307 to 328 of SEQ ID NO:2, nucleotides 308 to 329 of SEQ ID NO:2, nucleotides 309 to 330 of SEQ ID NO:2, nucleotides 310 to 331 of SEQ ID NO:2, nucleotides 311 to 332 of SEQ ID NO:2, nucleotides 312 to 333 of SEQ ID NO:2, nucleotides 313 to 334 of SEQ ID NO:2, nucleotides 314 to 335 of SEQ ID NO:2, nucleotides 315 to 336 of SEQ ID NO:2, nucleotides 316 to 337 of SEQ ID NO:2, nucleotides 317 to 338 of SEQ ID NO:2, nucleotides 318 to 339 of SEQ ID NO:2, nucleotides 319 to 340 of SEQ ID NO:2, nucleotides 320 to 341 of SEQ ID NO:2, nucleotides 321 to 342 of SEQ ID NO:2, nucleotides 322 to 343 of SEQ ID NO:2, nucleotides 323 to 344 of SEQ ID NO:2, nucleotides 324 to 345 of SEQ ID NO:2, nucleotides 325 to 346 of SEQ ID NO:2, nucleotides 326 to 347 of SEQ ID NO:2, nucleotides 327 to 348 of SEQ ID NO:2, nucleotides 328 to 349 of SEQ ID NO:2, nucleotides 329 to 350 of SEQ ID NO:2, nucleotides 330 to 351 of SEQ ID NO:2, nucleotides 331 to 352 of SEQ ID NO:2, nucleotides 332 to 353 of SEQ ID NO:2, nucleotides 333 to 354 of SEQ ID NO:2, nucleotides 334 to 355 of SEQ ID NO:2, nucleotides 335 to 356 of SEQ ID NO:2, nucleotides 336 to 357 of SEQ ID NO:2, nucleotides 337 to 358 of SEQ ID NO:2, nucleotides 338 to 359 of SEQ ID NO:2, nucleotides 339 to 360 of SEQ ID NO:2, nucleotides 340 to 361 of SEQ ID NO:2, nucleotides 341 to 362 of SEQ ID NO:2, nucleotides 342 to 363 of SEQ ID NO:2, nucleotides 343 to 364 of SEQ ID NO:2, nucleotides 344 to 365 of SEQ ID NO:2, nucleotides 345 to 366 of SEQ ID NO:2, nucleotides 346 to 367 of SEQ ID NO:2, nucleotides 347 to 368 of SEQ ID NO:2, nucleotides 348 to 369 of SEQ ID NO:2, nucleotides 349 to 370 of SEQ ID NO:2, and nucleotides 350 to 371 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 351 to 372 of SEQ ID NO:2, nucleotides 352 to 373 of SEQ ID NO:2, nucleotides 353 to 374 of SEQ ID NO:2, nucleotides 354 to 375 of SEQ ID NO:2, nucleotides 355 to 376 of SEQ ID NO:2, nucleotides 356 to 377 of SEQ ID NO:2, nucleotides 357 to 378 of SEQ ID NO:2, nucleotides 358 to 379 of SEQ ID NO:2, nucleotides 359 to 380 of SEQ ID NO:2, nucleotides 360 to 381 of SEQ ID NO:2, nucleotides 361 to 382 of SEQ ID NO:2, nucleotides 362 to 383 of SEQ ID NO:2, nucleotides 363 to 384 of SEQ ID NO:2, nucleotides 364 to 385 of SEQ ID NO:2, nucleotides 365 to 386 of SEQ ID NO:2, nucleotides 366 to 387 of SEQ ID NO:2, nucleotides 367 to 388 of SEQ ID NO:2, nucleotides 368 to 389 of SEQ ID NO:2, nucleotides 369 to 390 of SEQ ID NO:2, nucleotides 370 to 391 of SEQ ID NO:2, nucleotides 371 to 392 of SEQ ID NO:2, nucleotides 372 to 393 of SEQ ID NO:2, nucleotides 373 to 394 of SEQ ID NO:2, nucleotides 374 to 395 of SEQ ID NO:2, nucleotides 375 to 396 of SEQ ID NO:2, nucleotides 376 to 397 of SEQ ID NO:2, nucleotides 377 to 398 of SEQ ID NO:2, nucleotides 378 to 399 of SEQ ID NO:2, nucleotides 379 to 400 of SEQ ID NO:2; nucleotides 380 to 401 of SEQ ID NO:2, nucleotides 381 to 402 of SEQ ID NO:2, nucleotides 381 to 402 of SEQ ID NO:2, nucleotides 382 to 403 of SEQ ID NO:2, nucleotides 383 to 404 of SEQ ID NO:2, nucleotides 384 to 405 of SEQ ID NO:2, nucleotides 385 to 406 of SEQ ID NO:2, nucleotides 386 to 407 of SEQ ID NO:2, nucleotides 387 to 408 of SEQ ID NO:2, nucleotides 388 to 409 of SEQ ID NO:2, nucleotides 389 to 410 of SEQ ID NO:2, nucleotides 390 to 411 of SEQ ID NO:2, nucleotides 391 to 412 of SEQ ID NO:2, nucleotides 392 to 413 of SEQ ID NO:2, nucleotides 393 to 414 of SEQ ID NO:2, nucleotides 394 to 415 of SEQ ID NO:2, nucleotides 395 to 416 of SEQ ID NO:2, nucleotides 396 to 417 of SEQ ID NO:2, nucleotides 397 to 418 of SEQ ID NO:2, nucleotides 398 to 419 of SEQ ID NO:2, nucleotides 399 to 420 of SEQ ID NO:2, and nucleotides 400 to 421 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 401 to 422 of SEQ ID NO:2, nucleotides 402 to 423 of SEQ ID NO:2, nucleotides 403 to 424 of SEQ ID NO:2, nucleotides 404 to 425 of SEQ ID NO:2, nucleotides 405 to 426 of SEQ ID NO:2, nucleotides 406 to 427 of SEQ ID NO:2, nucleotides 407 to 428 of SEQ ID NO:2, nucleotides 408 to 429 of SEQ ID NO:2, nucleotides 409 to 430 of SEQ ID NO:2, nucleotides 410 to 431 of SEQ ID NO:2, nucleotides 411 to 432 of SEQ ID NO:2, nucleotides 412 to 433 of SEQ ID NO:2, nucleotides 413 to 434 of SEQ ID NO:2, nucleotides 414 to 435 of SEQ ID NO:2, nucleotides 415 to 436 of SEQ ID NO:2, nucleotides 416 to 437 of SEQ ID NO:2, nucleotides 417 to 438 of SEQ ID NO:2, nucleotides 418 to 439 of SEQ ID NO:2, nucleotides 419 to 440 of SEQ ID NO:2, nucleotides 420 to 441 of SEQ ID NO:2, nucleotides 421 to 442 of SEQ ID NO:2, nucleotides 422 to 443 of SEQ ID NO:2, nucleotides 423 to 444 of SEQ ID NO:2, nucleotides 424 to 445 of SEQ ID NO:2, nucleotides 425 to 446 of SEQ ID NO:2, nucleotides 426 to 447 of SEQ ID NO:2, nucleotides 427 to 448 of SEQ ID NO:2, nucleotides 428 to 449 of SEQ ID NO:2, nucleotides 429 to 450 of SEQ ID NO:2, nucleotides 430 to 451 of SEQ ID NO:2, nucleotides 431 to 452 of SEQ ID NO:2, nucleotides 432 to 453 of SEQ ID NO:2, nucleotides 433 to 454 of SEQ ID NO:2, nucleotides 434 to 455 of SEQ ID NO:2, nucleotides 435 to 456 of SEQ ID NO:2, nucleotides 436 to 457 of SEQ ID NO:2, nucleotides 437 to 458 of SEQ ID NO:2, nucleotides 438 to 459 of SEQ ID NO:2, nucleotides 439 to 460 of SEQ ID NO:2, nucleotides 440 to 461 of SEQ ID NO:2, nucleotides 441 to 462 of SEQ ID NO:2, nucleotides 442 to 463 of SEQ ID NO:2, nucleotides 443 to 464 of SEQ ID NO:2, nucleotides 444 to 465 of SEQ ID NO:2, nucleotides 445 to 466 of SEQ ID NO:2, nucleotides 446 to 467 of SEQ ID NO:2, nucleotides 447 to 468 of SEQ ID NO:2, nucleotides 448 to 469 of SEQ ID NO:2, nucleotides 449 to 470 of SEQ ID NO:2, and nucleotides 450 to 471 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 451 to 472 of SEQ ID NO:2, nucleotides 452 to 473 of SEQ ID NO:2, nucleotides 453 to 474 of SEQ ID NO:2, nucleotides 454 to 475 of SEQ ID NO:2, nucleotides 455 to 476 of SEQ ID NO:2, nucleotides 456 to 477 of SEQ ID NO:2, nucleotides 457 to 478 of SEQ ID NO:2, nucleotides 458 to 479 of SEQ ID NO:2, nucleotides 459 to 480 of SEQ ID NO:2, nucleotides 460 to 481 of SEQ ID NO:2, nucleotides 461 to 482 of SEQ ID NO:2, nucleotides 462 to 483 of SEQ ID NO:2, nucleotides 463 to 484 of SEQ ID NO:2, nucleotides 464 to 485 of SEQ ID NO:2, nucleotides 465 to 486 of SEQ ID NO:2, nucleotides 466 to 487 of SEQ ID NO:2, nucleotides 467 to 488 of SEQ ID NO:2, nucleotides 468 to 489 of SEQ ID NO:2, nucleotides 469 to 490 of SEQ ID NO:2, nucleotides 470 to 491 of SEQ ID NO:2, nucleotides 471 to 492 of SEQ ID NO:2, nucleotides 472 to 493 of SEQ ID NO:2, nucleotides 473 to 494 of SEQ ID NO:2, nucleotides 474 to 495 of SEQ ID NO:2, nucleotides 475 to 496 of SEQ ID NO:2, nucleotides 476 to 497 of SEQ ID NO:2, nucleotides 477 to 498 of SEQ ID NO:2, nucleotides 478 to 499 of SEQ ID NO:2, nucleotides 479 to 500 of SEQ ID NO:2, nucleotides 480 to 501 of SEQ ID NO:2, nucleotides 481 to 502 of SEQ ID NO:2, nucleotides 482 to 503 of SEQ ID NO:2, nucleotides 483 to 504 of SEQ ID NO:2, nucleotides 484 to 505 of SEQ ID NO:2, nucleotides 485 to 506 of SEQ ID NO:2, nucleotides 486 to 507 of SEQ ID NO:2, nucleotides 487 to 508 of SEQ ID NO:2, nucleotides 488 to 509 of SEQ ID NO:2, nucleotides 489 to 510 of SEQ ID NO:2, nucleotides 490 to 511 of SEQ ID NO:2, nucleotides 491 to 512 of SEQ ID NO:2, nucleotides 492 to 513 of SEQ ID NO:2, nucleotides 493 to 514 of SEQ ID NO:2, nucleotides 494 to 515 of SEQ ID NO:2, nucleotides 495 to 516 of SEQ ID NO:2, nucleotides 496 to 517 of SEQ ID NO:2, nucleotides 497 to 518 of SEQ ID NO:2, nucleotides 498 to 519 of SEQ ID NO:2, nucleotides 499 to 520 of SEQ ID NO:2, and nucleotides 500 to 521 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 501 to 522 of SEQ ID NO:2, nucleotides 502 to 523 of SEQ ID NO:2, nucleotides 503 to 524 of SEQ ID NO:2, nucleotides 504 to 525 of SEQ ID NO:2, nucleotides 505 to 526 of SEQ ID NO:2, nucleotides 506 to 527 of SEQ ID NO:2, nucleotides 507 to 528 of SEQ ID NO:2, nucleotides 508 to 529 of SEQ ID NO:2, nucleotides 509 to 530 of SEQ ID NO:2, nucleotides 510 to 531 of SEQ ID NO:2, nucleotides 511 to 532 of SEQ ID NO:2, nucleotides 512 to 533 of SEQ ID NO:2, nucleotides 513 to 534 of SEQ ID NO:2, nucleotides 514 to 535 of SEQ ID NO:2, nucleotides 515 to 536 of SEQ ID NO:2, nucleotides 516 to 537 of SEQ ID NO:2, nucleotides 517 to 538 of SEQ ID NO:2, nucleotides 518 to 539 of SEQ ID NO:2, nucleotides 519 to 540 of SEQ ID NO:2, nucleotides 520 to 541 of SEQ ID NO:2, nucleotides 521 to 542 of SEQ ID NO:2, nucleotides 522 to 543 of SEQ ID NO:2, nucleotides 523 to 544 of SEQ ID NO:2; nucleotides 524 to 545 of SEQ ID NO:2, nucleotides 525 to 546 of SEQ ID NO:2, nucleotides 526 to 547 of SEQ ID NO:2, nucleotides 527 to 548 of SEQ ID NO:2, nucleotides 528 to 549 of SEQ ID NO:2, nucleotides 529 to 550 of SEQ ID NO:2, nucleotides 530 to 551 of SEQ ID NO:2, nucleotides 531 to 552 of SEQ ID NO:2, nucleotides 532 to 553 of SEQ ID NO:2, nucleotides 533 to 554 of SEQ ID NO:2, nucleotides 534 to 555 of SEQ ID NO:2, nucleotides 535 to 556 of SEQ ID NO:2, nucleotides 536 to 557 of SEQ ID NO:2, nucleotides 537 to 558 of SEQ ID NO:2, nucleotides 538 to 559 of SEQ ID NO:2, nucleotides 539 to 560 of SEQ ID NO:2, nucleotides 540 to 561 of SEQ ID NO:2, nucleotides 541 to 562 of SEQ ID NO:2, nucleotides 542 to 563 of SEQ ID NO:2, nucleotides 543 to 564 of SEQ ID NO:2, nucleotides 544 to 565 of SEQ ID NO:2, nucleotides 545 to 566 of SEQ ID NO:2, nucleotides 546 to 567 of SEQ ID NO:2, nucleotides 547 to 568 of SEQ ID NO:2, nucleotides 548 to 569 of SEQ ID NO:2, nucleotides 549 to 570 of SEQ ID NO:2, and nucleotides 550 to 571 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 551 to 572 of SEQ ID NO:2, nucleotides 552 to 573 of SEQ ID NO:2, nucleotides 553 to 574 of SEQ ID NO:2, nucleotides 554 to 575 of SEQ ID NO:2, nucleotides 555 to 576 of SEQ ID NO:2, nucleotides 556 to 577 of SEQ ID NO:2, nucleotides 557 to 578 of SEQ ID NO:2, nucleotides 558 to 579 of SEQ ID NO:2, nucleotides 559 to 580 of SEQ ID NO:2, nucleotides 560 to 581 of SEQ ID NO:2, nucleotides 561 to 582 of SEQ ID NO:2, nucleotides 562 to 583 of SEQ ID NO:2, nucleotides 563 to 584 of SEQ ID NO:2, nucleotides 564 to 585 of SEQ ID NO:2, nucleotides 565 to 586 of SEQ ID NO:2, nucleotides 566 to 587 of SEQ ID NO:2, nucleotides 567 to 588 of SEQ ID NO:2, nucleotides 568 to 589 of SEQ ID NO:2, nucleotides 569 to 590 of SEQ ID NO:2, nucleotides 570 to 591 of SEQ ID NO:2, nucleotides 571 to 592 of SEQ ID NO:2, nucleotides 572 to 593 of SEQ ID NO:2, nucleotides 573 to 594 of SEQ ID NO:2, nucleotides 574 to 595 of SEQ ID NO:2, nucleotides 575 to 596 of SEQ ID NO:2, nucleotides 576 to 597 of SEQ ID NO:2, nucleotides 577 to 598 of SEQ ID NO:2, nucleotides 578 to 599 of SEQ ID NO:2, nucleotides 579 to 600 of SEQ ID NO:2, nucleotides 580 to 601 of SEQ ID NO:2, nucleotides 581 to 602 of SEQ ID NO:2, nucleotides 582 to 603 of SEQ ID NO:2, nucleotides 583 to 604 of SEQ ID NO:2, nucleotides 584 to 605 of SEQ ID NO:2, nucleotides 585 to 606 of SEQ ID NO:2, nucleotides 586 to 607 of SEQ ID NO:2, nucleotides 587 to 608 of SEQ ID NO:2, nucleotides 588 to 609 of SEQ ID NO:2, nucleotides 589 to 610 of SEQ ID NO:2, nucleotides 590 to 611 of SEQ ID NO:2, nucleotides 591 to 612 of SEQ ID NO:2, nucleotides 592 to 613 of SEQ ID NO:2, nucleotides 593 to 614 of SEQ ID NO:2, nucleotides 594 to 615 of SEQ ID NO:2, nucleotides 595 to 616 of SEQ ID NO:2, nucleotides 596 to 617 of SEQ ID NO:2, nucleotides 597 to 618 of SEQ ID NO:2, nucleotides 598 to 619 of SEQ ID NO:2, nucleotides 599 to 620 of SEQ ID NO:2, and nucleotides 600 to 621 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 601 to 622 of SEQ ID NO:2, nucleotides 602 to 623 of SEQ ID NO:2, nucleotides 603 to 624 of SEQ ID NO:2, nucleotides 604 to 625 of SEQ ID NO:2, nucleotides 605 to 626 of SEQ ID NO:2, nucleotides 606 to 627 of SEQ ID NO:2, nucleotides 607 to 628 of SEQ ID NO:2, nucleotides 608 to 629 of SEQ ID NO:2, nucleotides 609 to 630 of SEQ ID NO:2, nucleotides 610 to 631 of SEQ ID NO:2, nucleotides 611 to 632 of SEQ ID NO:2, nucleotides 612 to 633 of SEQ ID NO:2, nucleotides 613 to 634 of SEQ ID NO:2, nucleotides 614 to 635 of SEQ ID NO:2, nucleotides 615 to 636 of SEQ ID NO:2, nucleotides 616 to 637 of SEQ ID NO:2, nucleotides 617 to 638 of SEQ ID NO:2, nucleotides 618 to 639 of SEQ ID NO:2, nucleotides 619 to 640 of SEQ ID NO:2, nucleotides 620 to 641 of SEQ ID NO:2, nucleotides 621 to 642 of SEQ ID NO:2, nucleotides 622 to 643 of SEQ ID NO:2, nucleotides 623 to 644 of SEQ ID NO:2, nucleotides 624 to 645 of SEQ ID NO:2, nucleotides 625 to 646 of SEQ ID NO:2, nucleotides 626 to 647 of SEQ ID NO:2, nucleotides 627 to 648 of SEQ ID NO:2, nucleotides 628 to 649 of SEQ ID NO:2, nucleotides 629 to 650 of SEQ ID NO:2, nucleotides 630 to 651 of SEQ ID NO:2, nucleotides 631 to 652 of SEQ ID NO:2, nucleotides 632 to 653 of SEQ ID NO:2, nucleotides 633 to 654 of SEQ ID NO:2, nucleotides 634 to 655 of SEQ ID NO:2, nucleotides 635 to 656 of SEQ ID NO:2, nucleotides 636 to 657 of SEQ ID NO:2, nucleotides 637 to 658 of SEQ ID NO:2, nucleotides 638 to 659 of SEQ ID NO:2, nucleotides 639 to 660 of SEQ ID NO:2, nucleotides 640 to 661 of SEQ ID NO:2, nucleotides 641 to 662 of SEQ ID NO:2, nucleotides 642 to 663 of SEQ ID NO:2, nucleotides 643 to 664 of SEQ ID NO:2, nucleotides 644 to 665 of SEQ ID NO:2, nucleotides 645 to 666 of SEQ ID NO:2, nucleotides 646 to 667 of SEQ ID NO:2, nucleotides 647 to 668 of SEQ ID NO:2, nucleotides 648 to 669 of SEQ ID NO:2, nucleotides 649 to 670 of SEQ ID NO:2, and nucleotides 650 to 671 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 651 to 672 of SEQ ID NO:2, nucleotides 652 to 673 of SEQ ID NO:2, nucleotides 653 to 674 of SEQ ID NO:2, nucleotides 654 to 675 of SEQ ID NO:2, nucleotides 655 to 676 of SEQ ID NO:2, nucleotides 656 to 677 of SEQ ID NO:2, nucleotides 657 to 678 of SEQ ID NO:2, nucleotides 658 to 679 of SEQ ID NO:2, nucleotides 659 to 680 of SEQ ID NO:2, nucleotides 660 to 681 of SEQ ID NO:2, nucleotides 661 to 682 of SEQ ID NO:2, nucleotides 662 to 683 of SEQ ID NO:2, nucleotides 663 to 684 of SEQ ID NO:2, nucleotides 664 to 685 of SEQ ID NO:2, nucleotides 665 to 686 of SEQ ID NO:2, nucleotides 666 to 687 of SEQ ID NO:2, nucleotides 667 to 688 of SEQ ID NO:2, nucleotides 668 to 689 of SEQ ID NO:2, nucleotides 669 to 690 of SEQ ID NO:2, nucleotides 670 to 691 of SEQ ID NO:2, nucleotides 671 to 692 of SEQ ID NO:2, nucleotides 672 to 693 of SEQ ID NO:2, nucleotides 673 to 694 of SEQ ID NO:2, nucleotides 674 to 695 of SEQ ID NO:2, nucleotides 675 to 696 of SEQ ID NO:2, nucleotides 676 to 697 of SEQ ID NO:2, nucleotides 677 to 698 of SEQ ID NO:2, nucleotides 678 to 699 of SEQ ID NO:2, nucleotides 679 to 700 of SEQ ID NO:2, nucleotides 680 to 701 of SEQ ID NO:2, nucleotides 681 to 702 of SEQ ID NO:2, nucleotides 682 to 703 of SEQ ID NO:2, nucleotides 683 to 704 of SEQ ID NO:2, nucleotides 684 to 705 of SEQ ID NO:2, nucleotides 685 to 706 of SEQ ID NO:2, nucleotides 686 to 707 of SEQ ID NO:2, nucleotides 687 to 708 of SEQ ID NO:2, nucleotides 688 to 709 of SEQ ID NO:2, nucleotides 689 to 710 of SEQ ID NO:2, nucleotides 690 to 711 of SEQ ID NO:2, nucleotides 691 to 712 of SEQ ID NO:2, nucleotides 692 to 713 of SEQ ID NO:2, nucleotides 693 to 714 of SEQ ID NO:2, nucleotides 694 to 715 of SEQ ID NO:2, nucleotides 695 to 716 of SEQ ID NO:2, nucleotides 696 to 717 of SEQ ID NO:2, nucleotides 697 to 718 of SEQ ID NO:2, nucleotides 698 to 719 of SEQ ID NO:2, nucleotides 699 to 720 of SEQ ID NO:2, and nucleotides 700 to 721 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 701 to 722 of SEQ ID NO:2, nucleotides 702 to 723 of SEQ ID NO:2, nucleotides 703 to 724 of SEQ ID NO:2, nucleotides 704 to 725 of SEQ ID NO:2, nucleotides 705 to 726 of SEQ ID NO:2, nucleotides 706 to 727 of SEQ ID NO:2, nucleotides 707 to 728 of SEQ ID NO:2, nucleotides 708 to 729 of SEQ ID NO:2, nucleotides 709 to 730 of SEQ ID NO:2, nucleotides 710 to 731 of SEQ ID NO:2, nucleotides 711 to 732 of SEQ ID NO:2, nucleotides 712 to 733 of SEQ ID NO:2, nucleotides 713 to 734 of SEQ ID NO:2, nucleotides 714 to 735 of SEQ ID NO:2, nucleotides 715 to 736 of SEQ ID NO:2, nucleotides 716 to 737 of SEQ ID NO:2, nucleotides 717 to 738 of SEQ ID NO:2, nucleotides 718 to 739 of SEQ ID NO:2, nucleotides 719 to 740 of SEQ ID NO:2, nucleotides 720 to 741 of SEQ ID NO:2, nucleotides 721 to 742 of SEQ ID NO:2, nucleotides 722 to 743 of SEQ ID NO:2, nucleotides 723 to 744 of SEQ ID NO:2, nucleotides 724 to 745 of SEQ ID NO:2, nucleotides 725 to 746 of SEQ ID NO:2, nucleotides 726 to 747 of SEQ ID NO:2, nucleotides 727 to 748 of SEQ ID NO:2, nucleotides 728 to 749 of SEQ ID NO:2, nucleotides 729 to 750 of SEQ ID NO:2, nucleotides 730 to 751 of SEQ ID NO:2, nucleotides 731 to 752 of SEQ ID NO:2, nucleotides 732 to 753 of SEQ ID NO:2, nucleotides 733 to 754 of SEQ ID NO:2, nucleotides 734 to 755 of SEQ ID NO:2, nucleotides 735 to 756 of SEQ ID NO:2, nucleotides 736 to 757 of SEQ ID NO:2, nucleotides 737 to 758 of SEQ ID NO:2, nucleotides 738 to 759 of SEQ ID NO:2, nucleotides 739 to 760 of SEQ ID NO:2, nucleotides 740 to 761 of SEQ ID NO:2, nucleotides 741 to 762 of SEQ ID NO:2, nucleotides 742 to 763 of SEQ ID NO:2, nucleotides 743 to 764 of SEQ ID NO:2, nucleotides 744 to 765 of SEQ ID NO:2, nucleotides 745 to 766 of SEQ ID NO:2, nucleotides 746 to 767 of SEQ ID NO:2, nucleotides 747 to 768 of SEQ ID NO:2, nucleotides 748 to 769 of SEQ ID NO:2, nucleotides 749 to 770 of SEQ ID NO:2, and nucleotides 750 to 771 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 751 to 772 of SEQ ID NO:2, nucleotides 752 to 773 of SEQ ID NO:2, nucleotides 753 to 774 of SEQ ID NO:2, nucleotides 754 to 775 of SEQ ID NO:2, nucleotides 755 to 776 of SEQ ID NO:2, nucleotides 756 to 777 of SEQ ID NO:2, nucleotides 757 to 778 of SEQ ID NO:2, nucleotides 758 to 779 of SEQ ID NO:2, nucleotides 759 to 780 of SEQ ID NO:2, nucleotides 760 to 781 of SEQ ID NO:2, nucleotides 761 to 782 of SEQ ID NO:2, nucleotides 762 to 783 of SEQ ID NO:2, nucleotides 763 to 784 of SEQ ID NO:2, nucleotides 764 to 785 of SEQ ID NO:2, nucleotides 765 to 786 of SEQ ID NO:2, nucleotides 766 to 787 of SEQ ID NO:2, nucleotides 767 to 788 of SEQ ID NO:2, nucleotides 768 to 789 of SEQ ID NO:2, nucleotides 769 to 790 of SEQ ID NO:2, nucleotides 770 to 791 of SEQ ID NO:2, nucleotides 771 to 792 of SEQ ID NO:2, nucleotides 772 to 793 of SEQ ID NO:2, nucleotides 773 to 794 of SEQ ID NO:2, nucleotides 774 to 795 of SEQ ID NO:2, nucleotides 775 to 796 of SEQ ID NO:2, nucleotides 776 to 797 of SEQ ID NO:2, nucleotides 777 to 798 of SEQ ID NO:2, nucleotides 778 to 799 of SEQ ID NO:2, nucleotides 779 to 800 of SEQ ID NO:2, nucleotides 780 to 801 of SEQ ID NO:2, nucleotides 781 to 802 of SEQ ID NO:2, nucleotides 782 to 803 of SEQ ID NO:2, nucleotides 783 to 804 of SEQ ID NO:2, nucleotides 784 to 805 of SEQ ID NO:2, nucleotides 785 to 806 of SEQ ID NO:2, nucleotides 786 to 807 of SEQ ID NO:2, nucleotides 787 to 808 of SEQ ID NO:2, nucleotides 788 to 809 of SEQ ID NO:2, nucleotides 789 to 810 of SEQ ID NO:2, nucleotides 790 to 811 of SEQ ID NO:2, nucleotides 791 to 812 of SEQ ID NO:2, nucleotides 792 to 813 of SEQ ID NO:2, nucleotides 793 to 814 of SEQ ID NO:2, nucleotides 794 to 815 of SEQ ID NO:2, nucleotides 795 to 816 of SEQ ID NO:2, nucleotides 796 to 817 of SEQ ID NO:2, nucleotides 797 to 818 of SEQ ID NO:2, nucleotides 798 to 819 of SEQ ID NO:2, nucleotides 799 to 820 of SEQ ID NO:2, and nucleotides 800 to 821 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 801 to 822 of SEQ ID NO:2, nucleotides 802 to 823 of SEQ ID NO:2, nucleotides 803 to 824 of SEQ ID NO:2, nucleotides 804 to 825 of SEQ ID NO:2, nucleotides 805 to 826 of SEQ ID NO:2, nucleotides 806 to 827 of SEQ ID NO:2, nucleotides 807 to 828 of SEQ ID NO:2, nucleotides 808 to 829 of SEQ ID NO:2, nucleotides 809 to 830 of SEQ ID NO:2, nucleotides 810 to 831 of SEQ ID NO:2, nucleotides 811 to 832 of SEQ ID NO:2, nucleotides 812 to 833 of SEQ ID NO:2, nucleotides 813 to 834 of SEQ ID NO:2, nucleotides 814 to 835 of SEQ ID NO:2, nucleotides 815 to 836 of SEQ ID NO:2, nucleotides 816 to 837 of SEQ ID NO:2, nucleotides 817 to 838 of SEQ ID NO:2, nucleotides 818 to 839 of SEQ ID NO:2, nucleotides 819 to 840 of SEQ ID NO:2, nucleotides 820 to 841 of SEQ ID NO:2, nucleotides 821 to 842 of SEQ ID NO:2, nucleotides 822 to 843 of SEQ ID NO:2, nucleotides 823 to 844 of SEQ ID NO:2, nucleotides 824 to 845 of SEQ ID NO:2, nucleotides 825 to 846 of SEQ ID NO:2, nucleotides 826 to 847 of SEQ ID NO:2, nucleotides 827 to 848 of SEQ ID NO:2, nucleotides 828 to 849 of SEQ ID NO:2, nucleotides 829 to 850 of SEQ ID NO:2, nucleotides 830 to 851 of SEQ ID NO:2, nucleotides 831 to 852 of SEQ ID NO:2, nucleotides 832 to 853 of SEQ ID NO:2, nucleotides 833 to 854 of SEQ ID NO:2, nucleotides 834 to 855 of SEQ ID NO:2, nucleotides 835 to 856 of SEQ ID NO:2, nucleotides 836 to 857 of SEQ ID NO:2, nucleotides 837 to 858 of SEQ ID NO:2, nucleotides 838 to 859 of SEQ ID NO:2, nucleotides 839 to 860 of SEQ ID NO:2, nucleotides 840 to 861 of SEQ ID NO:2, nucleotides 841 to 862 of SEQ ID NO:2, nucleotides 842 to 863 of SEQ ID NO:2, nucleotides 843 to 864 of SEQ ID NO:2, nucleotides 844 to 865 of SEQ ID NO:2, nucleotides 845 to 866 of SEQ ID NO:2, nucleotides 846 to 867 of SEQ ID NO:2, nucleotides 847 to 868 of SEQ ID NO:2, nucleotides 848 to 869 of SEQ ID NO:2, nucleotides 849 to 870 of SEQ ID NO:2, and nucleotides 850 to 871 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 851 to 872 of SEQ ID NO:2, nucleotides 852 to 873 of SEQ ID NO:2, nucleotides 853 to 874 of SEQ ID NO:2, nucleotides 854 to 875 of SEQ ID NO:2, nucleotides 855 to 876 of SEQ ID NO:2, nucleotides 856 to 877 of SEQ ID NO:2, nucleotides 857 to 878 of SEQ ID NO:2, nucleotides 858 to 879 of SEQ ID NO:2, nucleotides 859 to 880 of SEQ ID NO:2, nucleotides 860 to 881 of SEQ ID NO:2, nucleotides 861 to 882 of SEQ ID NO:2, nucleotides 862 to 883 of SEQ ID NO:2, nucleotides 863 to 884 of SEQ ID NO:2, nucleotides 864 to 885 of SEQ ID NO:2, nucleotides 865 to 886 of SEQ ID NO:2, nucleotides 866 to 887 of SEQ ID NO:2, nucleotides 867 to 888 of SEQ ID NO:2, nucleotides 868 to 889 of SEQ ID NO:2, nucleotides 869 to 890 of SEQ ID NO:2, nucleotides 870 to 891 of SEQ ID NO:2, nucleotides 871 to 892 of SEQ ID NO:2, nucleotides 872 to 893 of SEQ ID NO:2, nucleotides 873 to 894 of SEQ ID NO:2, nucleotides 874 to 895 of SEQ ID NO:2, nucleotides 875 to 896 of SEQ ID NO:2, nucleotides 876 to 897 of SEQ ID NO:2, nucleotides 877 to 898 of SEQ ID NO:2, nucleotides 878 to 899 of SEQ ID NO:2, nucleotides 879 to 900 of SEQ ID NO:2, nucleotides 880 to 901 of SEQ ID NO:2, nucleotides 881 to 902 of SEQ ID NO:2, nucleotides 882 to 903 of SEQ ID NO:2, nucleotides 883 to 904 of SEQ ID NO:2, nucleotides 884 to 905 of SEQ ID NO:2, nucleotides 885 to 906 of SEQ ID NO:2, nucleotides 886 to 907 of SEQ ID NO:2, nucleotides 887 to 908 of SEQ ID NO:2, nucleotides 888 to 909 of SEQ ID NO:2, nucleotides 889 to 910 of SEQ ID NO:2, nucleotides 890 to 911 of SEQ ID NO:2, nucleotides 891 to 912 of SEQ ID NO:2, nucleotides 892 to 913 of SEQ ID NO:2, nucleotides 893 to 914 of SEQ ID NO:2, nucleotides 894 to 915 of SEQ ID NO:2, nucleotides 895 to 916 of SEQ ID NO:2, nucleotides 896 to 917 of SEQ ID NO:2, nucleotides 897 to 918 of SEQ ID NO:2, nucleotides 898 to 919 of SEQ ID NO:2, nucleotides 899 to 920 of SEQ ID NO:2, and nucleotides 900 to 921 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 901 to 922 of SEQ ID NO:2, nucleotides 902 to 923 of SEQ ID NO:2; nucleotides 903 to 924 of SEQ ID NO:2, nucleotides 904 to 925 of SEQ ID NO:2, nucleotides 905 to 926 of SEQ ID NO:2, nucleotides 906 to 927 of SEQ ID NO:2, nucleotides 907 to 928 of SEQ ID NO:2, nucleotides 908 to 929 of SEQ ID NO:2, nucleotides 909 to 930 of SEQ ID NO:2, nucleotides 910 to 931 of SEQ ID NO:2, nucleotides 911 to 932 of SEQ ID NO:2, nucleotides 912 to 933 of SEQ ID NO:2, nucleotides 913 to 934 of SEQ ID NO:2, nucleotides 914 to 935 of SEQ ID NO:2, nucleotides 915 to 936 of SEQ ID NO:2, nucleotides 916 to 937 of SEQ ID NO:2, nucleotides 917 to 938 of SEQ ID NO:2, nucleotides 918 to 939 of SEQ ID NO:2, nucleotides 919 to 940 of SEQ ID NO:2, nucleotides 920 to 941 of SEQ ID NO:2, nucleotides 921 to 942 of SEQ ID NO:2, nucleotides 922 to 943 of SEQ ID NO:2, nucleotides 923 to 944 of SEQ ID NO:2, nucleotides 924 to 945 of SEQ ID NO:2, nucleotides 925 to 946 of SEQ ID NO:2, nucleotides 926 to 947 of SEQ ID NO:2, nucleotides 927 to 948 of SEQ ID NO:2, nucleotides 928 to 949 of SEQ ID NO:2, nucleotides 929 to 950 of SEQ ID NO:2, nucleotides 930 to 951 of SEQ ID NO:2, nucleotides 931 to 952 of SEQ ID NO:2, nucleotides 932 to 953 of SEQ ID NO:2, nucleotides 933 to 954 of SEQ ID NO:2, nucleotides 934 to 955 of SEQ ID NO:2, nucleotides 935 to 956 of SEQ ID NO:2, nucleotides 936 to 957 of SEQ ID NO:2, nucleotides 937 to 958 of SEQ ID NO:2, nucleotides 938 to 959 of SEQ ID NO:2, nucleotides 939 to 960 of SEQ ID NO:2, nucleotides 940 to 961 of SEQ ID NO:2, nucleotides 941 to 962 of SEQ ID NO:2, nucleotides 942 to 963 of SEQ ID NO:2, nucleotides 943 to 964 of SEQ ID NO:2, nucleotides 944 to 965 of SEQ ID NO:2, nucleotides 945 to 966 of SEQ ID NO:2, nucleotides 946 to 967 of SEQ ID NO:2, nucleotides 947 to 968 of SEQ ID NO:2, nucleotides 948 to 969 of SEQ ID NO:2, nucleotides 949 to 970 of SEQ ID NO:2, and nucleotides 950 to 971 of SEQ ID NO:2.

As another example, a pool of siRNA of the invention derived from the *H. glycines* cct-6gene of SEQ ID NO:2 may comprise a multiplicity of RNA molecules selected from the group consisting of oligonucleotides substantially identical to nucleotides 951 to 972 of SEQ ID NO:2, nucleotides 952 to 973 of SEQ ID NO:2, nucleotides 953 to 974 of SEQ ID NO:2, nucleotides 954 to 975 of SEQ ID NO:2, nucleotides 955 to 976 of SEQ ID NO:2, nucleotides 956 to 977 of SEQ ID NO:2, nucleotides 957 to 978 of SEQ ID NO:2, nucleotides 958 to 979 of SEQ ID NO:2, nucleotides 959 to 980 of SEQ ID NO:2, nucleotides 960 to 981 of SEQ ID NO:2, nucleotides 961 to 982 of SEQ ID NO:2, nucleotides 962 to 983 of SEQ ID NO:2, nucleotides 963 to 984 of SEQ ID NO:2, nucleotides 964 to 985 of SEQ ID NO:2, nucleotides 965 to 986 of SEQ ID NO:2, nucleotides 966 to 987 of SEQ ID NO:2, nucleotides 967 to 988 of SEQ ID NO:2, nucleotides 968 to 989 of SEQ ID NO:2, nucleotides 969 to 990 of SEQ ID NO:2, nucleotides 970 to 991 of SEQ ID NO:2, nucleotides 971 to 992 of SEQ ID NO:2, nucleotides 972 to 993 of SEQ ID NO:2, nucleotides 973 to 994 of SEQ ID NO:2, nucleotides 974 to 995 of SEQ ID NO:2, nucleotides 975 to 996 of SEQ ID NO:2, nucleotides 976 to 997 of SEQ ID NO:2, nucleotides 977 to 998 of SEQ ID NO:2, nucleotides 978 to 999 of SEQ ID NO:2, nucleotides 979 to 1000 of SEQ ID NO:2, nucleotides 980 to 1001 of SEQ ID NO:2, nucleotides 981 to 1002 of SEQ ID NO:2, nucleotides 982 to 1003 of SEQ ID NO:2, nucleotides 983 to 1004 of SEQ ID NO:2, nucleotides 984 to 1005 of SEQ ID NO:2, nucleotides 985 to 1006 of SEQ ID NO:2, nucleotides 986 to 1007 of SEQ ID NO:2, nucleotides 987 to 1008 of SEQ ID NO:2, nucleotides 988 to 1009 of SEQ ID NO:2, nucleotides 989 to 1010 of SEQ ID NO:2, nucleotides 990 to 1011 of SEQ ID NO:2, nucleotides 991 to 1012 of SEQ ID NO:2, nucleotides 992 to 1013 of SEQ ID NO:2, nucleotides 993 to 1014 of SEQ ID NO:2, and nucleotides 994 to 1015 of SEQ ID NO:2.

A pool of siRNA of the invention derived from the *H. glycines* cct-6gene of SEQ ID NO:2 may also comprise any combination of RNA molecules having the specific 21 contiguous nucleotide sequences derived from SEQ ID NO:2 set forth above. Similarly, a pool of siRNA of the invention may comprise a multiplicity of RNA molecules having any 19 contiguous nucleotide sequences derived from SEQ ID NO:2, or a multiplicity of RNA molecules having any 20 contiguous nucleotide sequences derived from SEQ ID NO:2. Alternatively, the pool of the siRNA of the invention may comprise a multiplicity of RNA molecules having a combination of any 19, 20, and/or 21 contiguous nucleotide sequences derived from SEQ ID NO:2.

In another embodiment, a pool of siRNA of the invention derived from the *H. glycines* daf-21 gene of SEQ ID NO:3 may comprise a multiplicity of RNA molecules which are selected from the group consisting of oligonucleotides substantially identical to nucleotides 1 to 21 of SEQ ID NO:3, nucleotides 2 to 23 of SEQ ID NO:3, nucleotides 3 to 24 of SEQ ID NO:3, nucleotides 4 to 25 of SEQ ID NO:3, nucleotides 5 to 26 of SEQ ID NO:3, nucleotides 6 to 27 of SEQ ID NO:3, nucleotides 7 to 28 of SEQ ID NO:3, nucleotides 8 to 29 of SEQ ID NO:3, nucleotides 9 to 30 of SEQ ID NO:3, nucleotides 10 to 31 of SEQ ID NO:3, nucleotides 11 to 32 of SEQ ID NO:3, nucleotides 12 to 33 of SEQ ID NO:3, nucleotides 13 to 34 of SEQ ID NO:3, nucleotides 14 to 35 of SEQ ID NO:3, nucleotides 15 to 36 of SEQ ID NO:3, nucleotides 16 to 37 of SEQ ID NO:3, nucleotides 17 to 38 of SEQ ID NO:3, nucleotides 18 to 39 of SEQ ID NO:3, nucleotides 19 to 40 of SEQ ID NO:3, nucleotides 20 to 41 of SEQ ID NO:3, nucleotides 21 to 42 of SEQ ID NO:3, nucleotides 22 to 43 of SEQ ID NO:3, nucleotides 23 to 44 of SEQ ID NO:3, nucleotides 24 to 45 of SEQ ID NO:3, nucleotides 25 to 46 of SEQ ID NO:3, nucleotides 26 to 47 of SEQ ID NO:3, nucleotides 27 to 48 of SEQ ID NO:3, nucleotides 28 to 49 of SEQ ID NO:3, nucleotides 29 to 50 of SEQ ID NO:3, nucleotides 30 to 51 of SEQ ID NO:3, nucleotides 31 to 52 of SEQ ID NO:3, nucleotides 32 to 53 of SEQ ID NO:3, nucleotides 33 to 54 of SEQ ID NO:3, nucleotides 34 to 55 of SEQ ID NO:3, nucleotides 35 to 56 of SEQ ID NO:3, nucleotides 36 to 57 of SEQ ID NO:3, nucleotides 37 to 58 of SEQ ID NO:3, nucleotides 38 to 59 of SEQ ID NO:3, nucleotides 39 to 60 of SEQ ID NO:3, nucleotides 40 to 61 of SEQ ID NO:3, nucleotides 41 to 62 of SEQ ID NO:3, nucleotides 42 to 63 of SEQ ID NO:3, nucleotides 43 to 64 of SEQ ID NO:3, nucleotides 44 to 65 of SEQ ID NO:3, nucleotides 45 to 66 of SEQ ID NO:3, nucleotides 46 to 67 of SEQ ID NO:3, nucleotides 47 to 68 of SEQ ID NO:3, nucleotides 48 to 69 of SEQ ID NO:3, nucleotides 49 to 70 of SEQ ID NO:3, and nucleotides 50 to 71 of SEQ ID NO:3.

As another example, a pool of siRNA of the invention derived from the *H. glycines* daf-21 gene of SEQ ID NO:3 may comprise a multiplicity of RNA molecules selected from the group consisting of oligonucleotides substantially identical to nucleotides 51 to 72 of SEQ ID NO:3, nucleotides 52 to 73 of SEQ ID NO:3, nucleotides 53 to 74 of SEQ ID NO:3, nucleotides 54 to 75 of SEQ ID NO:3, nucleotides 55 to 76 of SEQ ID NO:3, nucleotides 56 to 77 of SEQ ID NO:3, nucleotides 57 to 78 of SEQ ID NO:3, nucleotides 58 to 79 of SEQ ID NO:3, nucleotides 59 to 80 of SEQ ID NO:3, nucleotides 60 to 81 of SEQ ID NO:3, nucleotides 61 to 82 of SEQ ID NO:3, nucleotides 62 to 83 of SEQ ID NO:3, nucleotides 63 to 84 of SEQ ID NO:3, nucleotides 64 to 85 of SEQ ID NO:3, nucleotides 65 to 86 of SEQ ID NO:3, nucleotides 66 to 87 of SEQ ID NO:3, nucleotides 67 to 88 of SEQ ID NO:3, nucleotides 68 to 89 of SEQ ID NO:3, nucleotides 69 to 90 of SEQ ID NO:3, nucleotides 70 to 91 of SEQ ID NO:3, nucleotides 71 to 92 of SEQ ID NO:3, nucleotides 72 to 93 of SEQ ID NO:3, nucleotides 73 to 94 of SEQ ID NO:3, nucleotides 74 to 95 of SEQ ID NO:3, nucleotides 75 to 96 of SEQ ID NO:3, nucleotides 76 to 97 of SEQ ID NO:3, nucleotides 77 to 98 of SEQ ID NO:3, nucleotides 78 to 99 of SEQ ID NO:3, nucleotides 79 to 100 of SEQ ID NO:3, nucleotides 80 to 101 of SEQ ID NO:3, nucleotides 81 to 102 of SEQ ID NO:3, nucleotides 82 to 103 of SEQ ID NO:3, nucleotides 83 to 104 of SEQ ID NO:3, nucleotides 84 to 105 of SEQ ID NO:3, nucleotides 85 to 106 of SEQ ID NO:3, nucleotides 86 to 107 of SEQ ID NO:3, nucleotides 87 to 108 of SEQ ID NO:3, nucleotides 88 to 109 of SEQ ID NO:3, nucleotides 89 to 110 of SEQ ID NO:3, nucleotides 90 to 111 of SEQ ID NO:3, nucleotides 91 to 112 of SEQ ID NO:3, nucleotides 92 to 113 of SEQ ID NO:3, nucleotides 93 to 14 of SEQ ID NO:3, nucleotides 94 to 115 of SEQ ID NO:3, nucleotides 95 to 116 of SEQ ID NO:3, nucleotides 96 to 117 of SEQ ID NO:3, nucleotides 97 to 118 of SEQ ID NO:3, nucleotides 98 to 119 of SEQ ID NO:3, nucleotides 99 to 120 of SEQ ID NO:3, and nucleotides 100 to 121 of SEQ ID NO:3.

As another example, a pool of siRNA of the invention derived from the *H. glycines* daf-21 gene of SEQ ID NO:3 may comprise a multiplicity of RNA molecules selected from the group consisting of oligonucleotides substantially identical to nucleotides 101 to 122 of SEQ ID NO:3, nucleotides 102 to 123 of SEQ ID NO:3, nucleotides 103 to 124 of SEQ ID NO:3, nucleotides 104 to 125 of SEQ ID NO:3, nucleotides 105 to 126 of SEQ ID NO:3, nucleotides 106 to 127 of SEQ ID NO:3, nucleotides 107 to 128 of SEQ ID NO:3, nucleotides 108 to 129 of SEQ ID NO:3, nucleotides 109 to 130 of SEQ ID NO:3, nucleotides 110 to 131 of SEQ ID NO:3, nucleotides 111 to 132 of SEQ ID NO:3, nucleotides 112 to 133 of SEQ ID NO:3, nucleotides 113 to 134 of SEQ ID NO:3, nucleotides 114 to 135 of SEQ ID NO:3, nucleotides 115 to 136 of SEQ ID NO:3, nucleotides 116 to 137 of SEQ ID NO:3, nucleotides 117 to 138 of SEQ ID NO:3, nucleotides 118 to 139 of SEQ ID NO:3, nucleotides 119 to 140 of SEQ ID NO:3, nucleotides 120 to 141 of SEQ ID NO:3, nucleotides 121 to 142 of SEQ ID NO:3, nucleotides 122 to 143 of SEQ ID NO:3, nucleotides 123 to 144 of SEQ ID NO:3, nucleotides 124 to 145 of SEQ ID NO:3, nucleotides 125 to 146 of SEQ ID NO:3, nucleotides 126 to 147 of SEQ ID NO:3, nucleotides 127 to 148 of SEQ ID NO:3, nucleotides 128 to 149 of SEQ ID NO:3, nucleotides 129 to 150 of SEQ ID NO:3, nucleotides 130 to 151 of SEQ ID NO:3, nucleotides 131 to 152 of SEQ ID NO:3, nucleotides 132 to 153 of SEQ ID NO:3, nucleotides 133 to 154 of SEQ ID NO:3, nucleotides 134 to 155 of SEQ ID NO:3, nucleotides 135 to 156 of SEQ ID NO:3, nucleotides 136 to 157 of SEQ ID NO:3, nucleotides 137 to 158 of SEQ ID NO:3, nucleotides 138 to 159 of SEQ ID NO:3, nucleotides 139 to 160 of SEQ ID NO:3, nucleotides 140 to 161 of SEQ ID NO:3, nucleotides 141 to 162 of SEQ ID NO:3, nucleotides 142 to 163 of SEQ ID NO:3, nucleotides 143 to 164 of SEQ ID NO:3, nucleotides 144 to 165 of SEQ ID NO:3, nucleotides 145 to 166 of SEQ ID NO:3, nucleotides 146 to 167 of SEQ ID NO:3, nucleotides 147 to 168 of SEQ ID NO:3, nucleotides 148 to 169 of SEQ ID NO:3, nucleotides 149 to 170 of SEQ ID NO:3, and nucleotides 150 to 171 of SEQ ID NO:3.

As another example, a pool of siRNA of the invention derived from the *H. glycines* daf-21 gene of SEQ ID NO:3 may comprise a multiplicity of RNA molecules selected from the group consisting of oligonucleotides substantially identical to nucleotides 151 to 172 of SEQ ID NO:3, nucleotides 152 to 173 of SEQ ID NO:3, nucleotides 153 to 174 of SEQ ID NO:3, nucleotides 154 to 175 of SEQ ID NO:3, nucleotides 155 to 176 of SEQ ID NO:3, nucleotides 156 to 177 of SEQ ID NO:3, nucleotides 157 to 178 of SEQ ID NO:3, nucleotides 158 to 179 of SEQ ID NO:3, nucleotides 159 to 180 of SEQ ID NO:3, nucleotides 160 to 181 of SEQ ID NO:3, nucleotides 161 to 182 of SEQ ID NO:3, nucleotides 162 to 183 of SEQ ID NO:3, nucleotides 163 to 184 of SEQ ID NO:3, nucleotides 164 to 185 of SEQ ID NO:3, nucleotides 165 to 186 of SEQ ID NO:3, nucleotides 166 to 187 of SEQ ID NO:3, nucleotides 167 to 188 of SEQ ID NO:3, nucleotides 168 to 189 of SEQ ID NO:3, nucleotides 169 to 190 of SEQ ID NO:3, nucleotides 170 to 191 of SEQ ID NO:3, nucleotides 171 to 192 of SEQ ID NO:3, nucleotides 172 to 193 of SEQ ID NO:3, nucleotides 173 to 194 of SEQ ID NO:3, nucleotides 174 to 195 of SEQ ID NO:3, nucleotides 175 to 196 of SEQ ID NO:3, nucleotides 176 to 197 of SEQ ID NO:3, nucleotides 177 to 198 of SEQ ID NO:3, nucleotides 178 to 199 of SEQ ID NO:3, nucleotides 179 to 200 of SEQ ID NO:3, nucleotides 180 to 201 of SEQ ID NO:3, nucleotides 181 to 202 of SEQ ID NO:3, nucleotides 182 to 203 of SEQ ID NO:3, nucleotides 183 to 204 of SEQ ID NO:3, nucleotides 184 to 205 of SEQ ID NO:3, nucleotides 185 to 206 of SEQ ID NO:3, nucleotides 186 to 207 of SEQ ID NO:3, nucleotides 187 to 208 of SEQ ID NO:3, nucleotides 188 to 209 of SEQ ID NO:3, nucleotides 189 to 210 of SEQ ID NO:3, nucleotides 190 to 211 of SEQ ID NO:3, nucleotides 191 to 212 of SEQ ID NO:3, nucleotides 192 to 213 of SEQ ID NO:3, nucleotides 193 to 214 of SEQ ID NO:3, nucleotides 194 to 215 of SEQ ID NO:3, nucleotides 195 to 216 of SEQ ID NO:3, nucleotides 196 to 217 of SEQ ID NO:3, nucleotides 197 to 218 of SEQ ID NO:3, nucleotides 198 to 219 of SEQ ID NO:3, nucleotides 199 to 220 of SEQ ID NO:3, and nucleotides 200 to 221 of SEQ ID NO:3.

As another example, a pool of siRNA of the invention derived from the *H. glycines* daf-21 gene of SEQ ID NO:3 may comprise a multiplicity of RNA molecules selected from the group consisting of oligonucleotides substantially identical to nucleotides 201 to 222 of SEQ ID NO:3, nucleotides 202 to 223 of SEQ ID NO:3, nucleotides 203 to 224 of SEQ ID NO:3, nucleotides 204 to 225 of SEQ ID NO:3, nucleotides 205 to 226 of SEQ ID NO:3, nucleotides 206 to 227 of SEQ ID NO:3, nucleotides 207 to 228 of SEQ ID NO:3, nucleotides 208 to 229 of SEQ ID NO:3, nucleotides 209 to 230 of SEQ ID NO:3, nucleotides 210 to 231 of SEQ ID NO:3, nucleotides 211 to 232 of SEQ ID NO:3, nucleotides 212 to 233 of SEQ ID NO:3, nucleotides 213 to 234 of SEQ ID NO:3, nucleotides 214 to 235 of SEQ ID NO:3, nucleotides 215 to 236 of SEQ ID NO:3, nucleotides 216 to 237 of SEQ ID NO:3, nucleotides 217 to 238 of SEQ ID NO:3, nucleotides 218 to 239 of SEQ ID NO:3, nucleotides 219 to 240 of SEQ ID NO:3, nucleotides 220 to 241 of SEQ ID NO:3, nucleotides 221 to 242 of SEQ ID NO:3, nucleotides 222 to 243 of SEQ ID NO:3, nucleotides 223 to 244 of SEQ ID NO:3, nucleotides 224 to 245 of SEQ ID NO:3, nucleotides 225 to 246 of SEQ ID NO:3, nucleotides 226 to 247 of SEQ ID NO:3, nucleotides 227 to 248 of SEQ ID NO:3, nucleotides 228 to 249 of SEQ ID NO:3, nucleotides 229 to 250 of SEQ ID NO:3, nucleotides 230 to 251 of SEQ ID NO:3, nucleotides 231 to 252 of SEQ ID NO:3, nucleotides 232 to 253 of SEQ ID NO:3, nucleotides 233 to 254 of SEQ ID NO:3, nucleotides 234 to 255 of SEQ ID NO:3, nucleotides 235 to 256 of SEQ ID NO:3, nucleotides 236 to 257 of SEQ ID NO:3, nucleotides 237 to 258 of SEQ ID NO:3, nucleotides 238 to 259 of SEQ ID NO:3, nucleotides 239 to 260 of SEQ ID NO:3, nucleotides 240 to 261 of SEQ ID NO:3, nucleotides 241 to 262 of SEQ ID NO:3, nucleotides 242 to 263 of SEQ ID NO:3, nucleotides 243 to 264 of SEQ ID NO:3, nucleotides 244 to 265 of SEQ ID NO:3, nucleotides 245 to 266 of SEQ ID NO:3, nucleotides 246 to 267 of SEQ ID NO:3, nucleotides 247 to 268 of SEQ ID NO:3, nucleotides 248 to 269 of SEQ ID NO:3, nucleotides 249 to 270 of SEQ ID NO:3, and nucleotides 250 to 271 of SEQ ID NO:3.

As another example, a pool of siRNA of the invention derived from the *H. glycines* daf-21 gene of SEQ ID NO:3 may comprise a multiplicity of RNA molecules selected from the group consisting of oligonucleotides substantially identical to nucleotides 251 to 272 of SEQ ID NO:3, nucleotides 252 to 273 of SEQ ID NO:3, nucleotides 253 to 274 of SEQ ID NO:3, nucleotides 254 to 275 of SEQ ID NO:3, nucleotides 255 to 276 of SEQ ID NO:3, nucleotides 256 to 277 of SEQ ID NO:3, nucleotides 257 to 278 of SEQ ID NO:3, nucleotides 258 to 279 of SEQ ID NO:3, nucleotides 259 to 280 of SEQ ID NO:3, nucleotides 260 to 281 of SEQ ID NO:3, nucleotides 261 to 282 of SEQ ID NO:3, nucleotides 262 to 283 of SEQ ID NO:3, nucleotides 263 to 284 of SEQ ID NO:3, nucleotides 264 to 285 of SEQ ID NO:3, nucleotides 265 to 286 of SEQ ID NO:3, nucleotides 266 to 287 of SEQ ID NO:3, nucleotides 267 to 288 of SEQ ID NO:3, nucleotides 268 to 289 of SEQ ID NO:3, nucleotides 269 to 290 of SEQ ID NO:3, nucleotides 270 to 291 of SEQ ID NO:3, nucleotides 271 to 292 of SEQ ID NO:3, nucleotides 272 to 293 of SEQ ID NO:3, nucleotides 273 to 294 of SEQ ID NO:3, nucleotides 274 to 295 of SEQ ID NO:3, nucleotides 275 to 296 of SEQ ID NO:3, nucleotides 276 to 297 of SEQ ID NO:3, nucleotides 277 to 298 of SEQ ID NO:3, nucleotides 278 to 299 of SEQ ID NO:3, nucleotides 279 to 300 of SEQ ID NO:3, nucleotides 280 to 301 of SEQ ID NO:3, nucleotides 281 to 302 of SEQ ID NO:3, nucleotides 282 to 303 of SEQ ID NO:3, nucleotides 283 to 304 of SEQ ID NO:3, nucleotides 284 to 305 of SEQ ID NO:3, nucleotides 285 to 306 of SEQ ID NO:3, nucleotides 286 to 307 of SEQ ID NO:3, nucleotides 287 to 308 of SEQ ID NO:3, nucleotides 288 to 309 of SEQ ID NO:3, nucleotides 289 to 310 of SEQ ID NO:3, nucleotides 290 to 311 of SEQ ID NO:3, nucleotides 291 to 312 of SEQ ID NO:3, nucleotides 292 to 313 of SEQ ID NO:3, nucleotides 293 to 314 of SEQ ID NO:3, nucleotides 294 to 315 of SEQ ID NO:3, nucleotides 295 to 316 of SEQ ID NO:3, nucleotides 296 to 317 of SEQ ID NO:3, nucleotides 297 to 318 of SEQ ID NO:3, nucleotides 298 to 319 of SEQ ID NO:3, nucleotides 299 to 320 of SEQ ID NO:3, and nucleotides 300 to 321 of SEQ ID NO:3.

As another example, a pool of siRNA of the invention derived from the *H. glycines* daf-21 gene of SEQ ID NO:3 may comprise a multiplicity of RNA molecules selected from the group consisting of oligonucleotides substantially identical to nucleotides 301 to 322 of SEQ ID NO:3, nucleotides 302 to 323 of SEQ ID NO:3, nucleotides 303 to 324 of SEQ ID NO:3, nucleotides 304 to 325 of SEQ ID NO:3, nucleotides 305 to 326 of SEQ ID NO:3, nucleotides 306 to 327 of SEQ ID NO:3, nucleotides 307 to 328 of SEQ ID NO:3, nucleotides 308 to 329 of SEQ ID NO:3, nucleotides 309 to 330 of SEQ ID NO:3, nucleotides 310 to 331 of SEQ ID NO:3, nucleotides 311 to 332 of SEQ ID NO:3, nucleotides 312 to 333 of SEQ ID NO:3, nucleotides 313 to 334 of SEQ ID NO:3, nucleotides 314 to 335 of SEQ ID NO:3, nucleotides 315 to 336 of SEQ ID NO:3, nucleotides 316 to 337 of SEQ ID NO:3, nucleotides 317 to 338 of SEQ ID NO:3, nucleotides 318 to 339 of SEQ ID NO:3, nucleotides 319 to 340 of SEQ ID NO:3, nucleotides 320 to 341 of SEQ ID NO:3, nucleotides 321 to 342 of SEQ ID NO:3, nucleotides 322 to 343 of SEQ ID NO:3, nucleotides 323 to 344 of SEQ ID NO:3, nucleotides 324 to 345 of SEQ ID NO:3, nucleotides 325 to 346 of SEQ ID NO:3, nucleotides 326 to 347 of SEQ ID NO:3, nucleotides 327 to 348 of SEQ ID NO:3, nucleotides 328 to 349 of SEQ ID NO:3, nucleotides 329 to 350 of SEQ ID NO:3, nucleotides 330 to 351 of SEQ ID NO:3, nucleotides 331 to 352 of SEQ ID NO:3, nucleotides 332 to 353 of SEQ ID NO:3, nucleotides 333 to 354 of SEQ ID NO:3, nucleotides 334 to 355 of SEQ ID NO:3, nucleotides 335 to 356 of SEQ ID NO:3, nucleotides 336 to 357 of SEQ ID NO:3, nucleotides 337 to 358 of SEQ ID NO:3, nucleotides 338 to 359 of SEQ ID NO:3, nucleotides 339 to 360 of SEQ ID NO:3, nucleotides 340 to 361 of SEQ ID NO:3, nucleotides 341 to 362 of SEQ ID NO:3, nucleotides 342 to 363 of SEQ ID NO:3, nucleotides 343 to 364 of SEQ ID NO:3, nucleotides 344 to 365 of SEQ ID NO:3, nucleotides 345 to 366 of SEQ ID NO:3, nucleotides 346 to 367 of SEQ ID NO:3, nucleotides 347 to 368 of SEQ ID NO:3, nucleotides 348 to 369 of SEQ ID NO:3, nucleotides 349 to 370 of SEQ ID NO:3, and nucleotides 350 to 371 of SEQ ID NO:3.

As another example, a pool of siRNA of the invention derived from the *H. glycines* daf-21 gene of SEQ ID NO:3 may comprise a multiplicity of RNA molecules selected from the group consisting of oligonucleotides substantially identical to nucleotides 351 to 372 of SEQ ID NO:3, nucleotides 352 to 373 of SEQ ID NO:3, nucleotides 353 to 374 of SEQ ID NO:3, nucleotides 354 to 375 of SEQ ID NO:3, nucleotides 355 to 376 of SEQ ID NO:3, nucleotides 356 to 377 of SEQ ID NO:3, nucleotides 357 to 378 of SEQ ID NO:3, nucleotides 358 to 379 of SEQ ID NO:3, nucleotides 359 to 380 of SEQ ID NO:3, nucleotides 360 to 381 of SEQ ID NO:3, nucleotides 361 to 382 of SEQ ID NO:3, nucleotides 362 to 383 of SEQ ID NO:3, nucleotides 363 to 384 of SEQ ID NO:3, nucleotides 364 to 385 of SEQ ID NO:3, nucleotides 365 to 386 of SEQ ID NO:3, nucleotides 366 to 387 of SEQ ID NO:3, nucleotides 367 to 388 of SEQ ID NO:3, nucleotides 368 to 389 of SEQ ID NO:3, nucleotides 369 to 390 of SEQ ID NO:3, nucleotides 370 to 391 of SEQ ID NO:3, nucleotides 371 to 392 of SEQ ID NO:3, nucleotides 372 to 393 of SEQ ID NO:3, nucleotides 373 to 394 of SEQ ID NO:3, nucleotides 374 to 395 of SEQ ID NO:3, nucleotides 375 to 396 of SEQ ID NO:3, nucleotides 376 to 397 of SEQ ID NO:3, nucleotides 377 to 398 of SEQ ID NO:3, nucleotides 378 to 399 of SEQ ID NO:3, nucleotides 379 to 400 of SEQ ID NO:3, nucleotides 380 to 401 of SEQ ID NO:3, nucleotides 381 to 402 of SEQ ID NO:3, nucleotides 382 to 403 of SEQ ID NO:3, nucleotides 383 to 404 of SEQ ID NO:3, nucleotides 384 to 405 of SEQ ID NO:3, nucleotides 385 to 406 of SEQ ID NO:3, nucleotides 386 to 407 of SEQ ID NO:3, nucleotides 387 to 408 of SEQ ID NO:3, nucleotides 388 to 409 of SEQ ID NO:3, nucleotides 389 to 410 of SEQ ID NO:3, nucleotides 390 to 411 of SEQ ID NO:3, nucleotides 391 to 412 of SEQ ID NO:3, nucleotides 392 to 413 of SEQ ID NO:3, nucleotides 393 to 414 of SEQ ID NO:3, nucleotides 394 to 415 of SEQ ID NO:3, nucleotides 395 to 416 of SEQ ID NO:3, nucleotides 396 to 417 of SEQ ID NO:3, nucleotides 397 to 418 of SEQ ID NO:3, nucleotides 398 to 419 of SEQ ID NO:3, nucleotides 399 to 420 of SEQ ID NO:3, and nucleotides 400 to 421 of SEQ ID NO:3.

As another example, a pool of siRNA of the invention derived from the *H. glycines* daf-21 gene of SEQ ID NO:3 may comprise a multiplicity of RNA molecules selected from the group consisting of oligonucleotides substantially identical to nucleotides 401 to 422 of SEQ ID NO:3, nucleotides 402 to 423 of SEQ ID NO:3, nucleotides 403 to 424 of SEQ ID NO:3, nucleotides 404 to 425 of SEQ ID NO:3, nucleotides 405 to 426 of SEQ ID NO:3, nucleotides 406 to 427 of SEQ ID NO:3, nucleotides 407 to 428 of SEQ ID NO:3, nucleotides 408 to 429 of SEQ ID NO:3, nucleotides 409 to 430 of SEQ ID NO:3, nucleotides 410 to 431 of SEQ ID NO:3, nucleotides 411 to 432 of SEQ ID NO:3, nucleotides 412 to 433 of SEQ ID NO:3, nucleotides 413 to 434 of SEQ ID NO:3, nucleotides 414 to 435 of SEQ ID NO:3, nucleotides 415 to 436 of SEQ ID NO:3, nucleotides 416 to 437 of SEQ ID NO:3, nucleotides 417 to 438 of SEQ ID NO:3, nucleotides 418 to 439 of SEQ ID NO:3, nucleotides 419 to 440 of SEQ ID NO:3, nucleotides 420 to 441 of SEQ ID NO:3, nucleotides 421 to 442 of SEQ ID NO:3, nucleotides 422 to 443 of SEQ ID NO:3, nucleotides 423 to 444 of SEQ ID NO:3, nucleotides 424 to 445 of SEQ ID NO:3, nucleotides 425 to 446 of SEQ ID NO:3, nucleotides 426 to 447 of SEQ ID NO:3, nucleotides 427 to 448 of SEQ ID NO:3, nucleotides 428 to 449 of SEQ ID NO:3, nucleotides 429 to 450 of SEQ ID NO:3, nucleotides 430 to 451 of SEQ ID NO:3, nucleotides 431 to 452 of SEQ ID NO:3, nucleotides 432 to 453 of SEQ ID NO:3, nucleotides 433 to 454 of SEQ ID NO:3, nucleotides 434 to 455 of SEQ ID NO:3, nucleotides 435 to 456 of SEQ ID NO:3, nucleotides 436 to 457 of SEQ ID NO:3, nucleotides 437 to 458 of SEQ ID NO:3, nucleotides 438 to 459 of SEQ ID NO:3, nucleotides 439 to 460 of SEQ ID NO:3, nucleotides 440 to 461 of SEQ ID NO:3, nucleotides 441 to 462 of SEQ ID NO:3, nucleotides 442 to 463 of SEQ ID NO:3, nucleotides 443 to 464 of SEQ ID NO:3, nucleotides 444 to 465 of SEQ ID NO:3, nucleotides 445 to 466 of SEQ ID NO:3, nucleotides 446 to 467 of SEQ ID NO:3, nucleotides 447 to 468 of SEQ ID NO:3, nucleotides 448 to 469 of SEQ ID NO:3, nucleotides 449 to 470 of SEQ ID NO:3, and nucleotides 450 to 471 of SEQ ID NO:3.

As another example, a pool of siRNA of the invention derived from the *H. glycines* daf-21 gene of SEQ ID NO:3 may comprise a multiplicity of RNA molecules selected from the group consisting of oligonucleotides substantially identical to nucleotides 451 to 472 of SEQ ID NO:3, nucleotides 452 to 473 of SEQ ID NO:3, nucleotides 453 to 474 of SEQ ID NO:1, nucleotides 454 to 475 of SEQ ID NO:3, nucleotides 455 to 476 of SEQ ID NO:3, nucleotides 456 to 477 of SEQ ID NO:3, nucleotides 457 to 478 of SEQ ID NO:3, nucleotides 458 to 479 of SEQ ID NO:3, nucleotides 459 to 480 of SEQ ID NO:3, nucleotides 460 to 481 of SEQ ID NO:3, nucleotides 461 to 482 of SEQ ID NO:3, nucleotides 462 to 483 of SEQ ID NO:3, nucleotides 463 to 484 of SEQ ID NO:3, nucleotides 464 to 485 of SEQ ID NO:3, nucleotides 465 to 486 of SEQ ID NO:3, nucleotides 466 to 487 of SEQ ID NO:3, nucleotides 467 to 488 of SEQ ID NO:3, nucleotides 468 to 489 of SEQ ID NO:3, nucleotides 469 to 490 of SEQ ID NO:3, nucleotides 470 to 491 of SEQ ID NO:3, nucleotides 471 to 492 of SEQ ID NO:3, nucleotides 472 to 493 of SEQ ID NO:3, nucleotides 473 to 494 of SEQ ID NO:3, nucleotides 474 to 495 of SEQ ID NO:3, nucleotides 475 to 496 of SEQ ID NO:3, nucleotides 476 to 497 of SEQ ID NO:3, nucleotides 477 to 498 of SEQ ID NO:3, nucleotides 478 to 499 of SEQ ID NO:3, nucleotides 479 to 500 of SEQ ID NO:3; nucleotides 480 to 501 of SEQ ID NO:3, nucleotides 481 to 502 of SEQ ID NO:3, nucleotides 482 to 503 of SEQ ID NO:3, nucleotides 483 to 504 of SEQ ID NO:3, nucleotides 484 to 505 of SEQ ID NO:3, nucleotides 485 to 506 of SEQ ID NO:3, nucleotides 486 to 507 of SEQ ID NO:3, nucleotides 487 to 508 of SEQ ID NO:3, nucleotides 488 to 509 of SEQ ID NO:3, nucleotides 489 to 510 of SEQ ID NO:3, nucleotides 490 to 511 of SEQ ID NO:3, nucleotides 491 to 512 of SEQ ID NO:3, nucleotides 492 to 513 of SEQ ID NO:3, nucleotides 493 to 514 of SEQ ID NO:3, nucleotides 494 to 515 of SEQ ID NO:3, nucleotides 495 to 516 of SEQ ID NO:3, nucleotides 496 to 517 of SEQ ID NO:3, nucleotides 497 to 518 of SEQ ID NO:3, nucleotides 498 to 519 of SEQ ID NO:3, nucleotides 499 to 520 of SEQ ID NO:3, and nucleotides 500 to 521 of SEQ ID NO:3.

As another example, a pool of siRNA of the invention derived from the *H. glycines* daf-21 gene of SEQ ID NO:3 may comprise a multiplicity of RNA molecules selected from the group consisting of oligonucleotides substantially identical to nucleotides 501 to 522 of SEQ ID NO:3, nucleotides 502 to 523 of SEQ ID NO:3, nucleotides 503 to 524 of SEQ ID NO:3, nucleotides 504 to 525 of SEQ ID NO:3, nucleotides 505 to 526 of SEQ ID NO:3, nucleotides 506 to 527 of SEQ ID NO:3, nucleotides 507 to 528 of SEQ ID NO:3, nucleotides 508 to 529 of SEQ ID NO:3, nucleotides 509 to 530 of SEQ ID NO:3, nucleotides 510 to 531 of SEQ ID NO:3, nucleotides 511 to 532 of SEQ ID NO:3, nucleotides 512 to 533 of SEQ ID NO:3, nucleotides 513 to 534 of SEQ ID NO:3, nucleotides 514 to 535 of SEQ ID NO:3, nucleotides 515 to 536 of SEQ ID NO:3, nucleotides 516 to 537 of SEQ ID NO:3, nucleotides 517 to 538 of SEQ ID NO:3, nucleotides 518 to 539 of SEQ ID NO:3, nucleotides 519 to 540 of SEQ ID NO:3, nucleotides 520 to 541 of SEQ ID NO:3, nucleotides 521 to 542 of SEQ ID NO:3, nucleotides 522 to 543 of SEQ ID NO:3, nucleotides 523 to 544 of SEQ ID NO:3; nucleotides 524 to 545 of SEQ ID NO:3, nucleotides 525 to 546 of SEQ ID NO:3, nucleotides 526 to 547 of SEQ ID NO:3, nucleotides 527 to 548 of SEQ ID NO:3, nucleotides 528 to 549 of SEQ ID NO:3, nucleotides 529 to 550 of SEQ ID NO:3, nucleotides 530 to 551 of SEQ ID NO:3, nucleotides 531 to 552 of SEQ ID NO:3, nucleotides 532 to 553 of SEQ ID NO:3, nucleotides 533 to 554 of SEQ ID NO:3, nucleotides 534 to 555 of SEQ ID NO:3, nucleotides 535 to 556 of SEQ ID NO:3, nucleotides 536 to 557 of SEQ ID NO:3, nucleotides 537 to 558 of SEQ ID NO:3, nucleotides 538 to 559 of SEQ ID NO:3, nucleotides 539 to 560 of SEQ ID NO:3, nucleotides 540 to 561 of SEQ ID NO:3, nucleotides 541 to 562 of SEQ ID NO:3, nucleotides 542 to 563 of SEQ ID NO:3, nucleotides 543 to 564 of SEQ ID NO:3, nucleotides 544 to 565 of SEQ ID NO:3, nucleotides 545 to 566 of SEQ ID NO:3, nucleotides 546 to 567 of SEQ ID NO:3, nucleotides 547 to 568 of SEQ ID NO:3, nucleotides 548 to 569 of SEQ ID NO:3, nucleotides 549 to 570 of SEQ ID NO:3, and nucleotides 550 to 571 of SEQ ID NO:3.

As another example, a pool of siRNA of the invention derived from the *H. glycines* daf-21 gene of SEQ ID NO:3 may comprise a multiplicity of RNA molecules selected from the group consisting of oligonucleotides substantially identical to nucleotides 551 to 572 of SEQ ID NO:3, nucleotides 552 to 573 of SEQ ID NO:3, nucleotides 553 to 574 of SEQ ID NO:3, nucleotides 554 to 575 of SEQ ID NO:3, nucleotides 555 to 576 of SEQ ID NO:3, nucleotides 556 to 577 of SEQ ID NO:3, nucleotides 557 to 578 of SEQ ID NO:3, nucleotides 558 to 579 of SEQ ID NO:3, nucleotides 559 to 580 of SEQ ID NO:3, nucleotides 560 to 581 of SEQ ID NO:3, nucleotides 561 to 582 of SEQ ID NO:3, nucleotides 562 to 583 of SEQ ID NO:3, nucleotides 563 to 584 of SEQ ID NO:3, nucleotides 564 to 585 of SEQ ID NO:3, nucleotides 565 to 586 of SEQ ID NO:3, nucleotides 566 to 587 of SEQ ID NO:3, nucleotides 567 to 588 of SEQ ID NO:3, nucleotides 568 to 589 of SEQ ID NO:3, nucleotides 569 to 590 of SEQ ID NO:3, nucleotides 570 to 591 of SEQ ID NO:3, nucleotides 571 to 592 of SEQ ID NO:3, nucleotides 572 to 593 of SEQ ID NO:3, nucleotides 573 to 594 of SEQ ID NO:3, nucleotides 574 to 595 of SEQ ID NO:3, nucleotides 575 to 596 of SEQ ID NO:3, nucleotides 576 to 597 of SEQ ID NO:3, nucleotides 577 to 598 of SEQ ID NO:3, nucleotides 578 to 599 of SEQ ID NO:3, nucleotides 579 to 600 of SEQ ID NO:3, nucleotides 580 to 601 of SEQ ID NO:3, nucleotides 581 to 602 of SEQ ID NO:3, nucleotides 582 to 603 of SEQ ID NO:3, nucleotides 583 to 604 of SEQ ID NO:3, nucleotides 584 to 605 of SEQ ID NO:3, nucleotides 585 to 606 of SEQ ID NO:3, nucleotides 586 to 607 of SEQ ID NO:3, nucleotides 587 to 608 of SEQ ID NO:3, nucleotides 588 to 609 of SEQ ID NO:3, nucleotides 589 to 610 of SEQ ID NO:3, nucleotides 590 to 611 of SEQ ID NO:3, nucleotides 591 to 612 of SEQ ID NO:3, nucleotides 592 to 613 of SEQ ID NO:3, nucleotides 593 to 614 of SEQ ID NO:3, nucleotides 594 to 615 of SEQ ID NO:3, nucleotides 595 to 616 of SEQ ID NO:3, nucleotides 596 to 617 of SEQ ID NO:3, nucleotides 597 to 618 of SEQ ID NO:3, nucleotides 598 to 619 of SEQ ID NO:3, nucleotides 599 to 620 of SEQ ID NO:3, and nucleotides 600 to 621 of SEQ ID NO:3.

As another example, a pool of siRNA of the invention derived from the *H. glycines* daf-21 gene of SEQ ID NO:3 may comprise a multiplicity of RNA molecules selected from the group consisting of oligonucleotides substantially identical to nucleotides 601 to 622 of SEQ ID NO:3, nucleotides 602 to 623 of SEQ ID NO:3, nucleotides 603 to 624 of SEQ ID NO:3, nucleotides 604 to 625 of SEQ ID NO:3, nucleotides 605 to 626 of SEQ ID NO:3, nucleotides 606 to 627 of SEQ ID NO:3, nucleotides 607 to 628 of SEQ ID NO:3, nucleotides 608 to 629 of SEQ ID NO:3, nucleotides 609 to 630 of SEQ ID NO:3, nucleotides 610 to 631 of SEQ ID NO:3, nucleotides 611 to 632 of SEQ ID NO:3, nucleotides 612 to 633 of SEQ ID NO:3, nucleotides 613 to 634 of SEQ ID NO:3, nucleotides 614 to 635 of SEQ ID NO:3, nucleotides 615 to 636 of SEQ ID NO:3, nucleotides 616 to 637 of SEQ ID NO:3, nucleotides 617 to 638 of SEQ ID NO:3, nucleotides 618 to 639 of SEQ ID NO:3, nucleotides 619 to 640 of SEQ ID NO:3, nucleotides 620 to 641 of SEQ ID NO:3, nucleotides 621 to 642 of SEQ ID NO:3, nucleotides 622 to 643 of SEQ ID NO:3, nucleotides 623 to 644 of SEQ ID NO:3, nucleotides 624 to 645 of SEQ ID NO:3, nucleotides 625 to 646 of SEQ ID NO:3, nucleotides 626 to 647 of SEQ ID NO:3, nucleotides 627 to 648 of SEQ ID NO:3, nucleotides 628 to 649 of SEQ ID NO:3, nucleotides 629 to 650 of SEQ ID NO:3, nucleotides 630 to 651 of SEQ ID NO:3, nucleotides 631 to 652 of SEQ ID NO:3, nucleotides 632 to 653 of SEQ ID NO:3, nucleotides 633 to 654 of SEQ ID NO:3, nucleotides 634 to 655 of SEQ ID NO:3, nucleotides 635 to 656 of SEQ ID NO:3, nucleotides 636 to 657 of SEQ ID NO:3, nucleotides 637 to 658 of SEQ ID NO:3, nucleotides 638 to 659 of SEQ ID NO:3, nucleotides 639 to 660 of SEQ ID NO:3, nucleotides 640 to 661 of SEQ ID NO:3, nucleotides 641 to 662 of SEQ ID NO:3, nucleotides 642 to 663 of SEQ ID NO:3, nucleotides 643 to 664 of SEQ ID NO:3, nucleotides 644 to 665 of SEQ ID NO:3, nucleotides 645 to 666 of SEQ ID NO:3, nucleotides 646 to 667 of SEQ ID NO:3, nucleotides 647 to 668 of SEQ ID NO:3, nucleotides 648 to 669 of SEQ ID NO:3, nucleotides 649 to 670 of SEQ ID NO:3, and nucleotides 650 to 671 of SEQ ID NO:3.

As another example, a pool of siRNA of the invention derived from the *H. glycines* daf-21 gene of SEQ ID NO:3 may comprise a multiplicity of RNA molecules selected from the group consisting of oligonucleotides substantially identical to nucleotides 651 to 672 of SEQ ID NO:3, nucleotides 652 to 673 of SEQ ID NO:3, nucleotides 653 to 674 of SEQ ID NO:3, nucleotides 654 to 675 of SEQ ID NO:3, nucleotides 655 to 676 of SEQ ID NO:3, nucleotides 656 to 677 of SEQ ID NO:3, nucleotides 657 to 678 of SEQ ID NO:3, nucleotides 658 to 679 of SEQ ID NO:3, nucleotides 659 to 680 of SEQ ID NO:3, nucleotides 660 to 681 of SEQ ID NO:3, nucleotides 661 to 682 of SEQ ID NO:3, nucleotides 662 to 683 of SEQ ID NO:3, nucleotides 663 to 684 of SEQ ID NO:3, nucleotides 664 to 685 of SEQ ID NO:3, nucleotides 665 to 686 of SEQ ID NO:3, nucleotides 666 to 687 of SEQ ID NO:3, nucleotides 667 to 688 of SEQ ID NO:3, nucleotides 668 to 689 of SEQ ID NO:3, nucleotides 669 to 690 of SEQ ID NO:3, nucleotides 670 to 691 of SEQ ID NO:3, nucleotides 671 to 692 of SEQ ID NO:3, nucleotides 672 to 693 of SEQ ID NO:3, nucleotides 673 to 694 of SEQ ID NO:3, nucleotides 674 to 695 of SEQ ID NO:3, nucleotides 675 to 696 of SEQ ID NO:3, nucleotides 676 to 697 of SEQ ID NO:3, nucleotides 677 to 698 of SEQ ID NO:3, nucleotides 678 to 699 of SEQ ID NO:3, nucleotides 679 to 700 of SEQ ID NO:3, nucleotides 680 to 701 of SEQ ID NO:3, nucleotides 681 to 702 of SEQ ID NO:3, nucleotides 682 to 703 of SEQ ID NO:3, nucleotides 683 to 704 of SEQ ID NO:3, nucleotides 684 to 705 of SEQ ID NO:3, nucleotides 685 to 706 of SEQ ID NO:3, nucleotides 686 to 707 of SEQ ID NO:3, nucleotides 687 to 708 of SEQ ID NO:3, nucleotides 688 to 709 of SEQ ID NO:3, nucleotides 689 to 710 of SEQ ID NO:3, nucleotides 690 to 711 of SEQ ID NO:3, nucleotides 691 to 712 of SEQ ID NO:3, nucleotides 692 to 713 of SEQ ID NO:3, nucleotides 693 to 714 of SEQ ID NO:3, nucleotides 694 to 715 of SEQ ID NO:3, nucleotides 695 to 716 of SEQ ID NO:3, nucleotides 696 to 717 of SEQ ID NO:3, nucleotides 697 to 718 of SEQ ID NO:3, nucleotides 698 to 719 of SEQ ID NO:3, nucleotides 699 to 720 of SEQ ID NO:3, and nucleotides 700 to 721 of SEQ ID NO:3.

As another example, a pool of siRNA of the invention derived from the *H. glycines* daf-21 gene of SEQ ID NO:3 may comprise a multiplicity of RNA molecules selected from the group consisting of oligonucleotides substantially identical to nucleotides 701 to 722 of SEQ ID NO:3, nucleotides 702 to 723 of SEQ ID NO:3, nucleotides 703 to 724 of SEQ ID NO:3, nucleotides 704 to 725 of SEQ ID NO:3, nucleotides 705 to 726 of SEQ ID NO:3, nucleotides 706 to 727 of SEQ ID NO:3, nucleotides 707 to 728 of SEQ ID NO:3, nucleotides 708 to 729 of SEQ ID NO:3, nucleotides 709 to 730 of SEQ ID NO:3, nucleotides 710 to 731 of SEQ ID NO:3, nucleotides 711 to 732 of SEQ ID NO:3, nucleotides 712 to 733 of SEQ ID NO:3, nucleotides 713 to 734 of SEQ ID NO:3, nucleotides 714 to 735 of SEQ ID NO:3, nucleotides 715 to 736 of SEQ ID NO:3, nucleotides 716 to 737 of SEQ ID NO:3, nucleotides 717 to 738 of SEQ ID NO:3, nucleotides 718 to 739 of SEQ ID NO:3, nucleotides 719 to 740 of SEQ ID NO:3, nucleotides 720 to 741 of SEQ ID NO:3, nucleotides 721 to 742 of SEQ ID NO:3, nucleotides 722 to 743 of SEQ ID NO:3, nucleotides 723 to 744 of SEQ ID NO:3, nucleotides 724 to 745 of SEQ ID NO:3, nucleotides 725 to 746 of SEQ ID NO:3, nucleotides 726 to 747 of SEQ ID NO:3, nucleotides 727 to 748 of SEQ ID NO:3, nucleotides 728 to 749 of SEQ ID NO:3, nucleotides 729 to 750 of SEQ ID NO:3, nucleotides 730 to 751 of SEQ ID NO:3, nucleotides 731 to 752 of SEQ ID NO:3, nucleotides 732 to 753 of SEQ ID NO:3, nucleotides 733 to 754 of SEQ ID NO:3, nucleotides 734 to 755 of SEQ ID NO:3, nucleotides 735 to 756 of SEQ ID NO:3, nucleotides 736 to 757 of SEQ ID NO:3, nucleotides 737 to 758 of SEQ ID NO:3, nucleotides 738 to 759 of SEQ ID NO:3, nucleotides 739 to 760 of SEQ ID NO:3, nucleotides 740 to 761 of SEQ ID NO:3, nucleotides 741 to 762 of SEQ ID NO:3, nucleotides 742 to 763 of SEQ ID NO:3, nucleotides 743 to 764 of SEQ ID NO:3, nucleotides 744 to 765 of SEQ ID NO:3, nucleotides 745 to 766 of SEQ ID NO:3, nucleotides 746 to 767 of SEQ ID NO:3, nucleotides 747 to 768 of SEQ ID NO:3, nucleotides 748 to 769 of SEQ ID NO:3, nucleotides 749 to 770 of SEQ ID NO:3, and nucleotides 750 to 771 of SEQ ID NO:3.

As another example, a pool of siRNA of the invention derived from the *H. glycines* daf-21 gene of SEQ ID NO:3 may comprise a multiplicity of RNA molecules selected from the group consisting of oligonucleotides substantially identical to nucleotides 751 to 772 of SEQ ID NO:3, nucleotides 752 to 773 of SEQ ID NO:3, nucleotides 753 to 774 of SEQ ID NO:3, nucleotides 754 to 775 of SEQ ID NO:3, nucleotides 755 to 776 of SEQ ID NO:3, nucleotides 756 to 777 of SEQ ID NO:3, nucleotides 757 to 778 of SEQ ID NO:3, nucleotides 758 to 779 of SEQ ID NO:3, nucleotides 759 to 780 of SEQ ID NO:3, nucleotides 760 to 781 of SEQ ID NO:3, nucleotides 761 to 782 of SEQ ID NO:3, nucleotides 762 to 783 of SEQ ID NO:3, nucleotides 763 to 784 of SEQ ID NO:3, nucleotides 764 to 785 of SEQ ID NO:3, nucleotides 765 to 786 of SEQ ID NO:3, nucleotides 766 to 787 of SEQ ID NO:3, nucleotides 767 to 788 of SEQ ID NO:3, nucleotides 768 to 789 of SEQ ID NO:3, nucleotides 769 to 790 of SEQ ID NO:3, nucleotides 770 to 791 of SEQ ID NO:3, and nucleotides 771 to 792 of SEQ ID NO:3.

A pool of siRNA of the invention derived from the *H. glycines* daf-21 gene of SEQ ID NO:3 may also comprise any combination of the RNA molecules having the specific 21 contiguous nucleotide sequences derived from SEQ ID NO:3 set forth above. Similarly, a pool of siRNA of the invention may comprise a multiplicity of RNA molecules having any 19 contiguous nucleotide sequences derived from SEQ ID NO:3, or a multiplicity of RNA molecules having any 20 contiguous nucleotide sequences derived from SEQ ID NO:3. Alternatively, the pool of the siRNA of the invention may comprise a multiplicity of RNA molecules having a combination of any 19, 20, and/or 21 contiguous nucleotide sequences derived from SEQ ID NO:3.

In another embodiment, a pool of siRNA of the invention derived from the *H. glycines* Y65B4BR.5a gene of SEQ ID NO:4 may comprise a multiplicity of RNA molecules which are selected from the group consisting of oligonucleotides substantially identical to nucleotides 1 to 21 of SEQ ID NO:4, nucleotides 2 to 23 of SEQ ID NO:4, nucleotides 3 to 24 of SEQ ID NO:4, nucleotides 4 to 25 of SEQ ID NO:4, nucleotides 5 to 26 of SEQ ID NO:4, nucleotides 6 to 27 of SEQ ID NO:4, nucleotides 7 to 28 of SEQ ID NO:4, nucleotides 8 to 29 of SEQ ID NO:4, nucleotides 9 to 30 of SEQ ID NO:4, nucleotides 10 to 31 of SEQ ID NO:4, nucleotides 11 to 32 of SEQ ID NO:4, nucleotides 12 to 33 of SEQ ID NO:4, nucleotides 13 to 34 of SEQ ID NO:4, nucleotides 14 to 35 of SEQ ID NO:4, nucleotides 15 to 36 of SEQ ID NO:4, nucleotides 16 to 37 of SEQ ID NO:4, nucleotides 17 to 38 of SEQ ID NO:4, nucleotides 18 to 39 of SEQ ID NO:4, nucleotides 19 to 40 of SEQ ID NO:4, nucleotides 20 to 41 of SEQ ID NO:4, nucleotides 21 to 42 of SEQ ID NO:4, nucleotides 22 to 43 of SEQ ID NO:4, nucleotides 23 to 44 of SEQ ID NO:4, nucleotides 24 to 45 of SEQ ID NO:4, nucleotides 25 to 46 of SEQ ID NO:4, nucleotides 26 to 47 of SEQ ID NO:4, nucleotides 27 to 48 of SEQ ID NO:4, nucleotides 28 to 49 of SEQ ID NO:4, nucleotides 29 to 50 of SEQ ID NO:4, nucleotides 30 to 51 of SEQ ID NO:4, nucleotides 31 to 52 of SEQ ID NO:4, nucleotides 32 to 53 of SEQ ID NO:4, nucleotides 33 to 54 of SEQ ID NO:4, nucleotides 34 to 55 of SEQ ID NO:4, nucleotides 35 to 56 of SEQ ID NO:4, nucleotides 36 to 57 of SEQ ID NO:4, nucleotides 37 to 58 of SEQ ID NO:4, nucleotides 38 to 59 of SEQ ID NO:4, nucleotides 39 to 60 of SEQ ID NO:4, nucleotides 40 to 61 of SEQ ID NO:4, nucleotides 41 to 62 of SEQ ID NO:4, nucleotides 42 to 63 of SEQ ID NO:4, nucleotides 43 to 64 of SEQ ID NO:4, nucleotides 44 to 65 of SEQ ID NO:4, nucleotides 45 to 66 of SEQ ID NO:4, nucleotides 46 to 67 of SEQ ID NO:4, nucleotides 47 to 68 of SEQ ID NO:4, nucleotides 48 to 69 of SEQ ID NO:4, nucleotides 49 to 70 of SEQ ID NO:4, and nucleotides 50 to 71 of SEQ ID NO:4.

As another example, a pool of siRNA of the invention derived from the *H. glycines* Y65B4BR.5a gene of SEQ ID NO:4 may comprise a multiplicity of RNA molecules selected from the group consisting of oligonucleotides substantially identical to nucleotides 51 to 72 of SEQ ID NO:4, nucleotides 52 to 73 of SEQ ID NO:4, nucleotides 53 to 74 of SEQ ID NO:4, nucleotides 54 to 75 of SEQ ID NO:4, nucleotides 55 to 76 of SEQ ID NO:4, nucleotides 56 to 77 of SEQ ID NO:4, nucleotides 57 to 78 of SEQ ID NO:4, nucleotides 58 to 79 of SEQ ID NO:4, nucleotides 59 to 80 of SEQ ID NO:4, nucleotides 60 to 81 of SEQ ID NO:4, nucleotides 61 to 82 of SEQ ID NO:4, nucleotides 62 to 83 of SEQ ID NO:4, nucleotides 63 to 84 of SEQ ID NO:4, nucleotides 64 to 85 of SEQ ID NO:4, nucleotides 65 to 86 of SEQ ID NO:4, nucleotides 66 to 87 of SEQ ID NO:4, nucleotides 67 to 88 of SEQ ID NO:4, nucleotides 68 to 89 of SEQ ID NO:4, nucleotides 69 to 90 of SEQ ID NO:4, nucleotides 70 to 91 of SEQ ID NO:4, nucleotides 71 to 92 of SEQ ID NO:4, nucleotides 72 to 93 of SEQ ID NO:4, nucleotides 73 to 94 of SEQ ID NO:4, nucleotides 74 to 95 of SEQ ID NO:4, nucleotides 75 to 96 of SEQ ID NO:4, nucleotides 76 to 97 of SEQ ID NO:4, nucleotides 77 to 98 of SEQ ID NO:4, nucleotides 78 to 99 of SEQ ID NO:4, nucleotides 79 to 100 of SEQ ID NO:4, nucleotides 80 to 101 of SEQ ID NO:4, nucleotides 81 to 102 of SEQ ID NO:4, nucleotides 82 to 103 of SEQ ID NO:4, nucleotides 83 to 104 of SEQ ID NO:4, nucleotides 84 to 105 of SEQ ID NO:4, nucleotides 85 to 106 of SEQ ID NO:4, nucleotides 86 to 107 of SEQ ID NO:4, nucleotides 87 to 108 of SEQ ID NO:4, nucleotides 88 to 109 of SEQ ID NO:4, nucleotides 89 to 110 of SEQ ID NO:4, nucleotides 90 to 111 of SEQ ID NO:4, nucleotides 91 to 112 of SEQ ID NO:4, nucleotides 92 to 113 of SEQ ID NO:4, nucleotides 93 to 114 of SEQ ID NO:4, nucleotides 94 to 115 of SEQ ID NO:4, nucleotides 95 to 116 of SEQ ID NO:4, nucleotides 96 to 117 of SEQ ID NO:4, nucleotides 97 to 118 of SEQ ID NO:4, nucleotides 98 to 119 of SEQ ID NO:4, nucleotides 99 to 120 of SEQ ID NO:4, and nucleotides 100 to 121 of SEQ ID NO:4.

As another example, a pool of siRNA of the invention derived from the *H. glycines* Y65B4BR.5a gene of SEQ ID NO:4 may comprise a multiplicity of RNA molecules selected from the group consisting of oligonucleotides substantially identical to nucleotides 101 to 122 of SEQ ID NO:4, nucleotides 102 to 123 of SEQ ID NO:4, nucleotides 103 to 124 of SEQ ID NO:4, nucleotides 104 to 125 of SEQ ID NO:4, nucleotides 105 to 126 of SEQ ID NO:4, nucleotides 106 to 127 of SEQ ID NO:4, nucleotides 107 to 128 of SEQ ID NO:4, nucleotides 108 to 129 of SEQ ID NO:4, nucleotides 109 to 130 of SEQ ID NO:4, nucleotides 110 to 131 of SEQ ID NO:4, nucleotides 111 to 132 of SEQ ID NO:4, nucleotides 112 to 133 of SEQ ID NO:4, nucleotides 113 to 134 of SEQ ID NO:4, nucleotides 114 to 135 of SEQ ID NO:4, nucleotides 115 to 136 of SEQ ID NO:4, nucleotides 116 to 137 of SEQ ID NO:4, nucleotides 117 to 138 of SEQ ID NO:4, nucleotides 118 to 139 of SEQ ID NO:4, nucleotides 119 to 140 of SEQ ID NO:4, nucleotides 120 to 141 of SEQ ID NO:4, nucleotides 121 to 142 of SEQ ID NO:4, nucleotides 122 to 143 of SEQ ID NO:4, nucleotides 123 to 144 of SEQ ID NO:4, nucleotides 124 to 145 of SEQ ID NO:4, nucleotides 125 to 146 of SEQ ID NO:4, nucleotides 126 to 147 of SEQ ID NO:4, nucleotides 127 to 148 of SEQ ID NO:4, nucleotides 128 to 149 of SEQ ID NO:4, nucleotides 129 to 150 of SEQ ID NO:4, nucleotides 130 to 151 of SEQ ID NO:4, nucleotides 131 to 152 of SEQ ID NO:4, nucleotides 132 to 153 of SEQ ID NO:4, nucleotides 133 to 154 of SEQ ID NO:4, nucleotides 134 to 155 of SEQ ID NO:4, nucleotides 135 to 156 of SEQ ID NO:4, nucleotides 136 to 157 of SEQ ID NO:4, nucleotides 137 to 158 of SEQ ID NO:4, nucleotides 138 to 159 of SEQ ID NO:4, nucleotides 139 to 160 of SEQ ID NO:4, nucleotides 140 to 161 of SEQ ID NO:4, nucleotides 141 to 162 of SEQ ID NO:4, nucleotides 142 to 163 of SEQ ID NO:4, nucleotides 143 to 164 of SEQ ID NO:4, nucleotides 144 to 165 of SEQ ID NO:4, nucleotides 145 to 166 of SEQ ID NO:4, nucleotides 146 to 167 of SEQ ID NO:4, nucleotides 147 to 168 of SEQ ID NO:4, nucleotides 148 to 169 of SEQ ID NO:4, nucleotides 149 to 170 of SEQ ID NO:4, and nucleotides 150 to 171 of SEQ ID NO:4.

As another example, a pool of siRNA of the invention derived from the *H. glycines* Y65B4BR.5a gene of SEQ ID NO:4 may comprise a multiplicity of RNA molecules selected from the group consisting of oligonucleotides substantially identical to nucleotides 151 to 172 of SEQ ID NO:4, nucleotides 152 to 173 of SEQ ID NO:4, nucleotides 153 to 174 of SEQ ID NO:4, nucleotides 154 to 175 of SEQ ID NO:4, nucleotides 155 to 176 of SEQ ID NO:4, nucleotides 156 to 177 of SEQ ID NO:4, nucleotides 157 to 178 of SEQ ID NO:4, nucleotides 158 to 179 of SEQ ID NO:4, nucleotides 159 to 180 of SEQ ID NO:4, nucleotides 160 to 181 of SEQ ID NO:4, nucleotides 161 to 182 of SEQ ID NO:4, nucleotides 162 to 183 of SEQ ID NO:4, nucleotides 163 to 184 of SEQ ID NO:4, nucleotides 164 to 185 of SEQ ID NO:4, nucleotides 165 to 186 of SEQ ID NO:4, nucleotides 166 to 187 of SEQ ID NO:4, nucleotides 167 to 188 of SEQ ID NO:4, nucleotides 168 to 189 of SEQ ID NO:4, nucleotides 169 to 190 of SEQ ID NO:4, nucleotides 170 to 191 of SEQ ID NO:4, nucleotides 171 to 192 of SEQ ID NO:4, nucleotides 172 to 193 of SEQ ID NO:4, nucleotides 173 to 194 of SEQ ID NO:4, nucleotides 174 to 195 of SEQ ID NO:4, nucleotides 175 to 196 of SEQ ID NO:4, nucleotides 176 to 197 of SEQ ID NO:4, nucleotides 177 to 198 of SEQ ID NO:4, nucleotides 178 to 199 of SEQ ID NO:4, nucleotides 179 to 200 of SEQ ID NO:4, nucleotides 180 to 201 of SEQ ID NO:4, nucleotides 181 to 202 of SEQ ID NO:4, nucleotides 182 to 203 of SEQ ID NO:4, nucleotides 183 to 204 of SEQ ID NO:4, nucleotides 184 to 205 of SEQ ID NO:4, nucleotides 185 to 206 of SEQ ID NO:4, nucleotides 186 to 207 of SEQ ID NO:4, nucleotides 187 to 208 of SEQ ID NO:4, nucleotides 188 to 209 of SEQ ID NO:4, nucleotides 189 to 210 of SEQ ID NO:4, nucleotides 190 to 211 of SEQ ID NO:4, nucleotides 191 to 212 of SEQ ID NO:4, nucleotides 192 to 213 of SEQ ID NO:4, nucleotides 193 to 214 of SEQ ID NO:4, nucleotides 194 to 215 of SEQ ID NO:4, nucleotides 195 to 216 of SEQ ID NO:4, nucleotides 196 to 217 of SEQ ID NO:4, nucleotides 197 to 218 of SEQ ID NO:4, nucleotides 198 to 219 of SEQ ID NO:4, nucleotides 199 to 220 of SEQ ID NO:4, and nucleotides 200 to 221 of SEQ ID NO:4.

As another example, a pool of siRNA of the invention derived from the *H. glycines* Y65B4BR.5a gene of SEQ ID NO:4 may comprise a multiplicity of RNA molecules selected from the group consisting of oligonucleotides substantially identical to nucleotides 201 to 222 of SEQ ID NO:4, nucleotides 202 to 223 of SEQ ID NO:4, nucleotides 203 to 224 of SEQ ID NO:4, nucleotides 204 to 225 of SEQ ID NO:4, nucleotides 205 to 226 of SEQ ID NO:4, nucleotides 206 to 227 of SEQ ID NO:4, nucleotides 207 to 228 of SEQ ID NO:4, nucleotides 208 to 229 of SEQ ID NO:4, nucleotides 209 to 230 of SEQ ID NO:4, nucleotides 210 to 231 of SEQ ID NO:4, nucleotides 211 to 232 of SEQ ID NO:4, nucleotides 212 to 233 of SEQ ID NO:4, nucleotides 213 to 234 of SEQ ID NO:4, nucleotides 214 to 235 of SEQ ID NO:4, nucleotides 215 to 236 of SEQ ID NO:4, nucleotides 216 to 237 of SEQ ID NO:4, nucleotides 217 to 238 of SEQ ID NO:4, nucleotides 218 to 239 of SEQ ID NO:4, nucleotides 219 to 240 of SEQ ID NO:4, nucleotides 220 to 241 of SEQ ID NO:4, nucleotides 221 to 242 of SEQ ID NO:4, nucleotides 222 to 243 of SEQ ID NO:4, nucleotides 223 to 244 of SEQ ID NO:4, nucleotides 224 to 245 of SEQ ID NO:4, nucleotides 225 to 246 of SEQ ID NO:4, nucleotides 226 to 247 of SEQ ID NO:4, nucleotides 227 to 248 of SEQ ID NO:4, nucleotides 228 to 249 of SEQ ID NO:4, nucleotides 229 to 250 of SEQ ID NO:4, nucleotides 230 to 251 of SEQ ID NO:4, nucleotides 231 to 252 of SEQ ID NO:4, nucleotides 232 to 253 of SEQ ID NO:4, nucleotides 233 to 254 of SEQ ID NO:4, nucleotides 234 to 255 of SEQ ID NO:4, nucleotides 235 to 256 of SEQ ID NO:4, nucleotides 236 to 257 of SEQ ID NO:4, nucleotides 237 to 258 of SEQ ID NO:4, nucleotides 238 to 259 of SEQ ID NO:4, nucleotides 239 to 260 of SEQ ID NO:4, nucleotides 240 to 261 of SEQ ID NO:4, nucleotides 241 to 262 of SEQ ID NO:4, nucleotides 242 to 263 of SEQ ID NO:4, nucleotides 243 to 264 of SEQ ID NO:4, nucleotides 244 to 265 of SEQ ID NO:4, nucleotides 245 to 266 of SEQ ID NO:4, nucleotides 246 to 267 of SEQ ID NO:4, nucleotides 247 to 268 of SEQ ID NO:4, nucleotides 248 to 269 of SEQ ID NO:4, nucleotides 249 to 270 of SEQ ID NO:4, and nucleotides 250 to 271 of SEQ ID NO:4.

As another example, a pool of siRNA of the invention derived from the *H. glycines* Y65B4BR.5a gene of SEQ ID NO:4 may comprise a multiplicity of RNA molecules selected from the group consisting of oligonucleotides substantially identical to nucleotides 251 to 272 of SEQ ID NO:4, nucleotides 252 to 273 of SEQ ID NO:4, nucleotides 253 to 274 of SEQ ID NO:4, nucleotides 254 to 275 of SEQ ID NO:4, nucleotides 255 to 276 of SEQ ID NO:4, nucleotides 256 to 277 of SEQ ID NO:4, nucleotides 257 to 278 of SEQ ID NO:4, nucleotides 258 to 279 of SEQ ID NO:4, nucleotides 259 to 280 of SEQ ID NO:4, nucleotides 260 to 281 of SEQ ID NO:4, nucleotides 261 to 282 of SEQ ID NO:4, nucleotides 262 to 283 of SEQ ID NO:4, nucleotides 263 to 284 of SEQ ID NO:4, nucleotides 264 to 285 of SEQ ID NO:4, nucleotides 265 to 286 of SEQ ID NO:4, nucleotides 266 to 287 of SEQ ID NO:4, nucleotides 267 to 288 of SEQ ID NO:4, nucleotides 268 to 289 of SEQ ID NO:4, nucleotides 269 to 290 of SEQ ID NO:4, nucleotides 270 to 291 of SEQ ID NO:4, nucleotides 271 to 292 of SEQ ID NO:4, nucleotides 272 to 293 of SEQ ID NO:4, nucleotides 273 to 294 of SEQ ID NO:4, nucleotides 274 to 295 of SEQ ID NO:4, nucleotides 275 to 296 of SEQ ID NO:4, nucleotides 276 to 297 of SEQ ID NO:4, nucleotides 277 to 298 of SEQ ID NO:4, nucleotides 278 to 299 of SEQ ID NO:4, nucleotides 279 to 300 of SEQ ID NO:4, nucleotides 280 to 301 of SEQ ID NO:4, nucleotides 281 to 302 of SEQ ID NO:4, nucleotides 282 to 303 of SEQ ID NO:4, nucleotides 283 to 304 of SEQ ID NO:4, nucleotides 284 to 305 of SEQ ID NO:4, nucleotides 285 to 306 of SEQ ID NO:4, nucleotides 286 to 307 of SEQ ID NO:4, nucleotides 287 to 308 of SEQ ID NO:4, nucleotides 288 to 309 of SEQ ID NO:4, nucleotides 289 to 310 of SEQ ID NO:4, nucleotides 290 to 311 of SEQ ID NO:4, nucleotides 291 to 312 of SEQ ID NO:4, nucleotides 292 to 313 of SEQ ID NO:4, nucleotides 293 to 314 of SEQ ID NO:4, nucleotides 294 to 315 of SEQ ID NO:4, nucleotides 295 to 316 of SEQ ID NO:4, nucleotides 296 to 317 of SEQ ID NO:4, nucleotides 297 to 318 of SEQ ID NO:4, nucleotides 298 to 319 of SEQ ID NO:4, nucleotides 299 to 320 of SEQ ID NO:4, and nucleotides 300 to 321 of SEQ ID NO:4.

As another example, a pool of siRNA of the invention derived from the *H. glycines* Y65B4BR.5a gene of SEQ ID NO:4 may comprise a multiplicity of RNA molecules selected from the group consisting of oligonucleotides substantially identical to nucleotides 301 to 322 of SEQ ID NO:4, nucleotides 302 to 323 of SEQ ID NO:4, nucleotides 303 to 324 of SEQ ID NO:4, nucleotides 304 to 325 of SEQ ID NO:4, nucleotides 305 to 326 of SEQ ID NO:4, nucleotides 306 to 327 of SEQ ID NO:4, nucleotides 307 to 328 of SEQ ID NO:4, nucleotides 308 to 329 of SEQ ID NO:4, nucleotides 309 to 330 of SEQ ID NO:4, nucleotides 310 to 331 of SEQ ID NO:4, nucleotides 311 to 332 of SEQ ID NO:4, nucleotides 312 to 333 of SEQ ID NO:4, nucleotides 313 to 334 of SEQ ID NO:4, nucleotides 314 to 335 of SEQ ID NO:4, nucleotides 315 to 336 of SEQ ID NO:4, nucleotides 316 to 337 of SEQ ID NO:4, nucleotides 317 to 338 of SEQ ID NO:4, nucleotides 318 to 339 of SEQ ID NO:4, nucleotides 319 to 340 of SEQ ID NO:4, nucleotides 320 to 341 of SEQ ID NO:4, nucleotides 321 to 342 of SEQ ID NO:4, nucleotides 322 to 343 of SEQ ID NO:4, nucleotides 323 to 344 of SEQ ID NO:4, nucleotides 324 to 345 of SEQ ID NO:4, nucleotides 325 to 346 of SEQ ID NO:4, nucleotides 326 to 347 of SEQ ID NO:4, nucleotides 327 to 348 of SEQ ID NO:4, nucleotides 328 to 349 of SEQ ID NO:4, nucleotides 329 to 350 of SEQ ID NO:4, nucleotides 330 to 351 of SEQ ID NO:4, nucleotides 331 to 352 of SEQ ID NO:4, nucleotides 332 to 353 of SEQ ID NO:4, nucleotides 333 to 354 of SEQ ID NO:4, nucleotides 334 to 355 of SEQ ID NO:4, nucleotides 335 to 356 of SEQ ID NO:4, nucleotides 336 to 357 of SEQ ID NO:4, nucleotides 337 to 358 of SEQ ID NO:4, nucleotides 338 to 359 of SEQ ID NO:4, nucleotides 339 to 360 of SEQ ID NO:4, nucleotides 340 to 361 of SEQ ID NO:4, nucleotides 341 to 362 of SEQ ID NO:4, nucleotides 342 to 363 of SEQ ID NO:4, nucleotides 343 to 364 of SEQ ID NO:4, nucleotides 344 to 365 of SEQ ID NO:4, nucleotides 345 to 366 of SEQ ID NO:4, nucleotides 346 to 367 of SEQ ID NO:4, nucleotides 347 to 368 of SEQ ID NO:4, nucleotides 348 to 369 of SEQ ID NO:4, nucleotides 349 to 370 of SEQ ID NO:4, and nucleotides 350 to 371 of SEQ ID NO:4.

As another example, a pool of siRNA of the invention derived from the *H. glycines* Y65B4BR.5a gene of SEQ ID NO:4 may comprise a multiplicity of RNA molecules selected from the group consisting of oligonucleotides substantially identical to nucleotides 351 to 372 of SEQ ID NO:4, nucleotides 352 to 373 of SEQ ID NO:4, nucleotides 353 to 374 of SEQ ID NO:4, nucleotides 354 to 375 of SEQ ID NO:4, nucleotides 355 to 376 of SEQ ID NO:4, nucleotides 356 to 377 of SEQ ID NO:4, nucleotides 357 to 378 of SEQ ID NO:4, nucleotides 358 to 379 of SEQ ID NO:4, nucleotides 359 to 380 of SEQ ID NO:4, nucleotides 360 to 381 of SEQ ID NO:4, nucleotides 361 to 382 of SEQ ID NO:4, nucleotides 362 to 383 of SEQ ID NO:4, nucleotides 363 to 384 of SEQ ID NO:4, nucleotides 364 to 385 of SEQ ID NO:4, nucleotides 365 to 386 of SEQ ID NO:4, nucleotides 366 to 387 of SEQ ID NO:4, nucleotides 367 to 388 of SEQ ID NO:4, nucleotides 368 to 389 of SEQ ID NO:4, nucleotides 369 to 390 of SEQ ID NO:4, nucleotides 370 to 391 of SEQ ID NO:4, nucleotides 371 to 392 of SEQ ID NO:4, nucleotides 372 to 393 of SEQ ID NO:4, nucleotides 373 to 394 of SEQ ID NO:4, nucleotides 374 to 395 of SEQ ID NO:4, nucleotides 375 to 396 of SEQ ID NO:4, nucleotides 376 to 397 of SEQ ID NO:4, nucleotides 377 to 398 of SEQ ID NO:4, nucleotides 378 to 399 of SEQ ID NO:4, nucleotides 379 to 400 of SEQ ID NO:4; nucleotides 380 to 401 of SEQ ID NO:4, nucleotides 381 to 402 of SEQ ID NO:4, nucleotides 382 to 403 of SEQ ID NO:4, nucleotides 383 to 404 of SEQ ID NO:4, nucleotides 384 to 405 of SEQ ID NO:4, nucleotides 385 to 406 of SEQ ID NO:4, nucleotides 386 to 407 of SEQ ID NO:4, nucleotides 387 to 408 of SEQ ID NO:4, nucleotides 388 to 409 of SEQ ID NO:4, nucleotides 389 to 410 of SEQ ID NO:4, nucleotides 390 to 411 of SEQ ID NO:4, nucleotides 391 to 412 of SEQ ID NO:4, nucleotides 392 to 413 of SEQ ID NO:4, nucleotides 393 to 414 of SEQ ID NO:4, nucleotides 394 to 415 of SEQ ID NO:4, nucleotides 395 to 416 of SEQ ID NO:4, nucleotides 396 to 417 of SEQ ID NO:4, nucleotides 397 to 418 of SEQ ID NO:4, nucleotides 398 to 419 of SEQ ID NO:4, nucleotides 399 to 420 of SEQ ID NO:4, and nucleotides 400 to 421 of SEQ ID NO:4.

As another example, a pool of siRNA of the invention derived from the *H. glycines* Y65B4BR.5a gene of SEQ ID NO:4 may comprise a multiplicity of RNA molecules selected from the group consisting of oligonucleotides substantially identical to nucleotides 401 to 422 of SEQ ID NO:4, nucleotides 402 to 423 of SEQ ID NO:4, nucleotides 403 to 424 of SEQ ID NO:4, nucleotides 404 to 425 of SEQ ID NO:4, nucleotides 405 to 426 of SEQ ID NO:4, nucleotides 406 to 427 of SEQ ID NO:4, nucleotides 407 to 428 of SEQ ID NO:4, nucleotides 408 to 429 of SEQ ID NO:4, nucleotides 409 to 430 of SEQ ID NO:4, nucleotides 410 to 431 of SEQ ID NO:4, nucleotides 411 to 432 of SEQ ID NO:4, nucleotides 412 to 433 of SEQ ID NO:4, nucleotides 413 to 434 of SEQ ID NO:4, nucleotides 414 to 435 of SEQ ID NO:4, nucleotides 415 to 436 of SEQ ID NO:4, nucleotides 416 to 430 of SEQ ID NO:4, nucleotides 417 to 438 of SEQ ID NO:4, nucleotides 418 to 439 of SEQ ID NO:4, nucleotides 419 to 440 of SEQ ID NO:4, nucleotides 420 to 441 of SEQ ID NO:4, nucleotides 421 to 442 of SEQ ID NO:4, nucleotides 422 to 443 of SEQ ID NO:4, nucleotides 423 to 444 of SEQ ID NO:4, nucleotides 424 to 445 of SEQ ID NO:4, nucleotides 425 to 446 of SEQ ID NO:4, nucleotides 426 to 447 of SEQ ID NO:4, nucleotides 427 to 448 of SEQ ID NO:4, nucleotides 428 to 449 of SEQ ID NO:4, nucleotides 429 to 450 of SEQ ID NO:4, nucleotides 430 to 451 of SEQ ID NO:4, nucleotides 431 to 452 of SEQ ID NO:4, nucleotides 432 to 453 of SEQ ID NO:4, nucleotides 433 to 454 of SEQ ID NO:4, nucleotides 434 to 455 of SEQ ID NO:4, nucleotides 435 to 456 of SEQ ID NO:4, nucleotides 436 to 457 of SEQ ID NO:4, nucleotides 437 to 458 of SEQ ID NO:4, nucleotides 438 to 459 of SEQ ID NO:4, nucleotides 439 to 460 of SEQ ID NO:4, nucleotides 440 to 461 of SEQ ID NO:4, nucleotides 441 to 462 of SEQ ID NO:4, nucleotides 442 to 463 of SEQ ID NO:4, nucleotides 443 to 464 of SEQ ID NO:4, nucleotides 444 to 465 of SEQ ID NO:4, nucleotides 445 to 466 of SEQ ID NO:4, nucleotides 446 to 467 of SEQ ID NO:4, nucleotides 447 to 468 of SEQ ID NO:4, nucleotides 448 to 469 of SEQ ID NO:4, nucleotides 449 to 470 of SEQ ID NO:4, and nucleotides 450 to 471 of SEQ ID NO:4.

As another example, a pool of siRNA of the invention derived from the *H. glycines* Y65B4BR.5a gene of SEQ ID NO:4 may comprise a multiplicity of RNA molecules selected from the group consisting of oligonucleotides substantially identical to nucleotides 451 to 472 of SEQ ID NO:4, nucleotides 452 to 473 of SEQ ID NO:4, nucleotides 453 to 474 of SEQ ID NO:4, nucleotides 454 to 475 of SEQ ID NO:4, nucleotides 455 to 476 of SEQ ID NO:4, nucleotides 456 to 477 of SEQ ID NO:4, nucleotides 457 to 478 of SEQ ID NO:4, nucleotides 458 to 479 of SEQ ID NO:4, nucleotides 459 to 480 of SEQ ID NO:4, nucleotides 460 to 481 of SEQ ID NO:4, nucleotides 461 to 482 of SEQ ID NO:4, nucleotides 462 to 483 of SEQ ID NO:4, nucleotides 463 to 484 of SEQ ID NO:4, nucleotides 464 to 485 of SEQ ID NO:4, nucleotides 465 to 486 of SEQ ID NO:4, nucleotides 466 to 487 of SEQ ID NO:4, nucleotides 467 to 488 of SEQ ID NO:4, nucleotides 468 to 489 of SEQ ID NO:4, nucleotides 469 to 490 of SEQ ID NO:4, nucleotides 470 to 491 of SEQ ID NO:4, nucleotides 471 to 492 of SEQ ID NO:4, nucleotides 472 to 493 of SEQ ID NO:4, nucleotides 473 to 494 of SEQ ID NO:4, nucleotides 474 to 495 of SEQ ID NO:4, nucleotides 475 to 496 of SEQ ID NO:4, nucleotides 476 to 497 of SEQ ID NO:4, nucleotides 477 to 498 of SEQ ID NO:4, nucleotides 478 to 499 of SEQ ID NO:4, nucleotides 479 to 500 of SEQ ID NO:4, nucleotides 480 to 501 of SEQ ID NO:4, nucleotides 481 to 502 of SEQ ID NO:4, nucleotides 482 to 503 of SEQ ID NO:4, nucleotides 483 to 504 of SEQ ID NO:4, nucleotides 484 to 505 of SEQ ID NO:4, nucleotides 485 to 506 of SEQ ID NO:4, nucleotides 486 to 507 of SEQ ID NO:4, nucleotides 487 to 508 of SEQ ID NO:4, nucleotides 488 to 509 of SEQ ID NO:4, nucleotides 489 to 510 of SEQ ID NO:4, nucleotides 490 to 511 of SEQ ID NO:4, nucleotides 491 to 512 of SEQ ID NO:4, nucleotides 492 to 513 of SEQ ID NO:4, nucleotides 493 to 514 of SEQ ID NO:4, nucleotides 494 to 515 of SEQ ID NO:4, nucleotides 495 to 516 of SEQ ID NO:4, nucleotides 496 to 517 of SEQ ID NO:4, nucleotides 497 to 518 of SEQ ID NO:4, nucleotides 498 to 519 of SEQ ID NO:4, nucleotides 499 to 520 of SEQ ID NO:4, and nucleotides 500 to 521 of SEQ ID NO:4.

As another example, a pool of siRNA of the invention derived from the *H. glycines* Y65B4BR.5a gene of SEQ ID NO:4 may comprise a multiplicity of RNA molecules selected from the group consisting of oligonucleotides substantially identical to nucleotides 501 to 522 of SEQ ID NO:4, nucleotides 502 to 523 of SEQ ID NO:4, nucleotides 503 to 524 of SEQ ID NO:4, nucleotides 504 to 525 of SEQ ID NO:4, nucleotides 505 to 526 of SEQ ID NO:4, nucleotides 506 to 527 of SEQ ID NO:4, nucleotides 507 to 528 of SEQ ID NO:4, nucleotides 508 to 529 of SEQ ID NO:4, nucleotides 509 to 530 of SEQ ID NO:4, nucleotides 510 to 531 of SEQ ID NO:4, nucleotides 511 to 532 of SEQ ID NO:4, nucleotides 512 to 533 of SEQ ID NO:4, nucleotides 513 to 534 of SEQ ID NO:4, nucleotides 514 to 535 of SEQ ID NO:4, nucleotides 515 to 536 of SEQ ID NO:4, nucleotides 516 to 537 of SEQ ID NO:4, nucleotides 517 to 538 of SEQ ID NO:4, nucleotides 518 to 539 of SEQ ID NO:4, nucleotides 519 to 540 of SEQ ID NO:4, nucleotides 520 to 541 of SEQ ID NO:4, nucleotides 521 to 542 of SEQ ID NO:4, nucleotides 522 to 543 of SEQ ID NO:4, nucleotides 523 to 544 of SEQ ID NO:4; nucleotides 524 to 545 of SEQ ID NO:4, nucleotides 525 to 546 of SEQ ID NO:4, nucleotides 526 to 547 of SEQ ID NO:4, nucleotides 527 to 548 of SEQ ID NO:4, nucleotides 528 to 549 of SEQ ID NO:4, nucleotides 529 to 550 of SEQ ID NO:4, nucleotides 530 to 551 of SEQ ID NO:4, nucleotides 531 to 552 of SEQ ID NO:4, nucleotides 532 to 553 of SEQ ID NO:4, nucleotides 533 to 554 of SEQ ID NO:4, nucleotides 534 to 555 of SEQ ID NO:4, nucleotides 535 to 556 of SEQ ID NO:4, nucleotides 536 to 557 of SEQ ID NO:4, nucleotides 537 to 558 of SEQ ID NO:4, nucleotides 538 to 559 of SEQ ID NO:4, nucleotides 539 to 560 of SEQ ID NO:4, nucleotides 540 to 561 of SEQ ID NO:4, nucleotides 541 to 562 of SEQ ID NO:4, nucleotides 542 to 563 of SEQ ID NO:4, nucleotides 543 to 564 of SEQ ID NO:4, nucleotides 544 to 565 of SEQ ID NO:4, nucleotides 545 to 566 of SEQ ID NO:4, nucleotides 546 to 567 of SEQ ID NO:4, nucleotides 547 to 568 of SEQ ID NO:4, nucleotides 548 to 569 of SEQ ID NO:4, nucleotides 549 to 570 of SEQ ID NO:4, and nucleotides 550 to 571 of SEQ ID NO:4.

As another example, a pool of siRNA of the invention derived from the *H. glycines* Y65B4BR.5a gene of SEQ ID NO:4 may comprise a multiplicity of RNA molecules selected from the group consisting of oligonucleotides substantially identical to nucleotides 551 to 572 of SEQ ID NO:4, nucleotides 552 to 573 of SEQ ID NO:4, nucleotides 553 to 574 of SEQ ID NO:4, nucleotides 554 to 575 of SEQ ID NO:4, nucleotides 555 to 576 of SEQ ID NO:4, nucleotides 556 to 577 of SEQ ID NO:4, nucleotides 557 to 578 of SEQ ID NO:4, nucleotides 558 to 579 of SEQ ID NO:4, nucleotides 559 to 580 of SEQ ID NO:4, nucleotides 560 to 581 of SEQ ID NO:4, nucleotides 561 to 582 of SEQ ID NO:4, nucleotides 562 to 583 of SEQ ID NO:4, nucleotides 563 to 584 of SEQ ID NO:4, nucleotides 564 to 585 of SEQ ID NO:4, nucleotides 565 to 586 of SEQ ID NO:4, nucleotides 566 to 587 of SEQ ID NO:4, nucleotides 567 to 588 of SEQ ID NO:4, nucleotides 568 to 589 of SEQ ID NO:4, nucleotides 569 to 590 of SEQ ID NO:4, nucleotides 570 to 591 of SEQ ID NO:4, nucleotides 571 to 592 of SEQ ID NO:4, nucleotides 572 to 593 of SEQ ID NO:4, nucleotides 573 to 594 of SEQ ID NO:4, nucleotides 574 to 595 of SEQ ID NO:4, nucleotides 575 to 596 of SEQ ID NO:4, nucleotides 576 to 597 of SEQ ID NO:4, nucleotides 577 to 598 of SEQ ID NO:4, nucleotides 578 to 599 of SEQ ID NO:4, nucleotides 579 to 600 of SEQ ID NO:4, nucleotides 580 to 601 of SEQ ID NO:4, nucleotides 581 to 602 of SEQ ID NO:4, nucleotides 582 to 603 of SEQ ID NO:4, nucleotides 583 to 604 of SEQ ID NO:4, nucleotides 584 to 605 of SEQ ID NO:4, nucleotides 585 to 606 of SEQ ID NO:4, nucleotides 586 to 607 of SEQ ID NO:4, nucleotides 587 to 608 of SEQ ID NO:4, nucleotides 588 to 609 of SEQ ID NO:4, nucleotides 589 to 610 of SEQ ID NO:4, nucleotides 590 to 611 of SEQ ID NO:4, nucleotides 591 to 612 of SEQ ID NO:4, nucleotides 592 to 613 of SEQ ID NO:4, nucleotides 593 to 614 of SEQ ID NO:4, nucleotides 594 to 615 of SEQ ID NO:4, nucleotides 595 to 616 of SEQ ID NO:4, nucleotides 596 to 617 of SEQ ID NO:4, nucleotides 597 to 618 of SEQ ID NO:4, nucleotides 598 to 619 of SEQ ID NO:4, nucleotides 599 to 620 of SEQ ID NO:4, and nucleotides 600 to 621 of SEQ ID NO:4.

As another example, a pool of siRNA of the invention derived from the *H. glycines* Y65B4BR.5a gene of SEQ ID NO:4 may comprise a multiplicity of RNA molecules selected from the group consisting of oligonucleotides substantially identical to nucleotides 601 to 622 of SEQ ID NO:4, nucleotides 602 to 623 of SEQ ID NO:4, nucleotides 603 to 624 of SEQ ID NO:4, nucleotides 604 to 625 of SEQ ID NO:4, nucleotides 605 to 626 of SEQ ID NO:4, nucleotides 606 to 627 of SEQ ID NO:4, nucleotides 607 to 628 of SEQ ID NO:4, nucleotides 608 to 629 of SEQ ID NO:4, nucleotides 609 to 630 of SEQ ID NO:4, nucleotides 610 to 631 of SEQ ID NO:4, nucleotides 611 to 632 of SEQ ID NO:4, nucleotides 612 to 633 of SEQ ID NO:4, nucleotides 613 to 634 of SEQ ID NO:4, nucleotides 614 to 635 of SEQ ID NO:4, nucleotides 615 to 636 of SEQ ID NO:4, nucleotides 616 to 637 of SEQ ID NO:4, nucleotides 617 to 638 of SEQ ID NO:4, nucleotides 618 to 639 of SEQ ID NO:4, nucleotides 619 to 640 of SEQ ID NO:4, nucleotides 620 to 641 of SEQ ID NO:4, nucleotides 621 to 642 of SEQ ID NO:4, nucleotides 622 to 643 of SEQ ID NO:4, nucleotides 623 to 644 of SEQ ID NO:4, nucleotides 624 to 645 of SEQ ID NO:4, nucleotides 625 to 646 of SEQ ID NO:4, nucleotides 626 to 647 of SEQ ID NO:4, nucleotides 627 to 648 of SEQ ID NO:4, nucleotides 628 to 649 of SEQ ID NO:4, nucleotides 629 to 650 of SEQ ID NO:4, nucleotides 630 to 651 of SEQ ID NO:4, nucleotides 631 to 652 of SEQ ID NO:4, nucleotides 632 to 653 of SEQ ID NO:4, nucleotides 633 to 654 of SEQ ID NO:4, nucleotides 634 to 655 of SEQ ID NO:4, nucleotides 635 to 656 of SEQ ID NO:4, nucleotides 636 to 657 of SEQ ID NO:4, nucleotides 637 to 658 of SEQ ID NO:4, nucleotides 638 to 659 of SEQ ID NO:4, nucleotides 639 to 660 of SEQ ID NO:4, nucleotides 640 to 661 of SEQ ID NO:4, nucleotides 641 to 662 of SEQ ID NO:4, nucleotides 642 to 663 of SEQ ID NO:4, nucleotides 643 to 664 of SEQ ID NO:4, nucleotides 644 to 665 of SEQ ID NO:4, nucleotides 645 to 666 of SEQ ID NO:4, nucleotides 646 to 667 of SEQ ID NO:4, nucleotides 647 to 668 of SEQ ID NO:4, nucleotides 648 to 669 of SEQ ID NO:4, nucleotides 649 to 670 of SEQ ID NO:4, and nucleotides 650 to 671 of SEQ ID NO:4.

As another example, a pool of siRNA of the invention derived from the *H. glycines* Y65B4BR.5a gene of SEQ ID NO:4 may comprise a multiplicity of RNA molecules selected from the group consisting of oligonucleotides substantially identical to nucleotides 651 to 672 of SEQ ID NO:4, nucleotides 652 to 673 of SEQ ID NO:4, nucleotides 653 to 674 of SEQ ID NO:4, nucleotides 654 to 675 of SEQ ID NO:4, nucleotides 655 to 676 of SEQ ID NO:4, nucleotides 656 to 677 of SEQ ID NO:4, nucleotides 657 to 678 of SEQ ID NO:4, nucleotides 658 to 679 of SEQ ID NO:4, nucleotides 659 to 680 of SEQ ID NO:4, nucleotides 660 to 681 of SEQ ID NO:4, nucleotides 661 to 682 of SEQ ID NO:4, nucleotides 662 to 683 of SEQ ID NO:4, nucleotides 663 to 684 of SEQ ID NO:4, nucleotides 664 to 685 of SEQ ID NO:4, nucleotides 665 to 686 of SEQ ID NO:4, nucleotides 666 to 687 of SEQ ID NO:4, nucleotides 667 to 688 of SEQ ID NO:4, nucleotides 668 to 689 of SEQ ID NO:4, nucleotides 669 to 690 of SEQ ID NO:4, nucleotides 670 to 691 of SEQ ID NO:4, nucleotides 671 to 692 of SEQ ID NO:4, nucleotides 672 to 693 of SEQ ID NO:4, nucleotides 673 to 694 of SEQ ID NO:4, nucleotides 674 to 695 of SEQ ID NO:4, nucleotides 675 to 696 of SEQ ID NO:4, nucleotides 676 to 697 of SEQ ID NO:4, nucleotides 677 to 698 of SEQ ID NO:4, nucleotides 678 to 699 of SEQ ID NO:4, nucleotides 679 to 700 of SEQ ID NO:4, nucleotides 680 to 701 of SEQ ID NO:4, nucleotides 681 to 702 of SEQ ID NO:4, nucleotides 682 to 703 of SEQ ID NO:4, nucleotides 683 to 704 of SEQ ID NO:4, nucleotides 684 to 705 of SEQ ID NO:4, nucleotides 685 to 706 of SEQ ID NO:4, nucleotides 686 to 707 of SEQ ID NO:4, nucleotides 687 to 708 of SEQ ID NO:4, nucleotides 688 to 709 of SEQ ID NO:4, nucleotides 689 to 710 of SEQ ID NO:4, nucleotides 690 to 711 of SEQ ID NO:4, nucleotides 691 to 712 of SEQ ID NO:4, nucleotides 692 to 713 of SEQ ID NO:4, nucleotides 693 to 714 of SEQ ID NO:4, nucleotides 694 to 715 of SEQ ID NO:4, nucleotides 695 to 716 of SEQ ID NO:4, nucleotides 696 to 717 of SEQ ID NO:4, nucleotides 697 to 718 of SEQ ID NO:4, nucleotides 698 to 719 of SEQ ID NO:4, nucleotides 699 to 720 of SEQ ID NO:4, and nucleotides 700 to 721 of SEQ ID NO:4.

As another example, a pool of siRNA of the invention derived from the *H. glycines* Y65B4BR.5a gene of SEQ ID NO:4 may comprise a multiplicity of RNA molecules selected from the group consisting of oligonucleotides substantially identical to nucleotides 701 to 722 of SEQ ID NO:4, nucleotides 702 to 723 of SEQ ID NO:4, nucleotides 703 to 724 of SEQ ID NO:4, nucleotides 704 to 725 of SEQ ID NO:4, nucleotides 705 to 726 of SEQ ID NO:4, nucleotides 706 to 727 of SEQ ID NO:4, nucleotides 707 to 728 of SEQ ID NO:4, nucleotides 708 to 729 of SEQ ID NO:4, nucleotides 709 to 730 of SEQ ID NO:4, nucleotides 710 to 731 of SEQ ID NO:4, nucleotides 711 to 732 of SEQ ID NO:4, nucleotides 712 to 733 of SEQ ID NO:4, nucleotides 713 to 734 of SEQ ID NO:4, nucleotides 714 to 735 of SEQ ID NO:4, nucleotides 715 to 736 of SEQ ID NO:4, nucleotides 716 to 737 of SEQ ID NO:4, nucleotides 717 to 738 of SEQ ID NO:4, nucleotides 718 to 739 of SEQ ID NO:4, nucleotides 719 to 740 of SEQ ID NO:4, nucleotides 720 to 741 of SEQ ID NO:4, nucleotides 721 to 742 of SEQ ID NO:4, nucleotides 722 to 743 of SEQ ID NO:4, nucleotides 723 to 744 of SEQ ID NO:4, nucleotides 724 to 745 of SEQ ID NO:4, nucleotides 725 to 746 of SEQ ID NO:4, nucleotides 726 to 747 of SEQ ID NO:4, nucleotides 727 to 748 of SEQ ID NO:4, nucleotides 728 to 749 of SEQ ID NO:4, nucleotides 729 to 750 of SEQ ID NO:4, nucleotides 730 to 751 of SEQ ID NO:4, nucleotides 731 to 752 of SEQ ID NO:4, nucleotides 732 to 753 of SEQ ID NO:4, nucleotides 733 to 754 of SEQ ID NO:4, nucleotides 734 to 755 of SEQ ID NO:4, nucleotides 735 to 756 of SEQ ID NO:4, nucleotides 736 to 757 of SEQ ID NO:4, nucleotides 737 to 758 of SEQ ID NO:4, nucleotides 738 to 759 of SEQ ID NO:4, nucleotides 739 to 760 of SEQ ID NO:4, nucleotides 740 to 761 of SEQ ID NO:4, nucleotides 741 to 762 of SEQ ID NO:4, nucleotides 742 to 763 of SEQ ID NO:4, nucleotides 743 to 764 of SEQ ID NO:4, nucleotides 744 to 765 of SEQ ID NO:4, nucleotides 745 to 766 of SEQ ID NO:4, nucleotides 746 to 767 of SEQ ID NO:4, nucleotides 747 to 768 of SEQ ID NO:4, nucleotides 748 to 769 of SEQ ID NO:4, nucleotides 749 to 770 of SEQ ID NO:4, and nucleotides 750 to 771 of SEQ ID NO:4.

As another example, a pool of siRNA of the invention derived from the *H. glycines* Y65B4BR.5a gene of SEQ ID NO:4 may comprise a multiplicity of RNA molecules selected from the group consisting of oligonucleotides substantially identical to nucleotides 751 to 772 of SEQ ID NO:4, nucleotides 752 to 773 of SEQ ID NO:4, nucleotides 753 to 774 of SEQ ID NO:4, nucleotides 754 to 775 of SEQ ID NO:4, nucleotides 755 to 776 of SEQ ID NO:4, nucleotides 756 to 777 of SEQ ID NO:4, nucleotides 757 to 778 of SEQ ID NO:4, nucleotides 758 to 779 of SEQ ID NO:4, nucleotides 759 to 780 of SEQ ID NO:4, nucleotides 760 to 781 of SEQ ID NO:4, nucleotides 761 to 782 of SEQ ID NO:4, nucleotides 762 to 783 of SEQ ID NO:4, nucleotides 763 to 784 of SEQ ID NO:4, nucleotides 764 to 785 of SEQ ID NO:4, nucleotides 765 to 786 of SEQ ID NO:4, nucleotides 766 to 787 of SEQ ID NO:4, nucleotides 767 to 788 of SEQ ID NO:4, nucleotides 768 to 789 of SEQ ID NO:4, nucleotides 769 to 790 of SEQ ID NO:4, nucleotides 770 to 791 of SEQ ID NO:4, nucleotides 771 to 792 of SEQ ID NO:4, nucleotides 772 to 793 of SEQ ID NO:4, nucleotides 773 to 794 of SEQ ID NO:4, nucleotides 774 to 795 of SEQ ID NO:4, nucleotides 775 to 796 of SEQ ID NO:4, nucleotides 776 to 797 of SEQ ID NO:4, nucleotides 777 to 798 of SEQ ID NO:4, nucleotides 778 to 799 of SEQ ID NO:4, nucleotides 779 to 800 of SEQ ID NO:4, nucleotides 780 to 801 of SEQ ID NO:4, nucleotides 781 to 802 of SEQ ID NO:4, nucleotides 782 to 803 of SEQ ID NO:4, nucleotides 783 to 804 of SEQ ID NO:4, and nucleotides 784 to 805 of SEQ ID NO:4.

A pool of siRNA of the invention derived from the *H. glycines* Y65B4BR.5A gene of SEQ ID NO:4 may also comprise any combination of RNA molecules having the specific 21 contiguous nucleotide sequences derived from SEQ ID NO:4 set forth above. Similarly, a pool of siRNA of the invention may comprise a multiplicity of RNA molecules having any 19 contiguous nucleotide sequences derived from SEQ ID NO:4, or a multiplicity of RNA molecules having any 20 contiguous nucleotide sequences derived from SEQ ID NO:4. Alternatively, the pool of the siRNA of the invention may comprise a multiplicity of RNA molecules having a combination of any 19, 20, and/or 21 contiguous nucleotide sequences derived from SEQ ID NO:4.

In another embodiment, a pool of siRNA of the invention derived from the *H. glycines* pat-10 gene of SEQ ID NO:5 may comprise a multiplicity of RNA molecules which are selected from the group consisting of oligonucleotides substantially identical to nucleotides 1 to 21 of SEQ ID NO:5, nucleotides 2 to 23 of SEQ ID NO:5, nucleotides 3 to 24 of SEQ ID NO:5, nucleotides 4 to 25 of SEQ ID NO:5, nucleotides 5 to 26 of SEQ ID NO:5, nucleotides 6 to 27 of SEQ ID NO:5, nucleotides 7 to 28 of SEQ ID NO:5, nucleotides 8 to 29 of SEQ ID NO:5, nucleotides 9 to 30 of SEQ ID NO:5, nucleotides 10 to 31 of SEQ ID NO:5, nucleotides 11 to 32 of SEQ ID NO:5, nucleotides 12 to 33 of SEQ ID NO:5, nucleotides 13 to 34 of SEQ ID NO:5, nucleotides 14 to 35 of SEQ ID NO:5, nucleotides 15 to 36 of SEQ ID NO:5, nucleotides 16 to 37 of SEQ ID NO:5, nucleotides 17 to 38 of SEQ ID NO:5, nucleotides 18 to 39 of SEQ ID NO:5, nucleotides 19 to 40 of SEQ ID NO:5, nucleotides 20 to 41 of SEQ ID NO:5, nucleotides 21 to 42 of SEQ ID NO:5, nucleotides 22 to 43 of SEQ ID NO:5, nucleotides 23 to 44 of SEQ ID NO:5, nucleotides 24 to 45 of SEQ ID NO:5, nucleotides 25 to 46 of SEQ ID NO:5, nucleotides 26 to 47 of SEQ ID NO:5, nucleotides 27 to 48 of SEQ ID NO:5, nucleotides 28 to 49 of SEQ ID NO:5, nucleotides 29 to 50 of SEQ ID NO:5, nucleotides 30 to 51 of SEQ ID NO:5, nucleotides 31 to 52 of SEQ ID NO:5, nucleotides 32 to 53 of SEQ ID NO:5, nucleotides 33 to 54 of SEQ ID NO:5, nucleotides 34 to 55 of SEQ ID NO:5, nucleotides 35 to 56 of SEQ ID NO:5, nucleotides 36 to 57 of SEQ ID NO:5, nucleotides 37 to 58 of SEQ ID NO:5, nucleotides 38 to 59 of SEQ ID NO:5, nucleotides 39 to 60 of SEQ ID NO:5, nucleotides 40 to 61 of SEQ ID NO:5, nucleotides 41 to 62 of SEQ ID NO:5, nucleotides 42 to 63 of SEQ ID NO:5, nucleotides 43 to 64 of SEQ ID NO:5, nucleotides 44 to 65 of SEQ ID NO:5, nucleotides 45 to 66 of SEQ ID NO:5, nucleotides 46 to 67 of SEQ ID NO:5, nucleotides 47 to 68 of SEQ ID NO:5, nucleotides 48 to 69 of SEQ ID NO:5, nucleotides 49 to 70 of SEQ ID NO:5, and nucleotides 50 to 71 of SEQ ID NO:5.

As another example, a pool of siRNA of the invention derived from the *H. glycines* pat-10 gene of SEQ ID NO:5 may comprise a multiplicity of RNA molecules selected from the group consisting of oligonucleotides substantially identical to nucleotides 51 to 72 of SEQ ID NO:5, nucleotides 52 to 73 of SEQ ID NO:5, nucleotides 53 to 74 of SEQ ID NO:5, nucleotides 54 to 75 of SEQ ID NO:5, nucleotides 55 to 76 of SEQ ID NO:5, nucleotides 56 to 77 of SEQ ID NO:5, nucleotides 57 to 78 of SEQ ID NO:5, nucleotides 58 to 79 of SEQ ID NO:5, nucleotides 59 to 80 of SEQ ID NO:5, nucleotides 60 to 81 of SEQ ID NO:5, nucleotides 61 to 82 of SEQ ID NO:5, nucleotides 62 to 83 of SEQ ID NO:5, nucleotides 63 to 84 of SEQ ID NO:5, nucleotides 64 to 85 of SEQ ID NO:5, nucleotides 65 to 86 of SEQ ID NO:5, nucleotides 66 to 87 of SEQ ID NO:5, nucleotides 67 to 88 of SEQ ID NO:5, nucleotides 68 to 89 of SEQ ID NO:5, nucleotides 69 to 90 of SEQ ID NO:5, nucleotides 70 to 91 of SEQ ID NO:5, nucleotides 71 to 92 of SEQ ID NO:5, nucleotides 72 to 93 of SEQ ID NO:5, nucleotides 73 to 94 of SEQ ID NO:5, nucleotides 74 to 95 of SEQ ID NO:5, nucleotides 75 to 96 of SEQ ID NO:5, nucleotides 76 to 97 of SEQ ID NO:5, nucleotides 77 to 98 of SEQ ID NO:5, nucleotides 78 to 99 of SEQ ID NO:5, nucleotides 79 to 100 of SEQ ID NO:5, nucleotides 80 to 101 of SEQ ID NO:5, nucleotides 81 to 102 of SEQ ID NO:5, nucleotides 82 to 103 of SEQ ID NO:5, nucleotides 83 to 104 of SEQ ID NO:5, nucleotides 84 to 105 of SEQ ID NO:5, nucleotides 85 to 106 of SEQ ID NO:5, nucleotides 86 to 107 of SEQ ID NO:5, nucleotides 87 to 108 of SEQ ID NO:5, nucleotides 88 to 109 of SEQ ID NO:5, nucleotides 89 to 110 of SEQ ID NO:5, nucleotides 90 to 111 of SEQ ID NO:5, nucleotides 91 to 112 of SEQ ID NO:5, nucleotides 92 to 113 of SEQ ID NO:5, nucleotides 93 to 114 of SEQ ID NO:5, nucleotides 94 to 115 of SEQ ID NO:5, nucleotides 95 to 116 of SEQ ID NO:5, nucleotides 96 to 117 of SEQ ID NO:5, nucleotides 97 to 118 of SEQ ID NO:5, nucleotides 98 to 119 of SEQ ID NO:5, nucleotides 99 to 120 of SEQ ID NO:5, and nucleotides 100 to 121 of SEQ ID NO:5.

As another example, a pool of siRNA of the invention derived from the *H. glycines* pat-10 gene of SEQ ID NO:5 may comprise a multiplicity of RNA molecules selected from the group consisting of oligonucleotides substantially identical to nucleotides 101 to 122 of SEQ ID NO:5, nucleotides 102 to 123 of SEQ ID NO:5, nucleotides 103 to 124 of SEQ ID NO:5, nucleotides 104 to 125 of SEQ ID NO:5, nucleotides 105 to 126 of SEQ ID NO:5, nucleotides 106 to 127 of SEQ ID NO:5, nucleotides 107 to 128 of SEQ ID NO:5, nucleotides 108 to 129 of SEQ ID NO:5, nucleotides 109 to 130 of SEQ ID NO:5, nucleotides 110 to 131 of SEQ ID NO:5, nucleotides 111 to 132 of SEQ ID NO:5, nucleotides 112 to 133 of SEQ ID NO:5, nucleotides 113 to 134 of SEQ ID NO:5, nucleotides 114 to 135 of SEQ ID NO:5, nucleotides 115 to 136 of SEQ ID NO:5, nucleotides 116 to 137 of SEQ ID NO:5, nucleotides 117 to 138 of SEQ ID NO:5, nucleotides 118 to 139 of SEQ ID NO:5, nucleotides 119 to 140 of SEQ ID NO:5, nucleotides 120 to 141 of SEQ ID NO:5, nucleotides 121 to 142 of SEQ ID NO:5, nucleotides 122 to 143 of SEQ ID NO:5, nucleotides 123 to 144 of SEQ ID NO:5, nucleotides 124 to 145 of SEQ ID NO:5, nucleotides 125 to 146 of SEQ ID NO:5, nucleotides 126 to 147 of SEQ ID NO:5, nucleotides 127 to 148 of SEQ ID NO:5, nucleotides 128 to 149 of SEQ ID NO:5, nucleotides 129 to 150 of SEQ ID NO:5, nucleotides 130 to 151 of SEQ ID NO:5, nucleotides 131 to 152 of SEQ ID NO:5, nucleotides 132 to 153 of SEQ ID NO:5, nucleotides 133 to 154 of SEQ ID NO:5, nucleotides 134 to 155 of SEQ ID NO:5, nucleotides 135 to 156 of SEQ ID NO:5, nucleotides 136 to 157 of SEQ ID NO:5, nucleotides 137 to 158 of SEQ ID NO:5, nucleotides 138 to 159 of SEQ ID NO:5, nucleotides 139 to 160 of SEQ ID NO:5, nucleotides 140 to 161 of SEQ ID NO:5, nucleotides 141 to 162 of SEQ ID NO:5, nucleotides 142 to 163 of SEQ ID NO:5, nucleotides 143 to 164 of SEQ ID NO:5, nucleotides 144 to 165 of SEQ ID NO:5, nucleotides 145 to 166 of SEQ ID NO:5, nucleotides 146 to 167 of SEQ ID NO:5, nucleotides 147 to 168 of SEQ ID NO:5, nucleotides 148 to 169 of SEQ ID NO:5, nucleotides 149 to 170 of SEQ ID NO:5, and nucleotides 150 to 171 of SEQ ID NO:5.

As another example, a pool of siRNA of the invention derived from the *H. glycines* pat-10 gene of SEQ ID NO:5 may comprise a multiplicity of RNA molecules selected from the group consisting of oligonucleotides substantially identical to nucleotides 151 to 172 of SEQ ID NO:5, nucleotides 152 to 173 of SEQ ID NO:5, nucleotides 153 to 174 of SEQ ID NO:5, nucleotides 154 to 175 of SEQ ID NO:5, nucleotides 155 to 176 of SEQ ID NO:5, nucleotides 156 to 177 of SEQ ID NO:5, nucleotides 157 to 178 of SEQ ID NO:5, nucleotides 158 to 179 of SEQ ID NO:5, nucleotides 159 to 180 of SEQ ID NO:5, nucleotides 160 to 181 of SEQ ID NO:5, nucleotides 161 to 182 of SEQ ID NO:5, nucleotides 162 to 183 of SEQ ID NO:5, nucleotides 163 to 184 of SEQ ID NO:5, nucleotides 164 to 185 of SEQ ID NO:5, nucleotides 165 to 186 of SEQ ID NO:5, nucleotides 166 to 187 of SEQ ID NO:5, nucleotides 167 to 188 of SEQ ID NO:5, nucleotides 168 to 189 of SEQ ID NO:5, nucleotides 169 to 190 of SEQ ID NO:5, nucleotides 170 to 191 of SEQ ID NO:5, nucleotides 171 to 192 of SEQ ID NO:5, nucleotides 172 to 193 of SEQ ID NO:5, nucleotides 173 to 194 of SEQ ID NO:5, nucleotides 174 to 195 of SEQ ID NO:5, nucleotides 175 to 196 of SEQ ID NO:5, nucleotides 176 to 197 of SEQ ID NO:5, nucleotides 177 to 198 of SEQ ID NO:5, nucleotides 178 to 199 of SEQ ID NO:5, nucleotides 179 to 200 of SEQ ID NO:5, nucleotides 180 to 201 of SEQ ID NO:5, nucleotides 181 to 202 of SEQ ID NO:5, nucleotides 182 to 203 of SEQ ID NO:5, nucleotides 183 to 204 of SEQ ID NO:5, nucleotides 184 to 205 of SEQ ID NO:5, nucleotides 185 to 206 of SEQ ID NO:5, nucleotides 186 to 207 of SEQ ID NO:5, nucleotides 187 to 208 of SEQ ID NO:5, nucleotides 188 to 209 of SEQ ID NO:5, nucleotides 189 to 210 of SEQ ID NO:5, nucleotides 190 to 211 of SEQ ID NO:5, nucleotides 191 to 212 of SEQ ID NO:5, nucleotides 192 to 213 of SEQ ID NO:5, nucleotides 193 to 214 of SEQ ID NO:5, nucleotides 194 to 215 of SEQ ID NO:5, nucleotides 195 to 216 of SEQ ID NO:5, nucleotides 196 to 217 of SEQ ID NO:5, nucleotides 197 to 218 of SEQ ID NO:5, nucleotides 198 to 219 of SEQ ID NO:5, nucleotides 199 to 220 of SEQ ID NO:5, and nucleotides 200 to 221 of SEQ ID NO:5.

As another example, a pool of siRNA of the invention derived from the *H. glycines* pat-10 gene of SEQ ID NO:5 may comprise a multiplicity of RNA molecules selected from the group consisting of oligonucleotides substantially identical to nucleotides 201 to 222 of SEQ ID NO:5, nucleotides 202 to 223 of SEQ ID NO:5, nucleotides 203 to 224 of SEQ ID NO:5, nucleotides 204 to 225 of SEQ ID NO:5, nucleotides 205 to 226 of SEQ ID NO:5, nucleotides 206 to 227 of SEQ ID NO:5, nucleotides 207 to 228 of SEQ ID NO:5, nucleotides 208 to 229 of SEQ ID NO:5, nucleotides 209 to 230 of SEQ ID NO:5, nucleotides 210 to 231 of SEQ ID NO:5, nucleotides 211 to 232 of SEQ ID NO:5, nucleotides 212 to 233 of SEQ ID NO:5, nucleotides 213 to 234 of SEQ ID NO:5, nucleotides 214 to 235 of SEQ ID NO:5, nucleotides 215 to 236 of SEQ ID NO:5, nucleotides 216 to 237 of SEQ ID NO:5, nucleotides 217 to 238 of SEQ ID NO:5, nucleotides 218 to 239 of SEQ ID NO:5, nucleotides 219 to 240 of SEQ ID NO:5, nucleotides 220 to 241 of SEQ ID NO:5, nucleotides 221 to 242 of SEQ ID NO:5, nucleotides 222 to 243 of SEQ ID NO:5, nucleotides 223 to 244 of SEQ ID NO:5, nucleotides 224 to 245 of SEQ ID NO:5, nucleotides 225 to 246 of SEQ ID NO:5, nucleotides 226 to 247 of SEQ ID NO:5, nucleotides 227 to 248 of SEQ ID NO:5, nucleotides 228 to 249 of SEQ ID NO:5, nucleotides 229 to 250 of SEQ ID NO:5, nucleotides 230 to 251 of SEQ ID NO:5, nucleotides 231 to 252 of SEQ ID NO:5, nucleotides 232 to 253 of SEQ ID NO:5, nucleotides 233 to 254 of SEQ ID NO:5, nucleotides 234 to 255 of SEQ ID NO:5, nucleotides 235 to 256 of SEQ ID NO:5, nucleotides 236 to 257 of SEQ ID NO:5, nucleotides 237 to 258 of SEQ ID NO:5, nucleotides 238 to 259 of SEQ ID NO:5, nucleotides 239 to 260 of SEQ ID NO:5, nucleotides 240 to 261 of SEQ ID NO:5, nucleotides 241 to 262 of SEQ ID NO:5, nucleotides 242 to 263 of SEQ ID NO:5, nucleotides 243 to 264 of SEQ ID NO:5, nucleotides 244 to 265 of SEQ ID NO:5, nucleotides 245 to 266 of SEQ ID NO:5, nucleotides 246 to 267 of SEQ ID NO:5, nucleotides 247 to 268 of SEQ ID NO:5, nucleotides 248 to 269 of SEQ ID NO:5, nucleotides 249 to 270 of SEQ ID NO:5, and nucleotides 250 to 271 of SEQ ID NO:5.

As another example, a pool of siRNA of the invention derived from the *H. glycines* pat-10 gene of SEQ ID NO:5 may comprise a multiplicity of RNA molecules selected from the group consisting of oligonucleotides substantially identical to nucleotides 251 to 272 of SEQ ID NO:5, nucleotides 252 to 273 of SEQ ID NO:5, nucleotides 253 to 274 of SEQ ID NO:5, nucleotides 254 to 275 of SEQ ID NO:5, nucleotides 255 to 276 of SEQ ID NO:5, nucleotides 256 to 277 of SEQ ID NO:5, nucleotides 257 to 278 of SEQ ID NO:5, nucleotides 258 to 279 of SEQ ID NO:5, nucleotides 259 to 280 of SEQ ID NO:5, nucleotides 260 to 281 of SEQ ID NO:5, nucleotides 261 to 282 of SEQ ID NO:5, nucleotides 262 to 283 of SEQ ID NO:5, nucleotides 263 to 284 of SEQ ID NO:5, nucleotides 264 to 285 of SEQ ID NO:5, nucleotides 265 to 286 of SEQ ID NO:5, nucleotides 266 to 287 of SEQ ID NO:5, nucleotides 267 to 288 of SEQ ID NO:5, nucleotides 268 to 289 of SEQ ID NO:5, nucleotides 269 to 290 of SEQ ID NO:5, nucleotides 270 to 291 of SEQ ID NO:5, nucleotides 271 to 292 of SEQ ID NO:5, nucleotides 272 to 293 of SEQ ID NO:5, nucleotides 273 to 294 of SEQ ID NO:5, nucleotides 274 to 295 of SEQ ID NO:5, nucleotides 275 to 296 of SEQ ID NO:5, nucleotides 276 to 297 of SEQ ID NO:5, nucleotides 277 to 298 of SEQ ID NO:5, nucleotides 278 to 299 of SEQ ID NO:5, nucleotides 279 to 300 of SEQ ID NO:5, nucleotides 280 to 301 of SEQ ID NO:5, nucleotides 281 to 302 of SEQ ID NO:5, nucleotides 282 to 303 of SEQ ID NO:5, nucleotides 283 to 304 of SEQ ID NO:5, nucleotides 284 to 305 of SEQ ID NO:5, nucleotides 285 to 306 of SEQ ID NO:5, nucleotides 286 to 307 of SEQ ID NO:5, nucleotides 287 to 308 of SEQ ID NO:5, nucleotides 288 to 309 of SEQ ID NO:5, nucleotides 289 to 310 of SEQ ID NO:5, nucleotides 290 to 311 of SEQ ID NO:5, nucleotides 291 to 312 of SEQ ID NO:5, nucleotides 292 to 313 of SEQ ID NO:5, nucleotides 293 to 314 of SEQ ID NO:5, nucleotides 294 to 315 of SEQ ID NO:5, nucleotides 295 to 316 of SEQ ID NO:5, nucleotides 296 to 317 of SEQ ID NO:5, nucleotides 297 to 318 of SEQ ID NO:5, nucleotides 298 to 319 of SEQ ID NO:5, nucleotides 299 to 320 of SEQ ID NO:5, and nucleotides 300 to 321 of SEQ ID NO:5.

As another example, a pool of siRNA of the invention derived from the *H. glycines* pat-10 gene of SEQ ID NO:5 may comprise a multiplicity of RNA molecules selected from the group consisting of oligonucleotides substantially identical to nucleotides 301 to 322 of SEQ ID NO:5, nucleotides 302 to 323 of SEQ ID NO:5, nucleotides 303 to 324 of SEQ ID NO:5, nucleotides 304 to 325 of SEQ ID NO:5, nucleotides 305 to 326 of SEQ ID NO:5, nucleotides 306 to 327 of SEQ ID NO:5, nucleotides 307 to 328 of SEQ ID NO:5, nucleotides 308 to 329 of SEQ ID NO:5, nucleotides 309 to 330 of SEQ ID NO:5, nucleotides 310 to 331 of SEQ ID NO:5, nucleotides 311 to 332 of SEQ ID NO:5, nucleotides 312 to 333 of SEQ ID NO:5, nucleotides 313 to 334 of SEQ ID NO:5, nucleotides 314 to 335 of SEQ ID NO:5, nucleotides 315 to 336 of SEQ ID NO:5, nucleotides 316 to 337 of SEQ ID NO:5, nucleotides 317 to 338 of SEQ ID NO:5, nucleotides 318 to 339 of SEQ ID NO:5, nucleotides 319 to 340 of SEQ ID NO:5, nucleotides 320 to 341 of SEQ ID NO:5, nucleotides 321 to 342 of SEQ ID NO:5, nucleotides 322 to 343 of SEQ ID NO:5, nucleotides 323 to 344 of SEQ ID NO:5, nucleotides 324 to 345 of SEQ ID NO:5, nucleotides 325 to 346 of SEQ ID NO:5, nucleotides 326 to 347 of SEQ ID NO:5, nucleotides 327 to 348 of SEQ ID NO:5, nucleotides 328 to 349 of SEQ ID NO:5, nucleotides 329 to 350 of SEQ ID NO:5, nucleotides 330 to 351 of SEQ ID NO:5, nucleotides 331 to 352 of SEQ ID NO:5, nucleotides 332 to 353 of SEQ ID NO:5, nucleotides 333 to 354 of SEQ ID NO:5, nucleotides 334 to 355 of SEQ ID NO:5, nucleotides 335 to 356 of SEQ ID NO:5, nucleotides 336 to 357 of SEQ ID NO:5, nucleotides 337 to 358 of SEQ ID NO:5, nucleotides 338 to 359 of SEQ ID NO:5, nucleotides 339 to 360 of SEQ ID NO:5, nucleotides 340 to 361 of SEQ ID NO:5, nucleotides 341 to 362 of SEQ ID NO:5, nucleotides 342 to 363 of SEQ ID NO:5, nucleotides 343 to 364 of SEQ ID NO:5, nucleotides 344 to 365 of SEQ ID NO:5, nucleotides 345 to 366 of SEQ ID NO:5, nucleotides 346 to 367 of SEQ ID NO:5, nucleotides 347 to 368 of SEQ ID NO:5, nucleotides 348 to 369 of SEQ ID NO:5, nucleotides 349 to 370 of SEQ ID NO:5, and nucleotides 350 to 371 of SEQ ID NO:5.

As another example, a pool of siRNA of the invention derived from the *H. glycines* pat-10 gene of SEQ ID NO:5 may comprise a multiplicity of RNA molecules selected from the group consisting of oligonucleotides substantially identical to nucleotides 351 to 372 of SEQ ID NO:5, nucleotides 352 to 373 of SEQ ID NO:5, nucleotides 353 to 374 of SEQ ID NO:5, nucleotides 354 to 375 of SEQ ID NO:5, nucleotides 355 to 376 of SEQ ID NO:5, nucleotides 356 to 377 of SEQ ID NO:5, nucleotides 357 to 378 of SEQ ID NO:5, nucleotides 358 to 379 of SEQ ID NO:5, nucleotides 359 to 380 of SEQ ID NO:5, nucleotides 360 to 381 of SEQ ID NO:5, nucleotides 361 to 382 of SEQ ID NO:5, nucleotides 362 to 383 of SEQ ID NO:5, nucleotides 363 to 384 of SEQ ID NO:5, nucleotides 364 to 385 of SEQ ID NO:5, nucleotides 365 to 386 of SEQ ID NO:5, nucleotides 366 to 387 of SEQ ID NO:5, nucleotides 367 to 388 of SEQ ID NO:5, nucleotides 368 to 389 of SEQ ID NO:5, nucleotides 369 to 390 of SEQ ID NO:5, nucleotides 370 to 391 of SEQ ID NO:5, nucleotides 371 to 392 of SEQ ID NO:5, nucleotides 372 to 393 of SEQ ID NO:5, nucleotides 373 to 394 of SEQ ID NO:5, nucleotides 374 to 395 of SEQ ID NO:5, nucleotides 375 to 396 of SEQ ID NO:5, nucleotides 376 to 397 of SEQ ID NO:5, nucleotides 377 to 398 of SEQ ID NO:5, nucleotides 378 to 399 of SEQ ID NO:5, nucleotides 379 to 400 of SEQ ID NO:5; nucleotides 380 to 401 of SEQ ID NO:5, nucleotides 381 to 402 of SEQ ID NO:5, nucleotides 382 to 403 of SEQ ID NO:5, nucleotides 383 to 404 of SEQ ID NO:5, nucleotides 384 to 405 of SEQ ID NO:5, nucleotides 385 to 406 of SEQ ID NO:5, nucleotides 386 to 407 of SEQ ID NO:5, nucleotides 387 to 408 of SEQ ID NO:5, nucleotides 388 to 409 of SEQ ID NO:5, nucleotides 389 to 410 of SEQ ID NO:5, nucleotides 390 to 411 of SEQ ID NO:5, nucleotides 391 to 412 of SEQ ID NO:5, nucleotides 392 to 413 of SEQ ID NO:5, nucleotides 393 to 414 of SEQ ID NO:5, nucleotides 394 to 415 of SEQ ID NO:5, nucleotides 395 to 416 of SEQ ID NO:5, nucleotides 396 to 417 of SEQ ID NO:5, nucleotides 397 to 418 of SEQ ID NO:5, nucleotides 398 to 419 of SEQ ID NO:5, nucleotides 399 to 420 of SEQ ID NO:5, and nucleotides 400 to 421 of SEQ ID NO:5.

As another example, a pool of siRNA of the invention derived from the *H. glycines* pat-10 gene of SEQ ID NO:5 may comprise a multiplicity of RNA molecules selected from the group consisting of oligonucleotides substantially identical to nucleotides 401 to 422 of SEQ ID NO:5, nucleotides 402 to 423 of SEQ ID NO:5, nucleotides 403 to 424 of SEQ ID NO:5, nucleotides 404 to 425 of SEQ ID NO:5, nucleotides 405 to 426 of SEQ ID NO:5, nucleotides 406 to 427 of SEQ ID NO:5, nucleotides 407 to 428 of SEQ ID NO:5, nucleotides 408 to 429 of SEQ ID NO:5, nucleotides 409 to 430 of SEQ ID NO:5, nucleotides 410 to 431 of SEQ ID NO:5, nucleotides 411 to 432 of SEQ ID NO:5, nucleotides 412 to 433 of SEQ ID NO:5, nucleotides 413 to 434 of SEQ ID NO:5, nucleotides 414 to 435 of SEQ ID NO:5, nucleotides 415 to 436 of SEQ ID NO:5, nucleotides 416 to 437 of SEQ ID NO:5, nucleotides 417 to 438 of SEQ ID NO:5, nucleotides 418 to 439 of SEQ ID NO:5, nucleotides 419 to 440 of SEQ ID NO:5, nucleotides 420 to 441 of SEQ ID NO:5, nucleotides 421 to 442 of SEQ ID NO:5, nucleotides 422 to 443 of SEQ ID NO:5, nucleotides 423 to 444 of SEQ ID NO:5, nucleotides 424 to 445 of SEQ ID NO:5, nucleotides 425 to 446 of SEQ ID NO:5, nucleotides 426 to 447 of SEQ ID NO:5, nucleotides 427 to 448 of SEQ ID NO:5, nucleotides 428 to 449 of SEQ ID NO:5, nucleotides 429 to 450 of SEQ ID NO:5, nucleotides 430 to 451 of SEQ ID NO:5, nucleotides 431 to 452 of SEQ ID NO:5, nucleotides 432 to 453 of SEQ ID NO:5, nucleotides 433 to 454 of SEQ ID NO:5, nucleotides 434 to 455 of SEQ ID NO:5, nucleotides 435 to 456 of SEQ ID NO:5, nucleotides 436 to 457 of SEQ ID NO:5, nucleotides 437 to 458 of SEQ ID NO:5, nucleotides 438 to 459 of SEQ ID NO:5, nucleotides 439 to 460 of SEQ ID NO:5, nucleotides 440 to 461 of SEQ ID NO:5, nucleotides 441 to 462 of SEQ ID NO:5, nucleotides 442 to 463 of SEQ ID NO:5, nucleotides 443 to 464 of SEQ ID NO:5, nucleotides 444 to 465 of SEQ ID NO:5, nucleotides 445 to 466 of SEQ ID NO:5, nucleotides 446 to 467 of SEQ ID NO:5, nucleotides 447 to 468 of SEQ ID NO:5, nucleotides 448 to 469 of SEQ ID NO:5, nucleotides 449 to 470 of SEQ ID NO:5, and nucleotides 450 to 471 of SEQ ID NO:5.

As another example, a pool of siRNA of the invention derived from the *H. glycines* pat-10 gene of SEQ ID NO:5 may comprise a multiplicity of RNA molecules selected from the group consisting of oligonucleotides substantially identical to nucleotides 451 to 472 of SEQ ID NO:5, nucleotides 452 to 473 of SEQ ID NO:5, nucleotides 453 to 474 of SEQ ID NO:5, nucleotides 454 to 475 of SEQ ID NO:5, nucleotides 455 to 476 of SEQ ID NO:5, nucleotides 456 to 477 of SEQ ID NO:5, nucleotides 457 to 478 of SEQ ID NO:5, nucleotides 458 to 479 of SEQ ID NO:5, nucleotides 459 to 480 of SEQ ID NO:5, nucleotides 460 to 481 of SEQ ID NO:5, nucleotides 461 to 482 of SEQ ID NO:5, nucleotides 462 to 483 of SEQ ID NO:5, nucleotides 463 to 484 of SEQ ID NO:5, nucleotides 464 to 485 of SEQ ID NO:5, nucleotides 465 to 486 of SEQ ID NO:5, nucleotides 466 to 487 of SEQ ID NO:5, nucleotides 467 to 488 of SEQ ID NO:5, nucleotides 468 to 489 of SEQ ID NO:5, nucleotides 469 to 490 of SEQ ID NO:5, nucleotides 470 to 491 of SEQ ID NO:5, nucleotides 471 to 492 of SEQ ID NO:5, nucleotides 472 to 493 of SEQ ID NO:5, nucleotides 473 to 494 of SEQ ID NO:5, nucleotides 474 to 495 of SEQ ID NO:5, nucleotides 475 to 496 of SEQ ID NO:5, nucleotides 476 to 497 of SEQ ID NO:5, nucleotides 477 to 498 of SEQ ID NO:5, nucleotides 478 to 499 of SEQ ID NO:5, nucleotides 479 to 500 of SEQ ID NO:5, nucleotides 480 to 501 of SEQ ID NO:5, nucleotides 481 to 502 of SEQ ID NO:5, nucleotides 482 to 503 of SEQ ID NO:5, nucleotides 483 to 504 of SEQ ID NO:5, nucleotides 484 to 505 of SEQ ID NO:5, nucleotides 485 to 506 of SEQ ID NO:5, nucleotides 486 to 507 of SEQ ID NO:5, nucleotides 487 to 508 of SEQ ID NO:5, nucleotides 488 to 509 of SEQ ID NO:5, nucleotides 489 to 510 of SEQ ID NO:5, nucleotides 490 to 511 of SEQ ID NO:5, nucleotides 491 to 512 of SEQ ID NO:5, nucleotides 492 to 513 of SEQ ID NO:5, nucleotides 493 to 514 of SEQ ID NO:5, nucleotides 494 to 515 of SEQ ID NO:5, nucleotides 495 to 516 of SEQ ID NO:5, nucleotides 496 to 517 of SEQ ID NO:5, nucleotides 497 to 518 of SEQ ID NO:5, nucleotides 498 to 519 of SEQ ID NO:5, nucleotides 499 to 520 of SEQ ID NO:5, and nucleotides 500 to 521 of SEQ ID NO:5.

As another example, a pool of siRNA of the invention derived from the *H. glycines* pat-10 gene of SEQ ID NO:5 may comprise a multiplicity of RNA molecules selected from the group consisting of oligonucleotides substantially identical to nucleotides 501 to 522 of SEQ ID NO:5, nucleotides 502 to 523 of SEQ ID NO:5, nucleotides 503 to 524 of SEQ ID NO:5, nucleotides 504 to 525 of SEQ ID NO:5, nucleotides 505 to 526 of SEQ ID NO:5, nucleotides 506 to 527 of SEQ ID NO:5, nucleotides 507 to 528 of SEQ ID NO:5, nucleotides 508 to 529 of SEQ ID NO:5, nucleotides 509 to 530 of SEQ ID NO:5, nucleotides 510 to 531 of SEQ ID NO:5, nucleotides 511 to 532 of SEQ ID NO:5, nucleotides 512 to 533 of SEQ ID NO:5, nucleotides 513 to 534 of SEQ ID NO:5, nucleotides 514 to 535 of SEQ ID NO:5, nucleotides 515 to 536 of SEQ ID NO:5, nucleotides 516 to 537 of SEQ ID NO:5, nucleotides 517 to 538 of SEQ ID NO:5, nucleotides 518 to 539 of SEQ ID NO:5, nucleotides 519 to 540 of SEQ ID NO:5, nucleotides 520 to 541 of SEQ ID NO:5, nucleotides 521 to 542 of SEQ ID NO:5, nucleotides 522 to 543 of SEQ ID NO:5, nucleotides 523 to 544 of SEQ ID NO:5; nucleotides 524 to 545 of SEQ ID NO:5, nucleotides 525 to 546 of SEQ ID NO:5, nucleotides 526 to 547 of SEQ ID NO:5, nucleotides 527 to 548 of SEQ ID NO:5, nucleotides 528 to 549 of SEQ ID NO:5, nucleotides 529 to 550 of SEQ ID NO:5, nucleotides 530 to 551 of SEQ ID NO:5, nucleotides 531 to 552 of SEQ ID NO:5, nucleotides 532 to 553 of SEQ ID NO:5, nucleotides 533 to 554 of SEQ ID NO:5, nucleotides 534 to 555 of SEQ ID NO:5, nucleotides 535 to 556 of SEQ ID NO:5, nucleotides 536 to 557 of SEQ ID NO:5, nucleotides 537 to 558 of SEQ ID NO:5, nucleotides 538 to 559 of SEQ ID NO:5, nucleotides 539 to 560 of SEQ ID NO:5, nucleotides 540 to 561 of SEQ ID NO:5, nucleotides 541 to 562 of SEQ ID NO:5, nucleotides 542 to 563 of SEQ ID NO:5, nucleotides 543 to 564 of SEQ ID NO:5, nucleotides 544 to 565 of SEQ ID NO:5, nucleotides 545 to 566 of SEQ ID NO:5, nucleotides 546 to 567 of SEQ ID NO:5, nucleotides 547 to 568 of SEQ ID NO:5, nucleotides 548 to 569 of SEQ ID NO:5, nucleotides 549 to 570 of SEQ ID NO:5, and nucleotides 550 to 571 of SEQ ID NO:5.

As another example, a pool of siRNA of the invention derived from the *H. glycines* pat-10 gene of SEQ ID NO:5 may comprise a multiplicity of RNA molecules selected from the group consisting of oligonucleotides substantially identical to nucleotides 551 to 572 of SEQ ID NO:5, nucleotides 552 to 573 of SEQ ID NO:5, nucleotides 553 to 574 of SEQ ID NO:5, nucleotides 554 to 575 of SEQ ID NO:5, nucleotides 555 to 576 of SEQ ID NO:5, nucleotides 556 to 577 of SEQ ID NO:5, nucleotides 557 to 578 of SEQ ID NO:5, nucleotides 558 to 579 of SEQ ID NO:5, nucleotides 559 to 580 of SEQ ID NO:5, nucleotides 560 to 581 of SEQ ID NO:5, nucleotides 561 to 582 of SEQ ID NO:5, nucleotides 562 to 583 of SEQ ID NO:5, nucleotides 563 to 584 of SEQ ID NO:5, nucleotides 564 to 585 of SEQ ID NO:5, nucleotides 565 to 586 of SEQ ID NO:5, nucleotides 566 to 587 of SEQ ID NO:5, nucleotides 567 to 588 of SEQ ID NO:5, nucleotides 568 to 589 of SEQ ID NO:5, nucleotides 569 to 590 of SEQ ID NO:5, nucleotides 570 to 591 of SEQ ID NO:5, nucleotides 571 to 592 of SEQ ID NO:5, nucleotides 572 to 593 of SEQ ID NO:5, nucleotides 573 to 594 of SEQ ID NO:5, nucleotides 574 to 595 of SEQ ID NO:5, nucleotides 575 to 596 of SEQ ID NO:5, nucleotides 576 to 597 of SEQ ID NO:5, nucleotides 577 to 598 of SEQ ID NO:5, nucleotides 578 to 599 of SEQ ID NO:5, nucleotides 579 to 600 of SEQ ID NO:5, nucleotides 580 to 601 of SEQ ID NO:5, nucleotides 581 to 602 of SEQ ID NO:5, nucleotides 582 to 603 of SEQ ID NO:5, nucleotides 583 to 604 of SEQ ID NO:5, nucleotides 584 to 605 of SEQ ID NO:5, nucleotides 585 to 606 of SEQ ID NO:5, nucleotides 586 to 607 of SEQ ID NO:5, nucleotides 587 to 608 of SEQ ID NO:5, nucleotides 588 to 609 of SEQ ID NO:5, nucleotides 589 to 610 of SEQ ID NO:5, nucleotides 590 to 611 of SEQ ID NO:5, nucleotides 591 to 612 of SEQ ID NO:5, nucleotides 592 to 613 of SEQ ID NO:5, nucleotides 593 to 614 of SEQ ID NO:5, nucleotides 594 to 615 of SEQ ID NO:5, nucleotides 595 to 616 of SEQ ID NO:5, nucleotides 596 to 617 of SEQ ID NO:5, nucleotides 597 to 618 of SEQ ID NO:5, nucleotides 598 to 619 of SEQ ID NO:5, nucleotides 599 to 620 of SEQ ID NO:5, and nucleotides 600 to 621 of SEQ ID NO:5.

As another example, a pool of siRNA of the invention derived from the *H. glycines* pat-10 gene of SEQ ID NO:5 may comprise a multiplicity of RNA molecules selected from the group consisting of oligonucleotides substantially identical to nucleotides 601 to 622 of SEQ ID NO:5, nucleotides 602 to 623 of SEQ ID NO:5, nucleotides 603 to 624 of SEQ ID NO:5, nucleotides 604 to 625 of SEQ ID NO:5, nucleotides 605 to 626 of SEQ ID NO:5, nucleotides 606 to 627 of SEQ ID NO:5, nucleotides 607 to 628 of SEQ ID NO:5, nucleotides 608 to 629 of SEQ ID NO:5, nucleotides 609 to 630 of SEQ ID NO:5, nucleotides 610 to 631 of SEQ ID NO:5, nucleotides 611 to 632 of SEQ ID NO:5, nucleotides 612 to 633 of SEQ ID NO:5, nucleotides 613 to 634 of SEQ ID NO:5, nucleotides 614 to 635 of SEQ ID NO:5, nucleotides 615 to 636 of SEQ ID NO:5, nucleotides 616 to 637 of SEQ ID NO:5, nucleotides 617 to 638 of SEQ ID NO:5, nucleotides 618 to 639 of SEQ ID NO:5, nucleotides 619 to 640 of SEQ ID NO:5, nucleotides 620 to 641 of SEQ ID NO:5, nucleotides 621 to 642 of SEQ ID NO:5, nucleotides 622 to 643 of SEQ ID NO:5, nucleotides 623 to 644 of SEQ ID NO:5, nucleotides 624 to 645 of SEQ ID NO:5, nucleotides 625 to 646 of SEQ ID NO:5, nucleotides 626 to 647 of SEQ ID NO:5, nucleotides 627 to 648 of SEQ ID NO:5, nucleotides 628 to 649 of SEQ ID NO:5, nucleotides 629 to 650 of SEQ ID NO:5, nucleotides 630 to 651 of SEQ ID NO:5, nucleotides 631 to 652 of SEQ ID NO:5, nucleotides 632 to 653 of SEQ ID NO:5, nucleotides 633 to 654 of SEQ ID NO:5, nucleotides 634 to 655 of SEQ ID NO:5, nucleotides 635 to 656 of SEQ ID NO:5, nucleotides 636 to 657 of SEQ ID NO:5, nucleotides 637 to 658 of SEQ ID NO:5, nucleotides 638 to 659 of SEQ ID NO:5, nucleotides 639 to 660 of SEQ ID NO:5, nucleotides 640 to 661 of SEQ ID NO:5, nucleotides 641 to 662 of SEQ ID NO:5, nucleotides 642 to 663 of SEQ ID NO:5, nucleotides 643 to 664 of SEQ ID NO:5, nucleotides 644 to 665 of SEQ ID NO:5, nucleotides 645 to 666 of SEQ ID NO:5, nucleotides 646 to 667 of SEQ ID NO:5, nucleotides 647 to 668 of SEQ ID NO:5, nucleotides 648 to 669 of SEQ ID NO:5, nucleotides 649 to 670 of SEQ ID NO:5, and nucleotides 650 to 671 of SEQ ID NO:5.

As another example, a pool of siRNA of the invention derived from the *H. glycines* pat-10 gene of SEQ ID NO:5 may comprise a multiplicity of RNA molecules selected from the group consisting of oligonucleotides substantially identical to nucleotides 651 to 672 of SEQ ID NO:5, nucleotides 652 to 673 of SEQ ID NO:5, nucleotides 653 to 674 of SEQ ID NO:5, nucleotides 654 to 675 of SEQ ID NO:5, nucleotides 655 to 676 of SEQ ID NO:5, nucleotides 656 to 677 of SEQ ID NO:5, nucleotides 657 to 678 of SEQ ID NO:5, nucleotides 658 to 679 of SEQ ID NO:5, nucleotides 659 to 680 of SEQ ID NO:5, nucleotides 660 to 681 of SEQ ID NO:5, nucleotides 661 to 682 of SEQ ID NO:5, nucleotides 662 to 683 of SEQ ID NO:5, nucleotides 663 to 684 of SEQ ID NO:5, nucleotides 664 to 685 of SEQ ID NO:5, nucleotides 665 to 686 of SEQ ID NO:5, nucleotides 666 to 687 of SEQ ID NO:5, nucleotides 667 to 688 of SEQ ID NO:5, nucleotides 668 to 689 of SEQ ID NO:5, nucleotides 669 to 690 of SEQ ID NO:5, nucleotides 670 to 691 of SEQ ID NO:5, nucleotides 671 to 692 of SEQ ID NO:5, nucleotides 672 to 693 of SEQ ID NO:5, nucleotides 673 to 694 of SEQ ID NO:5, nucleotides 674 to 695 of SEQ ID NO:5, nucleotides 675 to 696 of SEQ ID NO:5, nucleotides 676 to 697 of SEQ ID NO:5, nucleotides 677 to 698 of SEQ ID NO:5, nucleotides 678 to 699 of SEQ ID NO:5, nucleotides 679 to 700 of SEQ ID NO:5, and nucleotides 680 to 701 of SEQ ID NO:5.

A pool of siRNA of the invention derived from the *H. glycines* pat-10 gene of SEQ ID NO:5 may also comprise any combination of the RNA molecules having the specific 21 contiguous nucleotide sequences derived from SEQ ID NO:5 set forth above. Similarly, a pool of siRNA of the invention may comprise a multiplicity of RNA molecules having any 19 contiguous nucleotide sequences derived from SEQ ID NO:5, or a multiplicity of RNA molecules having any 20 contiguous nucleotide sequences derived from SEQ ID NO:5. Alternatively, the pool of the siRNA of the invention may comprise a multiplicity of RNA molecules having a combination of any 19, 20, and/or 21 contiguous nucleotide sequences derived from SEQ ID NO:5.

In another embodiment, a pool of siRNA of the invention derived from the *H. glycines* pat-10 gene of SEQ ID NO:6 may comprise a multiplicity of RNA molecules which are selected from the group consisting of oligonucleotides substantially identical to nucleotides 1 to 21 of SEQ ID NO:6, nucleotides 2 to 23 of SEQ ID NO:6, nucleotides 3 to 24 of SEQ ID NO:6, nucleotides 4 to 25 of SEQ ID NO:6, nucleotides 5 to 26 of SEQ ID NO:6, nucleotides 6 to 27 of SEQ ID NO:6, nucleotides 7 to 28 of SEQ ID NO:6, nucleotides 8 to 29 of SEQ ID NO:6, nucleotides 9 to 30 of SEQ ID NO:6, nucleotides 10 to 31 of SEQ ID NO:6, nucleotides 11 to 32 of SEQ ID NO:6, nucleotides 12 to 33 of SEQ ID NO:6, nucleotides 13 to 34 of SEQ ID NO:6, nucleotides 14 to 35 of SEQ ID NO:6, nucleotides 15 to 36 of SEQ ID NO:6, nucleotides 16 to 37 of SEQ ID NO:6, nucleotides 17 to 38 of SEQ ID NO:6, nucleotides 18 to 39 of SEQ ID NO:6, nucleotides 19 to 40 of SEQ ID NO:6, nucleotides 20 to 41 of SEQ ID NO:6, nucleotides 21 to 42 of SEQ ID NO:6, nucleotides 22 to 43 of SEQ ID NO:6, nucleotides 23 to 44 of SEQ ID NO:6, nucleotides 24 to 45 of SEQ ID NO:6, nucleotides 25 to 46 of SEQ ID NO:6, nucleotides 26 to 47 of SEQ ID NO:6, nucleotides 27 to 48 of SEQ ID NO:6, nucleotides 28 to 49 of SEQ ID NO:6, nucleotides 29 to 50 of SEQ ID NO:6, nucleotides 30 to 51 of SEQ ID NO:6, nucleotides 31 to 52 of SEQ ID NO:6, nucleotides 32 to 53 of SEQ ID NO:6, nucleotides 33 to 54 of SEQ ID NO:6, nucleotides 34 to 55 of SEQ ID NO:6, nucleotides 35 to 56 of SEQ ID NO:6, nucleotides 36 to 57 of SEQ ID NO:6, nucleotides 37 to 58 of SEQ ID NO:6, nucleotides 38 to 59 of SEQ ID NO:6, nucleotides 39 to 60 of SEQ ID NO:6, nucleotides 40 to 61 of SEQ ID NO:6, nucleotides 41 to 62 of SEQ ID NO:6, nucleotides 42 to 63 of SEQ ID NO:6, nucleotides 43 to 64 of SEQ ID NO:6, nucleotides 44 to 65 of SEQ ID NO:6, nucleotides 45 to 66 of SEQ ID NO:6, nucleotides 46 to 67 of SEQ ID NO:6, nucleotides 47 to 68 of SEQ ID NO:6, nucleotides 48 to 69 of SEQ ID NO:6, nucleotides 49 to 70 of SEQ ID NO:6, and nucleotides 50 to 71 of SEQ ID NO:6.

As another example, a pool of siRNA of the invention derived from the *H. glycines* pat-10 gene of SEQ ID NO:6 may comprise a multiplicity of RNA molecules selected from the group consisting of oligonucleotides substantially identical to nucleotides 51 to 72 of SEQ ID NO:6, nucleotides 52 to 73 of SEQ ID NO:6, nucleotides 53 to 74 of SEQ ID NO:6, nucleotides 54 to 75 of SEQ ID NO:6, nucleotides 55 to 76 of SEQ ID NO:6, nucleotides 56 to 77 of SEQ ID NO:6, nucleotides 57 to 78 of SEQ ID NO:6, nucleotides 58 to 79 of SEQ ID NO:6, nucleotides 59 to 80 of SEQ ID NO:6, nucleotides 60 to 81 of SEQ ID NO:6, nucleotides 61 to 82 of SEQ ID NO:6, nucleotides 62 to 83 of SEQ ID NO:6, nucleotides 63 to 84 of SEQ ID NO:6, nucleotides 64 to 85 of SEQ ID NO:6, nucleotides 65 to 86 of SEQ ID NO:6, nucleotides 66 to 87 of SEQ ID NO:6, nucleotides 67 to 88 of SEQ ID NO:6, nucleotides 68 to 89 of SEQ ID NO:6, nucleotides 69 to 90 of SEQ ID NO:6, nucleotides 70 to 91 of SEQ ID NO:6, nucleotides 71 to 92 of SEQ ID NO:6, nucleotides 72 to 93 of SEQ ID NO:6, nucleotides 73 to 94 of SEQ ID NO:6, nucleotides 74 to 95 of SEQ ID NO:6, nucleotides 75 to 96 of SEQ ID NO:6, nucleotides 76 to 97 of SEQ ID NO:6, nucleotides 77 to 98 of SEQ ID NO:6, nucleotides 78 to 99 of SEQ ID NO:6, nucleotides 79 to 100 of SEQ ID NO:6, nucleotides 80 to 101 of SEQ ID NO:6, nucleotides 81 to 102 of SEQ ID NO:6, nucleotides 82 to 103 of SEQ ID NO:6, nucleotides 83 to 104 of SEQ ID NO:6, nucleotides 84 to 105 of SEQ ID NO:6, nucleotides 85 to 106 of SEQ ID NO:6, nucleotides 86 to 107 of SEQ ID NO:6, nucleotides 87 to 108 of SEQ ID NO:6, nucleotides 88 to 109 of SEQ ID NO:6, nucleotides 89 to 110 of SEQ ID NO:6, nucleotides 90 to 111 of SEQ ID NO:6, nucleotides 91 to 112 of SEQ ID NO:6, nucleotides 92 to 113 of SEQ ID NO:6, nucleotides 93 to 114 of SEQ ID NO:6, nucleotides 94 to 115 of SEQ ID NO:6, nucleotides 95 to 116 of SEQ ID NO:6, nucleotides 96 to 117 of SEQ ID NO:6, nucleotides 97 to 118 of SEQ ID NO:6, nucleotides 98 to 119 of SEQ ID NO:6, nucleotides 99 to 120 of SEQ ID NO:6, and nucleotides 100 to 121 of SEQ ID NO:6.

As another example, a pool of siRNA of the invention derived from the *H. glycines* pat-10 gene of SEQ ID NO:6 may comprise a multiplicity of RNA molecules selected from the group consisting of oligonucleotides substantially identical to nucleotides 101 to 122 of SEQ ID NO:6, nucleotides 102 to 123 of SEQ ID NO:6, nucleotides 103 to 124 of SEQ ID NO:6, nucleotides 104 to 125 of SEQ ID NO:6, nucleotides 105 to 126 of SEQ ID NO:6, nucleotides 106 to 127 of SEQ ID NO:6, nucleotides 107 to 128 of SEQ ID NO:6, nucleotides 108 to 129 of SEQ ID NO:6, nucleotides 109 to 130 of SEQ ID NO:6, nucleotides 110 to 131 of SEQ ID NO:6, nucleotides 111 to 132 of SEQ ID NO:6, nucleotides 112 to 133 of SEQ ID NO:6, nucleotides 113 to 134 of SEQ ID NO:6, nucleotides 114 to 135 of SEQ ID NO:6, nucleotides 115 to 136 of SEQ ID NO:6, nucleotides 116 to 137 of SEQ ID NO:6, nucleotides 117 to 138 of SEQ ID NO:6, nucleotides 118 to 139 of SEQ ID NO:6, nucleotides 119 to 140 of SEQ ID NO:6, nucleotides 120 to 141 of SEQ ID NO:6, nucleotides 121 to 142 of SEQ ID NO:6, nucleotides 122 to 143 of SEQ ID NO:6, nucleotides 123 to 144 of SEQ ID NO:6, nucleotides 124 to 145 of SEQ ID NO:6, nucleotides 125 to 146 of SEQ ID NO:6, nucleotides 126 to 147 of SEQ ID NO:6, nucleotides 127 to 148 of SEQ ID NO:6, nucleotides 128 to 149 of SEQ ID NO:6, nucleotides 129 to 150 of SEQ ID NO:6, nucleotides 130 to 151 of SEQ ID NO:6, nucleotides 131 to 152 of SEQ ID NO:6, nucleotides 132 to 153 of SEQ ID NO:6, nucleotides 133 to 154 of SEQ ID NO:6, nucleotides 134 to 155 of SEQ ID NO:6, nucleotides 135 to 156 of SEQ ID NO:6, nucleotides 136 to 157 of SEQ ID NO:6, nucleotides 137 to 158 of SEQ ID NO:6, nucleotides 138 to 159 of SEQ ID NO:6, nucleotides 139 to 160 of SEQ ID NO:6, nucleotides 140 to 161 of SEQ ID NO:6, nucleotides 141 to 162 of SEQ ID NO:6, nucleotides 142 to 163 of SEQ ID NO:6, nucleotides 143 to 164 of SEQ ID NO:6, nucleotides 144 to 165 of SEQ ID NO:6, nucleotides 145 to 166 of SEQ ID NO:6, nucleotides 146 to 167 of SEQ ID NO:6, nucleotides 147 to 168 of SEQ ID NO:6, nucleotides 148 to 169 of SEQ ID NO:6, nucleotides 149 to 170 of SEQ ID NO:6, and nucleotides 150 to 171 of SEQ ID NO:6.

As another example, a pool of siRNA of the invention derived from the *H. glycines* pat-10 gene of SEQ ID NO:6 may comprise a multiplicity of RNA molecules selected from the group consisting of oligonucleotides substantially identical to nucleotides 151 to 172 of SEQ ID NO:6, nucleotides 152 to 173 of SEQ ID NO:6, nucleotides 153 to 174 of SEQ ID NO:6, nucleotides 154 to 175 of SEQ ID NO:6, nucleotides 155 to 176 of SEQ ID NO:6, nucleotides 156 to 177 of SEQ ID NO:6, nucleotides 157 to 178 of SEQ ID NO:6, nucleotides 158 to 179 of SEQ ID NO:6, nucleotides 159 to 180 of SEQ ID NO:6, nucleotides 160 to 181 of SEQ ID NO:6, nucleotides 161 to 182 of SEQ ID NO:6, nucleotides 162 to 183 of SEQ ID NO:6, nucleotides 163 to 184 of SEQ ID NO:6, nucleotides 164 to 185 of SEQ ID NO:6, nucleotides 165 to 186 of SEQ ID NO:6, nucleotides 166 to 187 of SEQ ID NO:6, nucleotides 167 to 188 of SEQ ID NO:6, nucleotides 168 to 189 of SEQ ID NO:6, nucleotides 169 to 190 of SEQ ID NO:6, nucleotides 170 to 191 of SEQ ID NO:6, nucleotides 171 to 192 of SEQ ID NO:6, nucleotides 172 to 193 of SEQ ID NO:6, nucleotides 173 to 194 of SEQ ID NO:6, nucleotides 174 to 195 of SEQ ID NO:6, nucleotides 175 to 196 of SEQ ID NO:6, nucleotides 176 to 197 of SEQ ID NO:6, nucleotides 177 to 198 of SEQ ID NO:6, nucleotides 178 to 199 of SEQ ID NO:6, nucleotides 179 to 200 of SEQ ID NO:6, nucleotides 180 to 201 of SEQ ID NO:6, nucleotides 181 to 202 of SEQ ID NO:6, nucleotides 182 to 203 of SEQ ID NO:6, nucleotides 183 to 204 of SEQ ID NO:6, nucleotides 184 to 205 of SEQ ID NO:6, nucleotides 185 to 206 of SEQ ID NO:6, nucleotides 186 to 207 of SEQ ID NO:6, nucleotides 187 to 208 of SEQ ID NO:6, nucleotides 188 to 209 of SEQ ID NO:6, nucleotides 189 to 210 of SEQ ID NO:6, nucleotides 190 to 211 of SEQ ID NO:6, nucleotides 191 to 212 of SEQ ID NO:6, nucleotides 192 to 213 of SEQ ID NO:6, nucleotides 193 to 214 of SEQ ID NO:6, nucleotides 194 to 215 of SEQ ID NO:6, nucleotides 195 to 216 of SEQ ID NO:6, nucleotides 196 to 217 of SEQ ID NO:6, nucleotides 197 to 218 of SEQ ID NO:6, nucleotides 198 to 219 of SEQ ID NO:6, nucleotides 199 to 220 of SEQ ID NO:6, and nucleotides 200 to 221 of SEQ ID NO:6.

As another example, a pool of siRNA of the invention derived from the *H. glycines* pat-10 gene of SEQ ID NO:6 may comprise a multiplicity of RNA molecules selected from the group consisting of oligonucleotides substantially identical to nucleotides 201 to 222 of SEQ ID NO:6, nucleotides 202 to 223 of SEQ ID NO:6, nucleotides 203 to 224 of SEQ ID NO:6, nucleotides 204 to 225 of SEQ ID NO:6, nucleotides 205 to 226 of SEQ ID NO:6, nucleotides 206 to 227 of SEQ ID NO:6, nucleotides 207 to 228 of SEQ ID NO:6, nucleotides 208 to 229 of SEQ ID NO:6, nucleotides 209 to 230 of SEQ ID NO:6, nucleotides 210 to 231 of SEQ ID NO:6, nucleotides 211 to 232 of SEQ ID NO:6, nucleotides 212 to 233 of SEQ ID NO:6, nucleotides 213 to 234 of SEQ ID NO:6, nucleotides 214 to 235 of SEQ ID NO:6, nucleotides 215 to 236 of SEQ ID NO:6, nucleotides 216 to 237 of SEQ ID NO:6, nucleotides 217 to 238 of SEQ ID NO:6, nucleotides 218 to 239 of SEQ ID NO:6, nucleotides 219 to 240 of SEQ ID NO:6, nucleotides 220 to 241 of SEQ ID NO:6, nucleotides 221 to 242 of SEQ ID NO:6, nucleotides 222 to 243 of SEQ ID NO:6, nucleotides 223 to 244 of SEQ ID NO:6, nucleotides 224 to 245 of SEQ ID NO:6, nucleotides 225 to 246 of SEQ ID NO:6, nucleotides 226 to 247 of SEQ ID NO:6, nucleotides 227 to 248 of SEQ ID NO:6, nucleotides 228 to 249 of SEQ ID NO:6, nucleotides 229 to 250 of SEQ ID NO:6, nucleotides 230 to 251 of SEQ ID NO:6, nucleotides 231 to 252 of SEQ ID NO:6, nucleotides 232 to 253 of SEQ ID NO:6, nucleotides 233 to 254 of SEQ ID NO:6, nucleotides 234 to 255 of SEQ ID NO:6, nucleotides 235 to 256 of SEQ ID NO:6, nucleotides 236 to 257 of SEQ ID NO:6, nucleotides 237 to 258 of SEQ ID NO:6, nucleotides 238 to 259 of SEQ ID NO:6, nucleotides 239 to 260 of SEQ ID NO:6, nucleotides 240 to 261 of SEQ ID NO:6, nucleotides 241 to 262 of SEQ ID NO:6, nucleotides 242 to 263 of SEQ ID NO:6, nucleotides 243 to 264 of SEQ ID NO:6, nucleotides 244 to 265 of SEQ ID NO:6, nucleotides 245 to 266 of SEQ ID NO:6, nucleotides 246 to 267 of SEQ ID NO:6, nucleotides 247 to 268 of SEQ ID NO:6, nucleotides 248 to 269 of SEQ ID NO:6, nucleotides 249 to 270 of SEQ ID NO:6, and nucleotides 250 to 271 of SEQ ID NO:6.

As another example, a pool of siRNA of the invention derived from the *H. glycines* pat-10 gene of SEQ ID NO:6 may comprise a multiplicity of RNA molecules selected from the group consisting of oligonucleotides substantially identical to nucleotides 251 to 272 of SEQ ID NO:6, nucleotides 252 to 273 of SEQ ID NO:6, nucleotides 253 to 274 of SEQ ID NO:6, nucleotides 254 to 275 of SEQ ID NO:6, nucleotides 255 to 276 of SEQ ID NO:6, nucleotides 256 to 277 of SEQ ID NO:6, nucleotides 257 to 278 of SEQ ID NO:6, nucleotides 258 to 279 of SEQ ID NO:6, nucleotides 259 to 280 of SEQ ID NO:6, nucleotides 260 to 281 of SEQ ID NO:6, nucleotides 261 to 282 of SEQ ID NO:6, nucleotides 262 to 283 of SEQ ID NO:6, nucleotides 263 to 284 of SEQ ID NO:6, nucleotides 264 to 285 of SEQ ID NO:6, nucleotides 265 to 286 of SEQ ID NO:6, nucleotides 266 to 287 of SEQ ID NO:6, nucleotides 267 to 288 of SEQ ID NO:6, nucleotides 268 to 289 of SEQ ID NO:6, nucleotides 269 to 290 of SEQ ID NO:6, nucleotides 270 to 291 of SEQ ID NO:6, nucleotides 271 to 292 of SEQ ID NO:6, nucleotides 272 to 293 of SEQ ID NO:6, nucleotides 273 to 294 of SEQ ID NO:6, nucleotides 274 to 295 of SEQ ID NO:6, nucleotides 275 to 296 of SEQ ID NO:6, nucleotides 276 to 297 of SEQ ID NO:6, nucleotides 277 to 298 of SEQ ID NO:6, nucleotides 278 to 299 of SEQ ID NO:6, nucleotides 279 to 300 of SEQ ID NO:6, nucleotides 280 to 301 of SEQ ID NO:6, nucleotides 281 to 302 of SEQ ID NO:6, nucleotides 282 to 303 of SEQ ID NO:6, nucleotides 283 to 304 of SEQ ID NO:6, nucleotides 284 to 305 of SEQ ID NO:6, nucleotides 285 to 306 of SEQ ID NO:6, nucleotides 286 to 307 of SEQ ID NO:6, nucleotides 287 to 308 of SEQ ID NO:6, nucleotides 288 to 309 of SEQ ID NO:6, nucleotides 289 to 310 of SEQ ID NO:6, nucleotides 290 to 311 of SEQ ID NO:6, nucleotides 291 to 312 of SEQ ID NO:6, nucleotides 292 to 313 of SEQ ID NO:6, nucleotides 293 to 314 of SEQ ID NO:6, nucleotides 294 to 315 of SEQ ID NO:6, nucleotides 295 to 316 of SEQ ID NO:6, nucleotides 296 to 317 of SEQ ID NO:6, nucleotides 297 to 318 of SEQ ID NO:6, nucleotides 298 to 319 of SEQ ID NO:6, nucleotides 299 to 320 of SEQ ID NO:6, and nucleotides 300 to 321 of SEQ ID NO:6.

As another example, a pool of siRNA of the invention derived from the *H. glycines* pat-10 gene of SEQ ID NO:6 may comprise a multiplicity of RNA molecules selected from the group consisting of oligonucleotides substantially identical to nucleotides 301 to 322 of SEQ ID NO:6, nucleotides 302 to 323 of SEQ ID NO:6, nucleotides 303 to 324 of SEQ ID NO:6, nucleotides 304 to 325 of SEQ ID NO:6, nucleotides 305 to 326 of SEQ ID NO:6, nucleotides 306 to 327 of SEQ ID NO:6, nucleotides 307 to 328 of SEQ ID NO:6, nucleotides 308 to 329 of SEQ ID NO:6, nucleotides 309 to 330 of SEQ ID NO:6, nucleotides 310 to 331 of SEQ ID NO:6, nucleotides 311 to 332 of SEQ ID NO:6, nucleotides 312 to 333 of SEQ ID NO:6, nucleotides 313 to 334 of SEQ ID NO:6, nucleotides 314 to 335 of SEQ ID NO:6, nucleotides 315 to 336 of SEQ ID NO:6, nucleotides 316 to 337 of SEQ ID NO:6, nucleotides 317 to 338 of SEQ ID NO:6, nucleotides 318 to 339 of SEQ ID NO:6, nucleotides 319 to 340 of SEQ ID NO:6, nucleotides 320 to 341 of SEQ ID NO:6, nucleotides 321 to 342 of SEQ ID NO:6, nucleotides 322 to 343 of SEQ ID NO:6, nucleotides 323 to 344 of SEQ ID NO:6, nucleotides 324 to 345 of SEQ ID NO:6, nucleotides 325 to 346 of SEQ ID NO:6, nucleotides 326 to 347 of SEQ ID NO:6, nucleotides 327 to 348 of SEQ ID NO:6, nucleotides 328 to 349 of SEQ ID NO:6, nucleotides 329 to 350 of SEQ ID NO:6, nucleotides 330 to 351 of SEQ ID NO:6, nucleotides 331 to 352 of SEQ ID NO:6, nucleotides 332 to 353 of SEQ ID NO:6, nucleotides 333 to 354 of SEQ ID NO:6, nucleotides 334 to 355 of SEQ ID NO:6, nucleotides 335 to 356 of SEQ ID NO:6, nucleotides 336 to 357 of SEQ ID NO:6, nucleotides 337 to 358 of SEQ ID NO:6, nucleotides 338 to 359 of SEQ ID NO:6, nucleotides 339 to 360 of SEQ ID NO:6, nucleotides 340 to 361 of SEQ ID NO:6, nucleotides 341 to 362 of SEQ ID NO:6, nucleotides 342 to 363 of SEQ ID NO:6, nucleotides 343 to 364 of SEQ ID NO:6, nucleotides 344 to 365 of SEQ ID NO:6, nucleotides 345 to 366 of SEQ ID NO:6, nucleotides 346 to 367 of SEQ ID NO:6, nucleotides 347 to 368 of SEQ ID NO:6, nucleotides 348 to 369 of SEQ ID NO:6, nucleotides 349 to 370 of SEQ ID NO:6, and nucleotides 350 to 371 of SEQ ID NO:6.

As another example, a pool of siRNA of the invention derived from the *H. glycines* pat-10 gene of SEQ ID NO:6 may comprise a multiplicity of RNA molecules selected from the group consisting of oligonucleotides substantially identical to nucleotides 351 to 372 of SEQ ID NO:6, nucleotides 352 to 373 of SEQ ID NO:6, nucleotides 353 to 374 of SEQ ID NO:6, nucleotides 354 to 375 of SEQ ID NO:6, nucleotides 355 to 376 of SEQ ID NO:6, nucleotides 356 to 377 of SEQ ID NO:6, nucleotides 357 to 378 of SEQ ID NO:6, nucleotides 358 to 379 of SEQ ID NO:6, nucleotides 359 to 380 of SEQ ID NO:6, nucleotides 360 to 381 of SEQ ID NO:6, nucleotides 361 to 382 of SEQ ID NO:6, nucleotides 362 to 383 of SEQ ID NO:6, nucleotides 363 to 384 of SEQ ID NO:6, nucleotides 364 to 385 of SEQ ID NO:6, nucleotides 365 to 386 of SEQ ID NO:6, nucleotides 366 to 387 of SEQ ID NO:6, nucleotides 367 to 388 of SEQ ID NO:6, nucleotides 368 to 389 of SEQ ID NO:6, nucleotides 369 to 390 of SEQ ID NO:6, nucleotides 370 to 391 of SEQ ID NO:6, nucleotides 371 to 392 of SEQ ID NO:6, nucleotides 372 to 393 of SEQ ID NO:6, nucleotides 373 to 394 of SEQ ID NO:6, nucleotides 374 to 395 of SEQ ID NO:6, nucleotides 375 to 396 of SEQ ID NO:6, nucleotides 376 to 397 of SEQ ID NO:6, nucleotides 377 to 398 of SEQ ID NO:6, nucleotides 378 to 399 of SEQ ID NO:6, nucleotides 379 to 400 of SEQ ID NO:6; nucleotides 380 to 401 of SEQ ID NO:6, nucleotides 381 to 402 of SEQ ID NO:6, nucleotides 382 to 403 of SEQ ID NO:6, nucleotides 383 to 404 of SEQ ID NO:6, nucleotides 384 to 405 of SEQ ID NO:6, nucleotides 385 to 406 of SEQ ID NO:6, nucleotides 386 to 407 of SEQ ID NO:6, nucleotides 387 to 408 of SEQ ID NO:6, nucleotides 388 to 409 of SEQ ID NO:6, nucleotides 389 to 410 of SEQ ID NO:6, nucleotides 390 to 411 of SEQ ID NO:6, nucleotides 391 to 412 of SEQ ID NO:6, nucleotides 392 to 413 of SEQ ID NO:6, nucleotides 393 to 414 of SEQ ID NO:6, nucleotides 394 to 415 of SEQ ID NO:6, nucleotides 395 to 416 of SEQ ID NO:6, nucleotides 396 to 417 of SEQ ID NO:6, nucleotides 397 to 418 of SEQ ID NO:6, nucleotides 398 to 419 of SEQ ID NO:6, nucleotides 399 to 420 of SEQ ID NO:6, and nucleotides 400 to 421 of SEQ ID NO:6.

As another example, a pool of siRNA of the invention derived from the *H. glycines* pat-10 gene of SEQ ID NO:6 may comprise a multiplicity of RNA molecules selected from the group consisting of oligonucleotides substantially identical to nucleotides 401 to 422 of SEQ ID NO:6, nucleotides 402 to 423 of SEQ ID NO:6, nucleotides 403 to 424 of SEQ ID NO:6, nucleotides 404 to 425 of SEQ ID NO:6, nucleotides 405 to 426 of SEQ ID NO:6, nucleotides 406 to 427 of SEQ ID NO:6, nucleotides 407 to 428 of SEQ ID NO:6, nucleotides 408 to 429 of SEQ ID NO:6, nucleotides 409 to 430 of SEQ ID NO:6, nucleotides 410 to 431 of SEQ ID NO:6, nucleotides 411 to 432 of SEQ ID NO:6, nucleotides 412 to 433 of SEQ ID NO:6, nucleotides 413 to 434 of SEQ ID NO:6, nucleotides 414 to 435 of SEQ ID NO:6, nucleotides 415 to 436 of SEQ ID NO:6, nucleotides 416 to 437 of SEQ ID NO:6, nucleotides 417 to 438 of SEQ ID NO:6, nucleotides 418 to 439 of SEQ ID NO:6, nucleotides 419 to 440 of SEQ ID NO:6, nucleotides 420 to 441 of SEQ ID NO:6, nucleotides 421 to 442 of SEQ ID NO:6, nucleotides 422 to 443 of SEQ ID NO:6, nucleotides 423 to 444 of SEQ ID NO:6, nucleotides 424 to 445 of SEQ ID NO:6, nucleotides 425 to 446 of SEQ ID NO:6, nucleotides 426 to 447 of SEQ ID NO:6, nucleotides 427 to 448 of SEQ ID NO:6, nucleotides 428 to 449 of SEQ ID NO:6, nucleotides 429 to 450 of SEQ ID NO:6, nucleotides 430 to 451 of SEQ ID NO:6, nucleotides 431 to 452 of SEQ ID NO:6, nucleotides 432 to 453 of SEQ ID NO:6, nucleotides 433 to 454 of SEQ ID NO:6, nucleotides 434 to 455 of SEQ ID NO:6, nucleotides 435 to 456 of SEQ ID NO:6, nucleotides 436 to 457 of SEQ ID NO:6, nucleotides 437 to 458 of SEQ ID NO:6, nucleotides 438 to 459 of SEQ ID NO:6, nucleotides 439 to 460 of SEQ ID NO:6, nucleotides 440 to 461 of SEQ ID NO:6, nucleotides 441 to 462 of SEQ ID NO:6, nucleotides 442 to 463 of SEQ ID NO:6, nucleotides 443 to 464 of SEQ ID NO:6, nucleotides 444 to 465 of SEQ ID NO:6, nucleotides 445 to 466 of SEQ ID NO:6, nucleotides 446 to 467 of SEQ ID NO:6, nucleotides 447 to 468 of SEQ ID NO:6, nucleotides 448 to 469 of SEQ ID NO:6, nucleotides 449 to 470 of SEQ ID NO:6, and nucleotides 450 to 471 of SEQ ID NO:6.

As another example, a pool of siRNA of the invention derived from the *H. glycines* pat-10 gene of SEQ ID NO:6 may comprise a multiplicity of RNA molecules selected from the group consisting of oligonucleotides substantially identical to nucleotides 451 to 472 of SEQ ID NO:6, nucleotides 452 to 473 of SEQ ID NO:6, nucleotides 453 to 474 of SEQ ID NO:6, nucleotides 454 to 475 of SEQ ID NO:6, nucleotides 455 to 476 of SEQ ID NO:6, nucleotides 456 to 477 of SEQ ID NO:6, nucleotides 457 to 478 of SEQ ID NO:6, nucleotides 458 to 479 of SEQ ID NO:6, nucleotides 459 to 480 of SEQ ID NO:6, nucleotides 460 to 481 of SEQ ID NO:6, nucleotides 461 to 482 of SEQ ID NO:6, nucleotides 462 to 483 of SEQ ID NO:6, nucleotides 463 to 484 of SEQ ID NO:6, nucleotides 464 to 485 of SEQ ID NO:6, nucleotides 465 to 486 of SEQ ID NO:6, nucleotides 466 to 487 of SEQ ID NO:6, nucleotides 467 to 488 of SEQ ID NO:6, nucleotides 468 to 489 of SEQ ID NO:6, nucleotides 469 to 490 of SEQ ID NO:6, nucleotides 470 to 491 of SEQ ID NO:6, nucleotides 471 to 492 of SEQ ID NO:6, nucleotides 472 to 493 of SEQ ID NO:6, nucleotides 473 to 494 of SEQ ID NO:6, nucleotides 474 to 495 of SEQ ID NO:6, nucleotides 475 to 496 of SEQ ID NO:6, nucleotides 476 to 497 of SEQ ID NO:6, nucleotides 477 to 498 of SEQ ID NO:6, nucleotides 478 to 499 of SEQ ID NO:6, nucleotides 479 to 500 of SEQ ID NO:6, nucleotides 480 to 501 of SEQ ID NO:6, nucleotides 481 to 502 of SEQ ID NO:6, nucleotides 482 to 503 of SEQ ID NO:6, nucleotides 483 to 504 of SEQ ID NO:6, nucleotides 484 to 505 of SEQ ID NO:6, nucleotides 485 to 506 of SEQ ID NO:6, nucleotides 486 to 507 of SEQ ID NO:6, nucleotides 487 to 508 of SEQ ID NO:6, nucleotides 488 to 509 of SEQ ID NO:6, nucleotides 489 to 510 of SEQ ID NO:6, nucleotides 490 to 511 of SEQ ID NO:6, nucleotides 491 to 512 of SEQ ID NO:6, nucleotides 492 to 513 of SEQ ID NO:6, nucleotides 493 to 514 of SEQ ID NO:6, nucleotides 494 to 515 of SEQ ID NO:6, nucleotides 495 to 516 of SEQ ID NO:6, nucleotides 496 to 517 of SEQ ID NO:6, nucleotides 497 to 518 of SEQ ID NO:6, nucleotides 498 to 519 of SEQ ID NO:6, nucleotides 499 to 520 of SEQ ID NO:6, and nucleotides 500 to 521 of SEQ ID NO:6.

As another example, a pool of siRNA of the invention derived from the *H. glycines* pat-10 gene of SEQ ID NO:6 may comprise a multiplicity of RNA molecules selected from the group consisting of oligonucleotides substantially identical to nucleotides 501 to 522 of SEQ ID NO:6, nucleotides 502 to 523 of SEQ ID NO:6, nucleotides 503 to 524 of SEQ ID NO:6, nucleotides 504 to 525 of SEQ ID NO:6, nucleotides 505 to 526 of SEQ ID NO:6, nucleotides 506 to 527 of SEQ ID NO:6, nucleotides 507 to 528 of SEQ ID NO:6, nucleotides 508 to 529 of SEQ ID NO:6, nucleotides 509 to 530 of SEQ ID NO:6, nucleotides 510 to 531 of SEQ ID NO:6, nucleotides 511 to 532 of SEQ ID NO:6, nucleotides 512 to 533 of SEQ ID NO:6, nucleotides 513 to 534 of SEQ ID NO:6, nucleotides 514 to 535 of SEQ ID NO:6, nucleotides 515 to 536 of SEQ ID NO:6, nucleotides 516 to 537 of SEQ ID NO:6, nucleotides 517 to 538 of SEQ ID NO:6, nucleotides 518 to 539 of SEQ ID NO:6, nucleotides 519 to 540 of SEQ ID NO:6, nucleotides 520 to 541 of SEQ ID NO:6, nucleotides 521 to 542 of SEQ ID NO:6, nucleotides 522 to 543 of SEQ ID NO:6, nucleotides 523 to 544 of SEQ ID NO:6; nucleotides 524 to 545 of SEQ ID NO:6, nucleotides 525 to 546 of SEQ ID NO:6, nucleotides 526 to 547 of SEQ ID NO:6, nucleotides 527 to 548 of SEQ ID NO:6, nucleotides 528 to 549 of SEQ ID NO:6, nucleotides 529 to 550 of SEQ ID NO:6, nucleotides 530 to 551 of SEQ ID NO:6, nucleotides 531 to 552 of SEQ ID NO:6, nucleotides 532 to 553 of SEQ ID NO:6, nucleotides 533 to 554 of SEQ ID NO:6, nucleotides 534 to 555 of SEQ ID NO:6, nucleotides 535 to 556 of SEQ ID NO:6, nucleotides 536 to 557 of SEQ ID NO:6, nucleotides 537 to 558 of SEQ ID NO:6, nucleotides 538 to 559 of SEQ ID NO:6, nucleotides 539 to 560 of SEQ ID NO:6, nucleotides 540 to 561 of SEQ ID NO:6, nucleotides 541 to 562 of SEQ ID NO:6, nucleotides 542 to 563 of SEQ ID NO:6, nucleotides 543 to 564 of SEQ ID NO:6, nucleotides 544 to 565 of SEQ ID NO:6, nucleotides 545 to 566 of SEQ ID NO:6, nucleotides 546 to 567 of SEQ ID NO:6, nucleotides 547 to 568 of SEQ ID NO:6, nucleotides 548 to 569 of SEQ ID NO:6, nucleotides 549 to 570 of SEQ ID NO:6, and nucleotides 550 to 571 of SEQ ID NO:6.

As another example, a pool of siRNA of the invention derived from the *H. glycines* pat-10 gene of SEQ ID NO:6 may comprise a multiplicity of RNA molecules selected from the group consisting of oligonucleotides substantially identical to nucleotides 551 to 572 of SEQ ID NO:6, nucleotides 552 to 573 of SEQ ID NO:6, nucleotides 553 to 574 of SEQ ID NO:6, nucleotides 554 to 575 of SEQ ID NO:6, nucleotides 555 to 576 of SEQ ID NO:6, nucleotides 556 to 577 of SEQ ID NO:6, nucleotides 557 to 578 of SEQ ID NO:6, nucleotides 558 to 579 of SEQ ID NO:6, nucleotides 559 to 580 of SEQ ID NO:6, nucleotides 560 to 581 of SEQ ID NO:6, nucleotides 561 to 582 of SEQ ID NO:6, nucleotides 562 to 583 of SEQ ID NO:6, nucleotides 563 to 584 of SEQ ID NO:6, nucleotides 564 to 585 of SEQ ID NO:6, nucleotides 565 to 586 of SEQ ID NO:6, nucleotides 566 to 587 of SEQ ID NO:6, nucleotides 567 to 588 of SEQ ID NO:6, nucleotides 568 to 589 of SEQ ID NO:6, nucleotides 569 to 590 of SEQ ID NO:6, nucleotides 570 to 591 of SEQ ID NO:6, nucleotides 571 to 592 of SEQ ID NO:6, nucleotides 572 to 593 of SEQ ID NO:6, nucleotides 573 to 594 of SEQ ID NO:6, nucleotides 574 to 595 of SEQ ID NO:6, nucleotides 575 to 596 of SEQ ID NO:6, nucleotides 576 to 597 of SEQ ID NO:6, nucleotides 577 to 598 of SEQ ID NO:6, nucleotides 578 to 599 of SEQ ID NO:6, nucleotides 579 to 600 of SEQ ID NO:6, nucleotides 580 to 601 of SEQ ID NO:6, nucleotides 581 to 602 of SEQ ID NO:6, nucleotides 582 to 603 of SEQ ID NO:6, nucleotides 583 to 604 of SEQ ID NO:6, nucleotides 584 to 605 of SEQ ID NO:6, nucleotides 585 to 606 of SEQ ID NO:6, nucleotides 586 to 607 of SEQ ID NO:6, nucleotides 587 to 608 of SEQ ID NO:6, nucleotides 588 to 609 of SEQ ID NO:6, nucleotides 589 to 610 of SEQ ID NO:6, nucleotides 590 to 611 of SEQ ID NO:6, nucleotides 591 to 612 of SEQ ID NO:6, nucleotides 592 to 613 of SEQ ID NO:6, nucleotides 593 to 614 of SEQ ID NO:6, nucleotides 594 to 615 of SEQ ID NO:6, nucleotides 595 to 616 of SEQ ID NO:6, nucleotides 596 to 617 of SEQ ID NO:6, nucleotides 597 to 618 of SEQ ID NO:6, nucleotides 598 to 619 of SEQ ID NO:6, nucleotides 599 to 620 of SEQ ID NO:6, and nucleotides 600 to 621 of SEQ ID NO:6.

As another example, a pool of siRNA of the invention derived from the *H. glycines* pat-10 gene of SEQ ID NO:6 may comprise a multiplicity of RNA molecules selected from the group consisting of oligonucleotides substantially identical to nucleotides 601 to 622 of SEQ ID NO:6, nucleotides 602 to 623 of SEQ ID NO:6, nucleotides 603 to 624 of SEQ ID NO:6, nucleotides 604 to 625 of SEQ ID NO:6, nucleotides 605 to 626 of SEQ ID NO:6, nucleotides 606 to 627 of SEQ ID NO:6, nucleotides 607 to 628 of SEQ ID NO:6, nucleotides 608 to 629 of SEQ ID NO:6, nucleotides 609 to 630 of SEQ ID NO:6, nucleotides 610 to 631 of SEQ ID NO:6, nucleotides 611 to 632 of SEQ ID NO:6, nucleotides 612 to 633 of SEQ ID NO:6, nucleotides 613 to 634 of SEQ ID NO:6, nucleotides 614 to 635 of SEQ ID NO:6, nucleotides 615 to 636 of SEQ ID NO:6, nucleotides 616 to 637 of SEQ ID NO:6, nucleotides 617 to 638 of SEQ ID NO:6, nucleotides 618 to 639 of SEQ ID NO:6, nucleotides 619 to 640 of SEQ ID NO:6, nucleotides 620 to 641 of SEQ ID NO:6, nucleotides 621 to 642 of SEQ ID NO:6, nucleotides 622 to 643 of SEQ ID NO:6, nucleotides 623 to 644 of SEQ ID NO:6, nucleotides 624 to 645 of SEQ ID NO:6, nucleotides 625 to 646 of SEQ ID NO:6, nucleotides 626 to 647 of SEQ ID NO:6, nucleotides 627 to 648 of SEQ ID NO:6, nucleotides 628 to 649 of SEQ ID NO:6, nucleotides 629 to 650 of SEQ ID NO:6, nucleotides 630 to 651 of SEQ ID NO:6, nucleotides 631 to 652 of SEQ ID NO:6, nucleotides 632 to 653 of SEQ ID NO:6, nucleotides 633 to 654 of SEQ ID NO:6, nucleotides 634 to 655 of SEQ ID NO:6, nucleotides 635 to 656 of SEQ ID NO:6, nucleotides 636 to 657 of SEQ ID NO:6, nucleotides 637 to 658 of SEQ ID NO:6, nucleotides 638 to 659 of SEQ ID NO:6, nucleotides 639 to 660 of SEQ ID NO:6, nucleotides 640 to 661 of SEQ ID NO:6, nucleotides 641 to 662 of SEQ ID NO:6, nucleotides 642 to 663 of SEQ ID NO:6, nucleotides 643 to 664 of SEQ ID NO:6, nucleotides 644 to 665 of SEQ ID NO:6, nucleotides 645 to 666 of SEQ ID NO:6, nucleotides 646 to 667 of SEQ ID NO:6, nucleotides 647 to 668 of SEQ ID NO:6, nucleotides 648 to 669 of SEQ ID NO:6, nucleotides 649 to 670 of SEQ ID NO:6, nucleotides 650 to 671 of SEQ ID NO:6, nucleotides 651 to 672 of SEQ ID NO:6, nucleotides 652 to 673 of SEQ ID NO:6, nucleotides 653 to 674 of SEQ ID NO:6, and nucleotides 654 to 675 of SEQ ID NO:6.

A pool of siRNA of the invention derived from the *H. glycines* pat-10 gene of SEQ ID NO:6 may also comprise any combination of RNA molecules having the specific 21 contiguous nucleotide sequences derived from SEQ ID NO:6 set forth above. Similarly, a pool of siRNA of the invention may comprise a multiplicity of RNA molecules having any 19 contiguous nucleotide sequences derived from SEQ ID NO:6, or a multiplicity of RNA molecules having any 20 contiguous nucleotide sequences derived from SEQ ID NO:6. Alternatively, the pool of the siRNA of the invention may comprise a multiplicity of RNA molecules having a combination of any 19, 20, and/or 21 contiguous nucleotide sequences derived from SEQ ID NO:6.

In another embodiment, a pool of dsRNA of the invention derived from the 5' UTR of the pat-10 gene set forth in SEQ ID NO:7 may comprise a multiplicity of RNA molecules which are selected from the group consisting of oligonucleotides substantially identical to nucleotides 1 to 21 of SEQ ID NO:7, nucleotides 2 to 23 of SEQ ID NO:7, nucleotides 3 to 24 of SEQ ID NO:7, nucleotides 4 to 25 of SEQ ID NO:7, nucleotides 5 to 26 of SEQ ID NO:7, nucleotides 6 to 27 of SEQ ID NO:7, nucleotides 7 to 28 of SEQ ID NO:7, nucleotides 8 to 29 of SEQ ID NO:7, nucleotides 9 to 30 of SEQ ID NO:7, nucleotides 10 to 31 of SEQ ID NO:7, nucleotides 11 to 32 of SEQ ID NO:7, nucleotides 12 to 33 of SEQ ID NO:7, nucleotides 13 to 34 of SEQ ID NO:7, nucleotides 14 to 35 of SEQ ID NO:7, nucleotides 15 to 36 of SEQ ID NO:7, nucleotides 16 to 37 of SEQ ID NO:7, nucleotides 17 to 38 of SEQ ID NO:7, nucleotides 18 to 39 of SEQ ID NO:7, nucleotides 19 to 40 of SEQ ID NO:7, nucleotides 20 to 41 of SEQ ID NO:7, nucleotides 21 to 42 of SEQ ID NO:7, nucleotides 22 to 43 of SEQ ID NO:7, nucleotides 23 to 44 of SEQ ID NO:7, nucleotides 24 to 45 of SEQ ID NO:7, nucleotides 25 to 46 of SEQ ID NO:7, nucleotides 26 to 47 of SEQ ID NO:7, nucleotides 27 to 48 of SEQ ID NO:7, nucleotides 28 to 49 of SEQ ID NO:7, nucleotides 29 to 50 of SEQ ID NO:7, nucleotides 30 to 51 of SEQ ID NO:7, nucleotides 31 to 52 of SEQ ID NO:7, nucleotides 32 to 53 of SEQ ID NO:7, nucleotides 33 to 54 of SEQ ID NO:7, nucleotides 34 to 55 of SEQ ID NO:7, nucleotides 35 to 56 of SEQ ID NO:7, nucleotides 36 to 57 of SEQ ID NO:7, nucleotides 37 to 58 of SEQ ID NO:7, nucleotides 38 to 59 of SEQ ID NO:7, nucleotides 39 to 60 of SEQ ID NO:7, nucleotides 40 to 61 of SEQ ID NO:7, nucleotides 41 to 62 of SEQ ID NO:7, nucleotides 42 to 63 of SEQ ID NO:7, nucleotides 43 to 64 of SEQ ID NO:7, nucleotides 44 to 65 of SEQ ID NO:7, nucleotides 45 to 66 of SEQ ID NO:7, nucleotides 46 to 67 of SEQ ID NO:7, nucleotides 47 to 68 of SEQ ID NO:7, and nucleotides 48 to 69 of SEQ ID NO:7.

dsRNA containing a nucleotide sequence identical to a portion of the target gene is preferred for inhibition. As disclosed herein, 100% sequence identity between the RNA and the target gene is not required to practice the present invention. Thus, the invention has the advantage of being able to tolerate sequence variations that might be expected due to genetic mutation, strain polymorphism, or evolutionary divergence. RNA sequences with insertions, deletions, and single point mutations relative to the target sequence may also be effective for inhibition. Thus, sequence identity may optimized by sequence comparison and alignment algorithms known in the art (see Gribskov and Devereux, Sequence Analysis Primer, Stockton Press, 1991, and references cited therein) and calculating the percent difference between the nucleotide sequences by, for example, the Smith-Waterman algorithm as implemented in the BESTFIT software program using default parameters (e.g., University of Wisconsin Genetic Computing Group). Greater than 90% sequence identity, or even 100% sequence identity, between the inhibitory RNA and the portion of the target gene is preferred. Alternatively, the duplex region of the RNA may be defined functionally as a nucleotide sequence that is capable of hybridizing with a portion of the target gene transcript under stringent conditions (e.g., 400 mM NaCl, 40 mM PIPES pH 6.4, 1 mM EDTA, 60° C. hybridization for 12-16 hours; followed by washing). The length of the substantially identical double-stranded nucleotide sequences may be at least about 19, 20, 21, 25, 50, 100, 200, 300, 400, 500, or 1000 bases. In a preferred embodiment, the length of the double-stranded nucleotide sequence is from approximately from about 21 to about 400 or 500 nucleotides in length.

Preferably, the dsRNA molecule of the present invention comprises one strand comprising a sequence substantially identical to a portion of a target gene from any parasitic nematode. Suitable parasitic nematode target genes are at least about 50-60%, preferably at least about 60-70%, and more preferably at least about 70-75%, 75-80%, 80-85%, 85-90%, or 90-95%, and most preferably at least about 96%, 97%, 98%, 99%, or more identical to a fragment of at least 19 contiguous nucleotides of a polynucleotide having the sequence set forth in SEQ ID NO:1, SEQ ID NO:2, SEQ ID NO:3, SEQ ID NO:4, SEQ ID NO:5, SEQ ID NO:6, or SEQ ID NO:7. Alternatively, suitable parasitic nematode target genes comprise a polynucleotide from a parasitic plant nematode that hybridizes under stringent conditions to a fragment of at least 19 contiguous nucleotides of a polynucleotide having the sequence set forth in SEQ ID NO:1, SEQ ID NO:2, SEQ ID NO:3, SEQ ID NO:4, SEQ ID NO:5, SEQ ID NO:6, or SEQ ID NO:7.

The dsRNA of the invention may optionally comprise a single stranded overhang at either or both ends. The double-stranded structure may be formed by a single self-complementary RNA strand (i.e. forming a hairpin loop) or two complementary RNA strands. RNA duplex formation may be initiated either inside or outside the cell. When the dsRNA of the invention forms a hairpin loop, it may optionally comprise an intron, as set forth in U.S. 2003/0180945A1 or a nucleotide spacer, which is a stretch of sequence between the complementary RNA strands to stabilize the hairpin transgene in cells. Methods for making various dsRNA molecules are set forth, for example, in WO 99/53050 and in U.S. Pat. No. 6,506,559. The RNA may be introduced in an amount that allows delivery of at least one copy per cell. Higher doses of double-stranded material may yield more effective inhibition.

In another embodiment, the invention provides an isolated recombinant expression vector comprising a nucleic acid encoding a dsRNA molecule as described above, wherein expression of the vector in a host plant cell results in increased tolerance to a parasitic nematode as compared to a wild-type variety of the host plant cell. As used herein, the term "vector" refers to a nucleic acid molecule capable of transporting another nucleic acid to which it has been linked. One type of vector is a "plasmid," which refers to a circular double stranded DNA loop into which additional DNA segments can be ligated. Another type of vector is a viral vector, wherein additional DNA segments can be ligated into the viral genome. Certain vectors are capable of autonomous replication in a host plant cell into which they are introduced. Other vectors are integrated into the genome of a host plant cell upon introduction into the host cell, and thereby are replicated along with the host genome. Moreover, certain vectors are capable of directing the expression of genes to which they are operatively linked. Such vectors are referred to herein as "expression vectors." In general, expression vectors of utility in recombinant DNA techniques are often in the form of plasmids. In the present specification, "plasmid" and "vector" can be used interchangeably as the plasmid is the most commonly used form of vector. However, the invention is intended to include such other forms of expression vectors, such as viral vectors (e.g., potato virus X, tobacco rattle virus, and Geminivirus), which serve equivalent functions.

The recombinant expression vectors of the invention comprise a nucleic acid of the invention in a form suitable for expression of the nucleic acid in a host plant cell, which means that the recombinant expression vector includes one or more regulatory sequences, selected on the basis of the host plant cells to be used for expression, which is operatively linked to the nucleic acid sequence to be expressed. With respect to a recombinant expression vector, "operatively linked" is intended to mean that the nucleotide sequence of interest is linked to the regulatory sequence(s) in a manner which allows for expression of the nucleotide sequence (e.g., in a host plant cell when the vector is introduced into the host plant cell). The term "regulatory sequence" is intended to include promoters, enhancers, and other expression control elements (e.g., polyadenylation signals). Such regulatory sequences are described, for example, in Goeddel, Gene Expression Technology: Methods in Enzymology 185, Academic Press, San Diego, Calif. (1990) and Gruber and Crosby, in: Methods in Plant Molecular Biology and Biotechnology, Eds. Glick and Thompson, Chapter 7, 89-108, CRC Press: Boca Raton, Fla., including the references therein. Regulatory sequences include those that direct constitutive expression of a nucleotide sequence in many types of host cells and those that direct expression of the nucleotide sequence only in certain host cells or under certain conditions. It will be appreciated by those skilled in the art that the design of the expression vector can depend on such factors as the choice of the host cell to be transformed, the level of expression of dsRNA desired, etc. The expression vectors of the invention can be introduced into plant host cells to thereby produce dsRNA molecules encoded by nucleic acids as described herein.

In accordance with the invention, the recombinant expression vector comprises a regulatory sequence operatively linked to a nucleotide sequence that is a template for one or both strands of the claimed dsRNA. In one embodiment, the nucleic acid molecule further comprises a promoter flanking either end of the nucleic acid molecule, wherein the promoters drive expression of each individual DNA strand, thereby generating two complementary RNAs that hybridize and form the dsRNA. In another embodiment, the nucleic acid molecule comprises a nucleotide sequence that is transcribed into both strands of the dsRNA on one transcription unit, wherein the sense strand is transcribed from the 5' end of the transcription unit and the antisense strand is transcribed from the 3' end, wherein the two strands are separated by 3 to 500 basepairs, and wherein after transcription, the RNA transcript folds on itself to form a hairpin.

According to the present invention, the introduced polynucleotide may be maintained in the plant cell stably if it is incorporated into a non-chromosomal autonomous replicon or integrated into the plant chromosomes. Alternatively, the introduced polynucleotide may be present on an extra-chromosomal non-replicating vector and be transiently expressed or transiently active. Whether present in an extra-chromosomal non-replicating vector or a vector that is integrated into a chromosome, the polynucleotide preferably resides in a plant expression cassette. A plant expression cassette preferably contains regulatory sequences capable of driving gene expression in plant cells that are operatively linked so that each sequence can fulfill its function, for example, termination of transcription by polyadenylation signals. Preferred polyadenylation signals are those originating from *Agrobacterium tumefaciens* t-DNA such as the gene 3 known as octopine synthase of the Ti-plasmid pTiACH5 (Gielen et al., 1984, EMBO J. 3:835) or functional equivalents thereof, but also all other terminators functionally active in plants are suitable. As plant gene expression is very often not limited on transcriptional levels, a plant expression cassette preferably contains other operatively linked sequences like translational enhancers such as the overdrive-sequence containing the 5'-untranslated leader sequence from tobacco mosaic virus enhancing the polypeptide per RNA ratio (Gallie et al., 1987, Nucl. Acids Research 15:8693-8711). Examples of plant expression vectors include those detailed in: Becker, D. et al., 1992, New plant binary vectors with selectable markers located proximal to the left border, Plant Mol. Biol. 20:1195-1197; Bevan, M. W., 1984, Binary *Agrobacterium* vectors for plant transformation, Nucl. Acid. Res. 12:8711-8721; and Vectors for Gene Transfer in Higher Plants; in: Transgenic Plants, Vol. 1, Engineering and Utilization, eds.: Kung and R. Wu, Academic Press, 1993, S. 15-38.

Plant gene expression should be operatively linked to an appropriate promoter conferring gene expression in a timely, cell type-preferred, or tissue-preferred manner. Promoters useful in the expression cassettes of the invention include any promoter that is capable of initiating transcription in a plant cell present in the plant's roots. Such promoters include, but are not limited to those that can be obtained from plants, plant viruses and bacteria that contain genes that are expressed in plants, such as *Agrobacterium* and *Rhizobium*. Preferably, the expression cassette of the invention comprises a root-specific promoter or a parasitic nematode feeding cell-specific promoter.

The promoter may be constitutive, inducible, developmental stage-preferred, cell type-preferred, tissue-preferred or organ-preferred. Constitutive promoters are active under most conditions. Examples of constitutive promoters include the CaMV 19S and 35S promoters (Odell et al., 1985, Nature 313:810-812), the sX CaMV 35S promoter (Kay et al., 1987, Science 236:1299-1302) the Sep1 promoter, the rice actin promoter (McElroy et al., 1990, Plant Cell 2:163-171), the *Arabidopsis* actin promoter, the ubiquitin promoter (Christensen et al., 1989, Plant Molec. Biol. 18:675-689); pEmu (Last et al., 1991, Theor. Appl. Genet. 81:581-588), the figwort mosaic virus 35S promoter, the Smas promoter (Velten et al., 1984, EMBO J. 3:2723-2730), the GRP1-8 promoter, the cinnamyl alcohol dehydrogenase promoter (U.S. Pat. No. 5,683,439), promoters from the T-DNA of *Agrobacterium*, such as mannopine synthase, nopaline synthase, and octopine synthase, the small subunit of ribulose biphosphate carboxylase (ssuRUBISCO) promoter, and the like. Promoters that express the dsRNA in a cell that is contacted by parasitic nematodes are preferred. Alternatively, the promoter may drive expression of the dsRNA in a plant tissue remote from the site of contact with the nematode, and the dsRNA may then be transported by the plant to a cell that is contacted by the parasitic nematode.

Inducible promoters are active under certain environmental conditions, such as the presence or absence of a nutrient or metabolite, heat or cold, light, pathogen attack, anaerobic conditions, and the like. For example, the promoters TobRB7, AtRPE, AtPyk10, Gemini19, and AtHMG1 have been shown to be induced by nematodes (for a review of nematode-inducible promoters, see Ann. Rev. Phytopathol. (2002) 40:191-219; see also U.S. Pat. No. 6,593,513). Method for isolating additional promoters, which are inducible by nematodes are set forth in U.S. Pat. Nos. 5,589,622 and 5,824,876. Other inducible promoters include the hsp80 promoter from *Brassica* is induced by heat shock; the PPDK promoter is induced by light; the PR-1 promoter from tobacco, *Arabidopsis*, and maize are inducible by infection with a pathogen; and the Adh1 promoter is induced by hypoxia and cold stress. Plant gene expression can also be facilitated via an inducible promoter (For review, see Gatz, 1997, Annu. Rev. Plant Physiol. Plant Mol. Biol. 48:89-108). Chemically inducible promoters are especially suitable if time-specific gene expression is desired. Examples of such promoters are a salicylic acid inducible promoter (PCT Application No. WO 95/19443), a tetracycline inducible promoter (Gatz et al., 1992, Plant J. 2:397-404) and an ethanol inducible promoter (PCT Application No. WO 93/21334).

Developmental stage-preferred promoters are preferentially expressed at certain stages of development. Tissue and organ preferred promoters include those that are preferentially expressed in certain tissues or organs, such as leaves, roots, seeds, or xylem. Examples of tissue preferred and organ preferred promoters include, but are not limited to fruit-preferred, ovule-preferred, male tissue-preferred, seed-preferred, integument-preferred, tuber-preferred, stalk-preferred, pericarp-preferred, and leaf-preferred, stigma-preferred, pollen-preferred, anther-preferred, a petal-preferred, sepal-preferred, pedicel-preferred, silique-preferred, stem-preferred, root-preferred promoters and the like. Seed preferred promoters are preferentially expressed during seed development and/or germination. For example, seed preferred promoters can be embryo-preferred, endosperm preferred and seed coat-preferred. See Thompson et al., 1989, BioEssays 10:108. Examples of seed preferred promoters include, but are not limited to cellulose synthase (celA), Cim1, gamma-zein, globulin-1, maize 19 kD zein (cZ19B1) and the like.

Other suitable tissue-preferred or organ-preferred promoters include the napin-gene promoter from rapeseed (U.S. Pat. No. 5,608,152), the USP-promoter from *Vicia faba* (Baeumlein et al, 1991, Mol Gen Genet. 225(3):459-67), the oleosin-promoter from *Arabidopsis* (PCT Application No. WO 98/45461), the phaseolin-promoter from *Phaseolus vulgaris* (U.S. Pat. No. 5,504,200), the Bce4-promoter from *Brassica* (PCT Application No. WO 91/13980), or the legumin B4 promoter (LeB4; Baeumlein et al., 1992, PlantJournal, 2(2): 233-9), as well as promoters conferring seed specific expression in monocot plants like maize, barley, wheat, rye, rice, etc. Suitable promoters to note are the lpt2 or lpt1-gene promoter from barley (PCT Application No. WO 95/15389 and PCT Application No. WO 95/23230) or those described in PCT Application No. WO 99/16890 (promoters from the barley hordein-gene, rice glutelin gene, rice oryzin gene, rice prolamin gene, wheat gliadin gene, wheat glutelin gene, oat glutelin gene, *Sorghum* kasirin-gene, and rye secalin gene).

Other promoters useful in the expression cassettes of the invention include, but are not limited to, the major chlorophyll a/b binding protein promoter, histone promoters, the Ap3 promoter, the β-conglycin promoter, the napin promoter, the soybean lectin promoter, the maize 15 kD zein promoter, the 22 kD zein promoter, the 27 kD zein promoter, the g-zein promoter, the waxy, shrunken 1, shrunken 2, and bronze promoters, the Zm13 promoter (U.S. Pat. No. 5,086,169), the maize polygalacturonase promoters (PG) (U.S. Pat. Nos. 5,412,085 and 5,545,546), and the SGB6 promoter (U.S. Pat. No. 5,470,359), as well as synthetic or other natural promoters.

In accordance with the present invention, the expression cassette comprises an expression control sequence operatively linked to a nucleotide sequence that is a template for one or both strands of the dsRNA. The dsRNA template comprises (a) a first stand having a sequence substantially identical to from about or from about 19 to about 400 or 500 consecutive nucleotides of SEQ ID NOs:1, 2, 3, 4, 5, 6 or 7; and (b) a second strand having a sequence substantially complementary to the first strand. In further embodiments, a promoter flanks either end of the template nucleotide sequence, wherein the promoters drive expression of each individual DNA strand, thereby generating two complementary RNAs that hybridize and form the dsRNA. In alternative embodiments, the nucleotide sequence is transcribed into both strands of the dsRNA on one transcription unit, wherein the sense strand is transcribed from the 5' end of the transcription unit and the antisense strand is transcribed from the 3' end, wherein the two strands are separated by 3 to 500 basepairs, and wherein after transcription, the RNA transcript folds on itself to form a hairpin.

The invention is also embodied in a transgenic plant capable of expressing the dsRNA of the invention and thereby inhibiting the target genes in parasitic nematodes. Suitable methods for transforming or transfecting host cells including plant cells can be found in Sambrook et al. (Molecular Cloning: A Laboratory Manual. 2$^{nd}$ Ed., Cold Spring Harbor Laboratory, Cold Spring Harbor Laboratory Press, Cold Spring Harbor, N.Y., 1989) and other laboratory manuals such as Methods in Molecular Biology, 1995, Vol. 44, *Agrobacterium* protocols, Ed: Gartland and Davey, Humana Press, Totowa, N.J. Any method may be used to transform the recombinant expression vector into plant cells to yield the transgenic plants of the invention. General methods for transforming dicotyledenous plants are disclosed, for example, in U.S. Pat. Nos. 4,940,838; 5,464,763, and the like. Methods for transforming specific dicotyledenous plants, for example, cotton, are set forth in U.S. Pat. Nos. 5,004,863; 5,159,135; and 5,846,797. Soybean transformation methods are set forth in U.S. Pat. Nos. 4,992,375; 5,416,011; 5,569,834; 5,824, 877; 6,384,301 and in EP 0301749B1. Other plant transformation methods are disclosed, for example, in U.S. Pat. Nos. 4,945,050; 5,188,958; 5,596,131; 5,981,840, and the like.

In accordance with this embodiment, the transgenic plant of the invention is produced by a method comprising the steps of selecting a parasitic nematode target gene from the group consisting of a *H. glycines* cct-6 gene, a *H. glycines* daf-21 gene, a *H. glycines* homolog of the *C. elegans* Y65B4BR.5a gene, and a *H. glycines* pat-10 gene, preparing an expression cassette comprising a first region that is substantially identical to a portion of the selected target gene and a second region which is complementary to the first region, transforming the expression cassette into a plant, and selecting progeny of the transformed plant which express the dsRNA construct of the invention.

Increased tolerance to nematode infection is a general trait for insertion into a wide variety of plants including but not limited to soybean, maize, barley, canola, wheat, cotton, tobacco, sugarbeet, potato, tomato, cabbage, cucumber, pea, and lettuce. In a preferred embodiment, the plant is a soybean plant.

The present invention also provides a method for inhibiting expression of a parasitic nematode target gene selected from the group consisting of a *H. glycines* cct-6 gene, a *H. glycines* daf-21 gene, a *H. glycines* homolog of the *C. elegans* Y65B4BR.5a gene, and a *H. glycines* pat-10 gene. In accordance with this embodiment, the method comprises the step of administering to the nematode a dsRNA in an amount sufficient to inhibit expression of the nucleic acid, wherein one strand of the dsRNA is substantially identical to a portion of SEQ ID NOs:1, 2, 3, 4, 5, 6 or 7. Oligonucleotides corresponding to a parasitic nematode target gene nucleotide sequence, for use as dsRNA in accordance with the invention, can be prepared by standard synthetic techniques, e.g., using an automated DNA synthesizer.

Physical methods of introducing dsRNA into parasitic nematodes include injection of a solution containing the dsRNA or soaking the parasitic nematode in a solution of the dsRNA. Preferably, the dsRNA of the invention is introduced into parasitic nematodes when the nematodes ingest transgenic plants containing expression vectors encoding the dsRNA.

The following examples are not intended to limit the scope of the claims to the invention, but are rather intended to be exemplary of certain embodiments. Any variations in the exemplified methods that occur to the skilled artisan are intended to fall within the scope of the present invention.

EXAMPLE 1

Identification and Isolation of Soybean Cyst Nematode Target Genes

Four soybean cyst nematode (SCN, *Heterodera glycines*) target candidate genes were identified through intensive datamining of the GENBANK SCN EST and *C. elegans* databases. The criteria used for datamining include EST sequence assembling, blast searches, expression of SCN target genes in pre-parasitic J2 stages and parasitic stages, no or very low homology of SCN target genes to soybean endogenous genes at nucleotide levels, essentiality of *C. elegans* homologues and their suitability for RNAi by feeding. The definition of essentiality for a gene includes, for example, developmental defects, lethality and sterility when the target gene is down-regulated or knocked-out by RNAi.

Using total RNA isolated from SCN J2 stage, RT-PCR was used to isolate cDNA fragments that were approximately 400 to 500 bp in length. The PCR products were cloned into TOPO pCR2.1 vector (Invitrogen, Carlsbad, Calif.) and inserts were confirmed by sequencing. RT-PCR was performed using primer sets (SEQ ID NOs:8-15 in FIG. 2) and the SuperScript One-Step RT-PCR with Platinum Taq DNA Polymerase kit (Invitrogen, Carlsbad, Calif., Cat. No. 10928-034). Briefly, total RNA was isolated from SCN J2 (race 3) using standard TRIzol method. RT-PCR reactions contained 0.5 µl SCN J2 total RNA (1 µg/µl), 0.5 µl forward primer (10 pmol/µl), 0.5 µl reverse primer (10 pmol/µl), 12.5 µl of 2×

Reaction Mix, 10.5 µl of ddH2O, 0.5 µl of RT/Platinum Taq Mix in a total volume of 25.0 µl. The reactions were run on a thermal cycler for 30 minutes at 50° C.; followed by 29 cycles at 94° C. for 15 seconds; 55° C. for 30 seconds, 72° C. for 1 minute; followed by 72° C. for 10 minutes, and terminating at 4° C.

Initially, partial cDNA sequences were isolated and used for target validation and for making dsRNA binary expression vectors. The *H. glycines* cct-6 partial cDNA isolated corresponds to nucleotides 859-1404 of SEQ ID NO:1 and was confirmed to be a *H. glycines* homolog of the *C. elegans* cct-6 gene. The *H. glycines* daf-21 partial cDNA isolated corresponds to nucleotides 103-502 of SEQ ID NO:3 and was confirmed to be a *H. glycines* homolog of the *C. elegans* daf-21 gene. The *H. glycines* Y65BR.5a partial cDNA isolated corresponds to nucleotides 96-595 of SEQ ID NO:4 and was confirmed to be a *H. glycines* homolog of the *C. elegans* Y65B4BR.5a gene. The *H. glycines* pat-10 partial cDNA isolated corresponds to nucleotides 1-400 of SEQ ID NO:5 and was confirmed to be a *H. glycines* homolog of the *C. elegans* pat-10 gene.

In order to obtain full-length cDNAs for four SCN targets, 5'cDNA ends were amplified by two different methods. One method utilizes the highly conserved spliced leader sequence (SL1) present in many nematode species. SL1 is located at 5' of many mRNAs resulted from trans-splicing of pre-mRNAs. For some genes, such as *H. glycines* daf-21, the SL1 method was not successful, so a RNA ligase-mediated rapid amplification of 5' and 3' cDNA ends was used (GeneRacer Kit by Invitrogen, Carlsbad, Calif., catalog No. L1500-01).

For the SL1 method, RT-PCR reactions were conducted using SuperScript One-Step kit (Invitrogen, Carlsbad, Calif., catalog No. 10928-034) and a primer set. The forward primer was a 22-mer SL1 sequence and reverse primers were gene specific and were located in previously cloned cDNA regions. The primers used to obtain the 5' portion of the *H. glycines* cct-6 cDNA were SEQ ID NOs:24 and 30. The primers used to obtain the 5' portion of the *H. glycines* Y65BR.5a cDNA were SEQ ID NOs:24 and 37. The primers used to obtain the 5' portion of the *H. glycines* pat-10 cDNA were SEQ ID NOs:15 and 24. Nested PCR reactions were subsequently performed to obtain 5' sequence using PfuUltra High-Fidelity DNA Polymerase (Stratagene, La Jolla, Calif., catalog No. 600380) and a primer set (for *H. glycines* cct-6: SEQ ID NOs: 24 and 31; for *H. glycines* Y65BR.5a: SEQ ID NOs: 24 and 38; for *H. glycines* pat-10: SEQ ID NOs: 24 and 34, all as shown in FIG. 2). The reactions were run on a thermal cycler for 2 minutes at 95° C.; followed by 30 cycles at 95° C. for 30 seconds; 55° C. for 30 seconds, 72° C. for 1.5 minutes; followed by 72° C. for 10 minutes, and terminating at 4° C. PCR products were cloned into pCR4-TOPO vector (Invitrogen, Carlsbad, Calif.) and sequenced.

The GeneRacer kit for 5' rapid amplification of cDNA ends was initiated with the treatment of total RNA with calf intestinal phosphatase to remove the 5'phosphates from truncated mRNA and non-mRNA. The dephosphorylated RNA was then treated with tobacco acid pyrophosphatase to remove of the 5'cap from full length mRNA, leaving an exposed 5'phosphate. The GeneRacer RNA Oligo was ligated to the 5'end of mature mRNA. The reverse-transcription reaction was carried out with SuperScript III RT and first-strand cDNAs were created.

The initial PCR reaction to obtain the 5' portion of the *H. glycines* daf-21 cDNA was conducted using a GeneRacer RNA Oligo and a gene specific reverse primer (SEQ ID NOs: 25 and 41, as shown in FIG. 2). A nested PCR reaction was subsequently performed using GeneRacer 5' nested primer and a gene specific reverse primer (SEQ ID NOs: 26 and 42, as shown in FIG. 2). In both initial and nested PCR, HotStar Taq DNA polymerase (Qiagen, Valencia, Calif., catalog No. 203203) was used. The reactions were run on a thermal cycler for 15 minutes at 95° C.; followed by 35 cycles at 94° C. for 1 minute; 52° C. for 30 seconds, 72° C. for 2 minutes; followed by 72° C. for 10 minutes, and terminating at 4° C. PCR products were cloned into pCR4-TOPO (Invitrogen, Carlsbad, Calif.) and sequenced.

3' cDNA ends of the target genes were amplified using the GeneRacer Kit (Invitrogen, Carlsbad, Calif., catalog No. L1500-01). The first-strand cDNAs were generated through reverse transcription using total RNA and the GeneRacer Oligo dT Primer (SEQ ID NO: 29 as shown in FIG. 2). The 3' RACE PCR was performed with the GeneRacer 3' Primer (SEQ ID NO: 27 as shown in FIG. 2) and a gene-specific forward primer. The 3' primer specific for *H. glycines* cct-6 is set forth as SEQ ID NO: 32; the 3' primer specific for daf-21 is set forth as SEQ ID NO: 43; the 3' primer specific for *H. glycines* Y65BR.5a is set forth as SEQ ID NO 39; and the 3' primer specific for pat-10 is set forth as SEQ ID NO: 35. Nested PCR reactions were subsequently conducted using the GeneRacer 3' Nested Primer (SEQ ID NO: 28) and a gene-specific forward primer. The 3' nested primer specific for *H. glycines* cct-6 is set forth as SEQ ID NO:33; the 3' nested primer specific for *H. glycines* daf-21 is set forth as SEQ ID NO:44; the 3' nested primer specific for *H. glycines* Y65BR.5a is set forth as SEQ ID NO:40; and the 3' nested primer specific for *H. glycines* pat-10 is set forth as SEQ ID NO:36. The reactions were run on a thermal cycler for 2 minutes at 94° C.; followed by 5 cycles at 94° C. for 30 seconds, 72° C. for 1.5 minutes; followed by 5 cycles at 94° C. for 30 seconds, 70° C. for 1.5 minutes; followed by 25 cycles at 94° C. for 30 seconds, 60° C. for 30 seconds, 72° C. for 1.5 minutes; followed by 72° C. at 10 minutes, and terminating at 4° C. PCR products were cloned into pCR4-TOPO (Invitrogen, Carlsbad, Calif.) and sequenced.

The sequences of the *H. glycines* cct-6 PCR fragments isolated above were assembled into two full-length cDNAs corresponding to the gene designated *H. glycines* cct-6, and these sequences are set forth as SEQ ID NO: 1 and SEQ ID NO:2. The two forms of the full-length cDNAs corresponding to *H. glycines* cct-6 are believed to result from alternative trans-splicing by SL1. The sequences of the *H. glycines* daf-21 PCR fragments isolated above were assembled into a single full-length cDNA corresponding to the gene designated as *H. glycines* daf-21, the sequence of which is set forth as SEQ ID NO:3. The sequences of the *H. glycines* Y65BR.5a PCR fragments isolated above were assembled into a single full-length cDNA corresponding to the gene designated as *H. glycines* Y65BR.5a, the sequence of which is set forth as SEQ ID NO:4. The sequences of the pat-10 PCR fragments isolated above were assembled into two cDNAs corresponding to *H. glycines* pat-10, one of which (SEQ ID NO:5) comprising the 5' UTR and the other (SEQ ID NO:6) comprising the SL1 leader sequence. The cDNA corresponding to SEQ ID NO:6 is believed to result from a lack of trans-splicing of pre-mRNA by SL1. SEQ ID NO:7 corresponds to a fragment of the *H. glycines* pat-10 5' UTR which was not cloned in the isolated PCR fragments but which is present in the GENBANK database (Accession NumberBG310753).

EXAMPLE 2

Target Validation on SCN J2 by RNAi Soaking

To validate the targets on SCN directly, RNAi was performed on SCN 2nd juveniles or J2 by in vitro "soaking." dsRNA was synthesized in vitro for a given target. Briefly, a primer set (each containing a T7 promoter primer sequence 5' TAATACGACTCACTATAGGGCAAGCTTG-GTACCGAGCTCG 3' (SEQ ID NO:49) and 5' TAATACGACTCACTATAGGGCGAATTGGGCCCTCTAGATGC 3' (SEQ ID NO:50)) was used to amplify the SCN targets cloned in the TOPO pCR2.1 vector. This resulted in a PCR product or SCN target gene flanked by two T7 promoter sequences in head-to-head configuration. The PCR product was purified with the Qiagen quick PCR purification kit (Qiagen, Valencia, Calif.). An in vitro RNA transcription kit (Ambion, Austin, Tex.) was then used to synthesize dsRNA using the purified PCR product as the template. The in vitro transcribed dsRNA was purified with the Qiagen RNeasy minikit (Qiagen, Valencia, Calif.). The dsRNA was eluted in nuclease-free water. S1 nuclease treatment experiment further confirmed the production of dsRNA, as the enzyme degraded single-stranded (ssRNA), but not dsRNA. The dsRNA concentration was determined by spectrometer at $OD_{260}$.

Freshly (~24 hr) hatched SCN J2s were washed 3-4 times with nuclease-free water (Sigma, St Louis, Mo., cat no 4502), were resuspended in water at 10-15 J2s/μl, and were added into 96-well assay plates (Costar, Cell Culture Cluster, cat. no. 3997). Each well contained about 50 to 75 J2s and approximately 0.6 μg/μl (final concentration) target dsRNA in a total volume of 30 μl. The plates were sealed with parafilm and placed in a sealed plastic container with wet paper towels covered with aluminum foil. The assay was performed at 23° C. in the dark and the phenotypes (immobilized vs. mobilized J2s) were assessed using a dissecting microscope and recorded on Day 5. dsRNA made from bacteria β-galactosidase (GUS) DNA fragment was used as a negative control. The experiments were performed twice with similar observations, i.e., immobilized J2s.

In a representative experiment, more than 95% of the nematodes incubated in water and more than 60% of the nematodes treated with GUS dsRNA demonstrated active mobility at 5 days after treatment. This indicated some nonspecific effect caused by dsRNA on SCN J2s, since GUS dsRNA was used as a negative control. However, fewer than 20% of the nematodes treated with dsRNA comprising a fragment of *H. glycines* Y65B4BR.5a gene corresponding to nucleotides 96-595 of SEQ ID NO:4 demonstrated activity, i.e. 80% of the *H. glycines* Y65B4BR.5a dsRNA-treated nematodes were immobilized. Fewer than 25% of the nematodes treated with ds RNA comprising a fragment of the *H. glycines* daf-21 gene corresponding to nucleotides 103-502 of SEQ ID NO:3 dsRNA demonstrated activity, i.e., 75% of the *H. glycines* daf-21 dsRNA-treated nematodes were immobilized. Fewer than 10% of the nematodes treated with dsRNA comprising a fragment of the *H. glycines* cct-6 gene corresponding to nucleotides 859-1404 of SEQ ID NO:1 demonstrated activity, i.e. 90% of the *H. glycines* cct-6 dsRNA-treated nematodes were immobilized. In the assay for activity of dsRNA corresponding to the *H. glycines* pat-10 gene, fewer than 47% of the nematodes treated with dsRNA corresponding to nucleotides 1-400 of SEQ ID NO:5 (1 μg/μl final concentration) demonstrated activity, i.e. 53% of the *H. glycines* pat-10 nematodes were immobilized, while 74% of the nematodes treated with GUS dsRNA and 92% of nematides treated with water demonstrated active mobility at 5 days after treatment. These results indicate that the four SCN target genes identified in Example 1 are essential to SCN J2 mobility.

EXAMPLE 3

Isolation and Demonstration of Essentiality of C. Elegans Homologs of SCN Target Genes RNAi was discovered in the free-living model nematode *C. elegans* (Fire et al., Nature 391: 806-811, 1998). One of the methods for introducing dsRNA into *C. elegans* is to feed the nematodes with bacteria expressing dsRNA, as *C. elegans* uses bacteria as its food sources (Timmons and Fire, Nature 395, 854, 1998). This method is also analogous to the delivery of dsRNA into SCN through feeding cells, the nutrient sources for SCN provided by plant host.

Homologs of the SCN target genes identified in Example 1 were isolated from *C. elegans* using PCR primers (SEQ ID NOs:16-23 in FIG. 2) and *C. elegans* genomic DNA as a template. The PCR products (~1 kb in length) isolated from exon-rich regions of genomic DNA and were cloned into the multiple cloning site of pLitmus28i (New England Biolabs, Beverly, Mass.), so that *C. elegans* gene fragments were flanked by two T7 promoters in a head-to-head configuration. The DNA sequences of *C. elegans* gene fragments used in RNAi assay were shown in FIG. 3 (SEQ ID NOs 45-48). F01F1.8a (SEQ ID NO:45) is the *C. elegans* homolog of *H. glycines* cct-6 (SEQ ID NOs:1 and 2); C47E8.5 (SEQ ID NO:46) is the *C. elegans* homolog of *H. glycines* daf-21 (SEQ ID NO:3); Y65B4BR.5a (SEQ ID NO:47) is the *C. elegans* homolog of *H. glycines* Y65BR.5a (SEQ ID NO:4); and F57C1.7 (SEQ ID NO:48) is the *C. elegans* homolog of *H. glycines* pat-10 (SEQ ID NOs: 5-7).

The pLitmus28i vectors with the target genes were then transformed into *E. coli* strain HT115(DE3). This strain is deficient in RNase III—an enzyme that degrades dsRNA. Therefore, dsRNA produced in HT115(DE3) is expected to be more stable. Upon IPTG (Isopropyl β-D-Thiogalactopyranoside) induction, T7 RNA polymerase, which is integrated in the genome of HT115(DE3), expresses and binds to the T7 promoters and transcribes dsRNA. The production of dsRNA in *E. coli* was confirmed by total RNA extraction using RiboPure-Bacteria Kit (Ambion, Austin, Tex., cat no 1925) and subsequent S1 nuclease treatment.

Briefly, the *C. elegans* RNAi feeding assay consisted growing the HT115(DE3) cultures overnight, centrifuging the HT115(DE3) cultures at 3000 rpm for 10 minutes, discarding the supernatant and resuspending the pellet in 1 ml of Induction Buffer A at room temperature, overnight. Induction Buffer A consisted of 10 ml of S-Media (Sulston and Brenner, Genetics 77: 95-104, 1974), 10 μl of IPTG (100 mg/ml), and 1 μl of Carbenicillin (50 mg/ml). The cultures were then spun down at 3000 rpm for 10 minutes, the supernatant discarded, and the pellet resuspended in Induction Buffer B to $OD_{600}$ around 0.6. Induction Buffer B consisted of 10 ml of S-Media, 5 μl of IPTG (100 mg/ml), and 1 μl of Carbenicillin (50 mg/ml). In a 96 well microtiter plate, 50 μl of the *E coli* cultures was added to each well. Approximately 3 μl of L1 larvae (10 to 15 L1s) were then added to each well. L1 larvae were chosen for RNAi assay in order to identify genes essential for post-embryonic development of the nematode. The plate was transferred into a container with wet paper towels, and placed in an incubator at approximately 25° C. for 5 days. For each target gene, two independent transformed HT115(DE3) colonies were picked for making the cultures. Each culture was triplicated, so a total of six wells were used for each *C. elegans* gene tested in the assay. The bacteria transformed with pLitmus28i alone (no inserts) was used as the control. The assay was examined and RNAi phenotypes of the *C. elegans* were analyzed.

By Day 5, in the control (pLitmus28i alone), L1 larvae developed into gravid adults and produced many progeny. The administration by feeding dsRNA substantially identical to the four *C. elegans* target genes resulted in arrest in development of nematodes, and the worms in all six wells for a given gene showed consistent RNAi phenotypes. dsRNA substantially identical to the *C. elegans* cct-6 gene (F01F1.8a (SEQ ID NO:45), the homolog of *H. glycines* cct-6(SEQ ID NOs:1 and 2)) caused L2 larval arrest, dsRNA substantially identical to *C. elegans* hsp-90(C47E8.5 (SEQ ID NO:46), the homolog of *H. glycines* daf-21 (SEQ ID NO:3)) caused L3 and L4 larval arrest, dsRNA substantially identical to the *C. elegans* Y65B4BR.5a gene (SEQ ID NO: 47), the homolog of *H. glycines* Y65BR.5a (SEQ ID NO:4)) caused young adult arrest, and dsRNA substantially identical to the *C. elegans* pat-10 gene (F57C1.7 (SEQ ID NO:48) the homolog of *H. glycines* pat-10 (SEQ ID NOs:5-7) caused L4 larval and young adult arrest. These data demonstrated that *C. elegans* homologs of the *H. glycines* target candidates identified in Example 1 are essential for *C. elegans* development. This further indicated that the selected target genes indeed play a key role for nematode development in both SCN and *C. elegans*.

EXAMPLE 4

Binary Vector Construction for Soybean Transformation

In order to evaluate whether the SCN targets are effective in vivo, cDNA fragments for four SCN target genes were used to make binary vectors. The vectors consist of an antisense fragment of the target (e.g. *H. glycines* cct-6), an intron, a sense fragment of target (e.g. *H. glycines* cct-6) and a vector backbone. In such vectors, dsRNA for a given SCN target (e.g *H. glycines* cct-6) was expressed under a Super promoter (Ni, M. et al., Plant Journal 7, 661-676, 1995). This promoter drives transgene expression at high level in many tissues including roots. The selection marker for transformation was a mutated AHAS gene from *Arabidopsis thaliana* that conferred tolerance to the herbicide ARSENAL (imazepyr, BASF Corporation, Mount Olive, N.J.). The expression of mutated AHAS was driven by the *Arabidopsis* actin 2 promoter. The pAW30 vector used as a control in the bioassay experiments set forth in Example 5 and in the molecular characterization experiments of Example 6 contained all of the elements described above, but did not contain sense or antisense fragments of any dsRNA transgene.

Figure 4B:
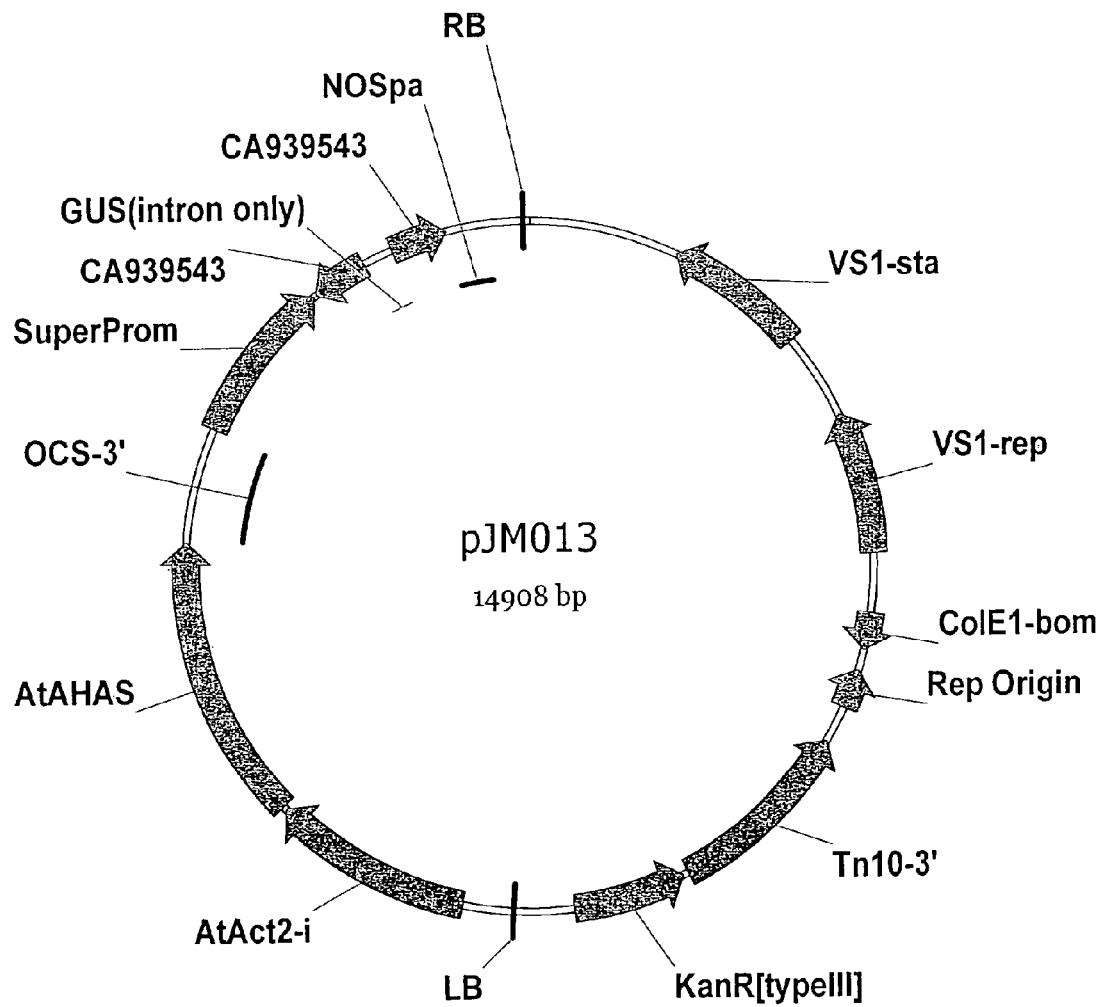
Figure 4C:
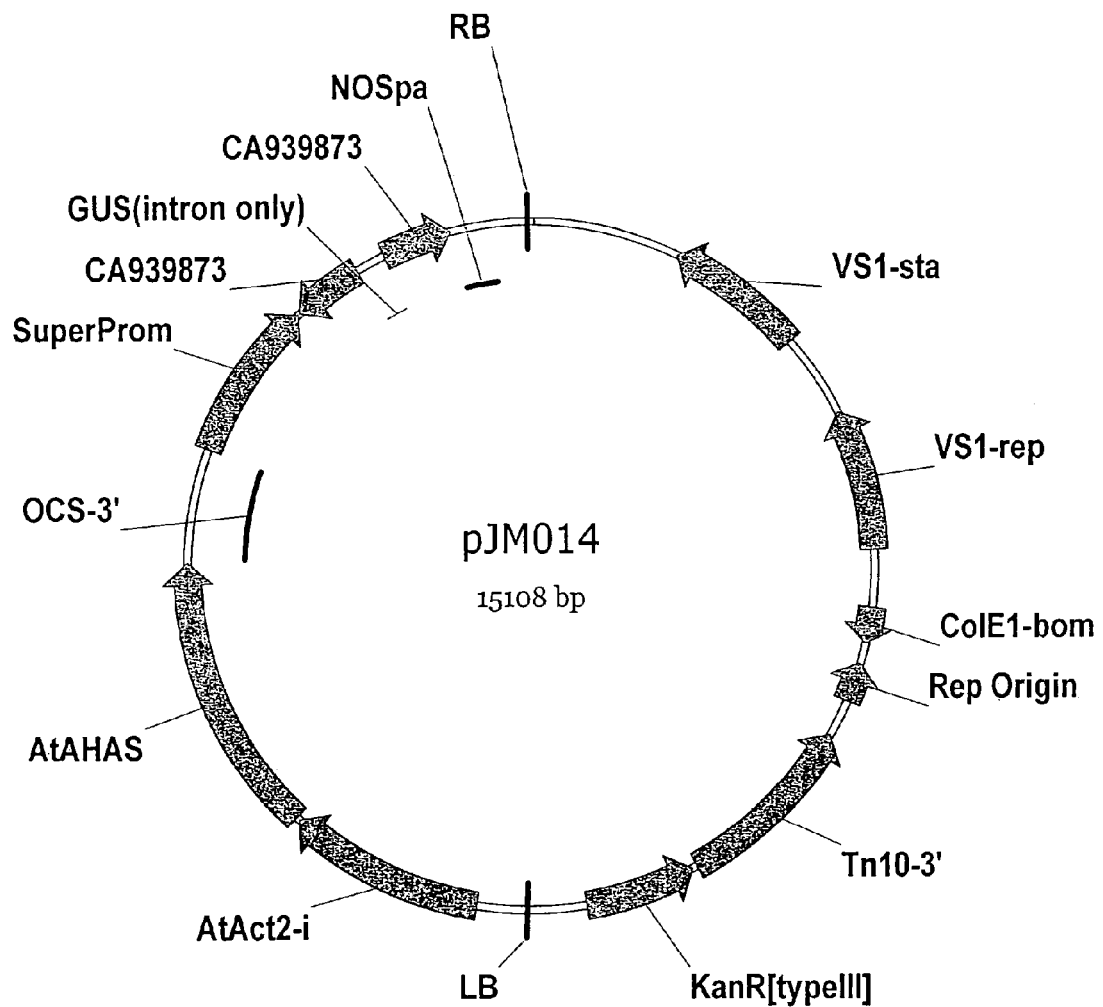
Figure 4E:
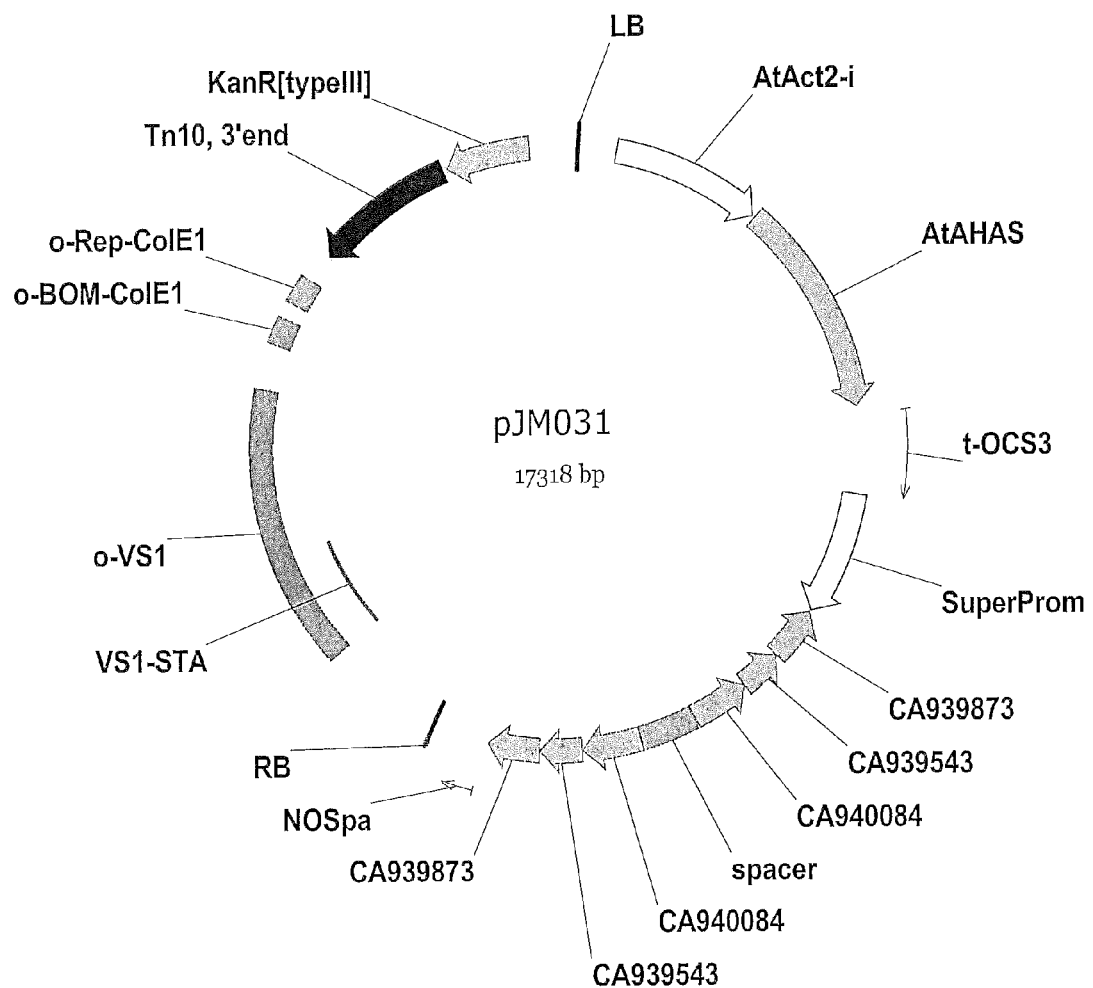

A gene fragment corresponding to nucleotides 1-400 of SEQ ID NO:5 was used to construct the binary vector pJM012 described in FIG. 4A. A gene fragment corresponding to nucleotides 73-472 of SEQ ID NO:3 was used to construct the binary vector pJM013 described in FIG. 4B. A gene fragment corresponding to nucleotides 96-595 of SEQ ID NO:4 was used to construct the binary vector pJM014 described in FIG. 4C. A gene fragment corresponding to nucleotides 859-1361 of SEQ ID NO:1 was used to construct the binary vector pWT-083 described in FIG. 4D. In a separate binary vector, pJM031 (FIG. 4E), three SCN target gene fragments (*H. glycines* cct-6(nucleotides 859-1361 of SEQ ID NO:1), *H. glycines* daf-21 (nucleotides 73-472 of SEQ ID NO:3) and *H. glycines* Y65BR.5a (nucleotides 96-595 of SEQ ID NO:4)) were linked together to use as one antisense fragment or one sense fragment. Such a vector results in production of dsRNAs for the three SCN targets simultaneously to achieve maximum RNAi efficacy for SCN control.

EXAMPLE 5

Generation of Transgenic Soybean Hairy-root and Nematode Bioassay

The soybean cyst nematode can be propagated on normal soybean root explants. However, this technique requires the continual establishment of root explants because these organs have a determinant period of growth in culture. In contrast, soybean hairy roots generated by infecting soybean cotyledons with *Agrobacterium rhizogenes* exhibit indeterminate growth in tissue culture providing an alternative to normal root explants for monoxenic propagation and study of soybean cyst nematode (Cho et. al., (1998) Plant Sci. 138, 53-65). The *A. rhizogenes* can transfer the T-DNA of binary vectors in trans, thereby enabling the production of transgenic hairy roots containing foreign genes inserted in the T-DNA plasmid. This method has been used to produce transgenic roots in several plant species (Christey, (1997) Doran, P. M. (ed) Hairy roots: culture and application, Harwood, Amsterdam, pp. 99-111). The transgenic hairy roots can then be used to study the effect of transgene expression on any given phenotype. In the present example, the transgenic hairy roots were used to study the effect of dsRNA generated from the pJM012 binary vector corresponding to the *H. glycines* pat-10 target gene designated pat-10 (SEQ ID NOs:5-7) in conferring cyst nematode resistance.

Binary vectors pJM012 and pAW30 (empty vector) were respectively transformed into *A. rhizogenes* K599 strain by electroporation (Cho et al., supra). The transformed *Agrobacterium* was used to induce soybean hairy-root formation using the following protocol. Briefly, approximately five days before *A. rhizogenes* inoculation, seeds from soybean cultivar Williams 82 (SCN-susceptible) were sterilized with 10% bleach for 10 min and germinated on 1% agar at 25° C. with 16 hour/day lighting. Approximately three days before *A. rhizogenes* inoculation, a frozen stock of *A. rhizogenes* Strain K599 containing the binary vector was streaked on LB+kanamycin (50 µg/ml) plates and incubated at 28° C. in darkness. Approximately one day before *A. rhizogenes* inoculation, a colony was picked from the plate and inoculated into liquid LB+kanamycin (50 µg/ml). The culture was shaken at 28° C. for approximately 16 hours. The concentration of *A. rhizogenes* in the liquid culture was adjusted to $OD_{600}$=1.0. Cotyledons were excised from the soybean seedling and the adaxial side was wounded several times with a scalpel. 15 µl of *A. rhizogenes* suspension was inoculated onto the wounded surface, and the cotyledon was placed with the adaxial side up on a 1% agar plate for 3 days at 25° C. under 16 hour/day lighting. The cotyledons were then transferred onto MS plates containing 500 µg/ml Carbenicillin (to suppress *A. rhizogenes*) and 1 µM ARSENAL. After culturing the cotyledons on selection media for 2 weeks, hairy roots were induced from the wounding site. The roots resistant to ARSENAL and growing on the selection media were harvested and transferred onto fresh selection media of the same composition and incubated at 25° C. in darkness. Two weeks after harvesting hairy roots and culturing them on selection media, the hairy roots were subcultured onto MS media containing Carbenicillin 500 µg/ml but not ARSENAL. Non-transgenic hairy roots from soybean cultivar Williams 82 (SCN susceptible) and Cyst X (SCN resistant) were also generated by using non-transformed *A. rhizogenes*, to serve as controls for nematode growth in the bioassay.

A bioassay to assess nematode resistance was performed on the transgenic hairy root transformed with the vectors pJM012 and pAW30, and on non-transgenic hairy roots from Williams 82 and Cyst X as controls. Two-week old hairy root cultures of each line that occupied at least half of the plate were inoculated with surface-decontaminated race 3 of soybean cyst nematode (SCN) second stage juveniles (j2) at the level of 2500 J2/plate. The plates were then sealed and put back into the incubator at 25° C. in darkness. Several independent hairy root lines were generated from each binary vector transformation and the lines used for bioassay. As an example of the nomenclature used for the transgenic lines, JM12L3 indicates Line 3 generated from transformation with pJM012. Four weeks after nematode inoculation, the cyst number in each plate was counted. For each line, several replicated plates (number of replicates indicated by n) were used and the average count (AVG), female index %, and standard error (SE) values calculated as shown in the Tables below. Results in each Table represent data from the same bioassay experiment.

As shown in Tables 1, 2 and 3, transgenic lines transformed with pJM012 show statistically significant reduction in female cyst count ranging from 15.4% (M12L15) to 77% (JM12L3) compared to susceptible control Williams 82 or lines L1 and L2 carrying the empty vector AW30L2.

TABLE 1

| | Event ID | | | | |
|---|---|---|---|---|---|
| | W82 | CystX | AW30L1 | JM12L24 | JM12 |
| AVG | 56.0 | 6.0 | 85.5 | 20.0 | 35.3 |
| Female index (%) | 100.0 | 10.7 | 152.7 | 35.7 | 62.9 |
| SE | 8.7 | 0.0 | 5.9 | 12.0 | 9.2 |
| N | 3 | 2 | 8 | 2 | 4 |

TABLE 2

| | Event ID | | | | | |
|---|---|---|---|---|---|---|
| | AW30L2 | JM12L3 | JM12L15 | JM12L26 | JM12L28 | JM12L29 |
| AVG | 61.7 | 26.5 | 9.5 | 22.0 | 17.5 | 22.5 |
| Female index (%) | 100.0 | 43.0 | 15.4 | 35.7 | 28.4 | 36.5 |
| SE | 16.3 | 6.6 | 9.1 | 9.0 | 5.3 | 10.4 |
| N | 6 | 6 | 4 | 6 | 4 | 4 |

TABLE 3

| | Event ID | | | |
|---|---|---|---|---|
| | W82 | CystX | JM12L15 | JM12L3 |
| AVG | 80.0 | 18.0 | 31.9 | 61.6 |
| Female index (%) | 100.0 | 22.5 | 39.8 | 77.0 |
| SE | 17.7 | 8.0 | 4.0 | 8.5 |
| N | 3 | 4 | 7 | 8 |

EXAMPLE 6

Molecular Characterization of dsRNA Transgene Expression

Genomic DNA from hairy root line JM12L3 was used in a PCR assay to test for the presence of *H. glycines* pat-10 anti-sense and sense fragments. The primers JMprim152 (5'-CTCGCTAGTCAAAAGTGTACCAAACA-3' (SEQ ID NO:51) and JMprim153 (5'CTGCACATCAA-CAAATTTTGGTCAT-3' (SEQ ID NO:52)) were used to assay for the anti-sense fragment. JMprim152 anneals to the Super promoter upstream of the anti-sense DNA and JMprim153 anneals to the intron spacer downstream of the *H. glycines* pat-10 anti-sense DNA. This PCR reaction amplified a DNA fragment of the expected size for the *H. glycines* pat-10 anti-sense DNA. No DNA fragment of the expected size was amplified in a control PCR reaction containing genomic DNA from a hairy root line that did not contain pJM12 sequence. The primers JMprim154 (5'-TGAC-CAAAATTTGTTGATGTGC-3' (SEQ ID NO:53)) and JMprim155 (5'-TCGCGTATTAAATGTATAATTGCG-3' (SEQ ID NO:54)) were used to detect the pat-10 sense fragment. JMprim154 anneals to the intron spacer upstream of the pat-10 sense DNA and JMprim155 anneals to the NOSpa terminator downstream of the pat-10 sense DNA. This PCR reaction amplified a DNA fragment of the expected size for the pat-10 sense DNA. No DNA fragment of the expected size was amplified in a control PCR reaction containing genomic DNA from a hairy root line that did not contain pJM12 sequence. These PCR tests confirm the presence of both anti-sense and sense pat-10 DNA in hairy root line JM12L3. Using similar methods, the presence of sense and anti-sense pat-10 DNA was confirmed for hairy root lines JM12L15, JM12L16, JM12L17, JM12L22, JM12L23, JM12L24, JM12L26, JM12L27, JM12L28, JM12L29, JM12L30, JM12L32, JM12L33, JM12L37, and JM12L38.

As another example, hairy root line WT83L3 was assayed for the presence of the *H. glycines* gene cct-6(SEQ ID NO:1) sense and anti-sense DNA fragments from the pWT83 vector. Genomic DNA from WT83L3 was used as the template in the PCR reactions. The primers JMprim152 (SEQ ID NO:51) and JMprim153 (SEQ ID NO:52)) were used to test for the *H. glycines* cct-6 sense sequence. JMprim152 anneals to the Super promoter upstream of the sense *H. glycines* cct-6 DNA and JMprim153 anneals to the intron spacer downstream of the sense *H. glycines* cct-6 DNA. This PCR reaction amplified a DNA fragment of the expected size for the sense *H. glycines* cct-6DNA. No DNA fragment of the expected size was amplified in a control PCR reaction containing genomic DNA from an empty vector control hairy root line. The primers JMprim154 (5'-TGACCAAAATTTGTTGATGTGC-3' (SEQ ID NO:55)) and JMprim155 (5'-TCGCGTATTAAAT- GTATAATTGCG-3' (SEQ ID NO:56)) were used to assay for the anti-sense *H. glycines* cct-6 fragment. JMprim154 anneals to the intron spacer upstream of the anti-sense *H. glycines* cct-6DNA and JMprim155 anneals to the NOSpa terminator downstream of the anti-sense *H. glycines* cct-6DNA. This PCR reaction amplified a DNA fragment of the expected size for the anti-sense *H. glycines* cct-6 DNA. No DNA fragment of the expected size was amplified in a control PCR reaction containing genomic DNA from a hairy root line that did not contain pWT83 sequence. These PCR tests confirm the presence of both sense and anti-sense *H. glycines* cct-6 DNA in hairy root line WT83L3. Using similar methods, the presence of sense and anti-sense *H. glycines* cct-6 DNA was confirmed for hairy root lines WT83L1, WT83L7, WT83L11, WT83L13, WT83L15, WT83L20, WT83L21, and WT83L27.

The following protocol was developed to verify the expression of SCN target dsRNA and the production of siRNAs in hairy roots. RNA samples in Formazol (Molecular Research Center, Cincinnati, Ohio) were run on a 15% acrylamide/bis (19:1)/7M urea gel in 1×Tris-borate/EDTA (TBE) at 200 volts (around 20 mA) for approximately 4 hours, or until the Bromophenol Blue dye was about 2 cm from the bottom of a 20 cm gel. The gel was transferred to Hybond-XL nylon membrane (Amersham Biosciences, Piscataway, N.J.) using a Trans-Blot Cell (Bio-Rad Laboratories, Hercules, Calif.) filled with 1×TBE at 500 mA, around 20 volts, for 2 hours. The membrane was then UV cross-linked. The bottom half of the membrane (below the xylene cyanol dye front) was hybridized with a $^{32}$P-labeled RNA probe that bound to the siRNA of interest, and the top half was used as a loading control by probing with a $^{32}$P-labeled cDNA probe specific for soybean 5.8S rRNA. The RNA probe was made using Ambion's Maxiscript T7 kit (Ambion, Austin Tex.), using the manufacture's protocol. A DNase treatment was used after the transcription reaction, and the probe was passed sequentially through two NucAway spin columns (Ambion, Austin, Tex.) to remove unincorporated nucleotides. The probe was cleaved to an average size of 50 bases in carbonate buffer. To do this, 15 μl of carbonate buffer (0.67% sodium bicarbonate, 1.27% sodium carbonate (weight/volume)) was added per 1 μl of probe. The sample was incubated at 60° C. for a time dependent on the length of the probe, using the formula t=(Li−Lf)/(k×Li×Lf), where t=time in minutes, Li=initial length of probe in kb, Lf=final length of probe in kb, and k=rate constant=0.11 $kb^{-1}$ $min^{-1}$. The reaction was neutralized with 1 μl 3M sodium acetate pH 5.0 per 15 μl of carbonate buffer. $2\times10^6$ counts per minute of radiolabeled probe was used per ml of hybridization solution.

RNA isolated from hairy root lines JM12L3, JM12L15, JM12L24, and JM12L26 was analyzed to detect siRNAs derived from *H. glycines* pat-10 (SEQ ID NO:5) using a $^{32}$P-labeled sense strand *H. glycines* pat-10 RNA probe in the protocol described above. RNA isolated from the transgenic hairy root line AW30L1 containing DNA from the empty vector pAW30 was analyzed simultaneously as a negative control. *H. glycines* pat-10 siRNA was detected in hairy root lines JM12L3, JM12L15, JM12L24, and JM12L26, but not in hairy root line AW30L1. Similar amounts of total RNA were demonstrated to have been loaded in each well of the gel by hybridization with a $^{32}$P-radiolabeled 5.8S cDNA probe. Three distinct siRNA species were detected in the RNA isolated from each of the four JM12 hairy root lines. The approximate sizes of these three siRNA species are 21, 22, and 24 to 25 nucleotides as determined by comparison to a RNA Decade ladder (Ambion, Austin Tex.) that was run on the same gel. Using similar methods, the presence of pat-10 siRNAs was confirmed for hairy root lines JM12L16 and JM12L17.

As another example, RNA isolated from hairy root lines WT83L3 and AW30L1(negative control) was analyzed to detect siRNAs derived from *H. glycines* cct-6(SEQ ID NO:1) using a sense strand $^{32}$P-labeled *H. glycines* cct-6RNA probe in the protocol described above. *H. glycines* cct-6 siRNA of approximately 21 nucleotides was detected in RNA isolated from WT83L3, but siRNA was not detected in RNA isolated from AW30L1. Similar amounts of total RNA were demonstrated to have been loaded in each well of the gel by hybridization with a $^{32}$P-labeled 5.8S cDNA probe. The approximate size of the *H. glycines* cct-6 siRNA detected in RNA isolated from hairy root line WT83L3 was determined by comparison to a RNA Decade ladder that was run on the same gel. Using similar methods, the presence of *H. glycines* cct-6 siRNAs was confirmed for hairy root lines WT83L1, WT83L11, WT83L13, WT83L15, WT83L20, WT83L21, and WT83L27, but was not detected in line WT83L7.

These results demonstrated that in soybean hairy-root, full-length dsRNA transgenes for *H. glycines* targets pat-10 and cct-6 were processed into siRNA. SCN uses its feeding tubes to withdraw nutrients from host feeding cells (or syncytium). The unique structure of nematode feeding tubes limits the size of molecules to approximately 20 kDa, (Bockenhoff and Grundler (1994) Parasitology. 109:249-254) that SCN can take up. The small size of the siRNAs produced in the hairy root lines described above would allow SCN to take up these molecules.

What is claimed is:

1. A transgenic plant capable of expressing a dsRNA comprising
    i) a first strand which comprises a fragment of at least 19 contiguous nucleotides of SEQ ID NO:5, SEQ ID NO:6, or SEQ ID NO:7; and
    ii) a second strand that is completely complementary to the first strand.

2. The transgenic plant of claim 1, wherein the dsRNA causes post-transcriptional gene silencing of a target gene in a parasitic nematode when said nematode feeds on the plant, wherein the target gene comprises a sequence selected from the group consisting of:
    a) a polynucleotide having the sequence as set forth in SEQ ID NO:5;
    b) a polynucleotide comprising at least 19 contiguous nucleotides of SEQ ID NO:5;
    c) a polynucleotide having the sequence as set forth in SEQ ID NO:6;
    d) a polynucleotide comprising at least 19 contiguous nucleotides of SEQ ID NO:6;
    e) a polynucleotide comprising the sequence as set forth in SEQ ID NO:7; and
    f) a polynucleotide comprising at least 19 contiguous nucleotides of SEQ ID NO:7.

3. The transgenic plant of claim 1, wherein the dsRNA comprises a multiplicity of RNA molecules each comprising a double stranded region having a length of 19, 20, or 21 nucleotides, wherein said RNA molecules are selected from the group consisting of:
    a) a polynucleotide having the sequence as set forth in SEQ ID NO:5;
    b) a polynucleotide comprising at least 19 contiguous nucleotides of SEQ ID NO:5;
    c) a polynucleotide having the sequence as set forth in SEQ ID NO:6;
    d) a polynucleotide comprising at least 19 contiguous nucleotides of SEQ ID NO:6;
    e) a polynucleotide comprising the sequence as set forth in SEQ ID NO:7; and
    f) a polynucleotide comprising at least 19 contiguous nucleotides of SEQ ID NO:7.

4. The transgenic plant of claim 1, which is a soybean plant.

5. A method of making a transgenic plant capable of expressing a dsRNA comprising a first strand that is identical to a portion of a pat-10 target gene in a parasitic nematode and a second strand that is complementary to the first strand, said method comprising the steps of:
    a) preparing a nucleic acid sequence comprising a fragment of at least 19 contiguous nucleotides of SEQ ID NO :5, SEQ ID NO:6, or SEQ ID NO:7 wherein the nucleic acid sequence is able to form a double-stranded transcript once expressed in the plant;
    b) contacting a recipient plant with said nucleic acid;
    c) producing one or more offspring of said recipient plant; and
    d) testing the offspring for expression of said double-stranded transcript.

6. The method of claim 5, wherein the target gene comprises a sequence selected from the group consisting of:
    a) a polynucleotide having the sequence as set forth in SEQ ID NO:5;
    b) a polynucleotide comprising at least 19 contiguous nucleotides of SEQ ID NO:5;
    c) a polynucleotide having the sequence as set forth in SEQ ID NO:6;
    d) a polynucleotide comprising at least 19 contiguous nucleotides of SEQ ID NO:6;
    e) a polynucleotide comprising the sequence as set forth in SEQ ID NO:7; and
    f) a polynucleotide comprising at least 19 contiguous nucleotides of SEQ ID NO:7.

7. The method of claim 5, wherein the portion of the target gene is from 19, 20, or 21 to at least 400 contiguous nucleotides of a sequence selected from the group consisting of:
    a) a polynucleotide having the sequence as set forth in SEQ ID NO:5;
    b) a polynucleotide comprising at least 19 contiguous nucleotides of SEQ ID NO:5;
    c) a polynucleotide having the sequence as set forth in SEQ ID NO:6;
    d) a polynucleotide comprising at least 19 contiguous nucleotides of SEQ ID NO:6;
    e) a polynucleotide comprising the sequence as set forth in SEQ ID NO:7; and
    f) a polynucleotide comprising at least 19 contiguous nucleotides of SEQ ID NO:7.

8. The method of claim 5, wherein the plant is a soybean plant.

9. The transgenic plant of claim 2, wherein the target gene comprises the polynucleotide having the sequence as set forth in SEQ ID NO:5.

10. The transgenic plant of claim 2, wherein the target gene comprises a fragment of at least 19 contiguous nucleotides of SEQ ID NO: 5.

11. The transgenic plant of claim 2, wherein the target gene comprises the polynucleotide having the sequence as set forth in SEQ ID NO:6.

12. The transgenic plant of claim 2, wherein the target gene comprises a fragment of at least 19 contiguous nucleotides of SEQ ID NO: 6.

13. The transgenic plant of claim 2, wherein the target gene comprises the polynucleotide having the sequence as set forth in SEQ ID NO:7.

14. The transgenic plant of claim 2, wherein the target gene comprises a fragment of at least 19 contiguous nucleotides of SEQ ID NO:7.

15. The transgenic plant of claim 3, wherein the RNA molecules are derived from the polynucleotide having the sequence as set forth in SEQ ID NO:5.

16. The transgenic plant of claim 3, wherein the RNA molecules comprise a fragment of at least 19 contiguous nucleotides of SEQ ID NO:5.

17. The transgenic plant of claim 3, wherein the RNA molecules are derived from the polynucleotide having the sequence as set forth in SEQ ID NO:6.

18. The transgenic plant of claim 3, wherein the RNA molecules comprise a fragment of at least 19 contiguous nucleotides of SEQ ID NO:6.

19. The transgenic plant of claim 3, wherein the RNA molecules are derived from the polynucleotide having the sequence as set forth in SEQ ID NO:7.

20. The transgenic plant of claim 3, wherein the RNA molecules comprise a fragment of at least 19 contiguous nucleotides of SEQ ID NO:7.

* * * * *

UNITED STATES PATENT AND TRADEMARK OFFICE
CERTIFICATE OF CORRECTION

| | |
|---|---|
| PATENT NO. | : 7,622,301 B2 |
| APPLICATION NO. | : 10/906472 |
| DATED | : November 24, 2009 |
| INVENTOR(S) | : Ren et al. |

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 603 days.

Signed and Sealed this

Twenty-sixth Day of October, 2010

David J. Kappos
*Director of the United States Patent and Trademark Office*

SEQUENCE LISTING

```
<160> NUMBER OF SEQ ID NOS: 56

<210> SEQ ID NO 1
<211> LENGTH: 1827
<212> TYPE: DNA
<213> ORGANISM: Heterodera glycines

<400> SEQUENCE: 1
ggtttaatta cccaagtttg agcttcaata acctttaatt ggaagccatt tgtctgctta      60
cctgttaaat ggcttccatc gcatgtttga acccaaaagc ggagttggcc cggcacgcgg     120
ccgcactgga gatgaacatc agcggtgcta aagggttgca ggaagtgatg aagaccaacc     180
```

-continued

```
tcgggccgaa gggcacgctg aaaatgcttg tctccggttc gggtgacctt aaagtgacta      240
aggacggcaa tgttttactc catgaaatgc aaatccaaca tccgactgct tcactgatcg      300
ccaaggcgtg caccgcgcaa aacgacgtca ccggcgacgg gaccacgtcg accgttctgc      360
tgattggcga actgctcaaa caggccgaga attacgtcag cgagggtgtc cacccccatt      420
tggtcaccga gggtttccaa ttggcccatg accatttgct ccaactgttg gccgcctcca      480
aaaagacgtt gcctatcgac cggccgctgc tcatcgaagt ggccaggacg acgttgcgca      540
caaaattgga ccaaaagttg gccgaccacg tcacggaatg tgttgtggac gccgttttgg      600
caattcgtcg ggatgaaaac gacacggagc ccgacttgca tatgattgaa attcagcaaa      660
tggaacacga gatggagacg gacacgcagc tgatccgtgg cctcgtgctt gaccacggcg      720
gccgacaccc ggacatgccg aagagtgtgc gaaacgtgca cattttgaca tgcaatgttt      780
cgttggagtt tgagaaaact gaggtcaatt cgggccttt ctacaagacg gcggctgagc      840
gtgaacgttt gctgcaagcg gagcgcgaat acatcacacg acgggtgctg aaaattgtgg      900
aactgaagga gacggtctgt gccggtggag atcaaggatt tgtggtgatt aatcaaaagg      960
gcattgatcc gccgtcgttg gatttgttgg cacagcacgg cattttggcc ctgcgacgtg     1020
ccaagcgtcg gaacatggaa cggctgcagt tggcctgcgg cggcgaggcg gtcaattcgg     1080
tggacgacct gacgccgat gtgctcggct gggcaggcag tgtttatgag catgtgctgg     1140
gcgaggacaa atacactttt gtggaggagt gcaaaagtcc caggtcggtc actttgctgc     1200
tcaaagggcc caacaagcac agcatcacgc agctgaagga cgccatttat gacggacagc     1260
gggcggttgc caatgcgttg aaagacggtg ccgttttgcc cggcgccggt gcatttgaaa     1320
ttgcgggata ttgtgcactg aaaaagcttg ccgacaatgt gaaagggcgt gccaaactcg     1380 gtgtttggc ttttgctgag gctttgctgg ttattccgaa aactttggcg gtcaatgccg     1440
gattcgacgc ccaggaggcc attgtcaagc tggtggagac gttcagtgct gctggtgagc     1500
tggtcggatt ggacctggag agcggagagc cgtgtgttcc tcagagcgtt gggacaatg     1560 tgtgcgtgaa gcaggcgagt ctgaacgcct gtcagaacat cgcctccaat ctgctggagg     1620
tggacgaggt gatgcgtgcc ggcatgcgcg acttgaaggg gggacagtga aaatgaacgg     1680
aacggaaatg aaggagcaac accaataaat cacaaaatgt taatggcttt ttctttgttg     1740
aactctgcgc tttattgttt gaatcagacc actgctgttt ttgcttttc aatctcgctt     1800 ttctgaacga atgaaaattt tgacaat                                        1827
```

<210> SEQ ID NO 2
<211> LENGTH: 1015
<212> TYPE: DNA
<213> ORGANISM: Heterodera glycines

<400> SEQUENCE: 2

```
gtttaattac ccaagtttga ggctgagcgt gagcgtttgc tgcaggcgga gcgcgaatac       60
atcacacgac gggtgctgaa aattgtggaa ctgaaggaga cggtctgtgc cggtggagat      120
caaggatttg tggtgattaa tcaaaagggc attgatccgc cgtcgttgga tttgttggca      180
cagcacggca ttttggccct gcgacgtgcc aagcgtcgga acatggaacg gctgcagttg      240
gcctgcggcg cgaggcggt caattcggtg gacgacctga cgcccgatgt gctcggctgg      300
gcaggcagtg tttatgagca tgtgctgggc gaggacaaat acactttgt ggaggagtgc      360 aaaagtccca ggtcggtcac tttgctgctc aaagggccca caagcacag catcacgcag      420
```

```
ctgaaggacg ccatttatga cggacagcgg gcggttgcca atgcgttgaa agacggtgcc      480
gttttgcccg gcgccggtgc atttgaaatt gcgggatatt gtgcactgaa aaagcttgcc      540
gacaatgtga aagggcgtgc caaactcggt gttttggctt ttgctgaggc tttgctggtt      600
attccgaaaa ctttggcggt caatgccgga ttcgacgccc aggaggccat tgtcaagctg      660
gtggagacgt tcagtgctgc tggtgagctg tcggattgg acctggagag cggagagccg       720
tgtgttcctc agagcgtttg gacaatgtg tgcgtgaagc aggcgagtct gaacgcctgt       780
cagaacatcg cctccaatct gctggaggtg gacgaggtga tgcgtgccgg catgcgcgac      840
ttgaaggggg gacagtgaaa atgaacggaa cggaaatgaa ggagcaacac caataaatca      900
caaaatgtta atggctttt ctttgttgaa ctctgcgctt tattgtttga atcagaccac       960
tgctgttttt gcttttcaa tctcgctttt ctgaacgaat gaaaattttg acaat           1015

<210> SEQ ID NO 3
<211> LENGTH: 763
<212> TYPE: DNA
<213> ORGANISM: Heterodera glycines

<400> SEQUENCE: 3
agcgcggctt cgaggtcatc tacatggtcg acccgattga cgagtactgc gtccagcagc       60
tcaaagaata cgacgggaag aagttggtca gtgtgaccaa ggaaggcctt gagctgccag      120
agagtgagga ggagaagaag aaatttgaag aggacaaggt caagttcgag aagctgtgca      180
aagtcattaa ggacatcttg acaagaaag tccaaaaggt ttctgtctca aaccgtttgg       240
tctcttctcc gtgttgcatt gtgaccggag agtacggatg gtctgccaac atggaacgga      300
tcatgaaggc ccaggcattg cgtgactcct ccacaatggg atacatggcg tccaaaaaga      360
acctggagat caaccctgac cattcaatca tcaagtcttt gcgcgaccgt gttgagaagg      420
agcaggacga caaaactgca aaggacctcg ttgtgctgct gtacgaaact tctctgctca      480
cctccggctt ttcattggag acccgcaac agcatgcgtc gcgaatttac cgaatggtga      540
aacttggact tgacatcccc gacgaggagg agccggccga gcaacagccg agcacttcgg      600
gcgagccgac aattgcggag aaaattgctg gtgccgaaga ggaggcctcg agaatggagg      660
aagttgactg aatggtgaca tcgtctatcc attcttggat ctcggctatt caatattttg      720
attcattgtt tttttgtttt cttgtttgac ataaatttga att                       763

<210> SEQ ID NO 4
<211> LENGTH: 805
<212> TYPE: DNA
<213> ORGANISM: Heterodera glycines

<400> SEQUENCE: 4
ggtttaatta cccaagtttg agcaattcga gtgctacaaa tagttcgaaa tggtaactgc       60
ggaagatacc gttaaaacaa aggaagaaga ccccaaaaaa acgacaacgg acgacggatc      120
gagttcagag gaagaagtgc ccgagctcga agagggcgac gttactgaag agcagaaaaa      180
agttgctgag gcgccggac tcagtgagca ggttgccgaa aagggctcca acaatcgcg       240 ttctgaaaag aaggctcgta aactattcag caaacttggc ctcaagcaag tgcacggcgt      300
ttcgcgcgta tgcatccgta atcgaagag cattttgttc gtcatcaaca agccggacgt      360
gtacaaaagt ccgggctccg acacatacgt cgttttggc gaggcaaaaa ttgaagattt       420
ggcacaacac gctcaaatca ctgacgtgga aatttgaaa ccgccctcaa tcattcgcga       480
tgttcgcaac cgaatcacac cggcggagga ggaaagcgat ggcgaagagg ctgatgctac      540
```

```
tggaattgaa gaaaaggata ttgagttggt gatgtcgcaa gcaaatgttt ctcgaaacaa      600
agctatcaaa gcattgaaaa aggctgacaa tgatttggtg aacgctatta tggcattgac      660
aatgtaggag gaagccagag gaattcagag aaaacattgt tgaccttcga atttttgctt      720
caatattttt cctacgggaa tcggttcttt taccattgct gattatgtta ctttacgaat      780
tttgcttata aaaattaaaa agcgt                                             805
```

<210> SEQ ID NO 5
<211> LENGTH: 701
<212> TYPE: DNA
<213> ORGANISM: Heterodera glycines
<400> SEQUENCE: 5

```
accgttttgt cctcctaccc atttcctaaa tcaataaca atccacagat cgctgagaaa       60
tggccgagaa catcgaagaa atccttgccg aaatcgacgg ctcccaaatt gaggagtacc     120
aacgcttttt cgatatgttc gaccgcgaa agaacggtta cataatggcc actcaaattg     180
ggcaaattat gaacgcgatg gagcaggact ttgacgagaa acccctcaga aaattgatcc     240
gaaaatttga cgcggacggc tcgggcaaat tggaattcga cgaattctgc gcgttggtgt     300
acactgtggc caacactgtg gacaaagaca cgttgcgaaa agagctgaga gaggcattcc     360
gactgtttga caaggagggc aatggttaca tttcgcgccc cacgctcaaa ggactgctgc     420
atgaaattgc acccgatctc agcgacaagg atttggaggc ggcggtggac gaaattgacg     480
aggacggcag cggaaagatc gaatttgagg aattttggga actgatggcg ggcgaaacgg     540
actaaacgaa cgatcagaaa gaggaaagaa agaacgaaag aaagtgatca attggcggaa     600
acggcggaac gtacaaaaaa cgtcctcaaa acaaaaataa ataaataatt cgccaattat     660 tattttttgca gcggaatttc ccattaaaat tcagtgaaag t                         701
```

<210> SEQ ID NO 6
<211> LENGTH: 675
<212> TYPE: DNA
<213> ORGANISM: Heterodera glycines
<400> SEQUENCE: 6

```
ggtttaatta cccaagtttg agatcgctga gaaatggccg agaacatcga agaaatcctt       60
gccgaaatcg acggctccca aattgaggag taccaacgct ttttcgatat gttcgaccgc     120
ggaaagaacg gttacataat ggccactcaa attgggcaaa ttatgaacgc gatggagcag     180
gactttgacg agaagaccct cagaaaattg atccgaaaat ttgacgcgga cggctcgggc     240
aaattggaat cgacgaatt ctgcgcgttg gtgtacactg tggccaacac tgtgacaaa     300 gacacgttgc gaaaagagct gagagaggca ttccgactgt ttgacaagga gggcaatggt     360
tacatttcgc gccccacgct caaaggactg ctgcatgaaa ttgcacccga tctcagcgac     420
aaggatttgg aggcggcggt ggacgaaatt gacgaggacg gcagcggaaa gatcgaattt     480
gaggaatttt gggaactgat ggcgggcgaa acgactaaa cgaacgatca gaaagaggaa     540
agaaagaacg aaagaaagtg atcaattggc ggaaacggcg gaacgtacaa aaaacgtcct     600
caaaacaaaa ataaataaat aattcgccaa ttattatttt tgcagcggaa tttcccatta     660
aaattcagtg aaagt                                                       675
```

<210> SEQ ID NO 7
<211> LENGTH: 69
<212> TYPE: DNA

-continued

```
<213> ORGANISM: Heterodera glycines

<400> SEQUENCE: 7
cgttttcgat cgtccttcct tttcttccct ctttttttt gctcctttaa ctcattttct    60
tgatccacc                                                           69

<210> SEQ ID NO 8
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 8
cggagcgcga atacatcaca                                               20

<210> SEQ ID NO 9
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 9
aagcctcagc aaaagccaaa                                               20

<210> SEQ ID NO 10
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 10
acgggaagaa gttggtcagt                                               20

<210> SEQ ID NO 11
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 11
gaagtttcgt acagcagcac                                               20

<210> SEQ ID NO 12
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 12
aaaaaacgac aacggacgac                                               20

<210> SEQ ID NO 13
<211> LENGTH: 20
<212> TYPE: DNA
<213> ORGANISM: Artificial Sequence
<220> FEATURE:
```

<223> OTHER INFORMATION: Description of Artificial Sequence: Synthetic
      primer

<400> SEQUENCE: 13
tcgagaaaca tttgcttgcg                                                     20

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 14
accgttttgt cctcctaccc                                                     20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 15
gggcgcgaaa tgtaaccatt                                                     20

<210> SEQ ID NO 16
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 16
aaagttgggc ttgttgaacg                                                     20

<210> SEQ ID NO 17
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 17
gcaccacgac agtgatatgg                                                     20

<210> SEQ ID NO 18
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 18
aatacgtttc ccgcatgaag                                                     20

<210> SEQ ID NO 19
<211> LENGTH: 20
<212> TYPE: DNA
<213> ORGANISM: Artificial Sequence
<220> FEATURE:
<223> OTHER INFORMATION: Description of Artificial Sequence: Synthetic primer

<400> SEQUENCE: 19
aatgatgcag caaacagcac                                             20

<210> SEQ ID NO 20
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 20
ggcttaattt tggctcagat ttt                                         23

<210> SEQ ID NO 21
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 21
aaagttctcg atcaatagag ggg                                         23

<210> SEQ ID NO 22
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 22
aactcctcga actcaatctt tcc                                         23

<210> SEQ ID NO 23
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 23
aagaatgtgt tttgtggagg aga                                         23

<210> SEQ ID NO 24
<211> LENGTH: 21
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 24
ggtttaatta cccaagtttg a                                           21

<210> SEQ ID NO 25
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

```
<400> SEQUENCE: 25
cgactggagc acgaggacac tga                                          23

<210> SEQ ID NO 26
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 26
ggacactgac atggactgaa ggagta                                       26

<210> SEQ ID NO 27
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 27
gctgtcaacg atacgctacg taacg                                        25

<210> SEQ ID NO 28
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 28
cgctacgtaa cggcatgaca gtg                                          23

<210> SEQ ID NO 29
<211> LENGTH: 60
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 29
gctgtcaacg atacgctacg taacggcatg acagtgtttt ttttttttt tttttttttt   60

<210> SEQ ID NO 30
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 30
ggtgcactcc tccacaaaag tgta                                         24

<210> SEQ ID NO 31
<211> LENGTH: 21
<212> TYPE: DNA
<213> ORGANISM: Artificial Sequence
<220> FEATURE:
<223> OTHER INFORMATION: Description of Artificial Sequence: Synthetic
      primer
```

<400> SEQUENCE: 31
atgctcataa acactgcctg c                                          21

<210> SEQ ID NO 32
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 32
ggatttgttg gcacagcacg gcat                                       24

<210> SEQ ID NO 33
<211> LENGTH: 23
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 33
gctcggctgg gcaggcagtg ttt                                        23

<210> SEQ ID NO 34
<211> LENGTH: 19
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 34
cgtcgaattc caatttgcc                                             19

<210> SEQ ID NO 35
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 35
tgaacgcgat ggagcaggac tttga                                      25

<210> SEQ ID NO 36
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 36
gacgaattct gcgcgttggt gtaca                                      25

<210> SEQ ID NO 37
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 37

```
tacacgtccg gcttgttgat ga                                              22
```

<210> SEQ ID NO 38
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 38

```
tcgatttacg gatgcatacg cg                                              22
```

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 39

```
gtcatcaaca agccggacgt gtaca                                           25
```

<210> SEQ ID NO 40
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 40

```
cattcgcgat gttcgcaacc gaat                                            24
```

<210> SEQ ID NO 41
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 41

```
attgtggagg agtcacgcaa tg                                              22
```

<210> SEQ ID NO 42
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 42

```
tgatccgttc catgttggca ga                                              22
```

<210> SEQ ID NO 43
<211> LENGTH: 26
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 43

```
gtctgccaac atggaacgga tcatga                                          26
```

<210> SEQ ID NO 44
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 44

```
ggcattgcgt gactcctcca caat                                            24
```

<210> SEQ ID NO 45
<211> LENGTH: 1178
<212> TYPE: DNA
<213> ORGANISM: Caenorhabditis elegans

<400> SEQUENCE: 45

```
aaagttgggc ttgttgaacg ggatggggaa tattatcaaa cacggcaaca gatcatagaa      60
acggacacac tgggggaat agaaaaacaa ttttaatatt tattctggtt gtggctgctt      120
caagttggtc ataccagcgc gcatcacttc atcaacaagc aagagattgc atgcaagtac     180
tgtcgccgac gagatactgt tcttcttcac cgtcacattg tcccaaattc cttgtggctc     240
gacagctcct ccggtttcga gatcgagtcc aacggcgata tctggtccag cggcggtttt     300
ctcctcaata agcttaacaa gtgtttcctg agcatcatat cctccattta cggccagtgt     360
ctttggaata acgagaagag cttgagcaaa cgcttcagct ccgagcttgg cacgtccctt     420
caggttctca acatcttttt tcaacatcac gtaggcagca atttcgaaag cagcagctcc     480
agggagaaca gcctctgaaa ataggttact agaacagaag ttaataaaat ttaaactcac     540
tgtcaacgat ggtgttgaaa acagcacgaa gtccatcatg aatagcatcc ttgatttgag     600
tgatggtatg cttgtttggt cccttgataa aagagtcac agattttgga gcacggcatt      660
cctcgataaa cgtgtatttc tcttctccaa gggaatgctc gtaaacgagt ccagcccatc     720
caagatcctc tggagtcaaa tcatcaactg agttgacggc ttctcctccg acggccagct     780
gaagacgttc catgttacgt ctcttggcac gacgaagagc aagaattcct tcggaagcaa     840
gcaagtcaag agatggagga tcgattcctt tctggttgat aacaacgaat cccttattct     900
taccatctgg agaattatca ataaccttct tcttcaactc aataatcttg tgaacacgac     960
gagtaatgaa ttcacgttcg gcagcgagaa gtgcctcacg ttccttggcg tcttgtagaa    1020
aaagtcccga gttgacttca gtcttctcgt attccaaaga aacgttgcaa gtgagaatgt    1080
aagcgtcttt aacgtgtctt ggcatatctg ggtgacgagc tccatgatcg agaactaatc    1140
cacgaacaag tgtggtatcc atatcactgt cgtggtgc                           1178
```

<210> SEQ ID NO 46
<211> LENGTH: 1099
<212> TYPE: DNA
<213> ORGANISM: Caenorhabditis elegans

<400> SEQUENCE: 46

```
aatacgtttc ccgcatgaag gagaaccaaa ctcaaatcta ctacatcacc ggagagtcca      60
aggatgttgt tgctgcttca gctttcgtcg agcgtgttaa gagccgcgga ttcgaagtcc     120
tctacatgtg cgacccaatt gatgagtact gcgtccaaca actcaaggag tatgatggaa     180
agaagcttgt ctccgtcacc aaggaaggac tcgagctccc agaaaccgag gaggagaaga     240
```

-continued

```
agaagttcga agaggacaag gttgcctacg aaaacctttg caaggtcatc aaggacattt      300
tggagaagaa ggttgagaag gttggagttt ctaaccgtct tgtctcttcc ccatgctgca      360
ttgtcacttc cgagtacgga tggtccgcta acatggagcg catcatgaaa gctcaagctc      420
ttcgtgattc ctctactatg ggatacatgg ccgccaagaa gcatctcgaa atcaacccag      480
accacgctat catgaagtaa gttacccaaa aactatttta aaatgaacat tcacaaacgt      540
ttttgctatt tcaggacact tcgtgatcgt gtcgaggtcg ataagaatga caagaccgtt      600
aaggatttgg ttgttcttct tttcgagact gctcttctcg cttccggatt ctcccttgag      660
gagccacaat ctcacgcttc ccgcatctac agaatgatca agcttggtct cgatatcgga      720
gatgacgaaa ttgaagattc tgctgttcca tcatcgtgca ccgctgaggc caagattgag      780
ggagctgagg aggatgcttc ccgcatggag gaggtcgact aaacatccta tttaatttat      840
catttgttac gagaagatct ccccaaaagc ccctccacag ttttattcat tgtttttcctg    900 tctatcgaac ccaaataaag ttccgtaatt aatttcatca atgttttttt ttgcaaacgt      960
gaacttttga agaagcacat ttgaacagtt tagatactcg agggaaatta aacagtttta    1020
gtttatacga aacatgattg caatcttatt cgagttggca tgtttcctga tcttggccag    1080
tgctgtttgc tgcatcatt                                                   1099
```

<210> SEQ ID NO 47
<211> LENGTH: 1152
<212> TYPE: DNA
<213> ORGANISM: Caenorhabditis elegans

<400> SEQUENCE: 47

```
ggcttaattt tggctcagat tttcctcaaa aacatgaaaa tccaatctag aataagtagt       60
aatgggtata ttctaagatt gtgcaaaagt tagcttgaat ttcctcgatt aaagctttcc     120
taccaagaaa aatgtgtgga tattttgaat ttacaagttt ttcatctttt ttttgtaata     180
ttctctttga aactcctgtt tctctcaaat ttgtaaactt tcataaacgt ttttttcagg     240
gttaccacat taaacaatga ccggaagcac cgaaactcgc cagaaggaag tcaaggaggt     300
tggttgttca aagtgacgtc taaaatattt aaatttctat atttcagcca caagttgacg     360
tttcggatga ttccgacaac gaggccgtcg agcaagagct caccgaggag caaagacgtg     420
tggccgaggc tgctggactt ggagatcaca tcgacaagca ggccaagcaa agccgctccg     480
agaagaaggc ccgcaagctc ttctccaagc tcggactcaa gcaagtgact ggtgtctccc     540
gtgtctgcat tcgcaagtcg aagaacatcc tcttcgtcat aaacaagcca gacgtgttca     600
agagcccagg atctgacacc tacatcatct tcggagaagc caagatcgag gatctcacccc   660 aacacgccca gatgtctgct attgagaact tgaagccaac tcgtgaggcc ccacaactca     720
agactgtcga agaggacgag aatgaggatg ttgaggtaat tcagtaactt aatcggatt      780 attacattaa ttgtacggtt taaggaggat tccaccggca ttgaggagaa ggacatcgag     840
cttgtcattt cccaagccaa caccacccgc aacaaggcca tcagggcgct taaggaagct     900
gacaatgaca tcgtcaatgc catcatgagc cttaccatgt agcttgtttc ctgatgacct     960
tgcagatact cttgttatcg ttgtatctct tgcttatccc gttttccgtt ccaagtaaac    1020
gtttatcagt cttttttaac ttttttgtta tgtttaaaaa acaattgcat cttcgaattg    1080
acctaccttt tacagaaaag aacaattaaa tcactgtttg tgtaaaacac ccctctattg    1140
atcgagaact tt                                                         1152
```

<210> SEQ ID NO 48
<211> LENGTH: 1166
<212> TYPE: DNA
<213> ORGANISM: Caenorhabditis elegans

<400> SEQUENCE: 48

```
aactcctcga actcaatctt tccggaaccg tcctcgtcaa tctcgtcgac agcctcctcg      60
agttgttgat cggtgaggtc atcggcgatt tctttgagaa gagccttcag agttggtcga     120
gaaatatatc cgttaccctg aaaaattaat aattaaagaa taaaaagcaa atctaaaag      180
tacaaacctc cttgtcgaaa agacggaaag cttcacgaag ttctttctcc aatgtttcct     240
tgtcgacagt gtttgcaacg gtgtacacga gagcgcagaa ctcgtcaaac tcgagctttc     300
cggaaccgtc agcgtcgaac ttgcggatca gtttacgaag ggtctaaaag aatgaagtta     360
gatgccacat agatttagaa aaatcaaaat catcaattct ataactaaat ttcataacat     420
atagttatat cttactttag tcgacataat aaatgctttt gttcagatgg aatatcaaaa     480
ttaattattt cacaaacatt agtaacatgt tttagtggcg aaaattaatt gaattcagtt     540
gagaaacaag ccgcagaaga taggtcggat aaaaacaaaa ttttaggcaa gagtaaccca     600
tttatatttt cggttatctt actcagttgg cctacctaat cattaccgtg aaacctaaat     660
ttaaaagagt tgaaaacttc ctaatttgaa ttatcactct tctgaagatc ccctaactct     720
acataaacca aaagttccaa aatgatttac cttctcatcg aaatcctgtt ccattccatg     780
catgatttga ccgatctgag tggccatgat gtatccttgc tttcctctgt cgaaggcatc     840
gaagaacttt tggtattcta gaaagtttta atgatgattt ttcaatcata aatataaaat     900
atcttaccct caatttggga tccgtcgatt tcagcaagaa tctcttcgat atcctcagcc     960
tataaaagta taaacatata aaattcaaa aagaaattta ttgaagacat gagaaagcgg    1020
gactcaccat gttgtcggag tttgttgtgc tctggataag cttcgtcggg cagaagcaac    1080
ggcgggagcg agtaggcgga ggaacccgag ggcgggcttt tctttctcac aacggcatca    1140
tcgtctcctc cacaaaacac attctt                                        1166
```

<210> SEQ ID NO 49
<211> LENGTH: 40
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 49

```
taatacgact cactataggg caagcttggt accgagctcg                            40
```

<210> SEQ ID NO 50
<211> LENGTH: 41
<212> TYPE: DNA
<213> ORGANISM: Artificial Sequence
<220> FEATURE:
<223> OTHER INFORMATION: Description of Artificial Sequence: Synthetic
     primer

<400> SEQUENCE: 50

```
taatacgact cactataggg cgaattgggc cctctagatg c                          41
```

<210> SEQ ID NO 51
<211> LENGTH: 26
<212> TYPE: DNA
<213> ORGANISM: Artificial Sequence
<220> FEATURE:

<223> OTHER INFORMATION: Description of Artificial Sequence: Synthetic
      primer

<400> SEQUENCE: 51
ctcgctagtc aaaagtgtac caaaca                                            26

<210> SEQ ID NO 52
<211> LENGTH: 25
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 52
ctgcacatca acaaattttg gtcat                                             25

<210> SEQ ID NO 53
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 53
tgaccaaaat tgttgatgt gc                                                 22

<210> SEQ ID NO 54
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 54
tcgcgtatta aatgtataat tgcg                                              24

<210> SEQ ID NO 55
<211> LENGTH: 22
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 55
tgaccaaaat ttgttgatgt gc                                                22

<210> SEQ ID NO 56
<211> LENGTH: 24
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 56
tcgcgtatta aatgtataat tgcg                                              24